(12) United States Patent
Inokuchi

(10) Patent No.: US 6,259,960 B1
(45) Date of Patent: *Jul. 10, 2001

(54) PART-INSPECTING SYSTEM

(75) Inventor: Masayuki Inokuchi, Tokyo (JP)

(73) Assignee: Joel Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,585

(22) Filed: Oct. 31, 1997

(51) Int. Cl.[7] .............................. G06F 19/00; G06G 7/66
(52) U.S. Cl. .................... 700/110; 700/109; 700/108; 250/306; 250/310; 382/56; 382/54
(58) Field of Search ..................... 364/468.02, 468.15, 364/468.16, 468.17; 250/306, 307, 310; 382/21, 27, 50, 52, 54, 56; 702/33–40

(56) References Cited

U.S. PATENT DOCUMENTS

| | | | |
|---|---|---|---|
| 5,107,206 | * | 4/1992 | Yanagi et al. ...................... 324/158 F |
| 5,127,064 | * | 6/1992 | Flinois et al. ............................ 382/56 |
| 5,233,580 | * | 8/1993 | Tanaka et al. ...................... 369/44.12 |
| 5,477,446 | * | 12/1995 | Takakura et al. ...................... 364/191 |
| 5,550,372 | * | 8/1996 | Yasue .................................... 250/310 |
| 5,655,029 | * | 8/1997 | Rutenberg et al. ................... 382/133 |
| 5,844,850 | * | 12/1998 | Tsutsui et al. ........................ 365/200 |
| 5,863,682 | * | 1/1999 | Abe et al. ............................... 430/30 |

\* cited by examiner

*Primary Examiner*—Paul P. Gordon
*Assistant Examiner*—Ramesh Patel
(74) *Attorney, Agent, or Firm*—Webb Ziesenheim Logsdon Orkin & Hanson, P.C.

(57) ABSTRACT

There is disclosed a part inspecting system that can be easily operated by a human operator. This system has an inspected part information database holding part search information, preliminary inspection information, and review information. The part search information contains information about the positions and sizes of defects present on inspected parts. The review information is obtained from a review apparatus that makes a detailed inspection of the inspected parts. Each inspected part is set on an inspected part-holding member. Apart kind discriminating means is provided to permit the user to enter the kind of the inspected part. A preliminary inspection reading fetches preliminary inspection information about the inspected part specified by the part kind discriminating from the inspected part information database. The user selects a desired one from defects contained in the fetched preliminary inspection information. The selected defect is reviewed, or undergone a detailed inspection. The resulting information is stored in the inspected part information database.

39 Claims, 73 Drawing Sheets

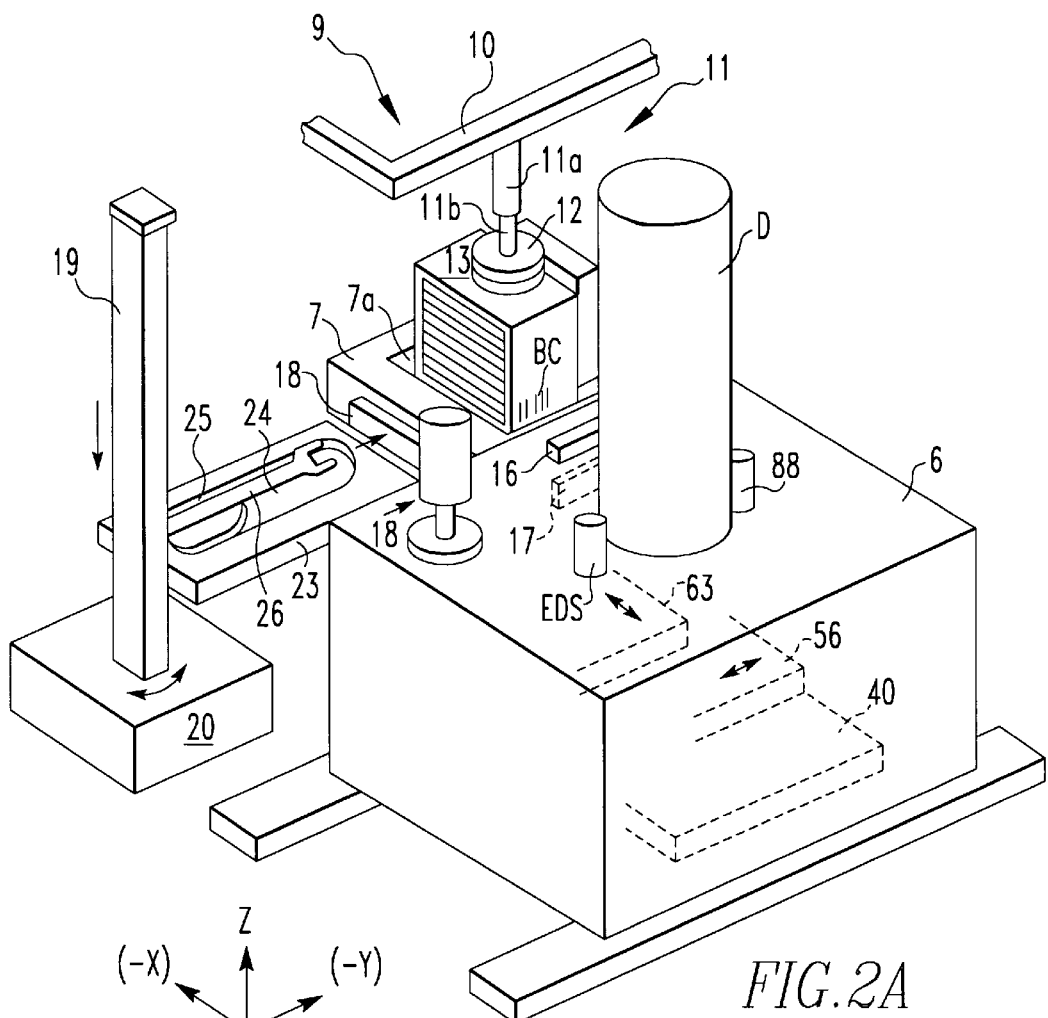
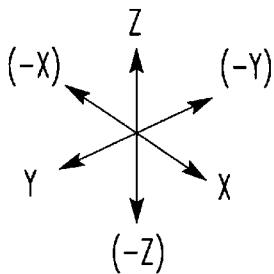
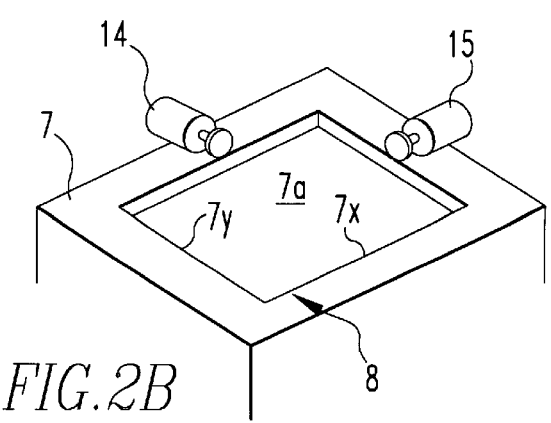
FIG. 2A
FIG. 2B

OPERATION OF TILTED IMAGE-TRACKING MEANS C12 (FIG.69)

OPERATION OF ROTATION-TRACKING MEANS C13 (FIG.68)

OPERATION OF MEANS C22 FOR CORRECTING MISALIGNMENT OF PATTERNED WAFER (FIG.49)

OPERATION OF MEANS C23 FOR CORRECTING MISALIGNMENT OF
UNPATTERNED WAFER (FIG.49)

OPERATION OF AUTOMATIC SHAPE-MONITORING MEANS C5 (FIG.50)

TRACKED AT 3000x

TRACKED AT 10,000x

TRACKED AT 30,000x

TILTED AND
MONITORED

ROTATED AND
MONITORED

ROTATED, TILTED
AND MONITORED

OBSERVATIONAL POINT INFORMATION
REGISTRATION-AND-MANAGEMENT MEANS C51 (FIG.56)

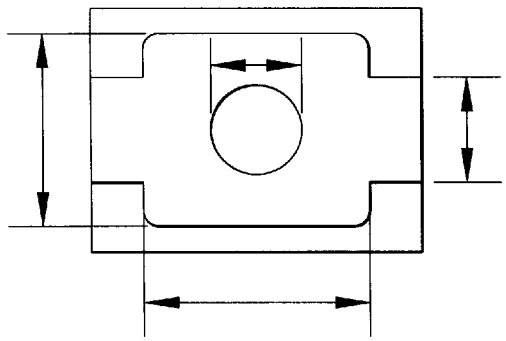
FIG.25A — MEASUREMENT AT TILT ANGLE 0°
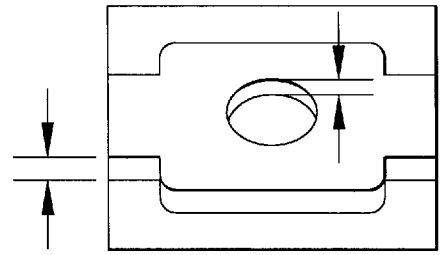
FIG.25B — MEASUREMENT OF HEIGHT AT TILT ANGLE α°
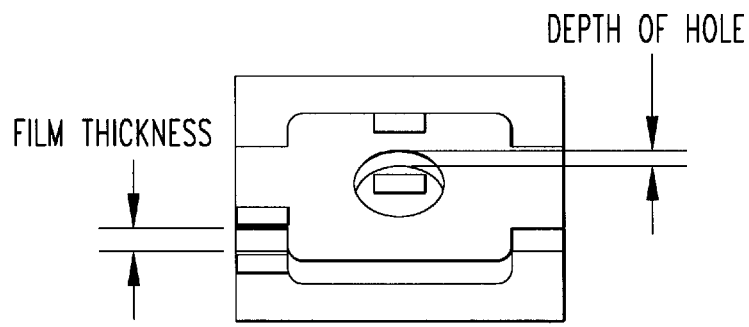
FIG.25C
OPERATION OF AUTOMATIC LENGTH-MEASURE MEANS C54
AT OBSERVED POINT (FIG.52)

OPERATION OF AUTOMATIC-MEASURING MEANS C54 (FIG.52)

OPERATION OF AUTOMATIC DEFECT IMAGE REVIEW EXECUTION MEANS C7 (FIG.62)

OPERATION OF DEFECT-CLASSIFYING MEANS C8

CLASSIFICATION OF ROUND DUST BY DIFS SERVER 3

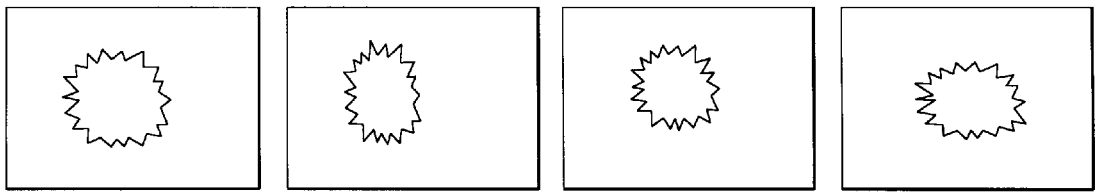

A) : A SET OF IMAGES RECOGNIZED AS ROUND DUST
AMOUNTS OF VARIOUS FEATURES OF IMAGES ARE FOUND.
THEY ARE STORED AS FEATURES OF ROUND DUST (TEACHING)

FIG.28A

CLASSIFICATION OF FIBROUS DUST PARTICLES BY DIFS SERVER 3

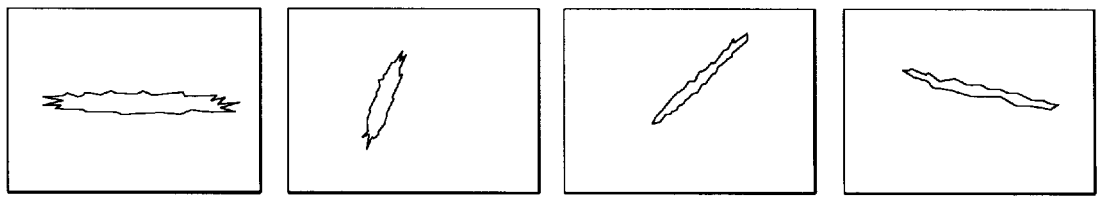

B) : A SET OF IMAGES RECOGNIZED AS FIBROUS DUST
PARTICLES. AMOUNTS OF VARIOUS FEATURES OF IMAGES
ARE FOUND. THEY ARE STORED AS FEATURES OF FIBEROUS
DUST (TEACHING).

FIG.28B

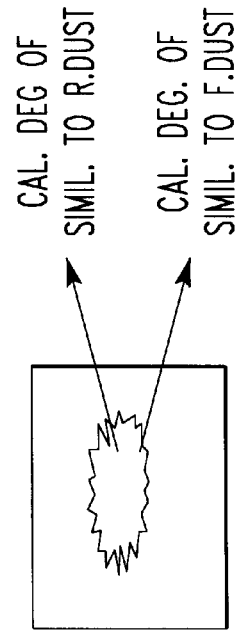

FIG. 28C

CLASSIFICATION BY REVIEW SEMS

SELECT SMALLER ONE
RESULT OF CLASSIFICATION = ROUND DUST

EX.: SUM OF SQUARES OF DIFFERENCES OF AMOUNTS OF FEATURES = 1029.3

EX.: SUM OF SQUARES OF DIFFERENCES OF AMOUNTS OF FEATURES = 3568.7

CAL. DEG. OF SIMIL. TO R.DUST

CAL. DEG. OF SIMIL. TO F.DUST c): CLASSIFICATION OF PHOTOGRAPHED IMAGES FIND VARIOUS AMOUNTS OF FEATURES. FIND DEGREE OF SIMILARITY TO FEATURES OF DUST OBTAINED BY LEARNING. TAKE THE CLOSER ONE AS RESULT OF CLASSIFICATION.

| MENU FOR ENTERING WAFER INFORMATION | |
|---|---|
| | ENTERED VALUE |
| TITLE | X X X X X X X X |
| PRODUCT NO. | X X X X X X X X |
| LOT NO. | X X X X X X X X |
| WAFER ID | X X X X X X X X |
| PROCESS STEP | X X X X X X X X |
| TEST RECIPE | X X X X X X X X |
| SLOT | X X X |
| ASSIGN    START | END |

FIG.32

CREATION OF PROCESSING REQUEST SLIP FOR CIM.

| PROCESSING REQUEST SLIP | |
|---|---|
| TITLE | ENTERED VALUE |
| CASSETTE ID | N N N N N N N N |
| PRODUCT NO. | X X X X X X X X |
| LOT NO. | X X X X X X X X |
| PROCESS STEP | X X X X X X X |
| KIND OF TEST | X X X X X |
| TEST APPA.ID | X X X X X X X X |
| WAFER ID | X X X X X X X |
| SLOT | X X X X X |
| TITLE OF RECIPE | X X X X X X X X |
| REGISTER | END |

| MENU FOR ENTERING WAFER INFORMATION ||
|---|---|
| TITLE | INPUT VALUE |
| PRODUCT NO. | X X X X X X X X |
| LOT NO. | X X X X X X X X |
| WAFER ID | X X X X X X X X |
| PROCESS STEP | X X X X X X X X |
| TEST RECIPE | X X X X X X X X |
| SLOT | X X X |
| ASSIGN    START | END |

FIG.46

|  | (X, Y) | SIZE | |
|---|---|---|---|
| #1 | ( , ) | | |
| #2 | ( , ) | | |
| #3 | ( , ) | | |
| ⋮ | ⋮ | | |

MANUALLY

MANUALLY $\theta = 0°$ $\theta = 10°$

MANUAL CENTERING $\theta = 10°$ $\theta = 20°$

MANUAL CENTERING $\theta = 20°$ $\theta = 30°$

MANUAL CENTERING $\theta = 30°$

φ = 0°

φ = 5°

φ = 5°

φ = 10°

φ = 10°

φ = 15°

φ = 15°

PART-INSPECTING SYSTEM

FIELD OF THE INVENTION

The present invention relates to a part-inspecting system for detecting the presence or absence of a defect (e.g., adhering foreign matter or defective pattern) on an inspected part, such as a silicon wafer, storing information used to identify the inspected part and information about defects, managing these kinds of information, and using the stored information for later operations to detect defects on parts. Especially, the invention relates to a part-inspecting system for performing accurate inspections with an electron microscope or the like.

BACKGROUND OF THE INVENTION

In principle, the "defect" referred to herein means every kind of defect, such as adhering foreign material deteriorating the quality of the inspected part and defective pattern. Where "foreign material" and a "defect" are used in the same sentence or paragraph, the former "foreign material" means a defect caused by adhesion of foreign material, while the latter "defect" means a defect due to other than adhesion of foreign material. The "defective pattern" referred to herein means a defect in a pattern formed on a part under inspection and does not embrace any defect such as adhesion of foreign material.

A part-inspecting system (technique J01) for performing detailed inspection according to information obtained by a preliminary inspection as illustrated in FIGS. 72–76 is known as a part-inspecting system of this kind. This system performs a preliminary inspection, using a commercially available optical part-inspecting apparatus. Information about the results of the preliminary inspection, such as the positions of defects on the inspected part and their size, is stored in memory. Then, the system performs a review inspection, or detailed inspection, with a review apparatus, by reference to the information obtained by the preliminary inspection. A review SEM (scanning electron microscope), an optical review apparatus using an optical microscope, or the like is used as the aforementioned review apparatus.

It is to be noted that "review" referred to herein is to perform detailed inspection of an object under inspection, for knowing the exact position of any defect or foreign material, its shape, or distribution. The "review SEM" using an electron microscope comprises a review SEM body and an EWS (engineering workstation) interfaced to the body by a communications cable.

The controller of the review SEM and the EWS are connected by a communications cable and housed in a common housing. The EWS connected with the SEM controller might be referred to as the SEM EWS. A display device DE for the SEM EWS and a display device D for the SEM controller are both held to the housing described above.

FIG. 72 schematically illustrates a conventional part-inspecting inspecting system of the above-described kind. An optical foreign material-inspecting apparatus 01, an optical defect-inspecting apparatus 02, a defect image filing system (DIFS) server 03 for storing information, an EWS (engineering workstation), etc. are connected by a network N such as Ethernet.

The optical foreign material-inspecting apparatus 01 and the optical defect-inspecting apparatus 02 detect foreign materials and defects on an inspected part and produce data regarding the positions and sizes of the detected foreign materials and defects. The outputs from these two kinds of apparatuses are similar in format. Accordingly, the optical foreign material-inspecting apparatus 01 and the optical defect-inspecting apparatus 02 are collectively referred to as the preliminary inspecting equipment (01, 02).

When a part to be inspected (i.e., a bare wafer on which no pattern is formed) is placed in position for inspection, the optical foreign material-inspecting apparatus 01 automatically detects the position and the size of adhering foreign material. Surfscan 6600 and Surfscan 7700 manufactured by TENCOR Corporation are available as such foreign material-inspecting apparatus. As a result of the inspection performed by the inspecting apparatus 01, a foreign material information file holding the position and the size of any foreign material and other data is delivered.

When a part to be inspected (i.e., a wafer on which a pattern is formed) is placed in position for inspection, the optical defect-inspecting apparatus 02 automatically detects the size and position of any defect (such as adhering foreign material, defective pattern, flaw, or the like). Apparatus 21XX manufactured by KLA Corporation is commercially available as this defect-inspecting apparatus 02.

The preliminary inspecting equipment (01, 02) consisting of the optical foreign material-inspecting apparatus 01 and the defect-inspecting apparatus 02 delivers foreign material information files and defect information files, which might be collectively referred to as preliminary inspection information files.

The preliminary inspection information files created by the optical foreign material-inspecting apparatus 01 and the defect-inspecting apparatus 02 are stored in computers ancillary to the optical foreign material-inspecting apparatus 01 and the defect-inspecting apparatus 02, respectively, or in the DIFS server 03.

Product serial numbers, lot numbers, wafer identification numbers or codes, data about process steps, data about the fabrication equipment, and date are stored in the preliminary inspection information files. Besides, the number of foreign materials, the number of defects, their positions on the wafer, their sizes, and other data are stored. The preliminary inspection information stored in the preliminary inspection information files can be displayed as shown in FIGS. 73A and 73B, for example.

FIGS. 73A and 73B show an example of preliminary inspection information displayed. FIG. 73A shows the contour of a wafer under inspection, as well as the positions of foreign materials or defects on the inspected part. FIG. 73B is a list of numbers given to the foreign materials or defects, their positions, their sizes, and other kinds of information. The preliminary inspection information permits one to grasp the situation and tendency of occurrence of defects produced during fabrication of inspected parts. Therefore, a preliminary inspection information file such as a foreign material information file or defect information file is indispensable for a yield management system.

More specifically, a semiconductor fabrication sequence fabricates 200 to 300 semiconductor chips on a bare wafer. If the result of a preliminary inspection needs an accurate inspection, each inspected part (such as a bare wafer or wafer on which semiconductor chips are being produced) is inspected accurately. If foreign materials or defects discovered by the accurate inspection are considered to degrade the quality of the inspected part below the acceptable level, then it is necessary to find and remove the cause of the defects.

If the operator can infer from the information about the preliminary inspection that the process sequence is at fault, the review SEM is used to know, or review, the shapes of foreign materials or defects or the circumstance. The review SEM can perform a quick review by using the information contained in the preliminary inspection information, i.e., the positions and sizes of the foreign materials or defects. A review SEM using a scanning electron microscope or an optical review SEM can be employed as the above-described review SEM.

When an inspected part should be reviewed by the use of the review SEM, the sample stage (not shown) of the review SEM is set on the part. Then, the initial magnification of the review SEM is set to 3000×, for example. Information (hereinafter referred to as the "optical inspection information") about the positions and sizes of foreign materials or defects previously obtained by the optical foreign material-inspecting apparatus 01 or the defect-inspecting apparatus 02 is read into the SEM EWS. At this time, images shown in FIGS. 73A and 73B are displayed on the display device DE connected with the SEM EWS.

The operator watches the images of FIGS. 73A and 73B, lists the numbers given to foreign materials or defects that might adversely affect the quality of the inspected part, and manually specifies the numbers given to the foreign material or defect that he or she wants to review.

The sample stage of the review SEM is moved according to the information about the position of the foreign material or defect bearing the specific number. The inspected part is moved so that an SEM image of the specified foreign material or defect is displayed in the middle of the display device D.

Then, an electron microscope image of the foreign material or defect specified by the review SEM is displayed on the display device D. At this time, if the position of the foreign material or defect found by the preliminary inspection using an optical microscope agrees with the coordinates of the foreign material or defect on the inspected part set on the sample stage of the review SEM, then it follows that the specified foreign material or defect is displayed in the center of the display device D. If they do not agree, it is necessary to correct the X- and Y-coordinates of the sample on the sample stage of the review SEM.

Generally, the position of the foreign material or defect found by the preliminary inspection using an optical microscope deviates from the coordinates of the foreign material or defect on the inspected part set on the sample stage of the review SEM. Therefore, the specified foreign material or defect is not first displayed in the center of the display device D. Normally, as shown in FIG. 74A, the foreign material or defect is displayed off the center of the viewing screen of the display device D. For example, the magnification of the foreign material or defect shown in FIG. 74A is 3000×. Where the image is magnified at such a magnification (say, 1000× or 3000×) while the foreign material or defect is off the center of the viewing screen, the magnified foreign material or defect is outside the viewing screen and hence impossible to observe. Therefore, where the foreign material or defect is magnified at a high magnification for observation, it is necessary to bring the displayed foreign material or defect in the center of the viewing screen of the display device D.

FIGS. 74A–74C illustrate SEM images of a foreign material or defect specified by the operator and displayed on the display device D. FIG. 74A shows a condition obtained immediately after the operator makes a designation. FIG. 74B shows a condition in which the foreign material or defect is brought into the center of the viewing screen of the display device D. FIG. 74C shows the image of FIG. 74B on a magnified scale.

When an image shown in FIG. 74A is displayed, the operator moves the center of a crisscross cursor Dk into the center of the foreign material or defect displayed together with the cursor, using a mouse. Then, he cricks on the left button. The sample stage (not shown) moves a distance corresponding to the amount of movement of the cursor Dk. As a result, the foreign material or defect moves into the center of the viewing screen of the display device D, as shown in FIG. 74B.

Under the condition of FIG. 74B, the image of the foreign material or defect is magnified, thus obtaining an image as shown in FIG. 74C. Then, the operator observes the displayed foreign material or defect. Thus, he can find the cause or kind of the foreign material or defect in the inspected part, identify the cause of the defect, and make a decision as to whether the defect is fatal.

The operator observes the inspected part in a two-dimensional plane in the sequence illustrated in FIGS. 74A–74C. If it is impossible to precisely judge the foreign material or defect on the part under inspection, the part may be rotated about a vertical line or tilted about a horizontal axis during observation.

Observation of Rotated Image

FIGS. 75A–75E illustrate the case where an observation is made while the foreign material or defect shown in FIG. 74C is tilted at an angle of 60° about a vertical axis parallel to the electron beam of the review SEM. FIG. 75A shows a state in which the angular position θ=0° (i.e., the state of FIG. 74C). FIG. 75B shows a state obtained by rotating the state of FIG. 75A through 10° (i.e., θ=10°). FIG. 75C shows a state obtained by translating an inspected part-holding member in the state of FIG. 75A so that the foreign material or defect is brought into the center of the viewing screen of the display device D. FIG. 75D shows a state obtained by rotating the state of FIG. 75C through 10° (i.e., θ=20°). FIG. 75E shows a state obtained by translating the inspected part-holding member in the state of FIG. 75C so that the foreign material or defect is brought into the center of the viewing screen of the display device D.

Where the operator wants to observe the foreign material or defect shown in FIG. 75A after rotating it through 60°, if the foreign material or defect is placed in the center of rotation, then the foreign material or defect will not move out of the field of view even if the foreign material or defect in the state of FIG. 75A is directly rotated through 60°. However, when the foreign material or defect is off the center of rotation, if the foreign material or defect is rotated through 60°, it will move out of the field of view, making the observation impossible.

Accordingly, the inspected part-holding member is first rotated through only 10°. The foreign material or defect shown in FIG. 75A is moved off the center of the field of view and takes the state of FIG. 75B. Under this condition, the holding member is translated to bring the foreign material or defect into the center of the field of view as shown in FIG. 75C.

Then, the inspected part-holding member is further rotated through 100 until θ=20°. The foreign material or defect shown in FIG. 75C moves off the center of the field of view and assumes the state of FIG. 75D. The holding member is translated to move the foreign material or defect into the middle of the field of view as shown in FIG. 75E.

The operator repeats these operations until the angular position reaches 60°. Under this condition, he can observe the foreign material or defect to review the cause of the generation of the foreign material or defect or its kind.

Observation of Tilted Image

FIGS. 76A–76E illustrate the case where an observation is made after tilting the image of the foreign material or defect shown in FIG. 74C by 45° around a horizontal axis vertical to the electron beam of the review SEM. FIG. 76A shows a state in which the tilt angle $\phi=0°$ (i.e., the state of FIGS. 74C and 75A). FIG. 76B shows a state obtained by tilting the state of FIG. 76A by 5° (i.e., $\phi=5°$) FIG. 76C shows a state obtained by translating the inspected part-holding member in the state of FIG. 76B so that the foreign material or defect is brought into the center of the viewing screen of the display device D. FIG. 76D shows a state obtained by tilting the state of FIG. 76C by 5° (i.e., $\phi=10°$). FIG. 76E shows a state obtained by translating the inspected part-holding member in the state of FIG. 76D so that the foreign material or defect is moved into the center of the viewing screen of the display device D.

When the operator wants to make an observation after tilting the image of the foreign material or defect shown in FIG. 76A at an angle of 45° ($\phi=45°$), the image is not tilted at 45° at once, for the same reason as described in connection with FIGS. 75A–75E. Rather, the tilt angle is increased in increments of 5°, for example. At each tilt angle, the foreign material or defect is moved into the center of the field of view. These operations are repeated. In this way, the operator can observe the foreign material or defect tilted at an angle of 45° (i.e., $\phi=45°$).

Where the inspected part is tilted as shown in FIGS. 76A–76E, as the distance between the foreign material or defect on the inspected part held on the holding member and the tilting axis of the holding member increases, the amount of deviation of the position of the foreign material or defect produced per unit tilt angle increases. Therefore, it is necessary to reduce the increment $\phi$ of the tilt angle according to the distance.

The operator classifies the foreign materials or defects from various points of view (e.g., causes of foreign materials or defects, shapes, and states), using the review SEM, according to the results of the review obtained by the method illustrated in connection with FIGS. 73A–76E. The results of the sorting are used as important information in a yield-managing system.

The prior art part-inspecting system makes use of the following known technique (J02) for measuring the dimensions of patterns on inspected parts by a length-measuring SEM. In order to monitor the processed part under inspection during a lithography or etching step of a semiconductor wafer fabrication sequence, this known technique uses the length-measuring SEM. Linewidths at certain measuring points on the wafer and hole diameters are monitored, using the length-measuring SEM. Hence, any process abnormality can be detected. As a result of the measurement, data about the measured lengths are produced. This data contains product serial numbers, lot numbers, wafer identification numbers, data about process steps, data about the fabrication equipment, and date. In addition, the number of measured points, the positions of the measured points, and linewidths are contained. The data about the measured lengths permits the operator to grasp the state and tendency of the fabrication process. Consequently, data about the measured lengths are indispensable for the production management system.

Problems with Technique (J01)

With the technique (J01) described above, the following problems take place:

(a) Since a review is made with a review SEM, it is necessary for the operator to specify individual defect locations, to enter them in a list, and to specify portions to be reviewed. Hence, the operator must always participate in these operations.

(b) Where foreign materials and defects are identified and classified according to the results of observations, the operator must participate in these operations. Since differences are produced among individual human operators, the result of sorting will differ among the individual operators.

(c) In performing observations, it is necessary to rotate and tilt the sample stage. If these operations are carried out, the field of view escapes. In consequence, the operator is required to perform a centering operation.

(d) In performing observations, the magnification needs to be modified to an appropriate value. Again, an operator's operation is necessary.

(e) Where the results of a review, or detailed inspection, are classified and stored in the DIFS server, the result of sorting differs among individual operators, because they differ in amount of knowledge and capability, and because intuitive judgments are often made. As a result, the reliability of the sorting tends to be impaired.

Problems with the Technique (J02)

(f) Since the length-measuring SEM is unable to tilt inspected parts, the instrument is limited to two-dimensional measurements, such as of linewidths as viewed from just above and of hole diameters. Step heights, heights, depths, film thicknesses, or the like cannot be measured during processing steps.

SUMMARY OF THE INVENTION

In view of the foregoing circumstances and the results of discussions, the present invention has been made.

It is an object of the present invention to satisfy the following requirements (001–0011)):

(001) The amount of operation that the operator must perform on a part-inspecting system is reduced.

(002) Information is obtained by a preliminary inspection of an inspected part. The review SEM can automatically read this preliminary inspection information from an inspected part information database.

(003) The review SEM automatically selects those defects from the preliminary inspection information which are required to be reviewed, and reviews only the selected defects. This shortens the review time.

(004) The review SEM can automatically move the selected defects into a review position according to information about the positions of the defects to be reviewed, the information being contained in the preliminary inspection information.

(005) The review SEM can automatically move the selected defects into an observational position set for inspected parts.

(006) The dimensions of inspected parts taken in the direction of thickness can be automatically calculated.

(007) The deviation of the center position of a defect in the review position from the center of the microscope image is measured. The defect can be automatically moved into the center of the microscope image.

(008) A microscope image can be automatically tilted by a desired specified angle without the defect coming out of the microscope image.

(009) Defects displayed in the microscope image can be displayed automatically in appropriate size.

(0010) Reviewed defects can be readily classified.

(0011) The operations (007)–(009) described above are carried out for each observation point. Abnormalities in reviewed images are detected. Defective shapes or patterns can be easily categorized.

Operation of the First Embodiment

Referring to FIGS. 1–5, 9 part-inspecting system according to a first embodiment of the present invention is constructed as described thus far, and has an inspected part information data base holding both preliminary inspection information and review information. The preliminary inspection information contains search information obtained from preliminarily inspected parts (W) and information about the positions and sizes of defects present on the inspected parts (W). The review is a detailed inspection performed, using a review apparatus comprising a microscope that performs a detailed inspection of the inspected parts (W).

An X-Y table (56+63on FIG. 2A) is placed inside a vacuum inspection chamber (6) of the review apparatus. This table moves an inspected part-holding member (65 on FIG. 5) along mutually perpendicular X- and Y-axes to bring a desired portion of the inspected part (W) held to the holding member (65) into the review position. A microscope image pickup means incorporated in the microscope for detailed inspection takes a microscope image according to a magnification determined by a microscope magnification-setting means. That is, the microscope image is stored as digital data.

Search information about the inspected part (W) set on the inspected part-holding member (65) is entered by a part search information input means (C41) of the review apparatus. This input means (C41) can consist of a manual input means or automatic input means. Where the part search information input means (C41) is a manual input means, it can comprise a display device, a means for displaying a menu on the viewing screen of the display device to prompt the user to enter part search information, a keyboard, and a means for storing inputs entered from the keyboard. Where the part search information input means (C41) is an automatic input means, it can be a reading means (16) for reading bar codes from a cassette (13) holding the inspected part (W) therein.

The review apparatus has a preliminary inspection information reading means (C42) for reading preliminary inspection information about that inspected part (W) from the inspected part information database which is specified by the part search information entered from the part search information input means (C41). Therefore, when a review, or detailed inspection, of the inspected part (W) is done by the review apparatus, the preliminary inspection information (e.g., information regarding the size of the inspected part (W), the size of the defect, and its position) about the inspected part (W) can be used.

A defect to be reviewed is selected from defects contained in the preliminary inspection information read in by the preliminary inspection information reading means (C42) of the review apparatus. The defect can be reviewed. A review information registration means (C43) stores review information obtained by the review in the inspected part information database. Accordingly, the review information stored in this database can be utilized through a computer that can gain access to the inspected part information database.

An inspected part-moving means moves the above-described X-Y table (56+63) to bring the inspected part (W) held to the inspected part-holding member (65) into target coordinates on the X-Y plane.

Misalignment-correcting means (C22) have set state coordinate deviation amount-detecting means for detecting the amount of deviation of the position, or coordinates, when the inspected part is placed in position and a reference point-coinciding moving means. The set state coordinate deviation amount-detecting means detects the amounts of deviation of the X- and Y-coordinates of the part position reference point on the review apparatus when the inspected part is set on the inspected part-holding member (65) from the x- and y-coordinates of the part position reference point of the inspected part (W) on the review apparatus, the x and y-coordinates being detected by the preliminary inspection apparatus. The reference point-coinciding moving means moves the inspected part (W) the detected amounts along the X- and Y-axes so that the x- and y-coordinates of the reference position of the part agree with the X- and Y-coordinates.

Accordingly, if the x- and y-coordinates of a desired portion (such as defect or foreign material) of the inspected part (W) detected by the preliminary inspection are different from the X- and Y-coordinates of the inspected portion when the part is set on the inspected part-holding member (65), this inspected portion can be precisely moved into the review position.

Operation of the Second Embodiment

In a part-inspecting system according to a second embodiment of the present invention, the set state coordinate deviation amount-detecting means detects the amounts of difference between the x- and y-coordinates of the part position reference point on the preliminary inspection apparatus detected by this preliminary inspection apparatus for the inspected part (W) and the X- and Y-coordinates of the reference point on the review apparatus when the part is set on the inspected part-holding member (65). A target coordinate-correcting means corrects target coordinates to be assumed by the part position reference point after movement of the inspected part, according to the amounts of deviation of the position of the inspected part. An inspected part-moving means moves the above-described X-Y table (56+63) to bring the inspected part (W) held to the inspected part-holding member (65) into the target coordinates on the X-Y plane.

Accordingly, if the coordinates of a desired portion (i.e., the position of a defect or foreign material on the inspected part (W) detected by the preliminary inspection) of the inspected part (W) detected by the preliminary inspection deviate from the coordinates of the inspected portion when the part is set on the inspected part-holding member (65), this inspected portion can be precisely moved into the review position.

Operation of the Third Embodiment

In a part-inspecting system according to a third embodiment of the present invention, an angular position-specifying means specifies the angular position of a rotating table (64) which can adjust the angular position of the inspected part-holding member (65) about an axis of rotation vertical to both X- and Y-axes.

A rotation control means rotates the rotating table (64) so that the inspected part (W) held to the inspected part-holding member (65) rotates into a target angular position corresponding to an angle specified by the angular position-specifying means within the X-Y plane. A set state angular position-detecting means detects the angular position of the inspected part (W) set on the inspected part-holding member (65) within the X-Y plane.

Misalignment-correcting means have an angular position deviation amount-detecting means and an angular position-coinciding rotating means. The angular position deviation amount-detecting means detects the amount of deviation of the angular position of the inspected part (W) within the X-Y plane detected by the preliminary inspection apparatus from the angular position within the X-Y plane when the part is set as described above. The angular position-coinciding rotating means rotates the rotating table through an angle corresponding to the detected amount of deviation of the angular position so that the angular position of the reference position of the inspected part (W) within the x-y plane coincides with the angular position of the inspected part (W) within the X-Y plane when the part is placed in position.

Accordingly, if the angular position of a desired inspected portion (i.e., the angular position of a defect or foreign material on the inspected part (W) detected by the preliminary inspection) on the inspected part (W) within the xy-plane deviates from the angular position within the XY-plane when the part is set as described above, this inspected portion can be precisely moved into the review position.

Operation of the Fourth Embodiment

In a part-inspecting system according to a fourth embodiment of the invention, an angular position-specifying means specifies the angular position of a rotating table(64) which can adjust the angular position of the inspected part-holding member (65) about an axis of rotation vertical to both X- and Y-axes.

A rotation control means rotates the rotating table (64) so that the that the inspected part (W) held to the inspected part-holding member (65) rotates into a target angular position corresponding to an angle specified by the angular position-specifying means within the X-Y plane. A set state angular position-detecting means detects the angular position of the inspected part set on the inspected part-holding member (65) within the X-Y plane.

An angular position deviation amount-detecting means detects the amount of deviation of the angular position of the inspected part (W) within the xy-plane detected by the preliminary inspection apparatus from the angular position within the XY-plane when the part is placed in position as described above.

A target position-correcting means corrects the target angular position of the inspected part (W) assumed during rotation according to the aforementioned amount of deviation of the angular position.

A rotation control means rotates the rotating table (64) so that the inspected part (W) held to the inspected part-holding member (65) rotates into a target angular position corrected as described above.

Accordingly, if the angular position of the inspected part (W) within the xy-plane detected by the preliminary inspection apparatus deviates from the angular position within the XY-plane when the part is set as described above, the target angular position of the inspected part. (W) assumed during rotation is corrected. Thus, the inspected portion can be precisely moved into the desired angular position.

Operation of the Fifth Embodiment

In a part-inspecting system according to a fifth embodiment of the invention, an inspected part information database holds information about an observational position set for the inspected part (W), a reference image that is a normal microscope image at that position, information about the magnification of the image, and observational information having feature amounts that are numerical values representative of features of the image.

An evaluation value is set according to the amount of features of an actual microscope image in an observational position set on the inspected part (W). Another evaluation value is determined according to the amount of features of the reference image. An automatic shape-monitoring means (C5) compares these two evaluation values and regards the microscope image as abnormal if the difference between these two evaluation values is in excess of a preset value.

The microscope image judged to be abnormal can be stored in memory together with a sort code indicating the abnormality. With respect to the reference image, information about the tilt of the reference image where the reference image is taken, information about the angular position of the inspected part (W) when the reference image is taken, and other kinds of information can be stored in memory, as well as the information about the magnification.

Operation of the Sixth Embodiment

In a part-inspecting system according to a sixth embodiment of the invention, the information about observations contains information for identifying a portion whose dimensions are to be measured. An automatic length-measuring means (C54) measures the dimensions of the portion identified by the above-described information for identifying the portion to be measured. This measurement is made on the actual microscope image in the observational position set for the inspected part (W).

Operation of the Seventh Embodiment

In a part-inspecting system according to a seventh embodiment of the invention, an automatic defect point moving means (C22) automatically moves a selected defect into the review position by moving the X-Y table (56+63) according to the information about the position of the defect, the information being contained in the preliminary inspection information. Therefore, the amount of work that the operator must perform in operating the review apparatus is reduced.

Operation of the Eighth Embodiment

In a part-inspecting system according to an eighth embodiment of the invention, an automatic centering means (C11) has a defect center position deviation amount-measuring means and a defect-moving means for moving the defect into the center position. The defect center position deviation amount-measuring means measures the deviation of the center of the defect from the center of the microscope image after the defect has been moved into the review position. The defect-moving means moves the defect an amount equal to the measured deviation so that the defect is brought into the center of the microscope image. Consequently, the image of the defect is invariably displayed at the center of the microscope image, thus facilitating observation of the defect.

Operation of the Ninth Embodiment

In a part-inspecting system according to a ninth embodiment of the invention, if an automatic field of view adjustment-commanding means commands an automatic adjustment of the field of view, an automatic field of view-adjusting means (C14) causes the microscope image magnification-setting means to set the magnification of the microscope image to a preset appropriate value according to the size of the defect on the microscope image.

Operation of the Tenth Embodiment

In a part-inspecting system according to a tenth embodiment of the invention, the inspected part information database has a defect image sorting database in which a microscope image of a defect produced on the inspected part (W) is stored, along with a sort code corresponding to the kind of the defect. The defect image sorting database stores plural numerical values as amounts featuring the defect, the numerical values being associated with the size and shape of the defect.

Accordingly, a sort code and a feature amount are stored in the defect image sorting database for each defect. When a sort code is attached for the defect of the inspected part (W), the feature amount of the defect is computed. Thus, a sort code corresponding to the computed feature amount can be automatically attached.

Operation of the Eleventh Embodiment

In a part-inspecting system according to an eleventh embodiment of the invention, the review apparatus is equipped with an intelligent defect information processing means (C21) for automatically selecting a defect that needs to be reviewed from the preliminary inspection information. This can reduce the burden imposed on the operator in operating the review apparatus. Hence, the efficiency of the work can be enhanced.

Operation of the Twelfth Embodiment

In a part-inspecting system according to a twelfth embodiment of the invention, a cassette placement portion is mounted adjacent to the vacuum inspection chamber (6) of the review apparatus, and a cassette (13) holding an inspected part (W) is placed on the cassette placement portion. An inspected part-transporting device (19–28+D3–D6+M3–M6) takes the inspected part (W) from the cassette (13) placed on the cassette placement portion, transports the part to the inspected part-holding member (65), and carries the inspected part (W) undergone an inspection from the inspected part-holding portion (65) to the cassette (13).

When the cassette (13) holding preliminary inspection information about the inspected part (W) in the cassette (13) is placed on the cassette placement portion, if the preliminary inspection information can be searched for, the part search information input means (C41) having a search information-detecting means (16) detects information used in searching for the inspected part (W).

The preliminary inspection information reading means (C42) of the review apparatus reads the preliminary inspection information about the inspected part (W) from the inspected part information database according to the search information detected by the part search information input means (C01).

Operation of the Thirteenth Embodiment

In a part-inspecting system according to a thirteenth embodiment of the invention, the review apparatus has an x-ray analyzer for making an x-ray analysis of the inspected part in the review position. An x-ray analysis execution-judging means makes a decision as to whether execution of an x-ray analysis is commanded or not. If the execution is commanded, an automatic x-ray analysis execution means automatically carries out an x-ray analysis.

Other objects and features of the invention will appear in the course of the description thereof, which follows.

BRIEF DESCRIPTION OF THE DRAWINGS

FIG. 2A is a perspective view of a wafer-transporting device and the body of a review SEM (scanning electron microscope) included in the system shown in FIG. 1, the wafer-transporting device acting to transport wafers into and out of a sample exchange chamber in the body of the review SEM;

FIG. 2B is a fragmentary perspective view of a cassette-positioning device shown in FIG. 2A;

FIG. 25A is a diagram showing a measurement image with a tilt angle of 0°, illustrating a function of an automatic observational point length-measuring means C54;

FIG. 25B is a diagram similar to FIG. 25A, but in which the tilt angle is α°;

FIG. 25C is a diagram similar to FIG. 25B, but illustrating a method of measuring a film thickness and a hole depth;

FIGS. 28A–28C are diagrams illustrating processing for classifying defects;

FIG. 32 is a diagram illustrating a menu displayed in step 3 of the flowchart of FIG. 31;

FIG. 46 is a diagram illustrating a menu displayed in step 103 of FIG. 44 to enter information about wafers;

DESCRIPTION OF THE PREFERRED EMBODIMENTS

In this specification, numbers preceded by an upper case C or G (e.g., "C41") refer to subheading in the specification.

Figure 1:
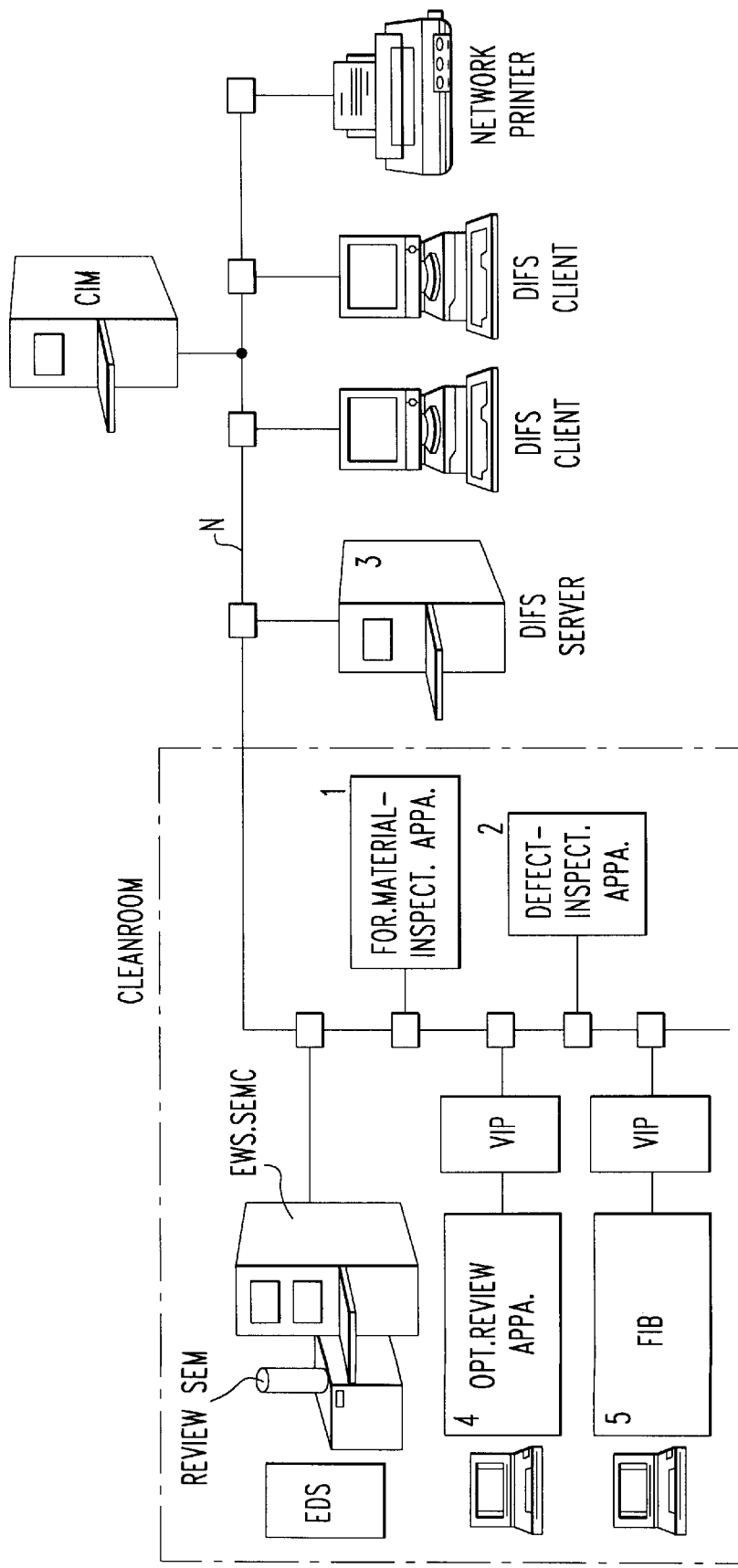
FIG. 1 is a diagram of a part-inspecting system according to Embodiment 1 of the present invention, illustrating the whole system.

Referring to FIG. 1, there is shown a part-inspecting system according to Embodiment 1 of the present invention. An optical foreign material-inspecting apparatus 1, an optical defect-inspecting apparatus 2, a defect image filing system (DIFS) server 3 for storing information, an EWS (engineering workstation), etc. are connected by a network N, such as Ethernet.

Figure 72:
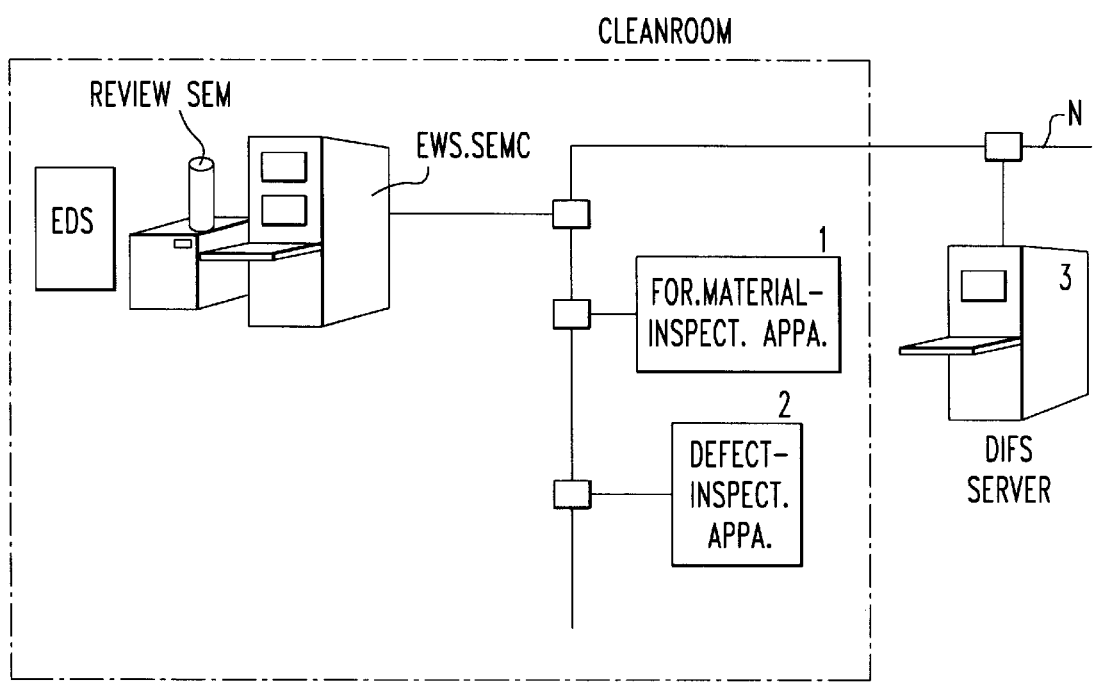
FIG. 72 is a schematic diagram of the prior art part-inspecting system.
Figures 73A, 73B:
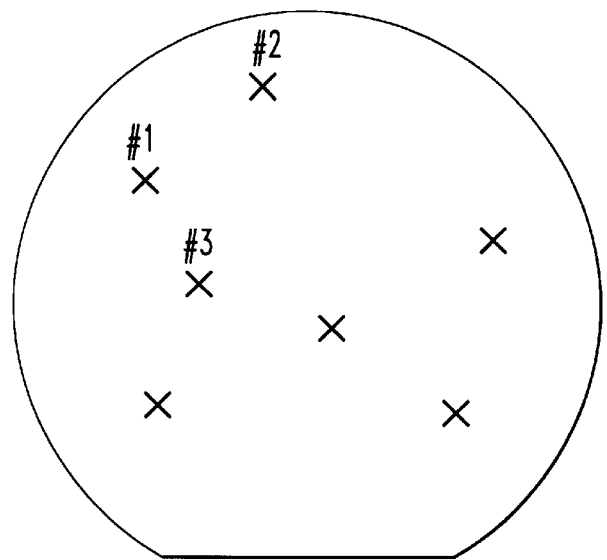
FIG. 73A is a diagram showing one example of displayed information including the contours of inspected parts and the positions of foreign materials or defects on the inspected parts.
FIG. 73B is a table of numbers given to foreign materials or defects, their positions, and their sizes.
Figure 74A:
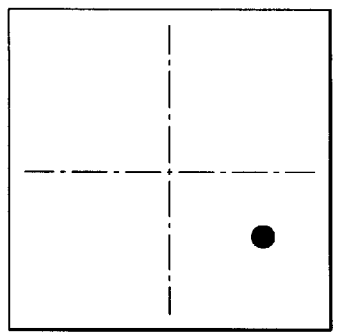
FIG. 74A is a diagram showing an SEM image of a foreign material or defect specified by an operator and displayed on a display device D1.
Figure 74B:
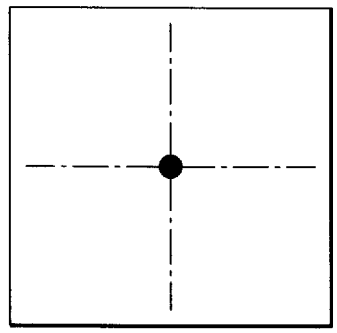
FIG. 74B is a diagram similar to FIG. 74A, but in which the foreign material or defect is displayed in the center of the viewing screen of the display device D1.
Figure 74C:
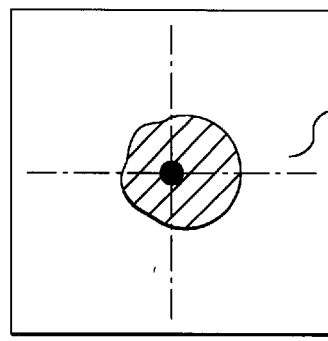
FIG. 74C is a diagram of an image obtained by magnifying the image of FIG. 74B.
Figure 75A:
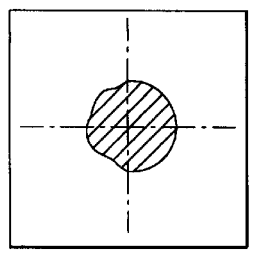
FIG. 75A is a diagram illustrating the image of foreign material or defect shown in FIG. 74C where the image is rotated through an angle of 0° (θ=0°) about a vertical axis parallel to the electron beam of the review SEM (i.e., in the same state as in FIG. 74C) before the image is rotated through 60°.
Figure 75B:
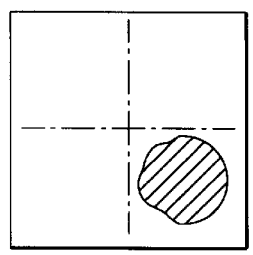
FIG. 75B is a diagram illustrating a state obtained by rotating the state of FIG. 75A through 10° (θ=10°)
Figure 75C:
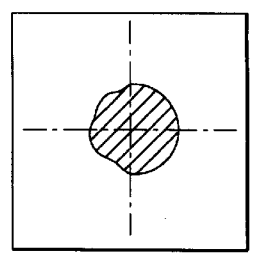
FIG. 75C is a diagram illustrating a state obtained by translating a sample table from the state of FIG. 75B such that the foreign material or defect is brought into the center of the viewing screen of the display device D1.
Figure 75D:
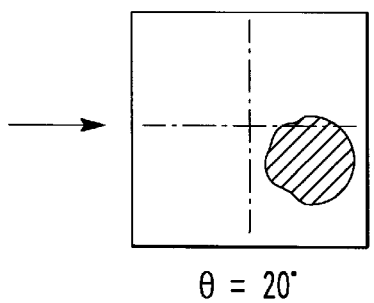
FIG. 75D is a diagram illustrating a state obtained by rotating the tables from the state of FIG. 75C through 10° so that θ=20°.
Figure 75E:
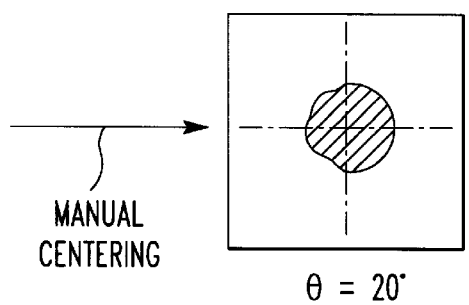
FIG. 75E is a diagram illustrating a state obtained by translating the sample table in the state of FIG. 75D so that the foreign material or defect is brought into the center of the viewing screen of the display device D1.
Figure 75F:
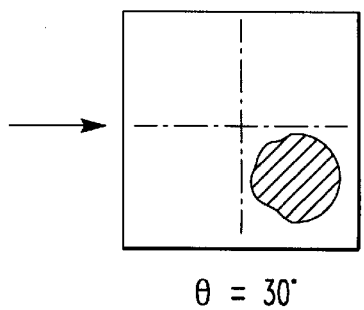
FIG. 75F is a diagram illustrating a state obtained by rotating the table from the state of FIG. 75C so that θ=3020.
Figure 75G:
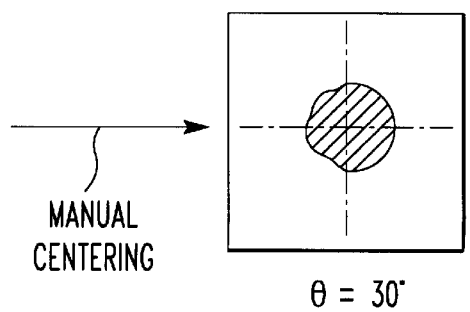
FIG. 75G is a diagram illustrating a state obtained by translating the sample table in the state of FIG. 75F so that the foreign material or defect is brought into the center of the viewing screen of the display device D1.
Figure 76A:
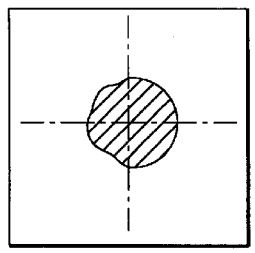
FIG. 76A is a diagram illustrating the image of foreign material or defect shown in FIG. 74C where the image is tilted at an angle of 0° (=0°) about a horizontal axis vertical to the electron bean the review SEM, i.e., in the same state as in FIGS. 74C and 75A before the image is rotated through 45°.
Figure 76B:
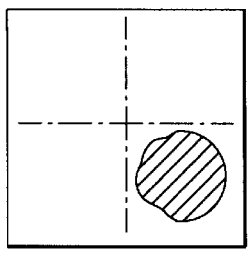
FIG. 76B is a diagram illustrating a state obtained by tilting the image in the state of FIG. 76A by 5° (φ=5°)
Figure 76C:
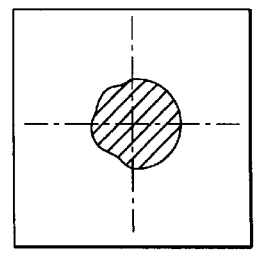
FIG. 76C is a diagram obtained by translating the sample table in the state of FIG. 76B so that the foreign material or defect is brought into the center of the viewing screen of the display device D1.
Figure 76D:
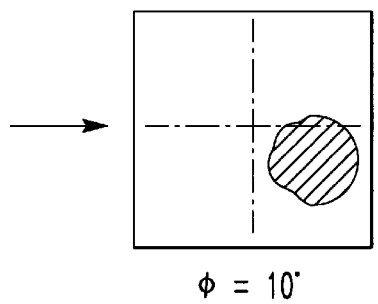
FIG. 76D is a diagram obtained by tilting the table in the state of FIG. 76C by 5° (φ=10° )
Figure 76E:
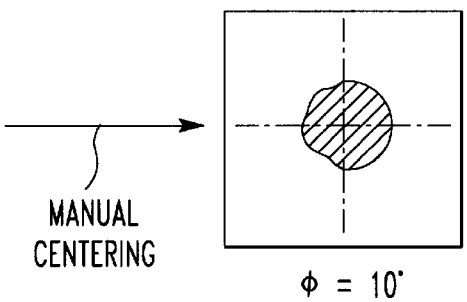
FIG. 76E is a diagram obtained by translating the sample table in the state of FIG. 76D so that the foreign material or defect is brought into the center of the viewing screen of the display device D1.
Figure 76F:
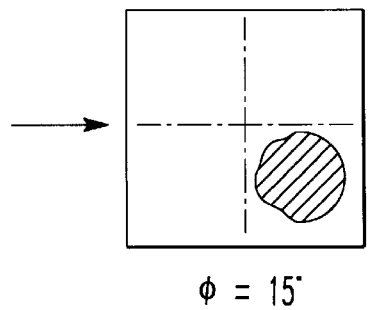
FIG. 76F is a diagram obtained by tilting the table in the state of FIG. 76C so that φ=10°.
Figure 76G:
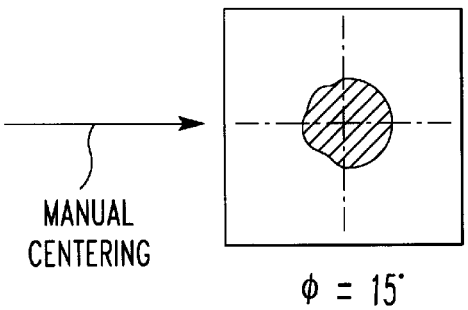
FIG. 76G is a diagram obtained by translating the sample table in the state of FIG. 76F so that the foreign material or defect is brought into the center of the viewing screen of the display devie D1.

The optical foreign material-inspecting apparatus 1 and the optical defect-inspecting apparatus 2 are commercially available apparatuses already described in connection with FIG. 72. In the present embodiment, these apparatuses 1 and 2 together form preliminary inspecting equipment (1, 2), which is used to detect foreign materials or defects on an inspected part, their positions, and their sizes before execution of a detailed inspection. In the present embodiment, information obtained as a result of an inspection made by the preliminary inspecting equipment (1, 2) is referred to as "preliminary inspection information". The functions of these apparatuses are as follows.

(1) Foreign Material-Inspecting Apparatus 1

The foreign material-inspecting apparatus 1 automatically detects foreign materials such as dust on a wafer, filing (i.e., arranging in order for preservation and reference) the positions and sizes of the foreign materials, and transmitting the created files, or preliminary inspection information, to the DIFS server 3.

(2) Defect-Inspecting Apparatus 2

The defect-inspecting apparatus 2 automatically detects foreign materials or defects on a wafer, filing the positions and sizes of the detected foreign materials or defects, and sending the created files, or preliminary inspection information, to the DIFS server 3.

(3) DIFS Server 3

The DIFS server 3 classifies the preliminary inspection information sent from the preliminary inspecting equipment (1, 2) and stores the classified information. Also, the server 3 stores various kinds of information about defects and images of the defects sent from the review SEM. Furthermore, the server 3 stores review information (including the results of detailed inspection and the results of x-ray analyses made by an EDS (energy-dispersive spectrometer) installed on the review SEM) such as information about sorting of the defects. In addition, the server 3 classifies data (i.e., results of tests made by a tester, i.e., resistance values and so on) sent from other equipment and process information (such as reaction furnace temperature, kinds of gases used in the fabrication process, and gas flow rates) obtained from equipment such as a CVD (chemical vapor deposition) system and an etcher and stores the classified data. The server 3 also serves to transmit data in response to a data request signal from other apparatus.

The DIFS server 3 manages the preliminary inspection information. This makes it unnecessary to save preliminary inspection information for each inspection apparatus, and facilitates management of the preliminary inspection information (such as backup, filing, and erasure). The DIFS database of information about inspected parts can be easily searched for the preliminary inspection information necessary for the review SEM without searching individual inspecting apparatuses.

(4) Review SEM

The review apparatus that is a detailed inspection apparatus of the present embodiment consists of a review SEM (scanning electron microscope). This review SEM comprises the body of a review SEM, an SEM controller (SEMC), and an EWS (engineering workstation).

The engineering workstation is connected with the review SEM and with the network N. This workstation transfers information to and from the foreign material-inspecting apparatus 1, the defect-inspecting apparatus 2, DIFS server 3, and other terminals (clients) that are connected with the review SEM and with the network N.

The controller of the review SEM and the EWS are connected by a communications cable and housed in a common housing. The display device DE of the EWS and the display device D of the SEM controller are held to the common housing.

The review SEM is equipped with the EDS (energy-dispersive x-ray spectrometer) that detects characteristic x-rays emanating from samples and makes qualitative and quantitative analyses of chemical elements contained in microscopic regions. The SEM controller incorporates video image processors (VIPs).

The video image processors (VIP) of the SEM controller receive images produced from various apparatuses, perform image processing necessary for automatic defect sorting, and communicate with the various apparatuses.

When an inspected part, such as a wafer, is meticulously inspected for defects, preliminary inspection information about the inspected wafer is read into the review SEM from the DIFS server 3 via the engineering workstation, the preliminary inspection information being obtained by inspections performed by the foreign material-inspecting apparatus 1 and the defect-inspecting apparatus 2. Then, the review SEM selects desired foreign material or defect and moves the sample stage into a position specified by the preliminary inspection information. The operator then makes observations.

The present system can operate either in a manual mode in which the operator is involved or an automatic mode in which the operator is not involved. In either mode of operation, images can be photographed and defects can be classified.

The DIFS server 3 manages the preliminary inspection information. This permits the preliminary inspection information necessary for a review to be read from the DIFS server 3 when the review SEM makes a review, or performs a detailed inspection, of the inspected part for which the preliminary inspection information has been created. Accordingly, the preliminary inspection information necessary for the review SEM can be automatically read simply by keying in the device name of a preset wafer cassette, the lot number, and the cassette identification (ID) number. Therefore, reviews, automatic defect sorting, and so on can be carried out unattended by providing a device that automatically reads the device name and the lot number of the set wafer cassette from a bar code on a label stuck on the cassette.

After the video image processors (VIPs) of the SEM controller automatically sorts defects, information about the sorting is sent to the DIFS (defect image filing system) server 3 through the network N, along with the accepted images (images of the defects) and information about the defects. The sent information is stored in the server 3 and managed.

(6) Video Image Processors (VIPs)

A plurality of video image processors (VIPs) are connected with the network N. These processors receive images entered from various apparatuses, perform image processing necessary for automatic defect sorting, and communicate with the various apparatuses. An optical review apparatus 4 and a focused ion beam (FIB) instrument 5 are connected with each video image processor. A length-measuring scanning electron microscope (SEM), a scanning electron microscope (SEM), a transmission electron microscope (TEM), and other instruments for producing images can be interfaced to the video image processors, which in turn are connected with the network N.

(7) Optical Review Apparatus 4

The optical review apparatus 4 connected with the network N via some of the video image processors are often used before the review SEM makes a review. This optical review apparatus 4 reads preliminary inspection information, previously observes each defective portion, find makes a decision as to whether it is necessary to make a review with the review SEM. The result of the decision can be indicated by a state of a flag (e.g., it is necessary to make a review with the SEM). This flag can be recorded in the preliminary inspection information. In this case, after reading the preliminary inspection information, the review SEM observes only the defective portion indicated by the flag. Generally, an optical review apparatus can make a review faster than a review SEM, such as JWS75XX manufactured by JEOL Co., Ltd., and so the throughput of the sorting can be improved by using an optical review apparatus.

(8) Focused Ion Beam (FIB) Instrument

The focused ion beam instrument 5 connected with the network N via some of the video image processors is used when a portion of a cross section of a wafer to be observed is processed by this instrument. Data loaded in the DIFS server can be sent to various apparatuses connected with the network N as the need arises. For example, by sending the preliminary inspection information containing information about sorting of defects to the focused ion beam instrument 5, those portions of a cross section which should be observed can be searched for quickly with this FIB instrument 5. The stage holding the wafer is placed in position, and then the wafer is processed.

(9) DIFS Client

The defect image filing system (DIFS) that is a computer terminal connected with the network N can be variously searched for preliminary inspection information, defect images, information about defects, information about x-ray analysis, information about tests, and data and process information obtained from other testing devices. The DIFS can display the contents or the results of summations in the form of table, graph, image, wafer map, and so on. Also, this filing system is able to find the correlations among various kinds of information, perform statistical processing, and image processing. The results can be displayed in the form of table, graph, image, wafer map, and so on.

The output from the DIFS client is appropriately processed (e.g., comments are added or the size is modified). Then, the output can be printed out by a printer. Although a printer connected with the network N is used in FIG. 1, the printer may be directly connected either with the DIFS server or with the client. The connection with the network N allows many clients to produce outputs. Besides, other system can also produce an output. This will contribute toward improvement of the efficiency of investment in the printer and the utilization efficiency and will achieve energy saving.

The DIFS server, client, printer, etc. can be mounted outside a cleanroom by connecting them by the network N as shown in FIG. 1. Since the apparatuses installed inside the cleanroom can be reduced in number, expensive space can be saved. Also, dust can be kept out. Furthermore, unattended operation of the plant is permitted by automating the transportation of wafers inside the cleanroom.

Construction of Review SEM

Figure 3:
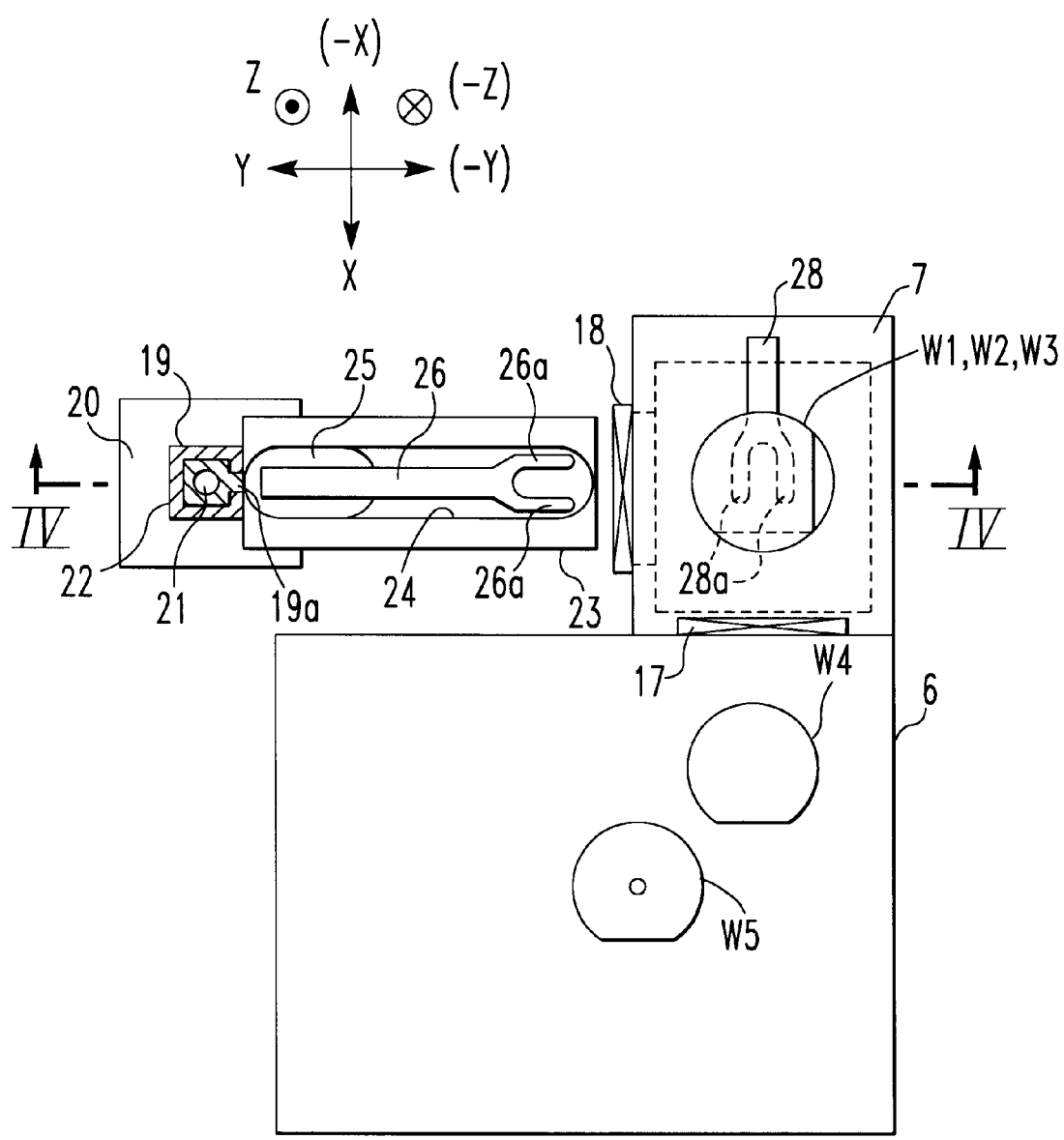
FIG. 3 is a plan view in cross section of the review SEM shown in FIG. 2A.
Figure 4:
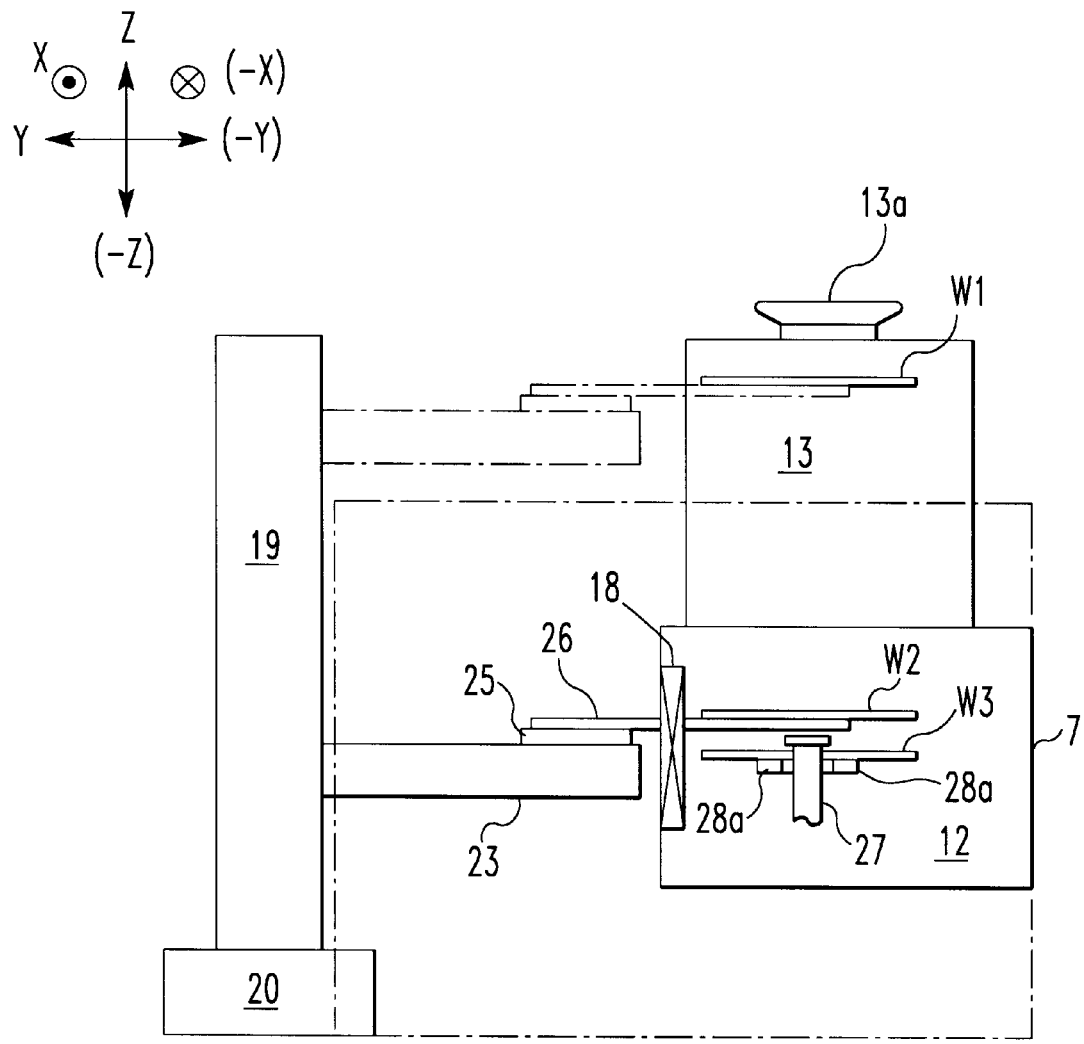
FIG. 4 is a plan view of a wafer-transporting device for transporting wafers between a wafer cassette shown in FIG. 2A and the sample exchange chamber in the body of the review SEM.

The construction of the review SEM shown in FIG. 1 is next described in detail by referring to FIGS. 2A–12. FIGS. 2A–2B illustrate the construction of the review SEM (scanning electron microscope). FIG. 2A is a perspective view of the body of the review SEM and a wafer-transporting device for moving wafers into and out of a sample exchange chamber in the body of the review SEM. FIG. 2B shows a cassette-positioning device. FIG. 3 is a plan view in cross section of the review SEM shown in FIG. 2A. FIG. 4 shows a wafer-transporting device for carrying wafers between a wafer cassette shown in FIG. 2A and the sample exchange chamber in the body of the review SEM.

Figure 5:
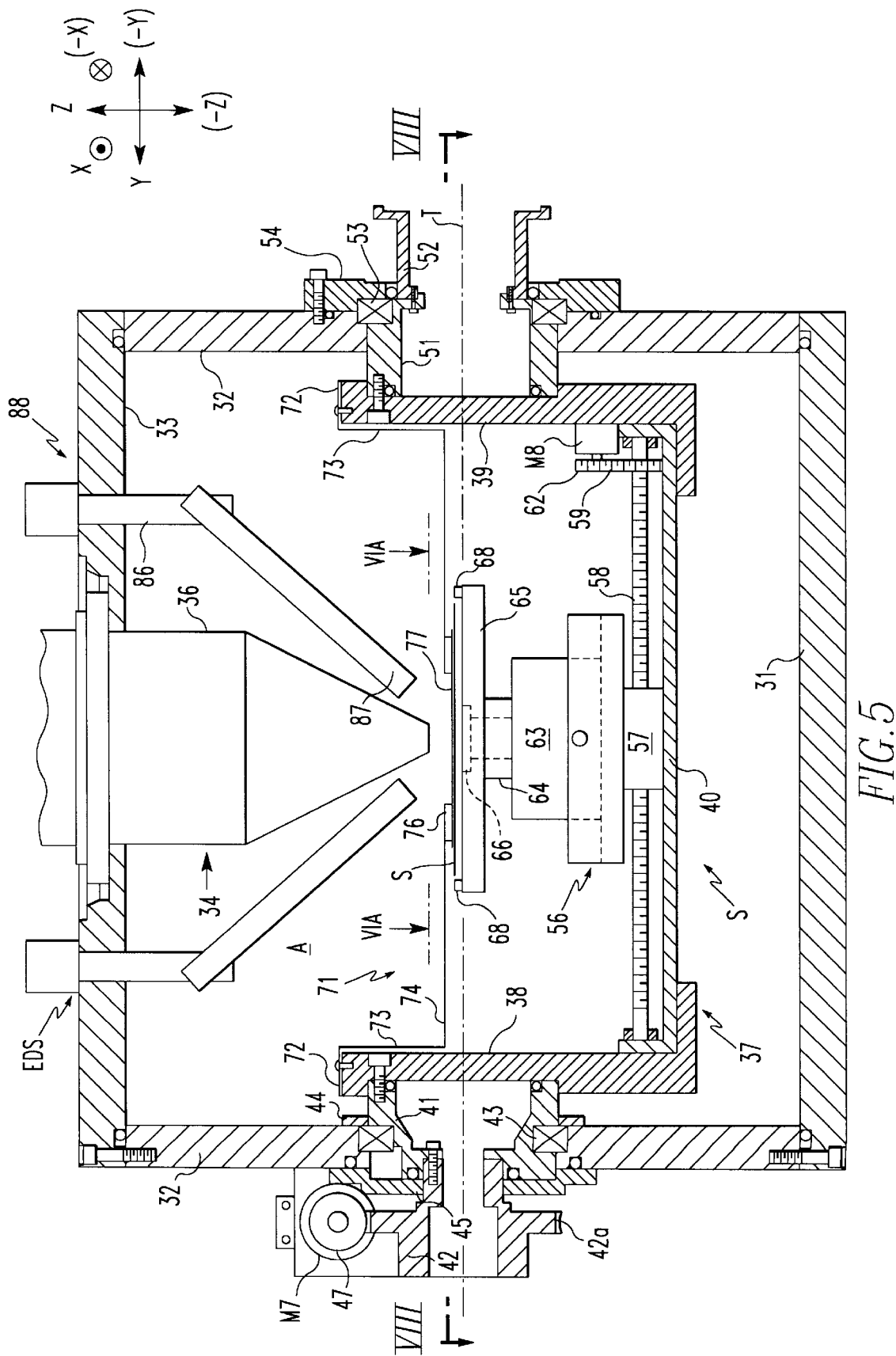
FIG. 5 is a cross-sectional view of main portions of the review SEM shown in FIG. 1.
Figure 6A:
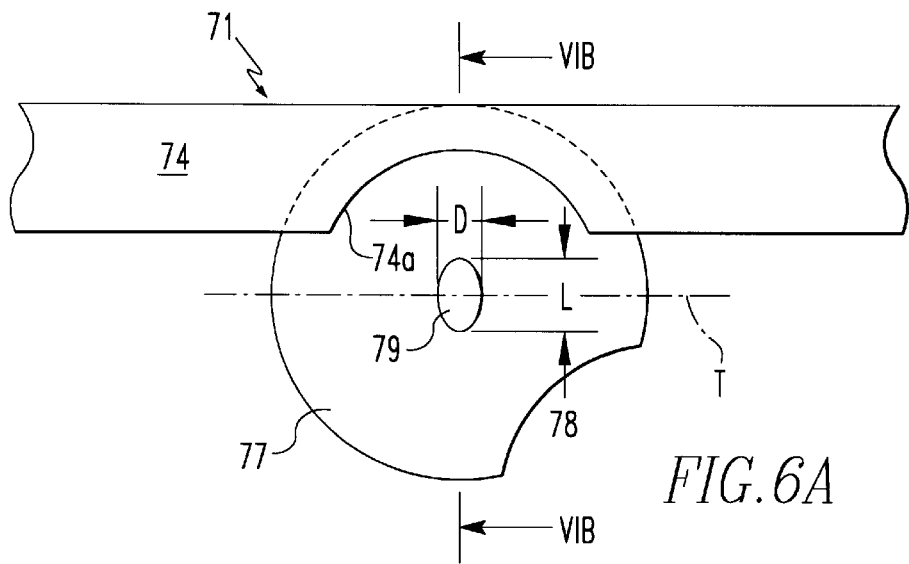
FIG. 6A is an end view taken along line VIA—VIA of FIG. 5, illustrating an electron beam passage hole formed in a cooling plate shown in FIG. 5.
Figure 6B:
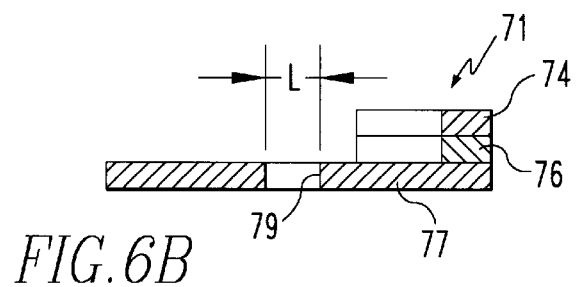
FIGS. 6B and 6C show cross sections taken along line VIB—VIB of FIG. 6A, illustrating cases in which the cooling plate is horizontal and tilted, respectively, and also illustrating variations in the effective diameter of the electron beam passage hole.
Figure 7:
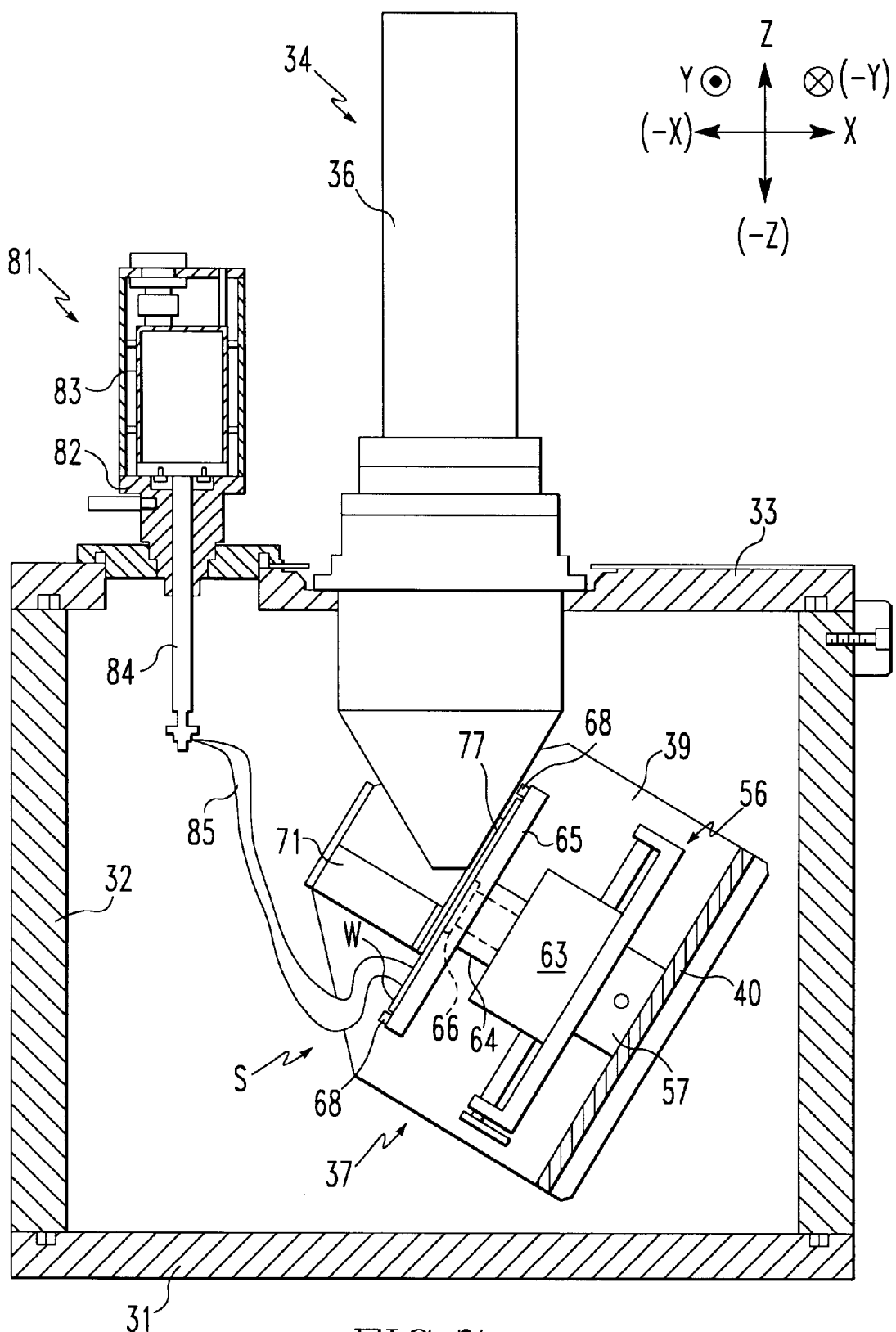
FIG. 7 is a side elevation in cross section of the review SEM shown in FIG. 1.
Figure 8:
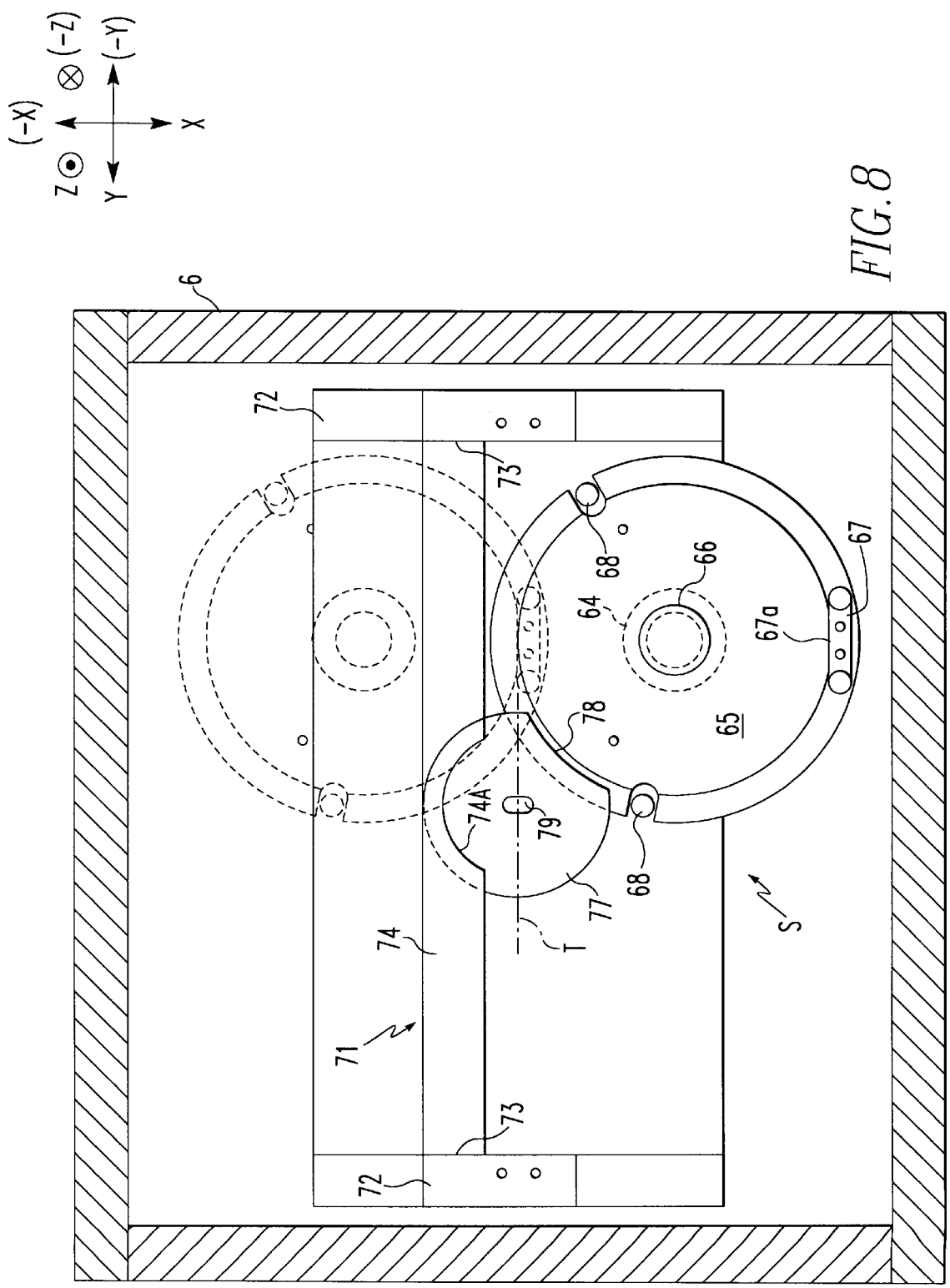
FIG. 8 is a cross-sectional view taken along line VIII—VIII of FIG. 5.

FIG. 5 is a front elevation in cross section of main portions of the review SEM shown in FIG. 1. FIG. 6A–6B show an electron beam passage hole in a cooling plate shown in FIG. 5. FIG. 6A is an end view taken along line VIA—VIA of FIG. 5. FIG. 6B shows two cases in one of which a cross section taken along VIB—VIB of FIG. 6A is horizontal. In the other case, the cross section is tilted. FIG. 6B illustrates the manner in which the effective diameter of the electron beam passage hole varies between these two cases. FIG. 7 is a side elevation in cross section of the review SEM shown in FIG. 1. FIG. 8 is a cross-sectional view taken along line VIII—VIII of FIG. 5. FIG. 9 illustrates a method of transferring a wafer W to a carrying table of a sample stage of this embodiment.

Figure 10:
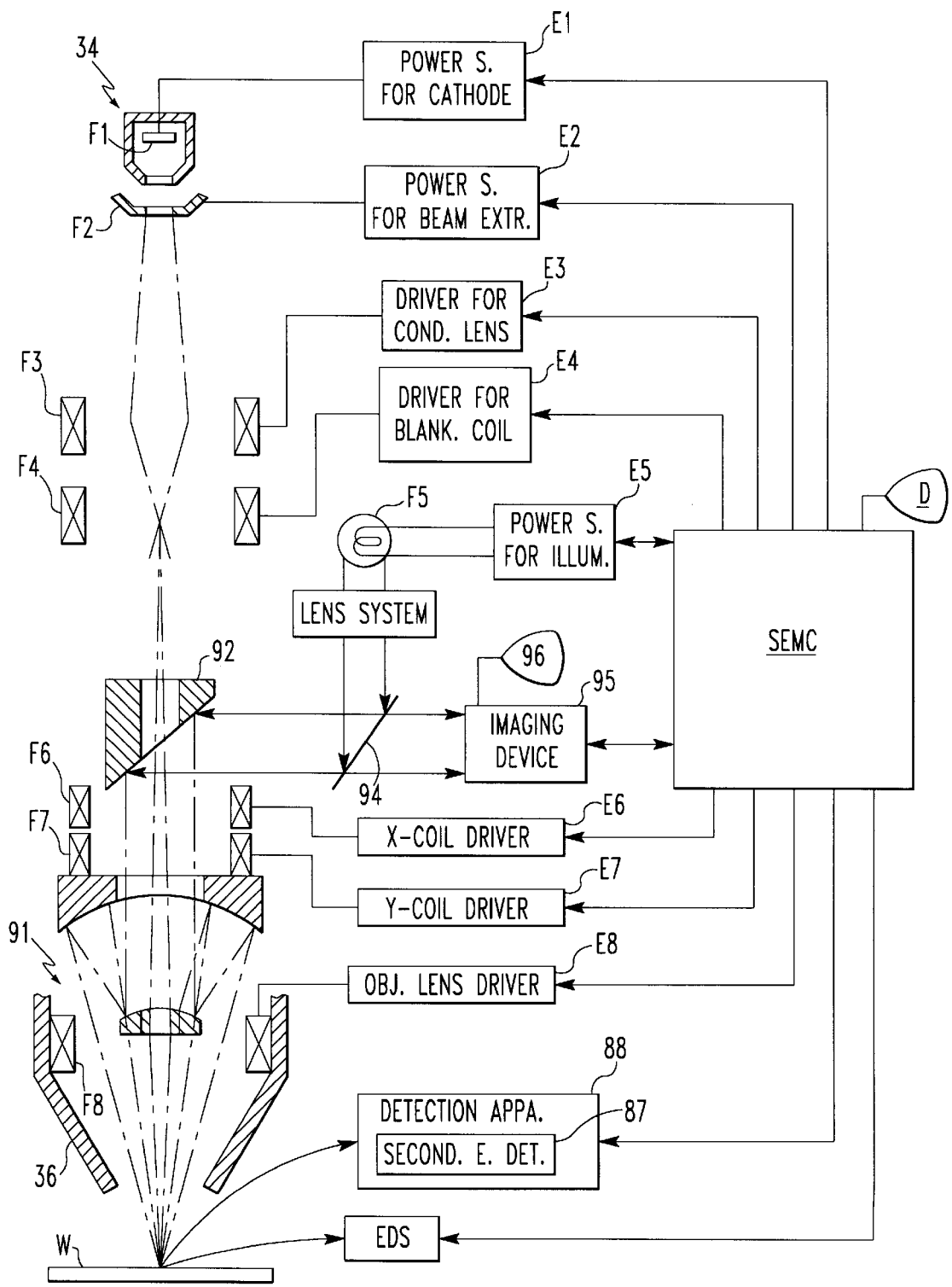
FIG. 10 is a block diagram of a scanning electron microscope (SEM) controller and components connected with the controller.
Figure 11:
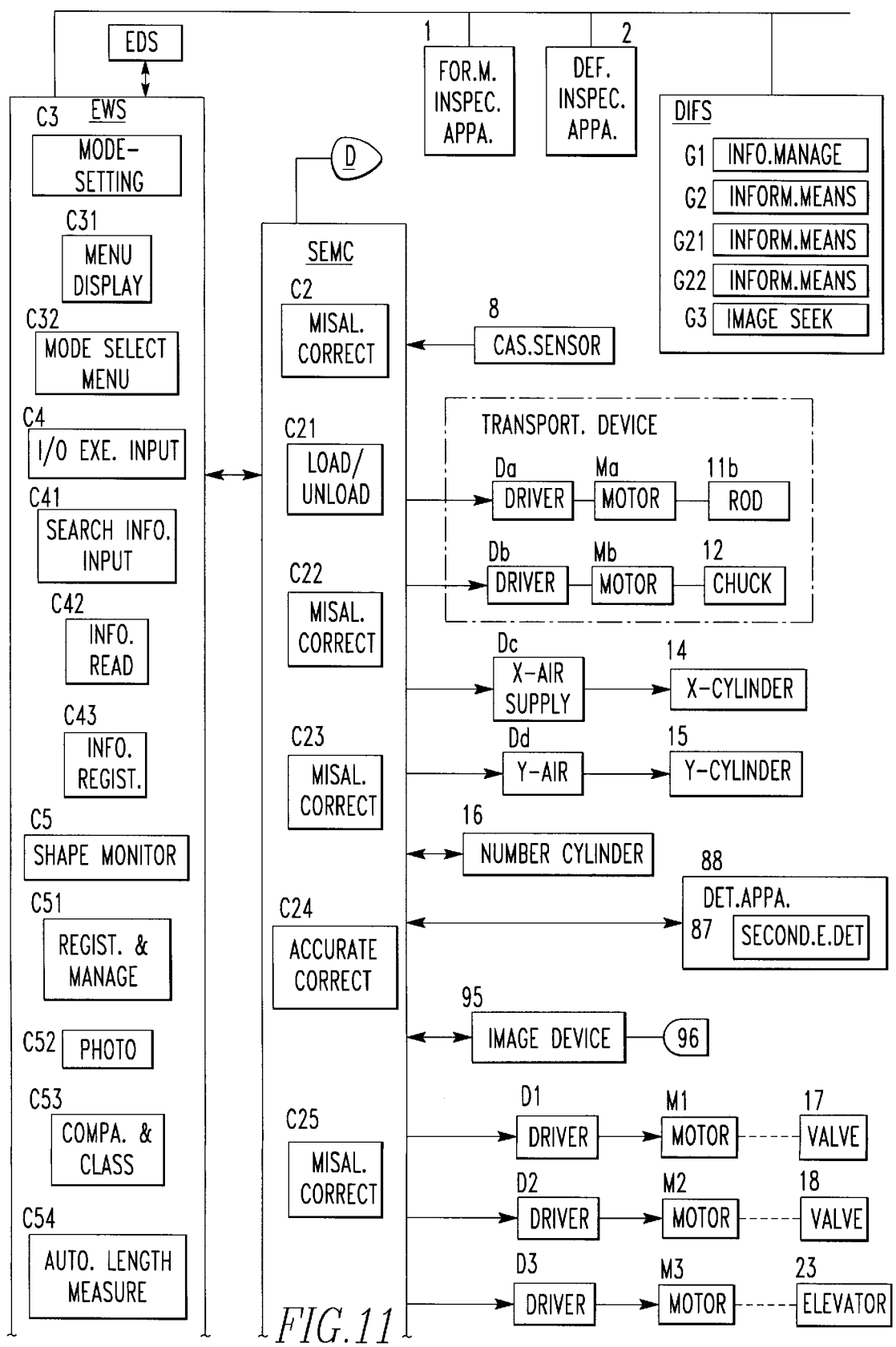
FIGS. 11 and 12 are block diagrams of the SEM (scanning electron microscope controller and components connected with the controller.
Figure 12:
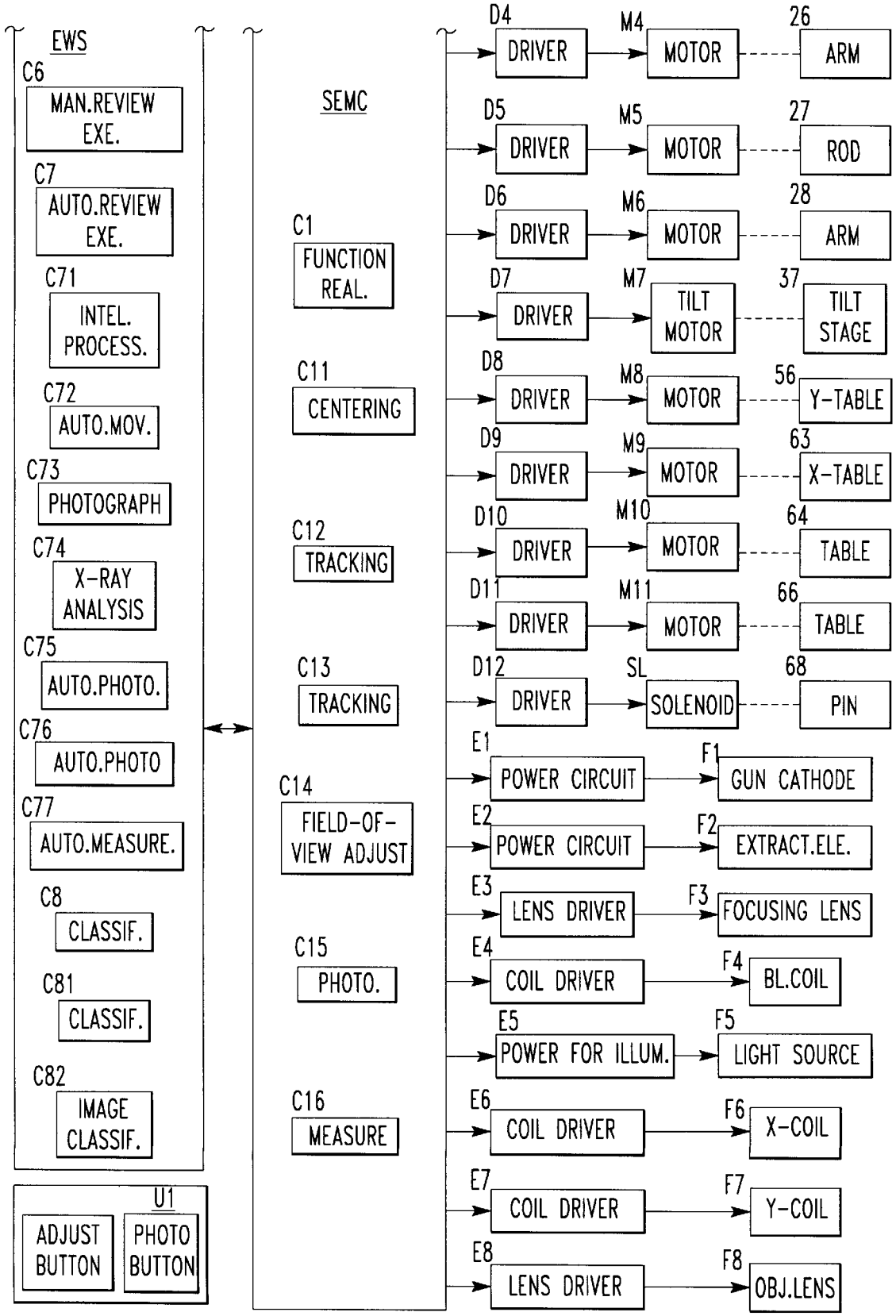

FIG. 10 is a block diagram of an SEM (scanning electron microscope) controller and components connected with this controller. FIGS. 11 and 12 are block diagrams of the SEM controller and the components connected with the controller.

For ease of understanding, it is assumed that coordinate axes, or X-, Y-, and Z-axes, are perpendicular to each other in the figures. The direction indicated by the arrow X is assumed to be a forward direction. The direction indicated by the arrow Y is assumed to be a leftward direction. The direction indicated by the arrow Z is assumed to be an upward direction. In this case, the direction opposite to the X-direction, or –X-direction, is a rearward direction. The direction opposite to the Y-direction is a rightward direction. The direction opposite to the Z-direction, or –Z-direction, is a downward direction.

Both X-direction and –X-direction are referred to as the longitudinal direction or a direction along the X-axis. Both Y-direction and –Y-direction are referred to as the horizontal direction or a direction along the Y-axis. Both Z-direction and –Z-direction are referred to as the vertical direction or a direction along the Z-axis.

The symbol "o" means a direction directed from the rear side to the front side of the sheet. The symbol "." means a direction directed from the front side to the rear side of the sheet.

In FIGS. 2A, 2B, and 3, there view SEM is provided with a sample exchange chamber (preliminary evacuation chamber) 7 adjacent to the left rear side surface (the side surface on the side of the –X-axis) of a vacuum inspection chamber (vacuum working room) 6 where various operations (e.g., observation, inspection, measurements of dimensions, and lithography) on samples such as a wafer of silicon are performed in a vacuum.

A recessed cassette placement portion 7a is formed in the top surface of the sample exchange chamber 7. A cassette sensor 8 is mounted on this top surface. Transportation rails 10 cooperating with a cassette-transporting device 9 is mounted above the recessed cassette placement portion 7a. A cassette-holding member 11 moves, using its self-propelled wheels (not shown), while held by the rails 10. The cassette-holding member 11 has an elevating rod 11b that is held by a rod support member 11a so as to be movable vertically.

A rack in mesh with a pinion (not shown) is formed on the elevating rod 11b. When the pinion is rotated by an elevating rod-driving motor Ma (FIG. 11), the rod 11b moves up or down. In FIG. 11, the rod-driving motor Ma is driven by an elevation motor driver circuit Da which is under control of the SEM controller.

A chuck 12 is attached to the bottom end of the elevating rod 11b. A gripped portion 13a (FIG. 4) is formed on the top surface of the cassette 13. The chuck 12 releasably grips this gripped portion 13a. A well-known mechanical chuck, vacuum-attracted chuck, or magnetically attracted chuck can be used as the chuck 12 having the function described above.

In FIG. 11, the chuck 12 is a mechanical chuck and is driven by a chuck-driving motor Mb, which in turn is driven by a chuck-operating motor-driving circuit Db under control of the SEM controller. The cassette-transporting device 9 is made up of these components 10–12, Ma, and, Mb.

The SEM (scanning electron microscope) controller orders the cassette-transporting device 9 to carry the cassette 13 from a given position into a set position, or the recessed cassette placement portion 7a shown in FIG. 1 and to convey the cassette 13 holding already reviewed wafers therein into other given position.

The cassette sensor 8 supplies a cassette presence/absence signal to the SEM controller to indicate whether any cassette is placed on the recessed cassette placement portion 7a. A plurality of wafers W are received at plural levels within the cassette 13 that has a wafer access opening 13a. This cassette 13 is transported by the cassette-transporting device 9 and placed onto the recessed cassette placement portion 7a.

As shown in FIG. 2B, an X-coordinate-setting cylinder 14 and a Y-coordinate-setting cylinder 15 are supported on the top surface of the sample exchange chamber 7. These cylinders 14 and 15 press the cassette 13 placed on the recessed cassette placement portion 7a in the X- and Y-directions, respectively, to place the cassette at the front end 7x and the left end 7y of the recessed cassette placement portion 7a.

In FIG. 11, the setting cylinders 14 and 15 are driven by an X air supply circuit Dc and a Y air supply circuit Dd, respectively, which in turn are controlled by the SEM controller.

A label on which a bar code BC indicating a cassette identification (ID) number is printed is stuck on the side surface of the cassette 13. A bar code reader or other cassette identification number reader 16 made of a CCD or the like is disposed opposite to the bar code BC. The reader 16 is operated in response to a control signal from the SEM controller, and the read signal is supplied to the SEM controller as shown in FIGS. 10 and 12.

In FIG. 10, if information about wafers received in the cassette is stored in the DIFS server 3, the engineering workstation (EWS) reads the information about the wafers accommodated in the cassette having a cassette identification number coincident with the bar code BC read by the code reader 16. Thus, the SEM controller can make use of this information. It is assumed that the foreign material-inspecting apparatus 1 or the defect-inspecting apparatus 2 inspects wafers in the cassette having some cassette identification numbers. If the file contains information about inspection of defects in the wafers held on the shelves inside the cassette, shelf numbers, and the cassette identification number described above, then the review SEM can make a review according to the preliminary inspection information read from the DIFS server 3.

An internal partitioning valve 17 (FIGS. 2A, 2B, and 3) is mounted between the vacuum inspection chamber 6 and the sample exchange chamber 7. This partitioning valve 17 can place these chambers 6 and 7 in communication with each other and hermetically isolate them from each other.

Referring to FIG. 10, the internal partitioning valve 17 is opened and closed by a partitioning valve-driving motor M1, which in turn is operated by an external partitioning valve-driving motor-driving circuit D1 under control of the review SEM controller.

The vacuum inspection chamber 6 and the sample exchange chamber 7 are pumped down by their respective vacuum pumps (not shown). An external partitioning valve 18 (FIGS. 2A, 2B, 3) is mounted on the left side surface (on the side of the Y-axis) of the sample exchange chamber 7. This partitioning valve 18 can hermetically close off the wafer access opening in the sample exchange chamber 7.

In FIG. 10, the external partitioning valve 18 is opened and closed by an external partitioning valve-driving motor M2, which in turn is operated by an external partitioning motor-driving circuit D2 under control of the SEM controller.

In FIG. 2, a vertically placed, hollow rectangular cylinder 19 is mounted opposite to the external partitioning valve 18 of the sample exchange chamber 7. The bottom end of this cylinder 19 is held to a motor casing 20. A reversible screw shaft 21 and a nut 22 are disposed inside the rectangular cylinder 19. The nut 22 is moved up and down by rotation of the screw shaft 21. An elevator 23 moving up and down in an interlocking relation to the vertically moving nut 22 is mounted on the right side surface of the rectangular cylinder 19. A vertically extending slit 19a is formed in the right side wall of the cylinder 19. A part of the nut 22 extends through the slit 19a and is connected to the elevator 23.

Referring again to FIG. 10, the elevator 23 and the vertically moving nut 22 are moved up and down by an elevating motor M3, which in turn is operated by an elevating motor-driving circuit D3 under control of the SEM controller.

A horizontally extending (along the Y-axis as viewed in FIG. 3) guide groove 24 is formed in the top surface of the elevator 23. A slider 25 is slidably mounted on the guide groove 24. An externally moving arm 26 is supported to the top surface of the slider 25.

In FIG. 10, the externally moving arm 26 and the slider 25 are moved by a slider-driving motor M4, which in turn is operated by a slider-driving circuit D4 under control of the SEM controller.

A wafer W is placed at the front end of the externally moving arm 26 and conveyed by this arm 26. The front end of the arm 26 is bifurcated into sample placement portions 26a. Well-known various structures can be used,as a device for moving the externally moving arm 26.

In FIG. 4, the position of the sample W received in the cassette 13 is indicated by W1. The externally moving arm 26 takes the sample W in this position W1 out of the cassette 13, and the arm 26 contracts to move the sample to the left, or in the Y-direction as viewed in FIG. 4. Then, the wafer W moves downward together with the elevator 23 and reaches a position where the wafer is opposite to the external partitioning valve 17.

Subsequently, the externally moving arm 26 is advanced to move the sample W from the external partitioning valve 18 into the sample exchange chamber 7. A vertically movable rod 27 and an internally moving arm 28 are disposed inside the sample exchange chamber 7. The internally moving arm 28 carries the wafer W between the sample exchange chamber 7 and the vacuum inspection chamber 6 while attaching the wafer W to the front end of the arm 28. The front end of the arm 28 bifurcates into the sample placement portions 28a. The vertically movable rod 27 can move up and down through the gap between the two sample placement portions 28a. Also, the rod 27 can vertically pass between the two sample placement portions 26a.

In FIG. 10, the vertically movable rod 27 is moved up and down by a rod-elevating motor M5, which in turn is operated by an elevating rod-driving circuit D5 under control of the SEM controller. The internally moving arm 28 is moved in the X- direction as viewed in FIG. 3 by an internally moving arm-driving motor M6. This motor M6 is operated by an internally moving arm-driving circuit D6 under control of the SEM controller. An inspected part-transporting device (19–28+D3–D6+M3–M6) for conveying the inspected part (wafer) between the cassette 13 and an inspected part-holding member (described later) is constituted by the components 19–28, D3–D6, and M3–M6.

The sample W is conveyed into the sample exchange chamber 7 by the externally moving arm 26 and then raised by the elevating rod 27 at a position W2. Under this condition, the arm 26 is retracted outwards. If the elevating rod 27 is subsequently lowered, the sample W also falls and becomes placed onto the internally moving arm 28. At this time, the position W3 of the sample W is below the position W2.

Then, the external partitioning valve 18 is closed to pump down the interior of the sample exchange chamber 7. Thereafter, the internal partitioning valve 17 is opened, and the internally moving arm 28 shown in FIG. 3 is advanced (i.e., moved in the X-direction) to convey the sample W into the vacuum inspection chamber (vacuum working room) 1. In this state, the position (i.e., the sample exchange position inside the vacuum chamber) of the sample W is indicated by W4. In this position W4, the sample W is transferred onto a sample-holding member (described later) of the sample table inside the vacuum inspection chamber 6, and then the internally moving arm 28 goes back into the sample exchange chamber 7.

The sample W moves into the position W inside the vacuum inspection chamber 6. The review SEM makes a review, i.e., detailed inspection for defects. On completion of this review, the inspected sample moved from the position W5 to the position W4 is transferred onto the internally moving arm 28. This arm 28 then moves the inspected and received sample W from the position W4 to the position W3. Then, the elevating rod 27 raises the sample W and moves it into a position above the position W2 across this position W2. At the same time, the internal partitioning valve 17 is closed off. Then, the sample exchange chamber 7 is opened to atmosphere, the external partitioning valve 18 is opened, and the externally moving arm 26 is advanced into the sample exchange chamber 7. The elevating rod 27 is lowered, and the sample W is placed on the externally moving arm 26 in the position W2. Thereafter, the arm 26 is moved to return the sample W from the position W2 to the cassette 13.

Then, an uninspected wafer W in the cassette 13 is carried into the vacuum inspection chamber 6 in the same way as in the above-described procedure, dimensions are measured, and the wafer is returned to the cassette 13 in the same manner as in the above-described method.

In FIG. 5, the vacuum inspection chamber 6 of the review SEM has a bottom wall member 31 supported on a floor (not shown). Frame-like side wall members 32 are held on the bottom wall member 31. A base plate 33 is held on the top ends of the side wall members 32. That is, the vacuum inspection chamber 6 is defined by the bottom wall member 31, the side wall members 32, and the base plate 33.

An SEM (scanning electron microscope) body 34 acting as an electron beam illumination machine is supported on the base plate 33. The SEM body 34 is composed of a microscope column 36 and components (such as an electron gun and electron lenses) mounted inside the column. These components will be described later in detail by referring to FIG. 10.

The bottom end of the microscope column 36 is located inside the vacuum inspection chamber 6 and tapers off downwardly. A tilt stage 37 for holding the wafer W (FIG. 5) below the electron-emitting portion (or, the lower end) of the microscope column is tiltably mounted to the side wall members 32 forming the vacuum inspection chamber 6.

In FIG. 5, the tilt stage 37 comprises an L-shaped left tilt member 38, an L-shaped right tilt member 39, and a bottom member 40 interconnecting the lower ends of the left and right tilt members. The left tilt member 38 of the tilt stage 37 is connected with a cylindrical inner shaft member 41, which has an outer end portion coupled to an external shaft member 42. The internal shaft member 41 is rotatably held to the left side wall member 32 via a bearing 43. This bearing 43 is held in position by an inner annular plate 44, which is fixedly mounted to the side wall members 32. The outer end of the inner shaft member 41 is placed in position by an outer annular plate 45.

The external shaft member 42 has a gear 42a driven by a worm 47 that is mounted to the output shaft of a tilt motor M7. The right tilt member 39 of the tilt stage 37 is joined to a cylindrical inner shaft member 51. This inner shaft member 51 has an outer end connected to an external shaft member 52. The inner shaft member 51 is rotatably held to the right side wall member 32 via a bearing 53. This bearing 53 is retained in position by an annular plate 54 fixedly secured to the side wall members 32. The outer end of the inner shaft member 51 is placed in position by the annular plate 54.

The left external shaft member 42, the inner shaft member 41, the tilt stage 37, the right inner shaft member 51, the external shaft member 52, and so on are coupled together into a subassembly as mentioned above. This subassembly is rotatably and tiltably held by bearings 43 and 53. Accordingly, when the left external shaft member 42 is rotated by the tilt motor M7, the tilt stage 37 tilts around the center lines of the bearings 43 and 53 (i.e., a tilting axis T). In FIG. 11, the tilt motor M7 for tilting the tilt stage 37 is operated by a tilt motor-driving circuit D7 under control of the SEM controller.

A Y-motion table 56 moving horizontally (i.e., along the Y-axis) is mounted to the top surface of the bottom member 40 of the tilt stage 37. The Y-motion table 56 has a nut portion 57 protruding from the bottom surface. This nut portion 57 is in mesh with a threaded shaft 58 rotatably held by the left and right tilt members 38 and 39, respectively. A gear 59 is mounted to the right end of the threaded shaft 58 and in mesh with a gear 62 driven by a Y-motion motor M8. Therefore, when the threaded shaft 58 is rotated by the Y-motion motor M8 via the gears 62 and 59, the Y-motion table 56 moves horizontally, i.e., along the Y-axis.

In FIG. 11, the Y-motion motor M8 for driving the Y-motion table 56 is operated by a horizontally moving motor-driving circuit D8 under control of the SEM controller. An X-motion table 63 is held on the Y-motion table 56. The X-motion table 63 is driven by an X-motion motor M9, which in turn is operated by an X-motion motor-driving circuit. D9 under control of the SEM controller. The Y-motion table 56 and the X-motion table 63 together form an X-Y table (56+63).

A cylindrical rotating table 64 is held to the X-motion table 63 so as to be rotatable about an axis perpendicular to the directions of movement of the Y-motion table 56 and the X-motion table 63, respectively. The aforementioned annular inspected part-holding member, 65, is fixedly mounted to the top end of the rotating table 64.

In FIG. 11, the rotating table 64 is rotated by a rotatable table-driving motor M10, which in turn is operated by a rotating table-driving circuit D10 under control of the SEM controller. An elevatable table 66 is held on the X-motion table 63 and extends through the cylindrical rotating table 64 and through the inspected part-holding member E5. This table 66 can move up and down between its upper and lower positions. In the lower position, the elevatable table 66 is flush with the top surface of the inspected part-holding member 65. The elevatable table 66 is moved up and down by an elevatable table-driving motor M11, which in turn is operated by an elevatable table-driving circuit D11 under control of the SEM controller A positioning fixing member 67 is disposed on the inspected part-holding member 65 near its outer periphery, as shown in the plan view of FIG. 8. Also, two positioning pins 68 capable of moving radially are positioned on the inspected part-holding member 65. The wafer W placed on the inspected part-holding member 65 is a substantially circular flat plate having a straight portion to be placed in position. This straight portion is formed by cutting away a part of a circular stock. The fixing member 67 has a positioning straight portion 67a against which the former straight portion formed along the outer periphery of the wafer W bears, the wafer W being placed on the inspected part-holding member 65.

The positioning movable pins 68 are always biased radially inwardly by springs (not shown). When positioning solenoids SL (FIG. 11) are energized, the pins 68 are held in their radially outer positions. The solenoids SL are operated by a solenoid-driving circuit D12 under control of the SEM controller.

The positioning solenoids SL (FIG. 11) are energized to hold the positioning movable pins 68 in their outer positions. Under this condition, the wafer W is placed on the inspected part-holding member 65. Then, the solenoids SL are deenergized to move the positioning pins 68 inwardly, thus holding the water in position on the inspected part-holding member 65. A stage S (FIGS. 5, 7, and 8) for supporting the wafer is formed by the components 37–68.

A method of placing the wafer W on the inspected part-holding member 65 is next described by referring to FIG. 9. The Y-motion table 56 and the X-motion table 63 are moved to bring the inspected part-holding member 65 into a position indicated by the phantom line in FIG. 8. This position will be referred to as the sample transfer position. Under this condition, the elevatable table 66 is kept in its lower position. The wafer W placed on the two sample placement portions 28a (FIGS. 3 and 9) of the internally moving arm 28 (FIG. 3) is moved into a location lying over the elevatable table 66 that is in the sample transfer position. The space between the two sample placement portions 28a is so determined that the elevatable table 66 can move up and down through the space.

Figure 9A:
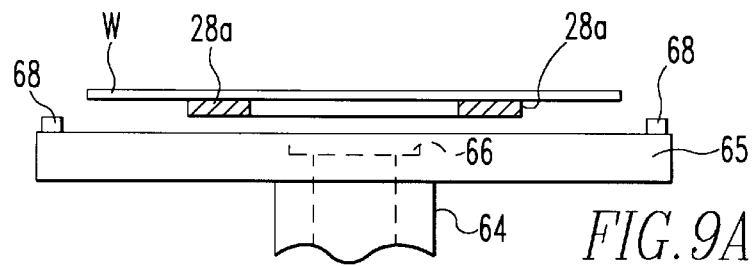
FIGS. 9(A)–9(E) are side elevations, illustrating the manner in which a wafer W is transferred to a carrying table of a sample stage of the review SEM shown in FIG. 1.
Figure 9B:
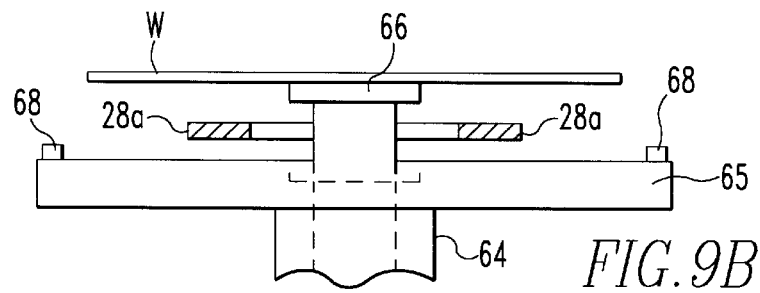
Figure 9C:
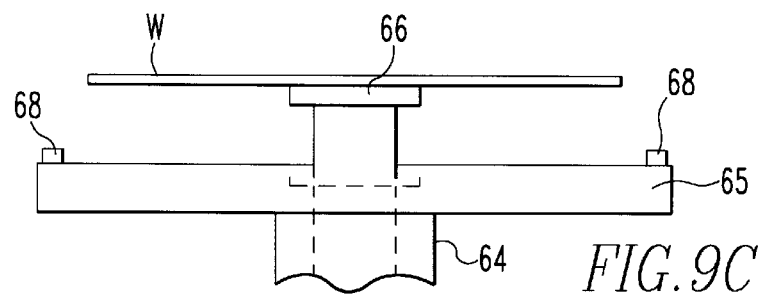
Figure 9D:
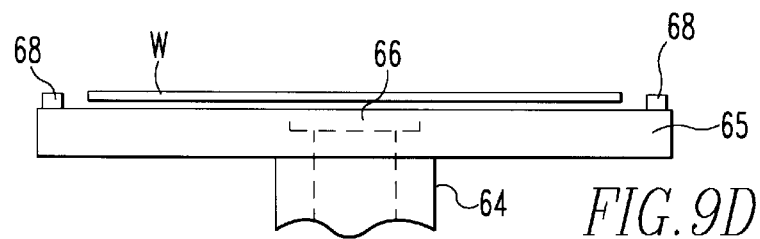
Figure 9E:
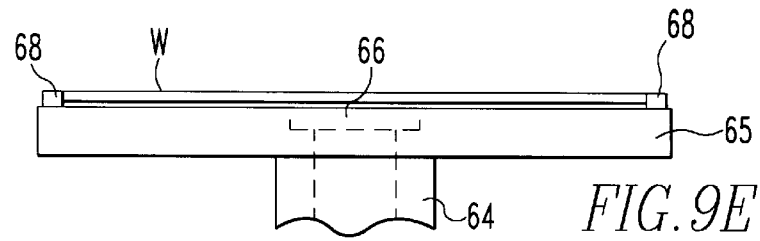

After the wafer W placed on the internally moving arm 28 has been carried into the sample transfer position (FIG. 9A), the elevatable table 66 is moved upward to raise the wafer (FIG. 9B) Then, the internally moving arm 28 is retracted (FIG. 9C) Subsequently, the positioning solenoids SL (FIG. 11) are energized to hold the positioning movable pins 68 in their outer positions. Under this condition, the elevatable table 66 is lowered. As a result, the wafer W held on the top surface of the table 66 is placed on the inspected part-holding member 65 (FIG. 9D). Then, the positioning solenoids SL are deenergized to move the positioning pins 68 inwardly, so that the wafer W is placed in position on the inspected part-holding member 65 (FIG. 9E). This inspected part-holding member 65 is so designed that, when the wafer W is placed in position on this holding member, the wafer W is placed within a plane containing the tilting axis T described above.

FIG. 7 is a side elevation of the left tilt member 38 and the right tilt member 39 of the tilt stage 37. As can be seen from this figure, each of these tilt members 38 and 39 is substantially pentagonal in shape. A cooling plate support member 71 has fixed portions 72 at its two opposite horizontal ends. These fixed portions 72 are mounted on the horizontal portions of the top ends of the tilt members 38 and 39. The cooling plate support member 71 has vertical portions 73 extending downward from the fixed portions 72 and a cooling plate support portion 74 interconnecting the lower ends of the vertical portions 73, as well as the fixed portions 72 at both ends.

The cooling plate support portion 74 of the cooling plate support member 71 is centrally provided with an arc-shaped cutout 74a (FIG. 8). A cooling plate 77 is firmly fixed to the outer bottom surface of the cutout 74a via a heat-insulating material 76. This cooling plate 77 is positioned close to the top surface of the wafer W held on the inspected part-holding member 65. That is, under the condition shown in FIG. 5, the cooling plate 77 is slightly above a plane containing the tilting axis T, i.e., the axis of rotation of the tilt stage 37 as it tilts. Since impurities such as gases in the vacuum inspection chamber 6 are absorbed on the low-temperature cooling plate 77, adhesion of impurities to the wafer W is prevented.

In FIG. 8, the cooling plate 77 is made of a substantially circular metal plate such as a copper plate having a high coefficient of thermal conductivity. An arc-shaped cutout 78 (FIG. 8) is formed in the outer surface of the cooling plate 77, for the following reason.

When the inspected part-holding member 65 is in the sample transfer position shown in FIG. 8, the wafer W carried into a position above the inspected part-holding member 65 is raised by upward movement of the elevatable table 66, and then downward movement brings the wafer W below the cooling plate 77 in placing the wafer W onto the inspected part-holding member 65.

Where the cooling plate 77 is circular, it overlaps with (as viewed in a plan view) the wafer on the inspected part-holding member 65 in the sample transfer position shown in FIG. 8. Therefore, if the cutout 78 were not formed in the cooling plate 77, the wafer W would be moved vertically between the upper and lower positions of the cooling plate 77. The formation of the arc-shaped cutout 78 in the cooling plate 77 permits miniaturization of the whole instrument.

Figure 6C:
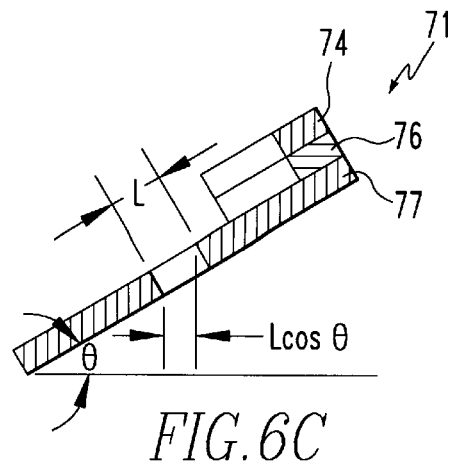

An electron beam passage hole 79 is formed in the center of the cooling plate 77 and located slightly above the intersection of the tilting axis T on the wafer W and the electron beam. In FIG. 6, the hole 79 is a slot extending vertical to the tilting axis T of the tilt stage 37. This slot has a major diameter L=6 mm and a minor diameter D=3, or the dimension taken in a direction vertical to the direction of the major diameter. When the tilt stage 37 is tilted, the electron passage hole 79 tilts about the tilting axis T perpendicular to the longitudinal direction of the hole 79. When the cooling plate 77 is tilted at an angle of θ, as shown in FIG. 3, the dimension decreases down to L cos θ (FIG. 3C) as viewed in the direction of travel of the electron beam, if th e thickness of the cooling plate 77 is neglected. When the plate is tilted at 60°, the major diameter L is set to 6 mm such that the dimension of the electron beam passage hole 79 as viewed in the direction of travel has a requisite inside diameter. That is, where θ=60°, L cos θ=6×(½)=3 mm.

In FIG. 7, a refrigerant container 81 holding liquid nitrogen therein is held to the base plate 33. The refrigerant container 81 and the cooling plate 77 are connected together by a heat-conducting member having a high coefficient of thermal conductivity to maintain the cooling plate 77 at low temperature.

In FIG. 5, a sensor-holding member 86 extends through, and is held to, the base plate 33. A secondary electron detector 87 is held to the front end of the sensor-holding member 86. The sensor-holding member 86, the secondary electron detector 87, a secondary electron amplification circuit (not shown), etc. together form a secondary electron detection apparatus, or an emitted particle detector, 88 (FIGS. 5 and 10).

The aforementioned energy dispersive x-ray spectrometer (EDS) (FIG. 10) is mounted to the left of the microscope column 36 and connected with the SEM controller as shown in FIGS. 10 and 12. The EDS operates according to a control signal from the SEM controller. The output signal from the EDS is fed to the SEM controller.

The SEM (scanning electron microscope) controller and the components of the SEM body 34 (FIGS. 5 and 7) connected with the SEM controller are shown in FIG. 10. The SEM body 34 comprises the microscope column 36, an electron gun cathode F1, an electron gun extraction electrode F2, a condenser lens F3, blanking coils F4, a light source F5 for illumination, an X-deflection coil F6 for scanning the electron beam along the X-axis, a Y-deflection coil F7 for scanning the beam along the Y-axis, and an objective lens F8 for focusing the electron beam onto the wafer W.

These components F1–F8 are operated by a power supply circuit E1 for the cathode, an electron beam extraction power supply circuit E2, a condenser lens-driving circuit E3, a blanking coil-driving circuit E4, a power supply circuit E5 for illumination, an X-deflection coil-driving circuit E6, a Y-deflection coil-driving circuit E7, and an objective lens-driving circuit E8, respectively. These circuits E1–E8 are operated according to control signals from the SEM controller. The components F1–F4, F6–F8, E1–E4, and E6–E8 together form an electron beam-scanning apparatus (F1–F4+ F6–F8+E1–E4+E6–F8)

In FIG. 10, a Cassegrain mirror 91 is mounted below the Y-deflection coil F7. A mirror 92 is disposed over the Cassegrain mirror 91. The light source F5 emits illuminating light which is collimated by a lens system 93. The collimated light is reflected by a half-mirror 94, passes through both mirror 92 and Cassegrain mirror 91, and impinges on the wafer W. Light reflected from the wafer W passes through the Cassegrain mirror 91, mirror 92, and half-mirror 94 and reaches an optical imaging device 95 comprising a CCD or the like. Thus, an optical image is taken. This image is displayed on a display device 96. Concurrently, the image is converted into digital data and supplied to the SEM controller.

Electric Circuit of Part-Inspecting Apparatus of FIG. 1

Figure 13:
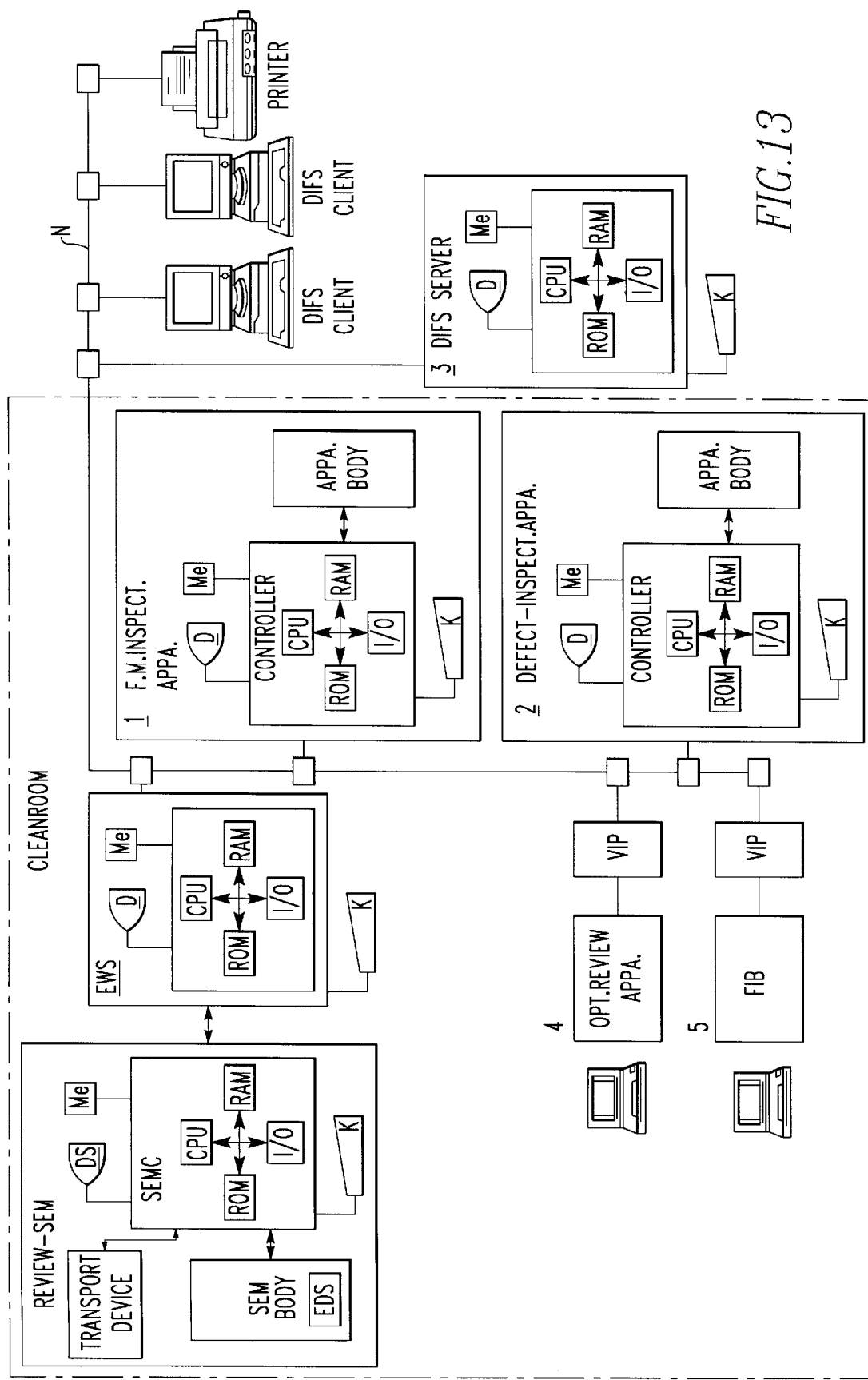
FIG. 13 is a block diagram of a controller shown in FIG. 1.

FIG. 13 is a block diagram of the control portion of FIG. 1. The SEM controller is made of a computer having a CPU, a ROM, a RAM, I/O, etc. The display device D, a memory Me, a keyboard K, etc. are connected with the SEM controller. The cassette 13 consisting of the components shown in FIGS. 11 and 12, a device for transporting wafers, and the components of the review body are connected with the SEM controller.

The SEM controller and the engineering workstation (EWS) interfaced to the SEM controller perform various kinds of processing in accordance with a program loaded in the memory in response to input signals to achieve the functions of the means shown in FIGS. 11 and 12.

In FIG. 13, the engineering workstation, the foreign material-detecting apparatus 1, the defect-inspecting apparatus 2, the DIFS server 3, etc. are composed of a computer with which the display device D, memory Me, keyboard K, etc. are connected. They carry out various kinds of processing in accordance with a program loaded in the memory of the computer.

(A) Functions of Preliminary Inspecting Equipment (1, 2)

Commercially available devices are used as the preliminary inspecting equipment (1, 2). However, a cassette-transporting device (not shown), a cassette placement portion (not shown), a cassette identification (ID) number reader (not shown) for reading a cassette number in the form of a bar code printed on a side surface of the cassette 13, a wafer exchange device (not shown) for conveying wafers between the cassette 13 and the preliminary inspecting equipment (1, 2), etc. are appended to the preliminary inspecting equipment (1, 2).

These cassette-transporting device, cassette identification (ID) number reader, wafer exchange device, etc. (none of which are shown) are operated according to control signals from the controller (FIG. 13) of the preliminary inspection equipment (1, 2). The signal read by the cassette identification (ID) number reader is supplied to the controller of the preliminary inspection equipment (1, 2).

The following means A1–A4 (not shown) are added to the preliminary inspection equipment (1, 2). The functions of the means A1–A4 are realized by a program stored either in the ROM of the controller (FIG. 13) or in the storage means Me connected with the controller.

(A1) Wafer Information Input Mode-Selecting Menu Display Means A1

This means A1 displays a menu permitting the operator to determine whether information about the inspected wafer is entered in a fully automated input mode. The preliminary inspection equipment (1, 2) operates according to the selected wafer input mode. If the fully automated input mode is not selected, a menu is displayed to permit the operator to manually enter information about the wafer.

(A2) Automatic Wafer Information Input Means (A2)

Where the fully automated wafer information input mode is selected, this input means A2 sends a cassette identification (ID) number read by the cassette identification number reader to a host computer for computer-integrated manufacturing (CIM), reads processing request slips, and reads wafer information from the slips.

(A3) Automatic Inspecting Means A3

This automatic inspecting means A3 automatically exchanges wafers between the cassette 13 placed on the above-described cassette placement portion (not shown) and the inspection position for the preliminary inspection equipment (1, 2), and automatically inspects wafers successively transported into the inspectionposition according to the wafer information either contained in the request slip or entered manually.

(A4) Automatic Inspection Result-Sending Means A4

This result-sending means A4 has a function of automatically sending the results of the inspection performed by the automatic inspection means A3 to the DIFS server 3.

(B) Functions of DIFS Clients, Host Computer for CIM, etc.

Each of the DIFS clients, the host computer, and other computers linked to the network N have means B1 (not shown) for creating processing request slips. The functions of this means B1 for creating processing request slips are as follows:

(B1) Means for Creating Processing Request Slips

This means B1 for creating processing request slips has a function of displaying the cassette identification numbers, information about wafers contained in the cassette 13 having the cassette identification numbers, a recipe for determining the contents of inspections, and a menu for entering other kinds of information. Also, this means B1 serves to register data displayed and entered from the displayed menu as digital data.

(C) Functions of Review SEM and of EWS

The SEM controller has functions of the means C1–C25 shown in FIGS. 11 and 12. The engineering workstation (EWS) has the functions of the means C3–C82 shown in FIGS. 11 and 12. The functions of the means C1–C25 are realized by a program stored in the memory connected with the SEM controller. The functions of the means C3–C62 are realized by a program stored in the memory connected with the EWS. The program for implementing the functions of the means C1–C82 may be stored in either one of the memories connected with the EWS and with SEM controller, respectively. The program for realizing the functions of the means C1–C82 may be totally stored in the memory connected with the SEM controller, in which case the EWS may be omitted.

Where any defect is reviewed with the review SEM, it is necessary to move the defect into the review position, using the x- and y-coordinates on the preliminary inspection apparatus which have been detected by the preliminary inspection equipment (1, 2). For this purpose, any one of the following methods can be adopted:

(a) Before the movement, the position of the inspected part is corrected (correction of misalignment) so that the X- and Y-coordinates of the inspected part on the review SEM agree with the x- and y-coordinates on the preliminary inspection equipment (1, 2).

(b) The movement is made while converting the x- and y-coordinates into X- and Y-coordinates. This method (b) is implemented by the following sequence:

(1) It is assumed that the x- and y-coordinates of an inspected part on the preliminary inspection equipment (1, 2) are known. The position of this inspected part is detected in two or more detection position $P_1$, $P_2$, etc. The X- and Y-coordinates of these detection positions are detected. Let $(X_0, Y_0)$ be the origin of the xy-coordinate system. A first straight line segment is drawn from the origin of the XY-coordinate system to the origin $(X_0, Y_0)$ of the xy-coordinate system. A second straight line segment is drawn from the position given by the X- and Y-coordinates to the position given by the x- and y-coordinates. The angle θ made between these first and second line segments is calculated from the known x- and y-coordinates and from the detected X- and Y-coordinates.

(2) When the defect detected by the preliminary inspection apparatus is moved into the review position for the review SEM, the X- and Y-coordinates of the defect on the review SEM are computed from the known x- and y-coordinates of the defect on the preliminary inspection apparatus, using the values of $X_0$, $Y_0$, and θ.

(3) The inspected part is moved so that the defect is brought into the review position.

Where the method (a) or (b) is executed, it is necessary to make a coordinate transformation between the x- and y-coordinates and the X- and Y-coordinates. Methods of calculating coordinate transformation parameters necessary to make a coordinate transformation are next described.

Method 1 of Calculating Coordinate Transformation Parameters

Figure 14:
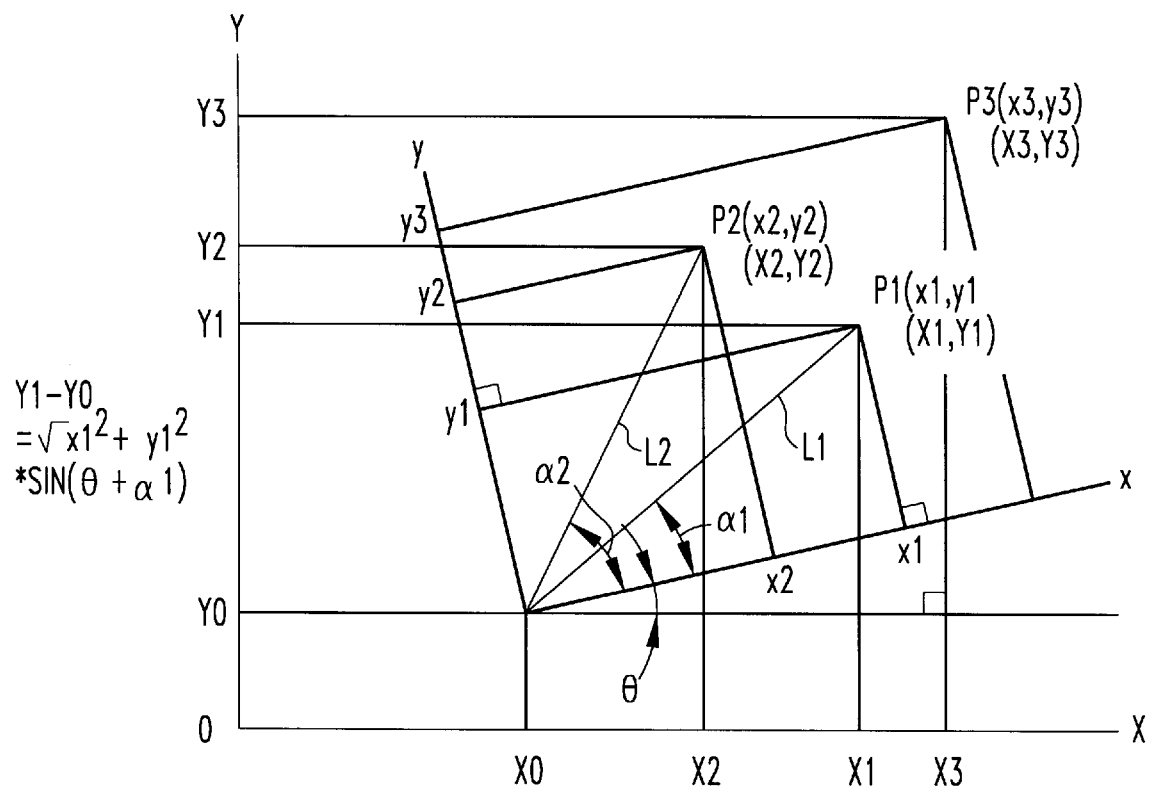
FIG. 14 is a diagram illustrating a method of converting the x- and y-coordinates, of a defect detected by a preliminary inspection into X- and Y-coordinates where the x- and y-coordinates of an inspected part on a preliminary inspection device are different from the X- and Y-coordinates on a review SEM that is a detailed inspection apparatus.

FIG. 14 illustrates a method of transforming the x- and y-coordinates of a defect detected by a preliminary inspection into X- and Y-coordinates were the x- and y-coordinates of the inspected part on the preliminary inspection apparatus are different from the X- and Y-coordinates on the review SEM, or detailed inspection apparatus. Also, one example of a method of calculating coordinate transformation parameters is $$\sqrt{x1^2 + y1^2} \cos(\theta + \alpha 1) = X1 - X0 \quad (1)$$

$$\sqrt{x1^2 + y1^2} \sin(\theta + \alpha 1) = X1 - X0 \quad (2)$$

$$\sqrt{x2^2 + y2^2} \cos(\theta + \alpha 2) = X2 - X0 \quad (3)$$

$$\tan \alpha 1 = (y1/x1), \tan \alpha 2 = (y2/x2)$$

(x1, y1), (x2, y2): coordinates of points $P_1$, $P_2$ on xy-coordinate axes (X1, Y1), (X2, Y2): coordinates of points $P_1$, $P_2$ on XY-coordinate axes $$X3 = X0 + \sqrt{x3^2 + y3^2} \cos(\theta + \alpha 3) \quad (4)$$

$$Y3 = Y0 + \sqrt{x3^2 + y3^2} \sin(\theta + \alpha 3) \quad (5)$$

where $\tan \alpha 3 = (y3/x3)$ generally $$Xi = Xo + \sqrt{xi^2 + yi^2} \cos(\theta + \alpha i) \quad (6)$$

$$Yi + Yo + \sqrt{xi^2 + yi^2} \sin(\theta + \alpha i) \quad (7)$$

where $\tan \alpha i = (yi/xi)$

In FIG. 14, part position detection positions $P_1$, $P_2$, and $P_3$ are set on the inspected part and measured in terms of the xy-coordinate system for the preliminary inspection apparatus. These positions are given by $P_1$ ($x_1$, $y_1$), $P_2$($x_2$, $y_2$), and $P_3$ ($x_3$, $y_3$), respectively, where the xy-coordinate system for the preliminary inspection apparatus is used. These detection positions $P_1$, $P_2$, and $P_3$ are given by $P_1$ ($X_1$, $Y_1$), $P_2$ ($X_2$, $Y_2$), and $P_3$ ($X_3$, $y_3$), respectively, where the XY-coordinate system is used. It is now assumed that the origin O of the XY-coordinate system is shifted by $X_0$ and $Y_0$ with respect to the origin of the xy-coordinate system, and that the XY-coordinate system is shifted by θ° with respect to the xy-coordinate system.

If $X_0$, $Y_0$, and θ are all zero, the x- and y-coordinates of the part position detection positions $P_1$, $P_2$, and $P_3$ set on the inspected part and measured on the preliminary inspection apparatus are the same as the X- and Y-coordinates, respectively. In this case, the relation $(x_i, y_i)=(X_i, Y_i)$ holds and, therefore, when the defect at the coordinates $(x_i, y_i)$ is moved into the review position of the review SEM, the coordinates $(x_i, y_i)$ can be directly used as target coordinates into which the defect in the inspected part should be brought after the movement.

However, the above-described $X_0$, $Y_0$, and θ are generally nonzero. Therefore, it is necessary to transform the X- and Y-coordinates $(x_i, y_i)$ of the defect point on the inspected part measured by the preliminary inspection apparatus into coordinates $(X_i, Y_i)$ of the review SEM.

Where the coordinates $(X_1, Y_1)$, $(X_2, Y_2)$ of the positions $P_1$ and $P_2$ are actually detected and measurement values are obtained, equations (1), (2), and (3) of FIG. 14 hold. In these equations (1)–(3), $X_1$, $Y_1$, $X_2$, $Y_2$, $x_1$, $y_1$, $x_2$, $y_2$, $\alpha_1$, and $\alpha_2$ are known and so unknown factors are $X_0$, $Y_0$, and θ. Since the three equations (1)–(3) exist for the three unknown values, these unknown values can be found from the equations (1)–(3). If so, the X- and Y-coordinates of the point $P_3$ can be calculated from the equations (1)–(3) without measurements. That is, $X_3$ and $Y_3$ can be found from equations (4) and (5) of FIG. 14. Once the $X_0$, $Y_0$, and $\theta$ are found, the X- and Y-coordinates ($X_i$, $Y_i$) of a point $P_i$ on the review SEM are found, using equations (6) and (7) of FIG. 14, the point $P_i$ being given by x- and y-coordinates ($x_i$, $y_i$).

Also, the X- and Y-coordinates can be made coincident with the x- and y-coordinates by moving the inspected part W over a distance given by $X_0$ and $Y_0$ within the XY-coordinate system and rotating the part through angle $\theta$. When the defect at the coordinates ($x_i$, $y_i$) measured on the preliminary inspection apparatus is moved into the review position on the review SEM, the coordinates ($x_i$, $y_i$) can be directly used as the target coordinates to be assumed by the defect on the inspected part after movement.

Method 2 of Calculating Coordinate Transformation Parameters

Figure 15:
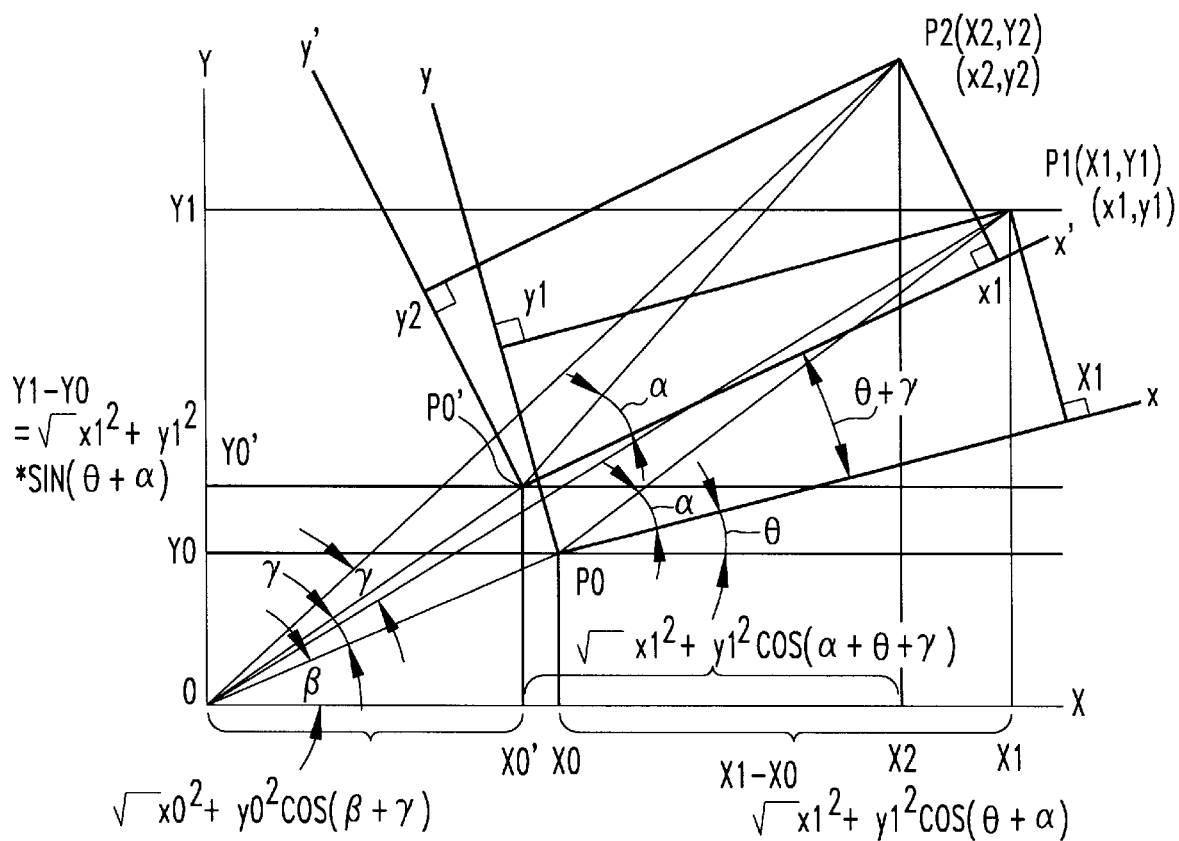
FIG. 15 is a diagram similar to FIG. 14, but illustrating another method.

FIG. 15 illustrates a second method of transforming the x- and y-coordinates of a defect detected by a preliminary inspection into X- and Y-coordinates where the x- and y-coordinates of the inspected part on the preliminary inspection apparatus are different from the X- and Y-coordinates on the review SEM, or detailed inspection apparatus.

In FIG. 15, a part position detection position $P_1$ is set on the inspected part and measured in terms of the xy-coordinate system for the preliminary inspection apparatus. The x- and y-coordinates of the part detection position $P_1$ are given by $P_1$ ($x_1$, $y_1$), while the X- and Y-coordinates of the part detection position $P_1$ is given by $P_1$ ($X_1$, $Y_1$). It is now assumed that the origin O of the XY-coordinate system is shifted by $X_0$ and $Y_0$ with respect to the origin of the xy-coordinate system, and that the XY-coordinate system is shifted by $\theta°$ with respect to the xy-coordinate system. If the $X_0$, $Y_0$, and $\theta$ are found, the X- and Y-coordinates ($x_i$, $y_i$) of the point $P_i$ on the review SEM are found from equations (6) and (7) of FIG. 14, the point $P_i$ being given by ($x_i$, $y_i$), as previously described in connection with FIG. 14.

A method of calculating the coordinate transformation parameters $X_0$, $Y_0$, and $\theta$ in a manner different from the method of FIG. 14 is next described.

The following equations (1) and (2) hold about point $P_1$:

$$\sqrt{x1^2 + y1^2}\cos(\theta + \alpha) = X1 - X0 \quad (1)$$

$$\sqrt{x1^2 + y1^2}\sin(\theta + \alpha) = Y1 - Y0 \quad (2)$$

$x_1$, $y_1$: coordinates of point $P_1$ on xy-coordinate axes
$X_1$, $Y_1$: measurement coordinates point $P_1$ on XY-coordinate axes $\tan\alpha = (y1/x1) \therefore \alpha = \tan^{-1}=(y1/x1)$ When an inspected part is rotated through angle $\gamma$, points $P_1$ and $P_2$ are moved into points $P'_0$, $P_2$. With respect to point $P_2$, $$\sqrt{X0^2 + Y0^2}\cos(\beta + \gamma) + \sqrt{x1^2 + y1^2}\cos(\alpha + \theta + \gamma) = X2 \quad (3)$$

where $\tan\beta = (Y0/X0)$
$x_2$: measurement coordinate of point $P_2$ on xy-coordinate axes. Equations (1) and (2) hold in FIG. 15. It is assumed that, when the inspected part is rotated through angle $\gamma°$ within the xy-coordinate system for the review SEM, the origin $P_0$ of the xy-coordinate system is rotated into $P_0'$ and that the point $P_1$ ($X_1$, $Y_1$) is rotated into the point $P_2$ ($X_2$, $Y_2$). In this case, equation (3) of FIG. 15 holds. These coordinates ($X_1$, $Y_1$) and ($X_2$, $Y_2$) are known by performing measurements with the review SEM. The three unknown values $X_0$, $Y_0$, and $\theta$ are determined, using the three equations (1)–(3) of FIG. 15. Then, the X- and Y-coordinates ($x_i$, $y_i$) of the point $P_i$ on the review SEM are determined, using equations (6) and (7) of FIG. 14, the point $P_i$ being given by x- and y-coordinates ($x_i$, $y_i$). Accordingly, as previously described in conjunction with FIG. 14, the position $P_i$ of the defect given by x- and y-coordinates ($x_i$, $y_i$) can be brought into the review position by moving the inspected part within the XY-coordinate system for the review SEM. The position of a defect or foreign material detected by the preliminary inspection apparatus can be adopted as the part position detection positions $P_1$ and $P_2$ of FIG. 14 and as the part position detection position $P_1$ of FIG. 15. The functions of the various means C1–C25 of the review SEM are next described.

(C1) Commonly Used Function-Realizing Means C1

The commonly used function-realizing means C1 has the following means C11–C15 that are activated when the user depresses buttons for selecting the functions of these means C11–C15 or clicks on icons displayed on a FUNCTION-SELECTING menu in the manual operation mode, i.e., during execution of a manual review of a defect. In the automatic mode (i.e., when the automatic misalignment correcting means, automatic shape-monitoring means, automatic defect image review execution means, and other means are in operation), the commonly used function-realizing means C1 is operated automatically in accordance with a program.

Figure 16:
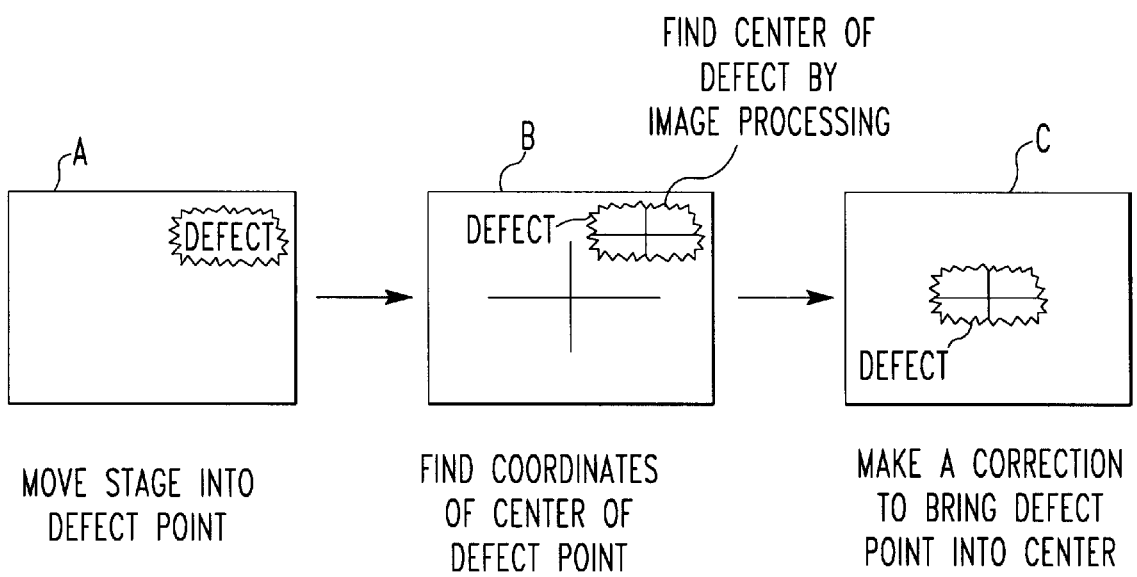
FIG. 16A is a diagram showing an image of a defect point moved into an inspection position (scanned by an electron beam) by an automatic centering means C11.
FIG. 16B is a diagram showing a deviation of the center of the defect point shown in FIG. 16A from the scanning center of the electron beam.
FIG. 16C is a diagram showing the manner in which the defect point shown in FIGS. 16A and 16B is brought into the center position by adjusting driver circuits E6 and E7 for X- and Y-deflection coils F6 and F7, respectively.
Figure 65:
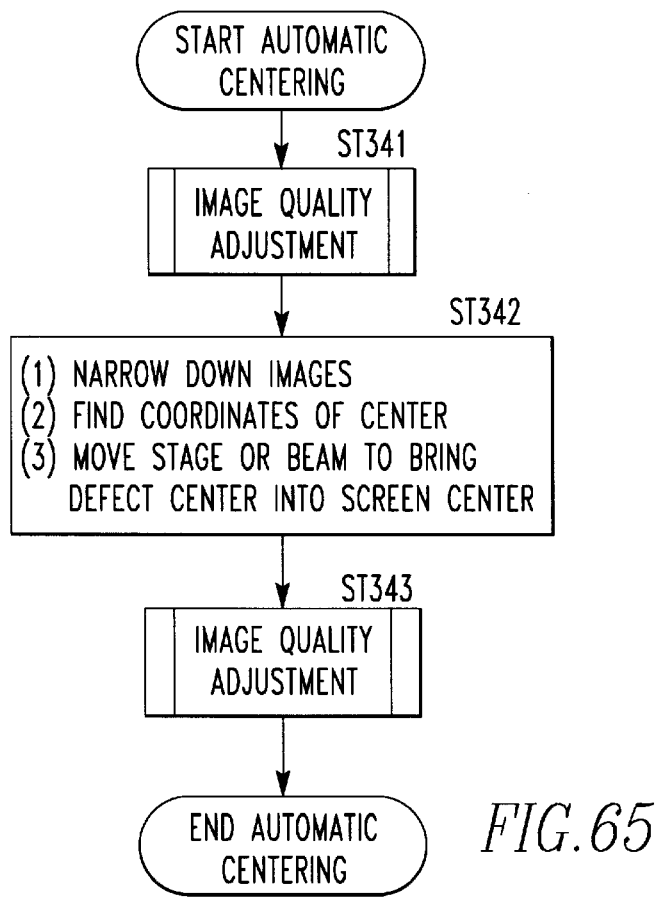
FIG. 65 is a flowchart illustrating subroutines of steps 314 and 322 of FIGS. 60 and 64, respectively, to perform automatic centering, the subroutines being also executed in steps 363, 372, and 382.

(C11) Automatic Centering Means C11: (FIGS. 16 and 65)

This automatic centering means C11 has a function of moving a specified defect position into the inspection position scanned by the electron beam. In the manual mode of operation, the defect image is automatically brought into the center of the display image simply by selecting a desired defect to be reviewed from plural defects. Thus, an appropriate observed image is displayed. In the automatic centering of the defect point, fine adjustments are made by adjusting the energizing voltages applied to the deflection coils F6 and F7 for the electron beam. If such fine adjustments do not suffice, the X-Y table is driven.

FIGS. 16A–16C illustrate the functions of the automatic centering means C11. FIG. 16A shows an image obtained when a defect point has been moved into the inspection position scanned by the electron beam. FIG. 16B shows a deviation of the center of the defect point from the center of the position scanned by the electron beam. FIG. 16C shows a state obtained by adjusting the driver circuits E6 and E7 for the X- and Y-deflection coils F6 and F7, respectively, shown in FIG. 10 such that the defect point is brought into the center.

If the X- and Y-coordinates of the defect on the preliminary inspection equipment (1, 2) deviate from the X- and Y-coordinates on the review SEM because of the detection accuracy of the preliminary inspection equipment (1, 2), the accuracy of the position of the sample stage, or the accuracy of the position of the stage of the review SEM, the defect position cannot be always brought into the center of the viewing screen. For instance, if the defect image deviates from the field of view in FIG. 16, this automatic centering means C11 brings the defect into the screen center by the following sequence.

(a) The image of the defect point is accepted by making at least one of automatic brightness adjustment, automatic contrast adjustment, and automatic focusing adjustment. The automatic brightness adjustment consists of modifying the offset of the output voltage from the secondary electron detector of the review SEM so that the average brightness of the taken image is within a given range. The automatic focusing adjustment consists of altering the objective lens current or objective lens voltage in such a way that the focal distance of the objective lens is changed, thus focusing the beam on the surface of the object under investigation. The automatic contrast adjustment consists of modifying the sensitivity of the secondary electron detector and the gain of the amplifier so that the dynamic range (from black level to white level) of the photographed image does not outside the upper and lower limits of the A/D converter. As a result, faithful reproduction is accomplished.

(b) The accepted image of the defect point is processed, the defect point is recognized, and the coordinates of the center of the defect point are found.

(c) The center of the defect point is moved into the center of the field of view by movement of the stage or beam. This will hereinafter be referred to as centering.

(d) At least one of the automatic brightness adjustment and automatic focusing adjustment is again made to accept a defect image.

Figure 69:
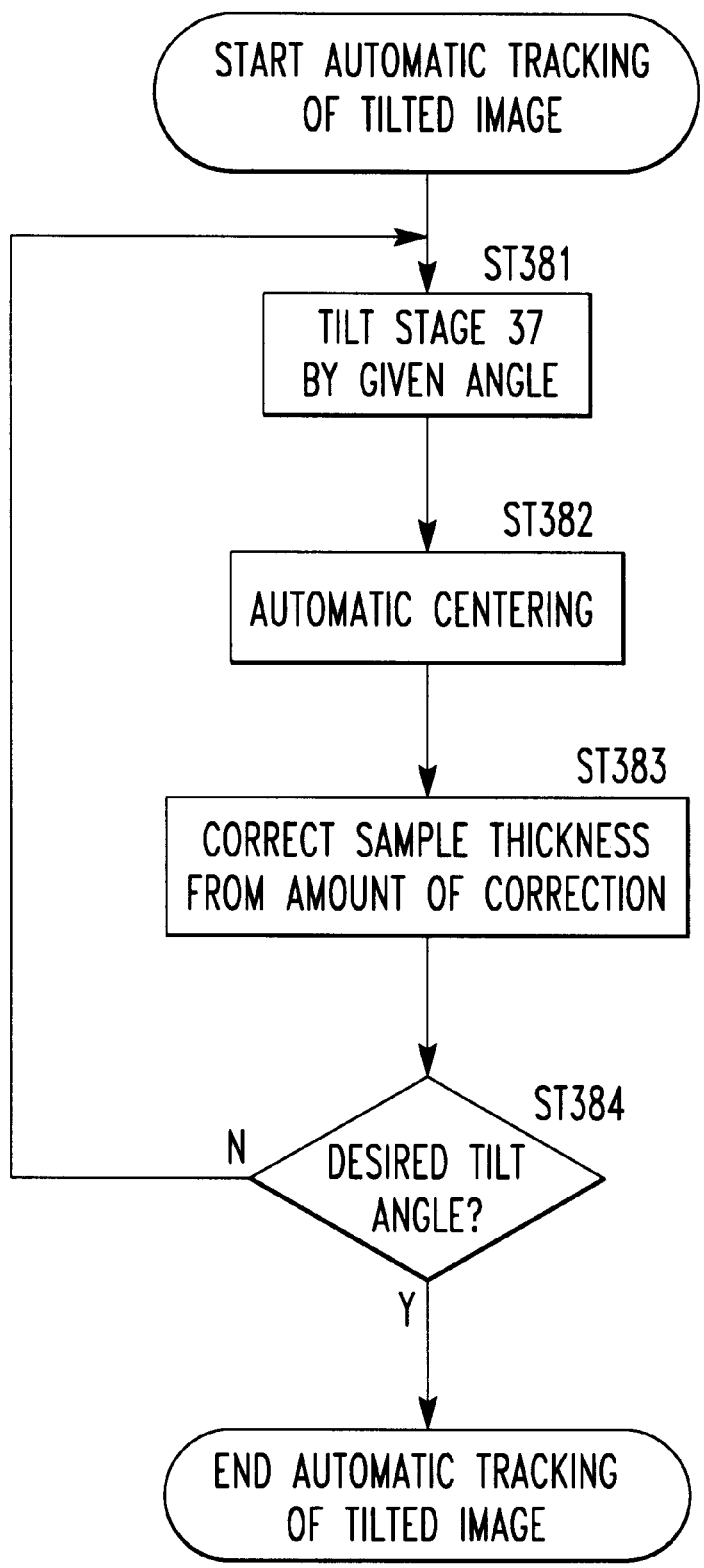
FIG. 69 is a flowchart illustrating subroutines of steps 278 and 328 of FIGS. 60 arid 64, respectively, to automatically track a tilted image.

(C12) Tilted Image Tracking Means C12: (FIGS. 17, 18, and 69)

When the inspected part-holding member 65 is tilted and the defect image is observed, the image is moved simultaneously with the tilt. This tracking means C12 recognizes the defect image by image processing techniques whenever the holding member is tilted by an increment of angle, until a specified angular position is reached. In this way, the automatic centering is performed.

Figure 17A:
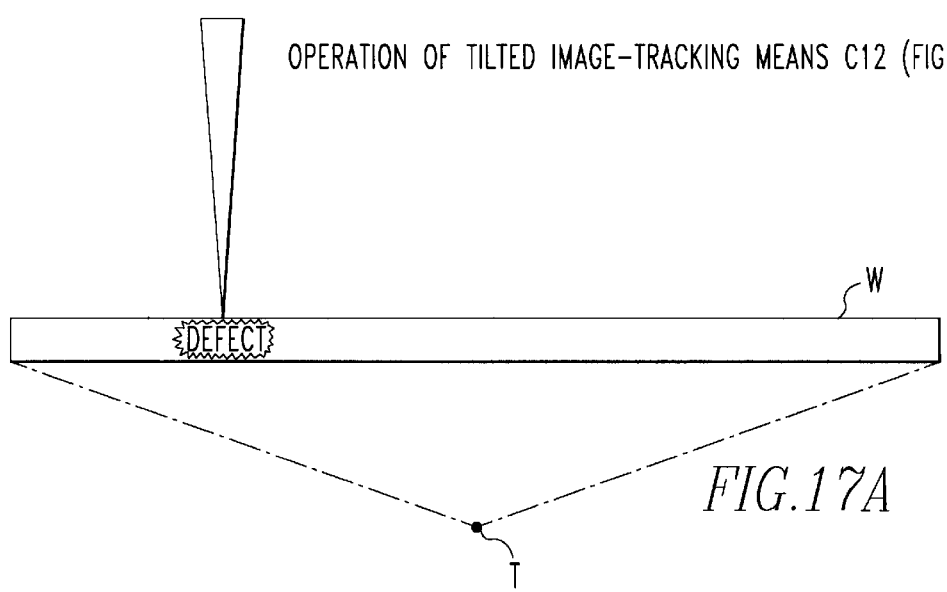
FIG. 17A is a side elevation illustrating the manner in which the electron beam of the review SEM shown in FIG. 1 is focused at the center of a defect point where an inspected part-holding member 65 is tilted at an angle of 0° about a tilting axis T shown in FIGS. 5 and 8.
Figure 17B:
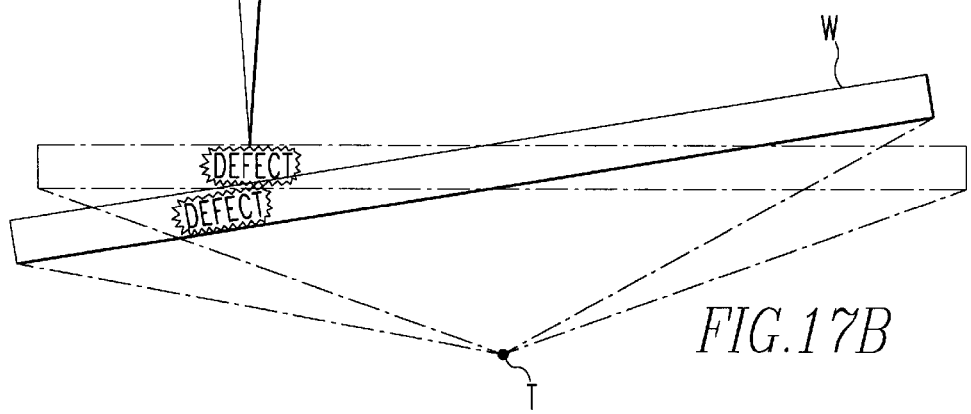
FIG. 17B is a side elevation similar to FIG. 17A, but in which the defect is located off the scanning center by simply tilting the inspected part-holding member 65 where the defect point deviates from the tilting axis T.
Figure 17C:
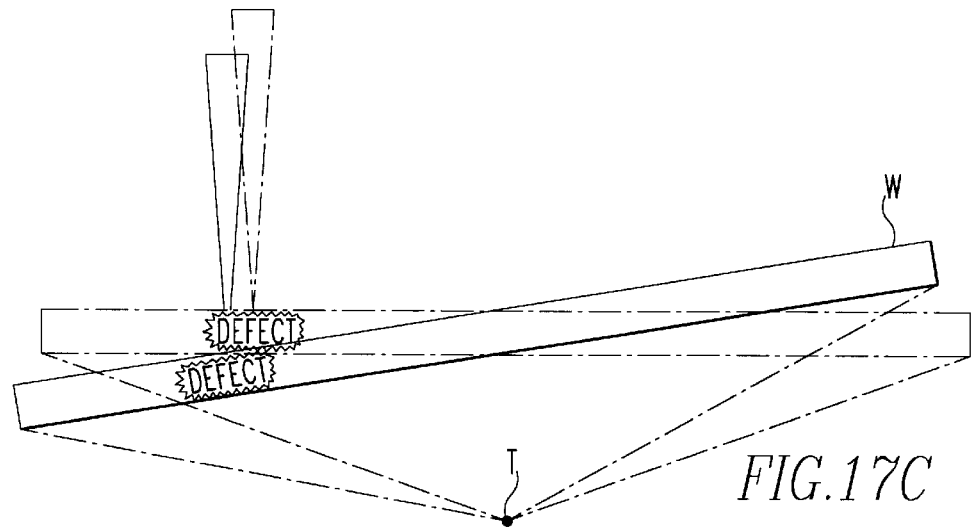
FIG. 17C is a side elevation similar to FIGS. 17A and 17B, but in which the defect point is brought into the scanning center by adjusting driver circuits E6 and E7 for X- and Y-deflection coils F6 and F7, respectively, and driver circuits E3 and E8 for a condenser lens F3 and an objective lens F8, respectively.
Figure 18:
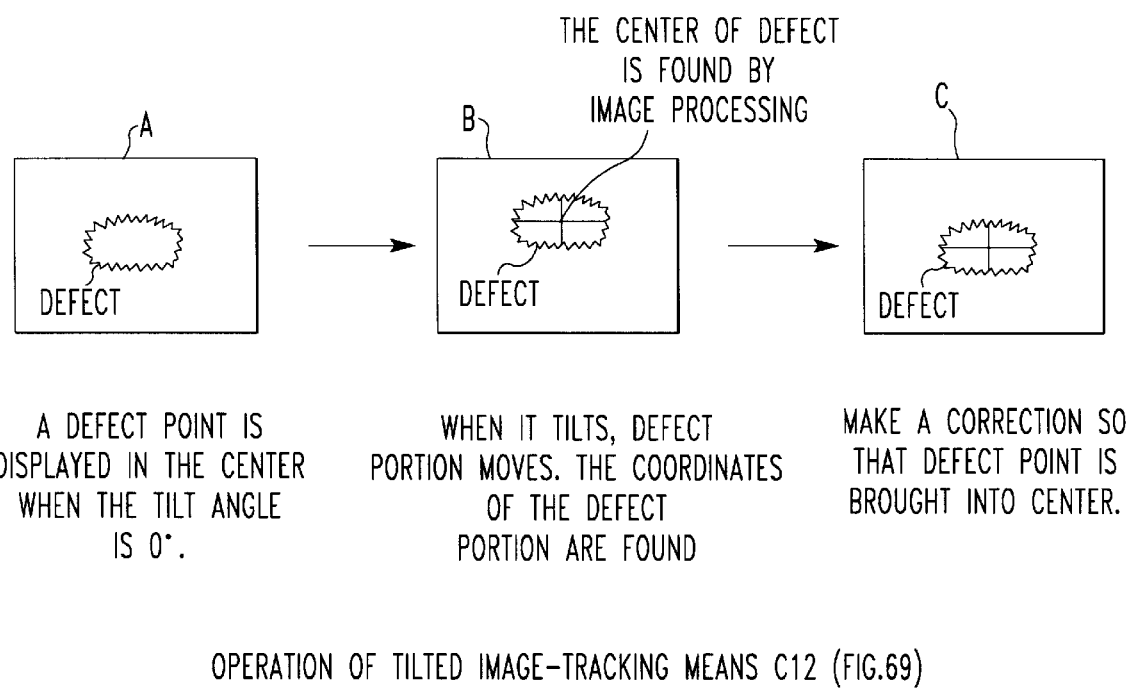
FIGS. 18A–18C are plan views corresponding to FIGS. 17A–17C, respectively.

FIGS. 17A–17C illustrate the manner in which a defect point deviates from the inspection position (scanning center of the electron beam) when the inspected part-holding member 65 is tilted about the tilting axis T (FIGS. 5 and 8). FIG. 17A shows a state in which the tilt angle is 0° and the electron beam is focused at the center of the defect point. FIG. 17B shows a state in which the inspected part-holding member 65 is simply tilted when the defect point is off the tilting axis T. The defect point is off the scanning center. FIG. 17C shows a state in which the driver circuits E6, E7 for the X- and Y-deflection coils F6, F7 and the driver circuits E3, E8 for the focusing lens F3 and the objective lens F8 are adjusted so that the defect point is brought into the scanning center.

FIGS. 18A–18C show a state in which a defect point is moved off the inspection position (scanning center of the electron beam) when the inspected part-holding member 65 is tilted about the tilting axis T (FIGS. 5 and 8). FIG. 18A shows an image obtained when the tilt angle is 0° and the electron beam is focused at the center of the defect point. FIG. 18B shows an image moved off the scanning center when the defect point is off the tilting axis T and the inspected part-holding member 65 is simply tilted. FIG. 18C shows an image produced when the driver circuits E6, E7 for the X- and Y-deflection coils F6, F7 and the driver circuits E3, E8 for the focusing lens F3 and the objective lens F8 are so adjusted that the defect point is brought into the scanning center.

When the automatic brightness/focusing adjustment is in operation, the tilted image tracking means C12 performs automatic brightness/focusing adjustment when the automatic centering ends. Where the tilted image tracking means C12 is operated when the inspected part-holding member 65 is tilted, the defect image varies as follows.

(a) A defect point shown in FIGS. 17A and 18A is obtained by tilting the inspected part-holding member 65 at an angle of 65°. As can be seen from FIG. 18A, the defect point image is in the center of the viewing screen.

(b) When the inspected part-holding member 65 is tilted by $\alpha°$ from the state shown in FIGS. 17A and 18A, the defect point image is off the center of the viewing screen. This state is shown in FIGS. 17B (indicated by the solid line) and 18B.

(c) When the scanning center of the electron beam is moved as shown in FIG. 17C, the defect point image is moved into the center of the viewing screen.

(d) The steps (b) and (c) described above are repeated until a final tilt angle is reached.

Generally, it is common practice to perform calculations and to provide control so as to prevent the image from shifting even if the inspected part-holding member 65 is tilted. In practice, however, the thickness of the wafer W deviates from a calculated value, or the wafer is warped, producing differences with calculated values. As a result, image shift takes place.

The tilted image tracking means C12 calculates the thickness of the wafer from the amount of movement of the image due to tilt of $\alpha°$ and makes a correction to minimize the calculational error. This correction permits such a control that any large image shift is prevented if the inspected part-holding member 65 is subsequently tilted by $\alpha°$. In practice, the defect image shifts due to the insufficient accuracy of the stage, limited calculational accuracy, and differences in wafer warpage between individual products even if such an amendment is made. Hence, the above-described centering is carried out.

As can be seen from FIG. 17, if the wafer-supporting stage S (FIGS. 5, 7, and 8) is tilted, the position taken in the direction of the height shifts, resulting in defocusing. The present function can correct the height and so the control is provided without defocusing.

Figure 19:
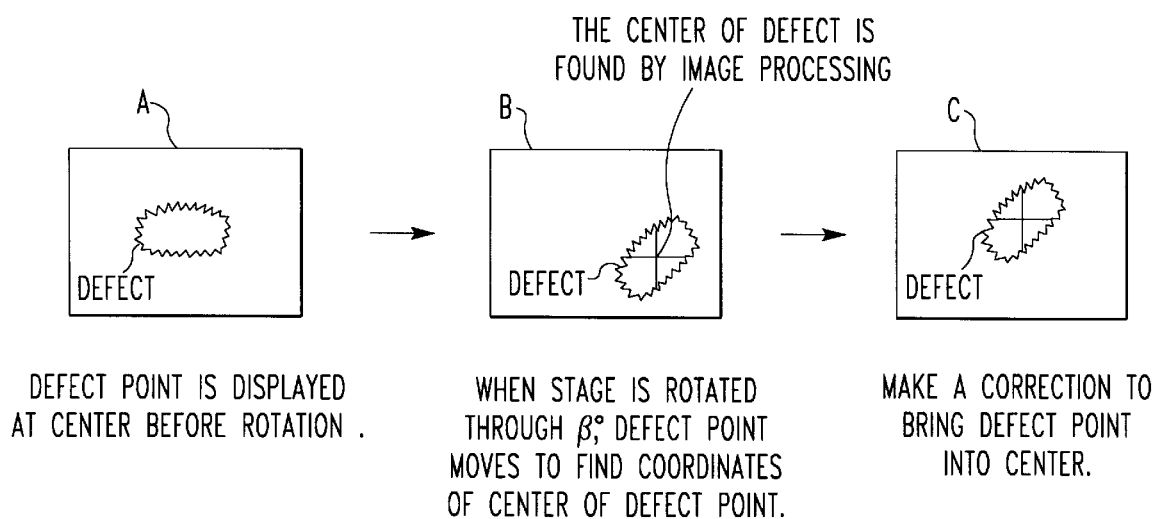
FIG. 19A is a plan view illustrating the manner in which the electron beam of the review SEM shown in FIG. 1 is focused at the center of a defect point when the inspected part-holding member 65 is not yet rotated with a rotating table 64 shown in FIGS. 5 and 8.
FIG. 19B is a plan view similar to FIG. 19A, but in which the defect point located off the center of rotation is moved off the scanning center by rotating the inspected part-holding member 65 through β°.
FIG. 19C is a plan view similar to FIGS. 19A and 19B, but in which the defect point is brought into the scanning center by adjusting the driver circuits E6 and E7 for X- and Y-deflection coils F6 and F7, respectively.
Figure 68:
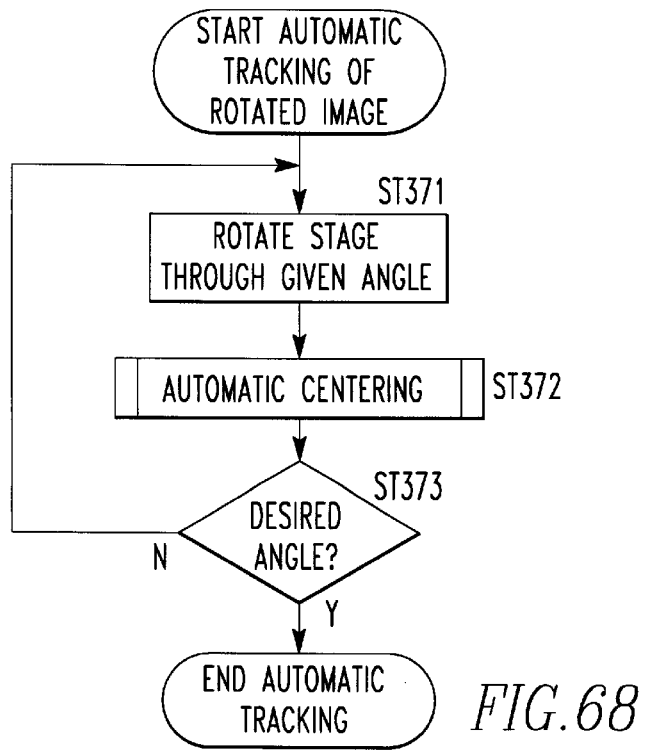
FIG. 68 is a flowchart illustrating subroutines of steps 284 and 326 of FIGS. 60 and 64, respectively, to automatically track a rotated image.

(C13) Rotated Image Tracking Means C13: (FIGS. 19 and 68)

When the operator wants to observe a defect point while rotating it, as the stage moves, the image shifts. Therefore, whenever the image rotates through an increment of angle, the defect image is recognized by image processing techniques, thus performing automatic centering. Where the function of the automatic brightness/focusing adjustment is in operation, this adjustment is made at the end of the automatic centering.

FIGS. 19A–19C show the manner in which the defect point moves out of the inspection point (scanning center of the electron beam) as the inspected part-holding member 65 is rotated with the rotating table 64 (FIGS. 5 and 8). FIG. 19A shows an image obtained when the electron beam is focused at the center of the defect point before rotation of the inspected part-holding member 65. FIG. 19B shows an image derived when the inspected part-holding member 65 is rotated through $\beta°$ when the defect point is off the center of rotation. As a result, the defect point is off the scanning center. FIG. 19C shows an image produced by adjusting the driver circuits E6 and E7 for the X- and Y-deflection coils F6 and F7, respectively, so that the defect point is brought into the scanning center.

Where the rotated image tracking means C13 is operated when the wafer-supporting stage S is rotated, the defect image varies in the manner described below.

(a) In FIG. 19A, the defect image is in the center of the viewing screen before rotation of the wafer-supporting stage S.

(b) When the wafer-supporting stage is rotated through β° from the state of FIG. 19A, the defect image moves off the center of the viewing screen as shown in FIG. 19B.

(c) In FIG. 19C, automatic centering is performed to bring the defect point image into the screen center.

(d) The steps (b) and (c) are repeated until a final angular position is reached.

Figure 67:
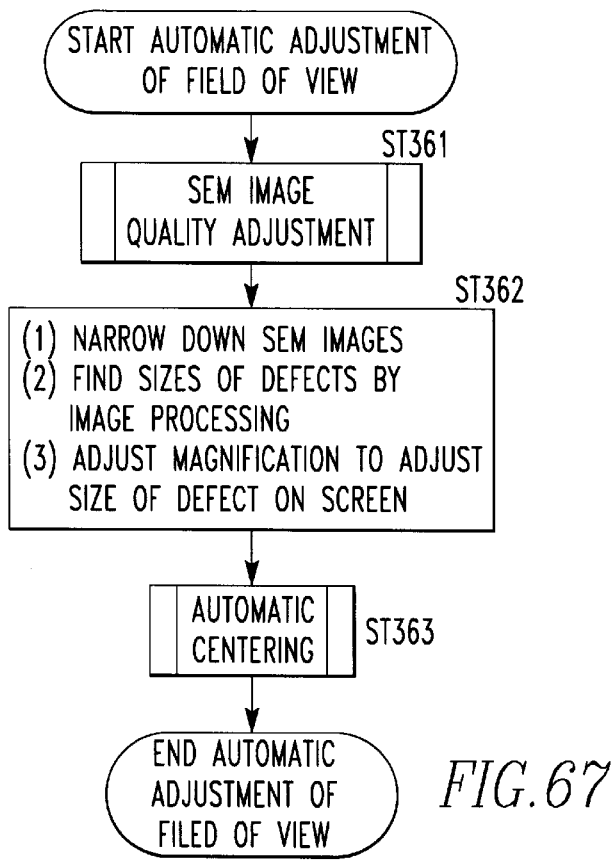
FIG. 67 is a flowchart illustrating subroutines of steps 293 and 323 of FIGS. 61 and 64, respectively, to automatically adjust the field of view.

(C14) Automatic Field of View Adjusting Means C14: (FIG. 67)

This means C14 processes the accepted image and modifies the magnification so that the obtained defect comes within the field of view. Also, this adjustment means C14 makes automatic brightness adjustment, automatic contrast adjustment, automatic focusing adjustment, and automatic centering. This function of the automatic field of view adjusting means C14 makes it unnecessary for the operator to manually adjust the magnification while watching the viewing screen or to adjust the brightness or focusing. In the manual review mode, if the operator depresses the "automatic field of view" button, this automatic field of view adjusting means C14 is set into operation. In the automatic review mode, this adjustment means C14 is automatically operated.

For example, it is assumed that the displayed microscope image has a height of V and a width of H. Any defect image is displayed with a height of V and a width of H. The magnification can be so set that one of these two dimensions is v=V/2 or h=H/2 and that the other is v≦V/2 or h≦H/2.

Figure 64:
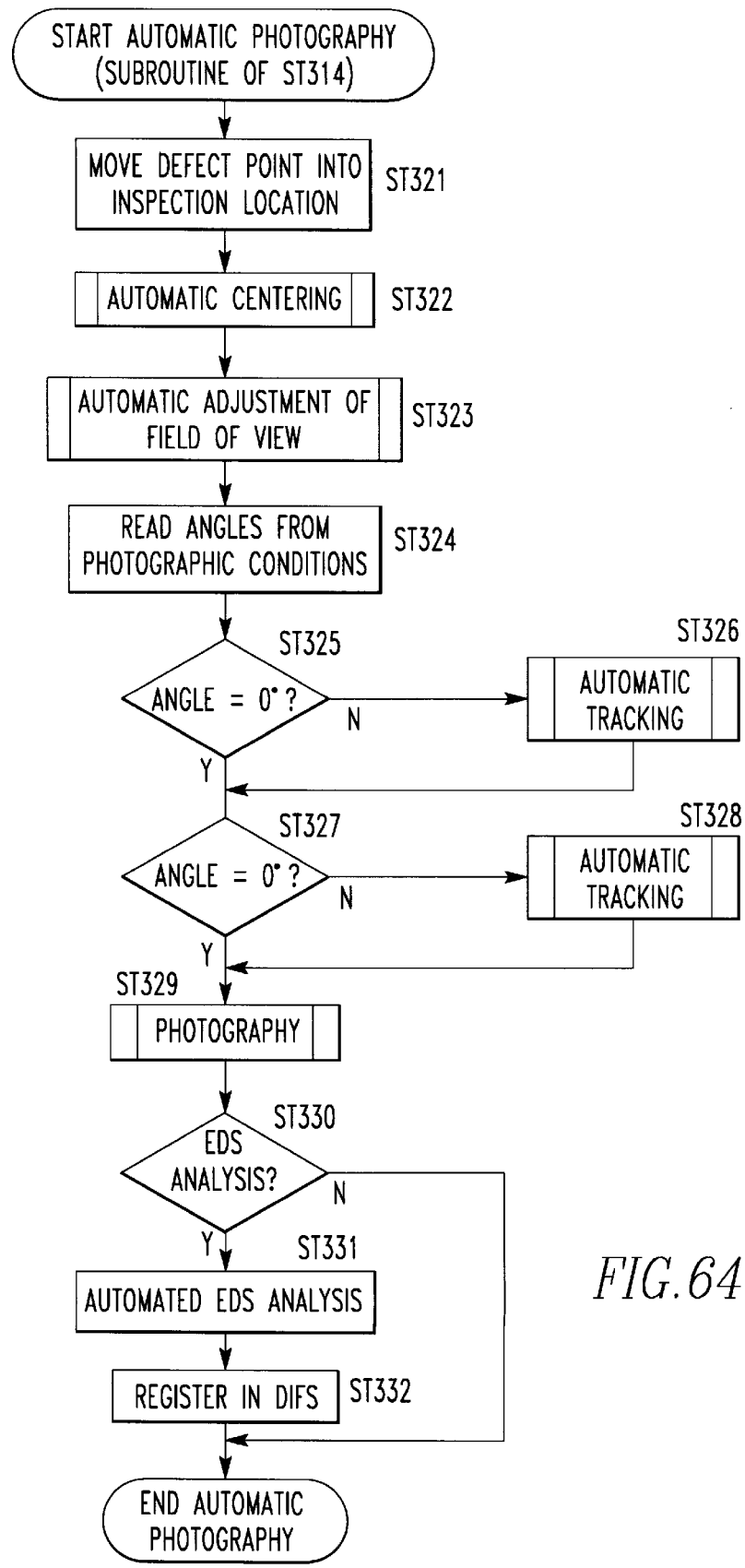
FIG. 64 is a flowchart illustrating a subroutine of step 314 of FIG. 62 to automatically photograph foreign materials and defects.

(C15) Defect Image Photographing Means C15: (FIG. 64)

This photographing means C15 can photograph (or, store as digital data) a defect image displayed on the display device D of the review SEM. In the manual review mode, if the operator depresses the "photography" button, this defect image photographing means C15 is set into operation. In the automatic review mode, the photographing means C15 is automatically operated according to a program. Photographed images are classified by the aforementioned defect sorting means and sent to the DIFS server 3 along with the results of the sorting. The server 3 registers the received data in the DIFS database.

(C16) Defect Image Portion Measuring Means C16

This measuring means C16 measures various sizes (such as the lengths taken along the X- and Y-axes, the area, and the height of the defect portion) of the defect image (review image) displayed on the display device D of the review SEM. In the manual mode, a portion of the displayed review image to be measured is specified within the XY-coordinate system with a mouse. Then, a "measurement button" is depressed. The various dimensions of the measured portion are automatically measured. If the bottom surface and the top surface of a step portion are specified, and if a "height measurement button" is depressed, the dimension between these two surfaces, or height, is automatically measured.

The height measurement is carried out by slightly tilting the stage and performing processing similar to the processing of the automatic length-measuring means C54 for the observed point. In making measurements, the size of the specified surface can be decreased. Also, plural portions can be specified. Simultaneously, the maximum heights of these specified portions can be found. Furthermore, the height around any defect point (the height of the substrate) can be found. The height of the defect portion above the substrate can be found by subtracting the substrate height from the defect portion height.

(C2) Automatic Misalignment Correcting Means C2

This automatic misalignment correcting means C2 has the following means C21–C25, automatically loads and unloads wafers, and corrects misalignment. The functions of these means C21–C25 are described below.

(C21) Automatic Wafer Load/Unload Means C21 (Steps 114, 127, and 147 of a Flowchart Described Below)

This automatic wafer load/unload means C21 transfers (loads) a wafer from the cassette 13 placed in position (the recessed cassette placement portion 7a) onto the inspected part-holding member 65 or unloads the wafer. Also, the automatic wafer load/unload means C21 causes the cassette identification number reader 16 to read the bar code printed on the label stuck on the cassette 13, sends the read cassette identification number to the DIFS server 3, and fetches information about defects on the wafer in the cassette 13 from the DIFS database.

That is, the automatic wafer load/unload means C21 executes the following processing steps successively:

(1) When the wafer cassette 13 is placed in position, the load/unload means C21 instructs the bar code reader to read the device number and the lot number.

(2) The load/unload means C21 searches the database for the device number and lot number and fetches information about defects on the wafer W in the cassette 13.

(3) After the wafer has been loaded, i.e., placed in the inspection position, defect information involved with the wafer is determined. In loading the wafer, an orientation flat state or notches are detected by an aligner. Adjustments are made so that they are in a given direction and that the origin of the wafer agrees with the origin of the system with a certain degree of accuracy.

Figure 20:
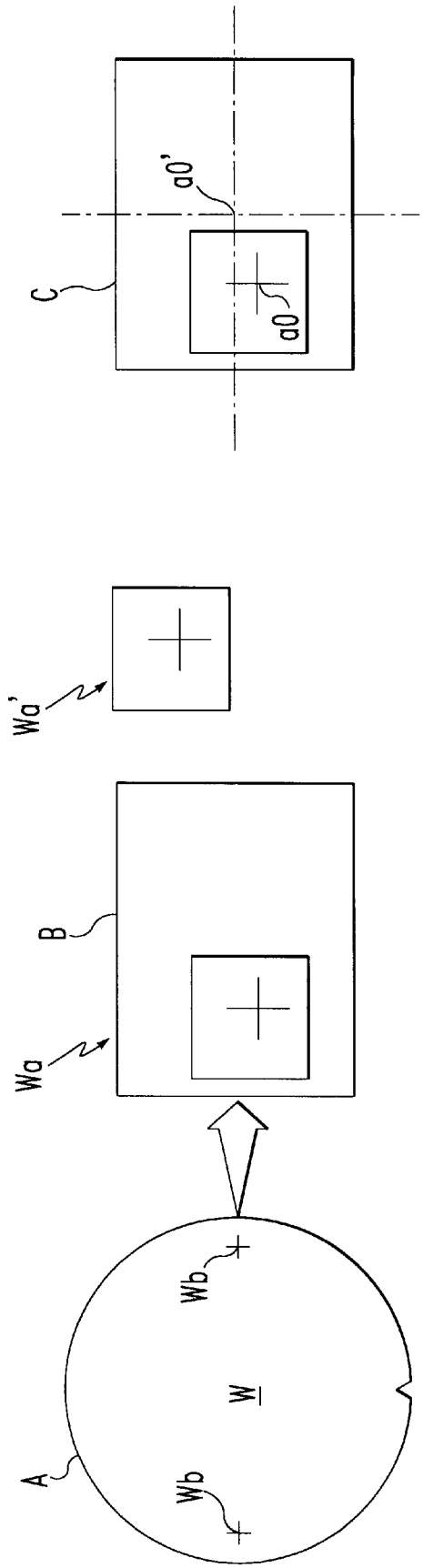
FIG. 20A is a plan view of a wafer w having a pattern and aligned to positions indicated by +.
FIG. 20B illustrates an image Wa at an alignment position and a reference alignment image Wa' stored in a DIFS database.
FIG. 20C is a diagram illustrating the deviation of a detected center position $a_0$ of the reference alignment image Wa' shown in FIG. 20B from a set center position $a_0$' of the reference alignment image Wa', the deviation being used by a misalignment-correcting means C22 to calculate misalignment-correcting value 1.

(C22) Misalignment Correcting Means C22 for Patterned Wafers (FIGS. 20, 49, and Step 168 of a Flowchart Described Later)

This misalignment correcting means C22 accurately corrects the position of the wafer placed in position by the automatic wafer load/unload means C21. That is, after the wafer has been loaded, the wafer-supporting stage S is moved into plural alignment reference positions to precisely determine the origin of the wafer and its rotation. Then, the offsets (the amounts of deviations from the set positions) from the reference points are found.

The offsets of the reference points are found by photographing an alignment image in the same way as when the observed point is photographed by the automatic photographing means C52, comparing the detected pattern with alignment images stored as references (referred to as the alignment marks), and calculating the offsets from the deviations of the alignment images. These offsets will hereinafter be referred to as first misalignment correcting values.

FIGS. 20A–20C illustrate the first misalignment correcting values calculated by the misalignment correcting means C22 for patterned wafers. FIG. 20A is a plan view of a patterned wafer W for which an alignment position is established at a position indicated by +. FIG. 20B shows an image Wa at the alignment position and a reference alignment image Wa' stored in the DIFS database of the DIFS server 3. FIG. 20C shows a deviation of the center ao of a detected alignment image from a set position $a_0$' of the center of the alignment image. The offsets (first misalignment correcting values) can be calculated from the deviation of the center position ao from the set position, taking account of the magnification of the image.

(C23) Misalignment Correcting Means C23 for Bare Wafers (FIGS. 21, 49 and Step 163 of a Flowchart Described Later)

This misalignment: correcting means C23 observes the edges of the wafer and finds the radius of some circle and the coordinates of the center in such a manner that a point on an arc on the wafer edges agrees best with a point on the circle provided that the wafer is a bare (i.e., unpatterned) wafer.

For example, the least squares method is used for this calculation. The misalignment correcting means C23 makes such a correction that the center of the circle found as described above becomes the center of the observed wafer or the origin of the wafer. Furthermore, an orientation flat state or notches are observed, and the angular position of the wafer is corrected.

Figure 21:
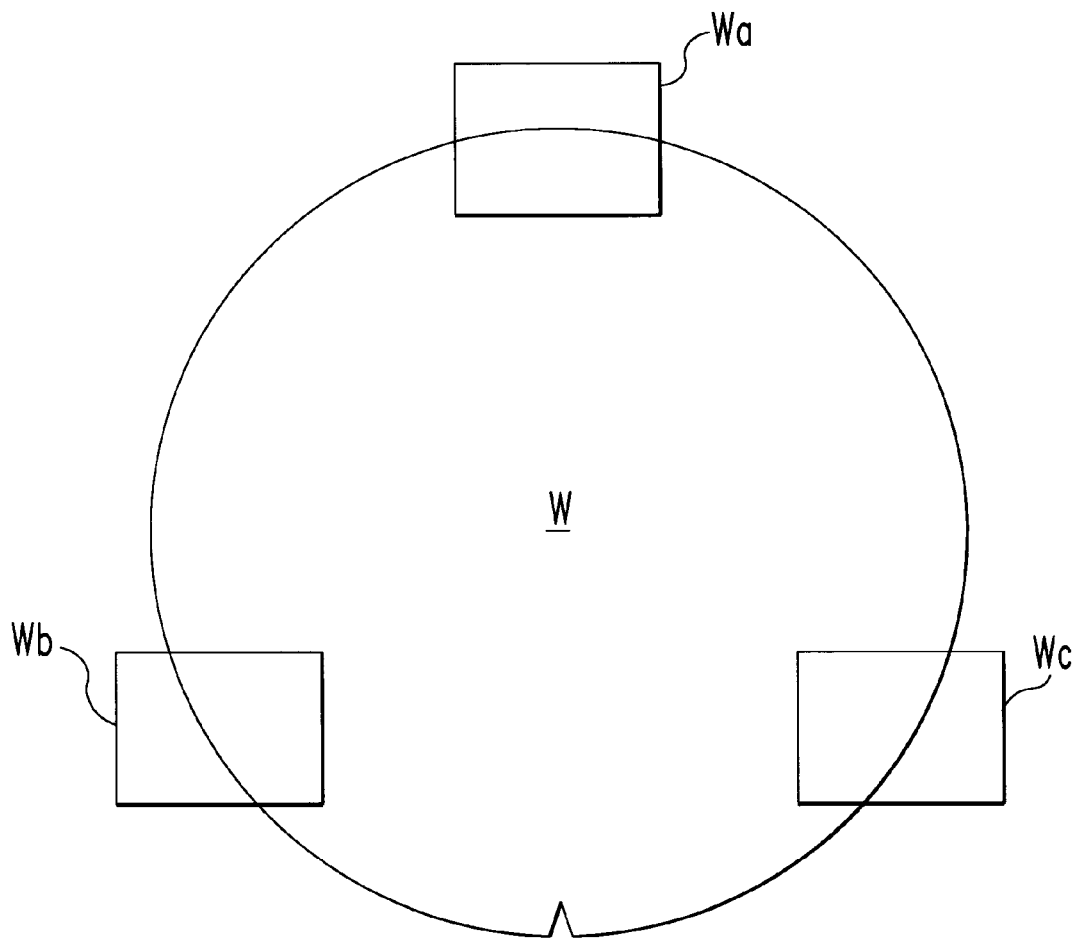
FIG. 21 is a diagram illustrating a misalignment-correcting method using a misalignment-correcting means C23 for an unpatterned wafer.

FIG. 21 illustrates a method of correcting misalignment by the misalignment correcting means C23 for unpatterned wafers.

(a) Images of portions Wa–Wc of a wafer W to be photographed are processed, the edges of the wafer W are detected, and points on arcs drawing the detected edges are extracted.

(b) The radius R and the coordinates of the center are found by the least squares method such that the points on the arcs Wa–Wc draw a circle.

The photographed portion can be only one, if the edges of the wafer can be detected with high accuracy. Any desired portions may be photographed. Also, the photographed portions may be arbitrary in number.

Figure 22:
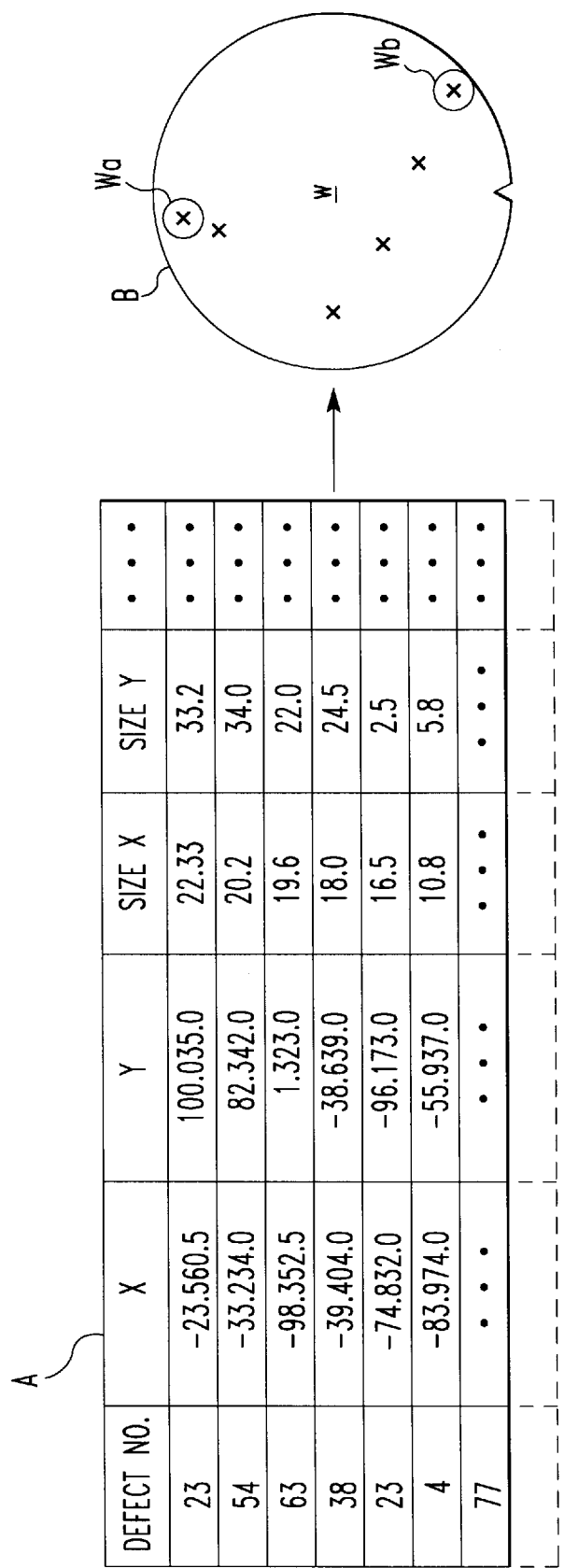
FIG. 22A is a table of defects having dimensions taken in the X-direction, the dimensions ranging from 10.0 to 25.0 which have been arranged in order of their sizes and searched for by the misalignment-correcting means C24.
FIG. 22B is a diagram obtained by mapping the defects listed in FIG. 22A onto a wafer W.
Figure 49:
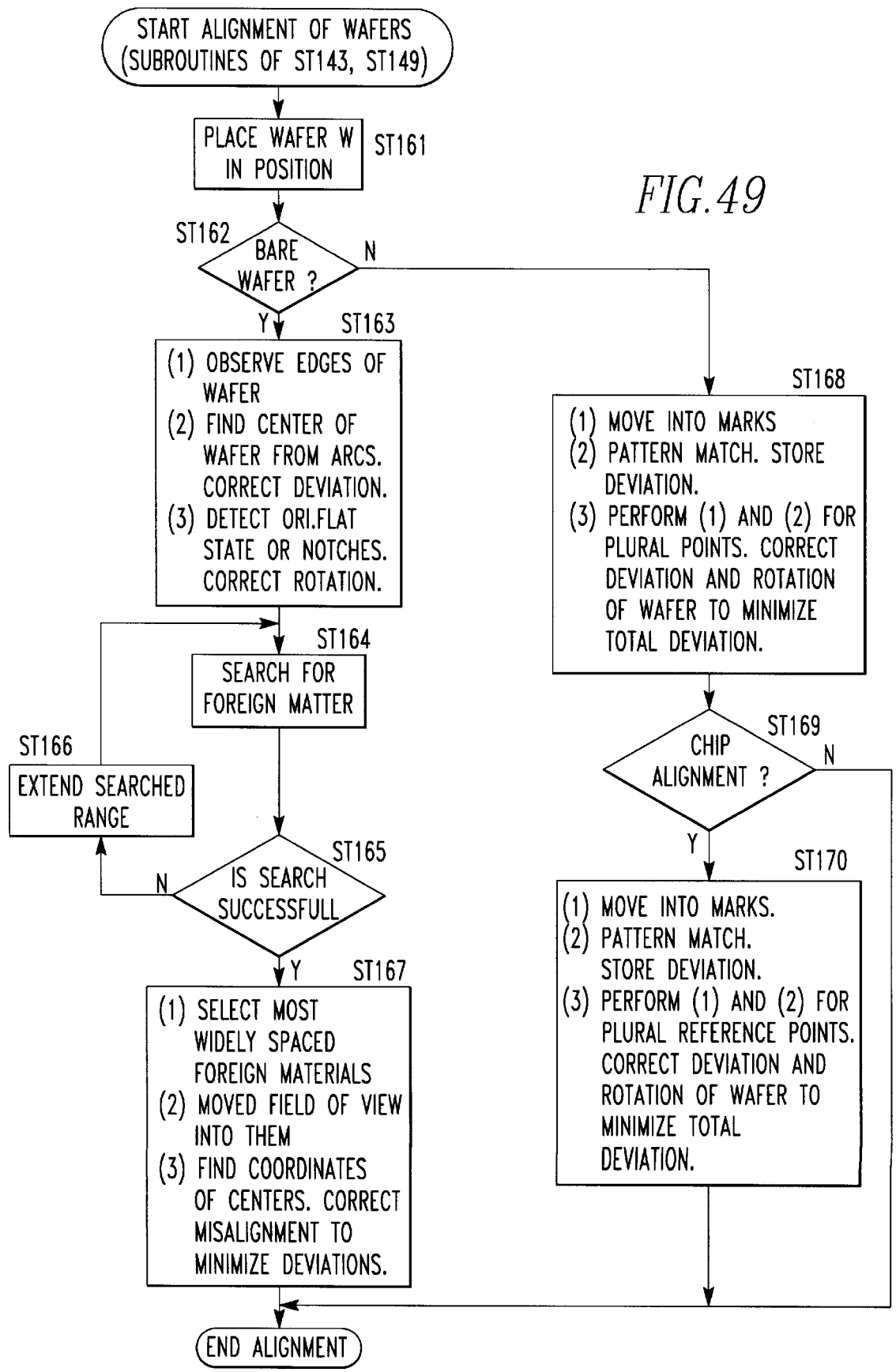
FIG. 49 is a flowchart illustrating a subroutine of steps 143 and 149 to align wafers.

(C24) Accurate Misalignment Correcting Means C24, Using Defect Points (FIGS. 22, 49 and steps 164–017)

The misalignment correcting function for bare wafers can accurately find the coordinates of the center of the wafer or of the origin from the edges of the wafer. However, with this function alone, any defect portion may, in practice, not be precisely brought into a desired location due to errors contained in the coordinates of the defect portion (i.e., errors in defect information) and due to positional error in the stage of the review SEM. In order to solve this problem, the accurate misalignment correcting means C24 makes such a correction that the coordinates of a defect contained in the defect information coincide with the coordinates of the observed defect point. In particular, the correcting means C24 automatically executes the following processing. FIGS. 22A and 22B illustrate the function of the accurate misalignment correcting means C24. FIG. 22A is a table of defects which have been found by searching for defects having X dimensions of 10.0 to 25.0 and are arranged in increasing order. FIG. 22B is a view obtained by mapping the defects of FIG. 22A onto the wafer W.

(a) The defect information (FIG. 22A) about the wafer W is searched for defect points having sizes lying in a specified range. Among them, some points Wa and Wb (FIG. 22B) spaced from each other most remotely are extracted, movements are made up to these points Wa and Wb, the centers of the recognized defects are found, and amounts of corrections are calculated, taking account of the average value of such deviations. They will be referred to as second misalignment correcting values.

(b) If any defect point is found from the specified range of sizes, the range is extended, and the searching is again attempted.

(c) In performing automatic centering to photograph defect points, the centers of the defective points are found. Therefore, a map of amounts of corrections on the wafer is created, using the deviations. The corrections can be made over the whole wafer surface by finding coordinates, by interpolation, on the map for which correcting values are unknown. These correcting values will be referred to as third misalignment correcting values.

(d) Where no defect point is found, searching is attempted while switching the correcting values from the third misalignment correcting values to the second misalignment correcting values and then to the first misalignment correcting values.

The accurate misalignment correcting means C24 can also be applied to patterned wafers. Accurate alignments can be made by performing similar processing on defects on each chip even after "chip misalignment correction" described later is performed.

(C25) Chip Misalignment Correcting Means C25 for Patterned Wafers (FIG. 49 and Step 170)

The chip misalignment correcting means C25 automatically performs an alignment operation for each chip observed if the positional accuracy of the alignment function for patterned wafers is not sufficiently high. This enhances the positional accuracy in the manner described below.

(a) The coordinates of a certain pattern (alignment mark) relative to the origin of a chip are previously stored. The pattern will be used to make alignments inside or outside the chip.

(b) Before observing the chip, the field of view is moved into the position of the alignment mark. An image of the alignment mark is photographed and compared in pattern with the stored alignment mark or marks.

(c) Deviations of the coordinates found by the comparison are corrected.

The accuracy of the positions, or coordinates, inside the chip can be enhanced by the operations described thus far. The functions of the means C3–C81 of the engineering workstation (EWS) are next described.

Figure 44:
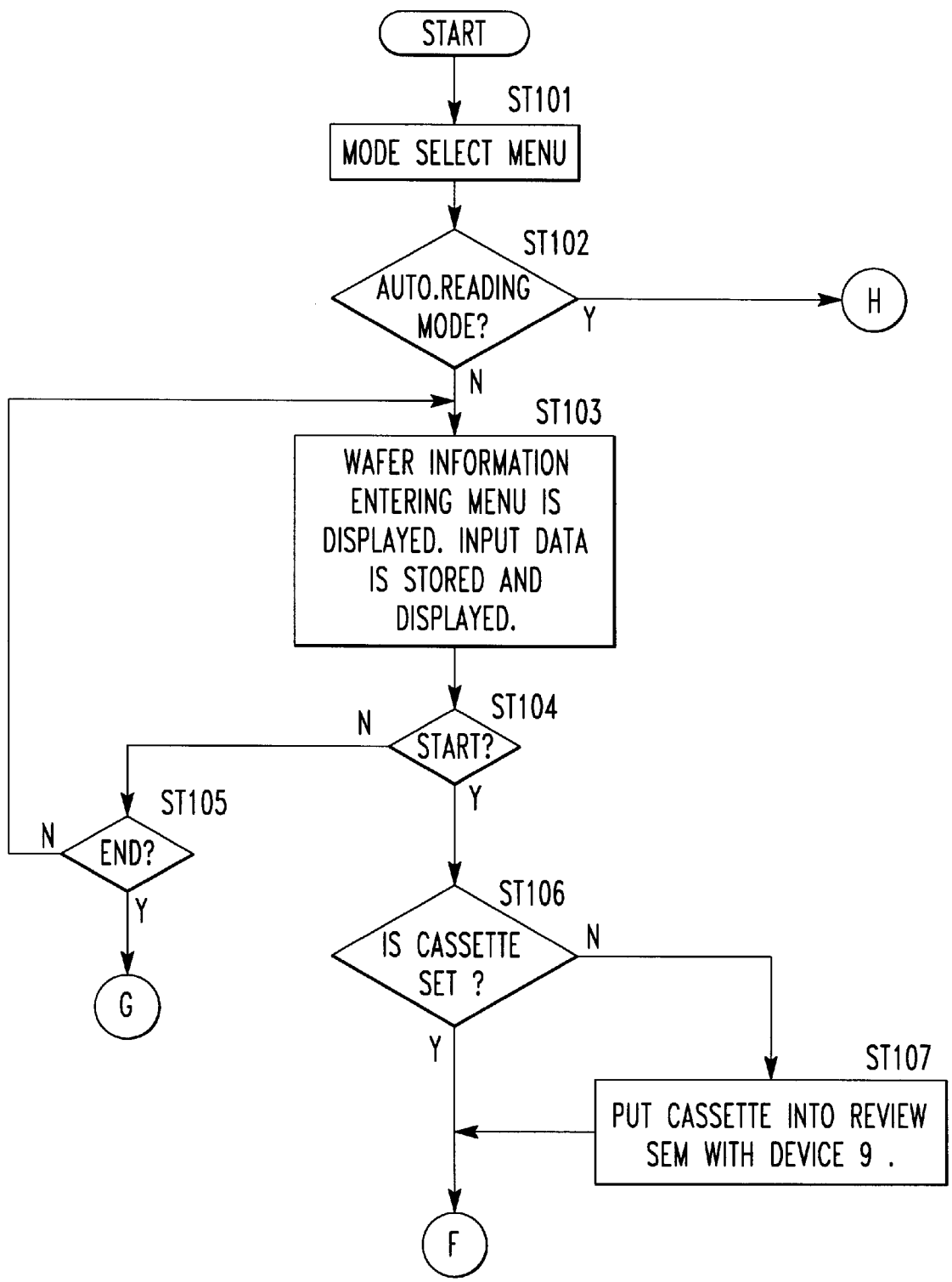
FIG. 44 is a flowchart illustrating processing performed by the review SEM in accordance with a program stored in the memory of the SEM controller.
Figure 45:
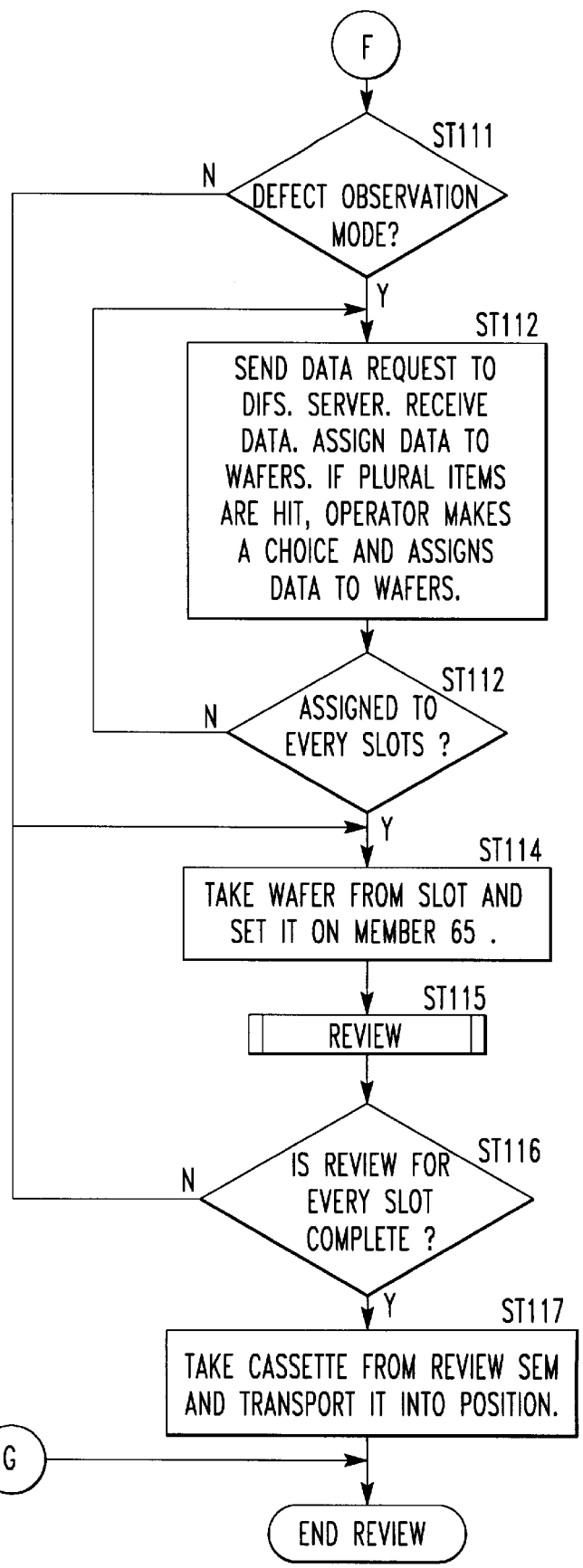
FIG. 45 is a flowchart illustrating processing performed subsequently to the processing of FIG. 44.
Figure 47:
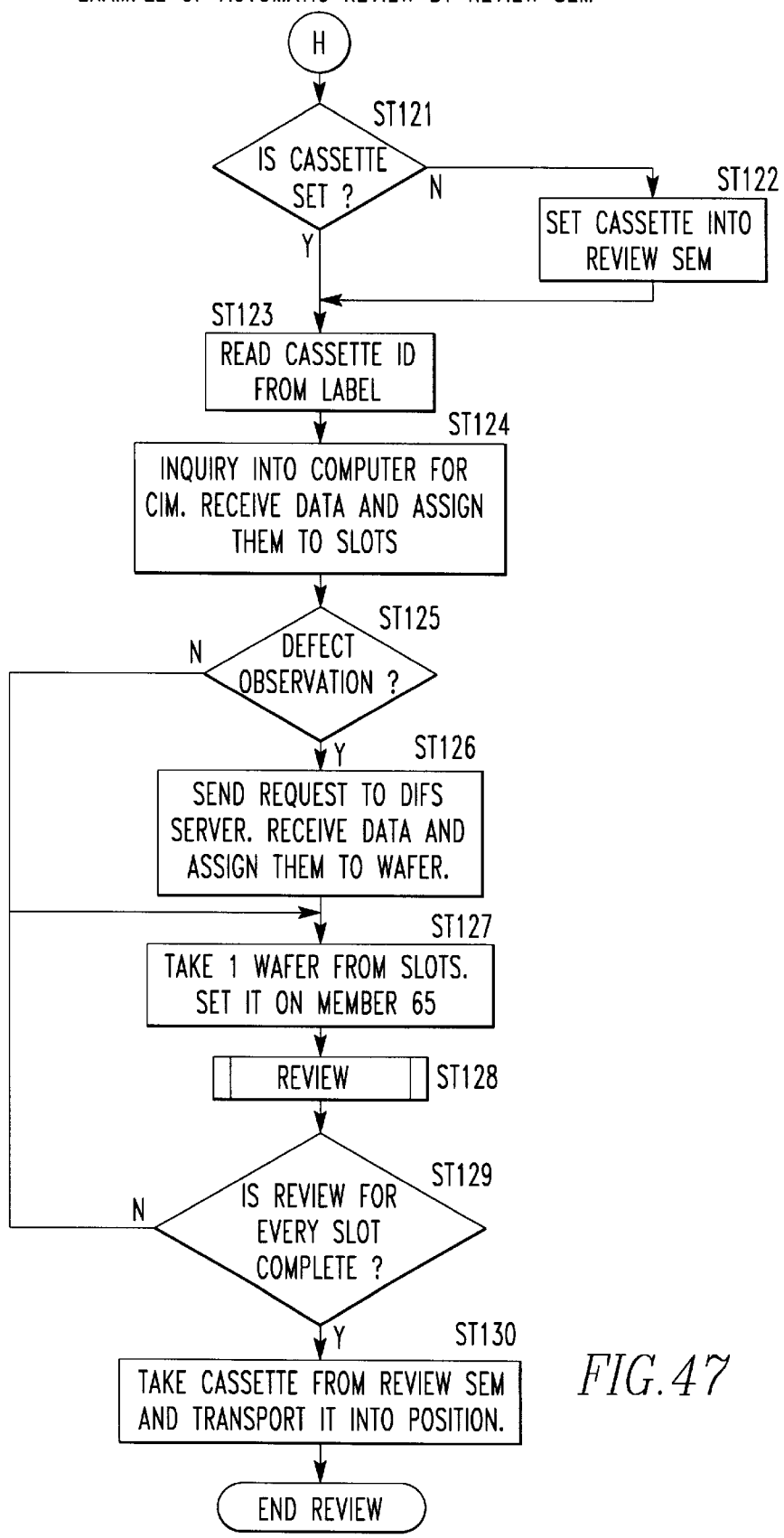
FIG. 47 is a flowchart illustrating processing performed subsequently to the processing of FIG. 44.

(C3) Operation Mode Establishing Means C3 (Steps 101 and 102 of FIG. 44, Step 111 of FIG. 45, and Step 125 of FIG. 47)

This operation mode establishing means C3 has a function of establishing the mode of operation of the SEM controller.

(C31) Wafer Information Input Mode Selecting Menu Displaying Means C31 (Step 101 of FIG. 44)

This mode selecting means C31 has a function of displaying a menu to permit the user to determine whether information about a wafer to be reviewed is entered in the fully automated input mode. The SEM controller operates according to the selected wafer information input mode. If the fully automated input mode is not selected, the controller displays a menu for promoting the user to manually enter wafer information.

(C32) Mode Selecting Menu Displaying Means C32 (Step 101 of FIG. 44)

This menu displaying means C32 permits the user to make a selection between the wafer information automatically reading mode and the manual input mode, to make a selection between the foreign material/defect observation mode and the shape-monitoring mode, and to make a selection between the automatic review mode and the manual mode.

(C4) Input/Output Execution Means C4 (Step 103 of FIG. 44 and Step 112 of FIG. 45)

This input/output execution means C4 executes the passing of information into and out of the preliminary inspection equipment (1, 2) and the DIFS server 3 connected via the review SEM and via the network N.

(C41) Part Search Information Input Means C41 (Step 103 of FIG. 44)

This part search information input means C41 has a function of entering part search information necessary for the review SEM to search the DIFS server for information about preliminary inspection of an inspected part and to read the information. This information input means C41 can be made of a manually input means or an automatic input means. Where this input means C41 consists of a manually input means, this means C41 can comprise the display device D, a means for displaying a menu for entering part search information on the display device D, a keyboard, and a means for storing information entered from the keyboard. Where the part search information input means is made of an automatic input means, it can be composed of the bar code reader 16 for reading a code from the cassette 13 in which the inspected part W is received. (C42) Preliminary Inspection Information Reading Means C42 (step 112 of FIG. 45 and steps 124, 126 of FIG. 47):

This preliminary inspection information reading means C42 has a function of reading information about preliminary inspection of the inspected part W from the search part information database, the inspected part W corresponding to the part search information entered from the part search information input means C41.

Accordingly, when the review SEM reviews, or performs detailed inspection of, the inspected part W, preliminary inspection information (such as the size of the part W, the sizes of defects, and positional information) about the inspected part W can be used. Any desired defect to be reviewed is selected from defects contained in the preliminary inspection information read by the preliminary inspection information reading means C42 of the review SEM. This selected defect can be reviewed.

Figure 51:
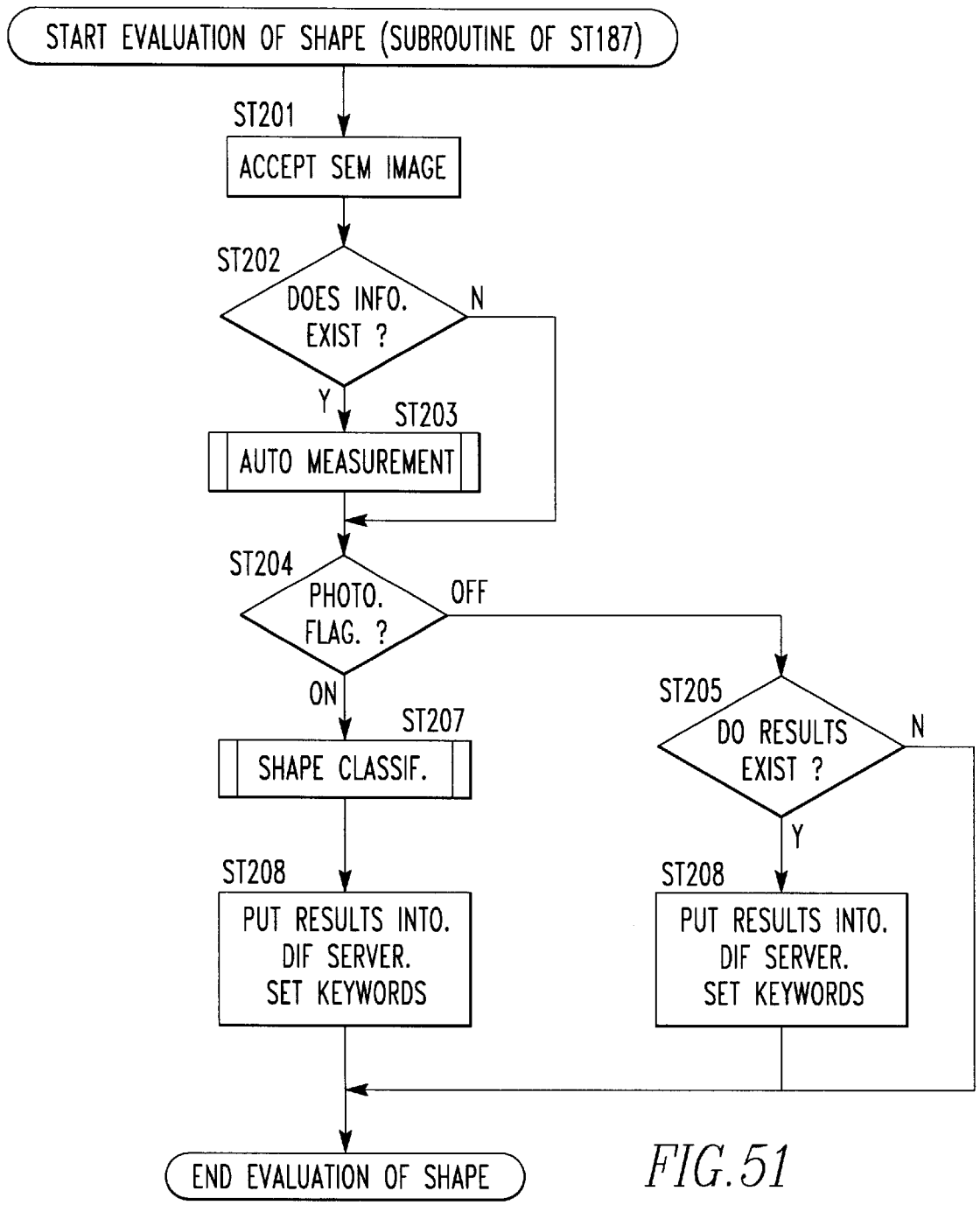
FIG. 51 is a flowchart illustrating a subroutine of step 187 of FIG. 50 to evaluate shapes.

(C43) Review Information Registration Means C43 (Steps 206 and 208 of FIG. 51)

The review information registration means C43 stores review information obtained by the review in the DIFS database (i.e., the database about information about inspected parts). Therefore, a computer that can be accessed to the inspected part information database can use the review information stored in the DIFS database.

Figure 23:
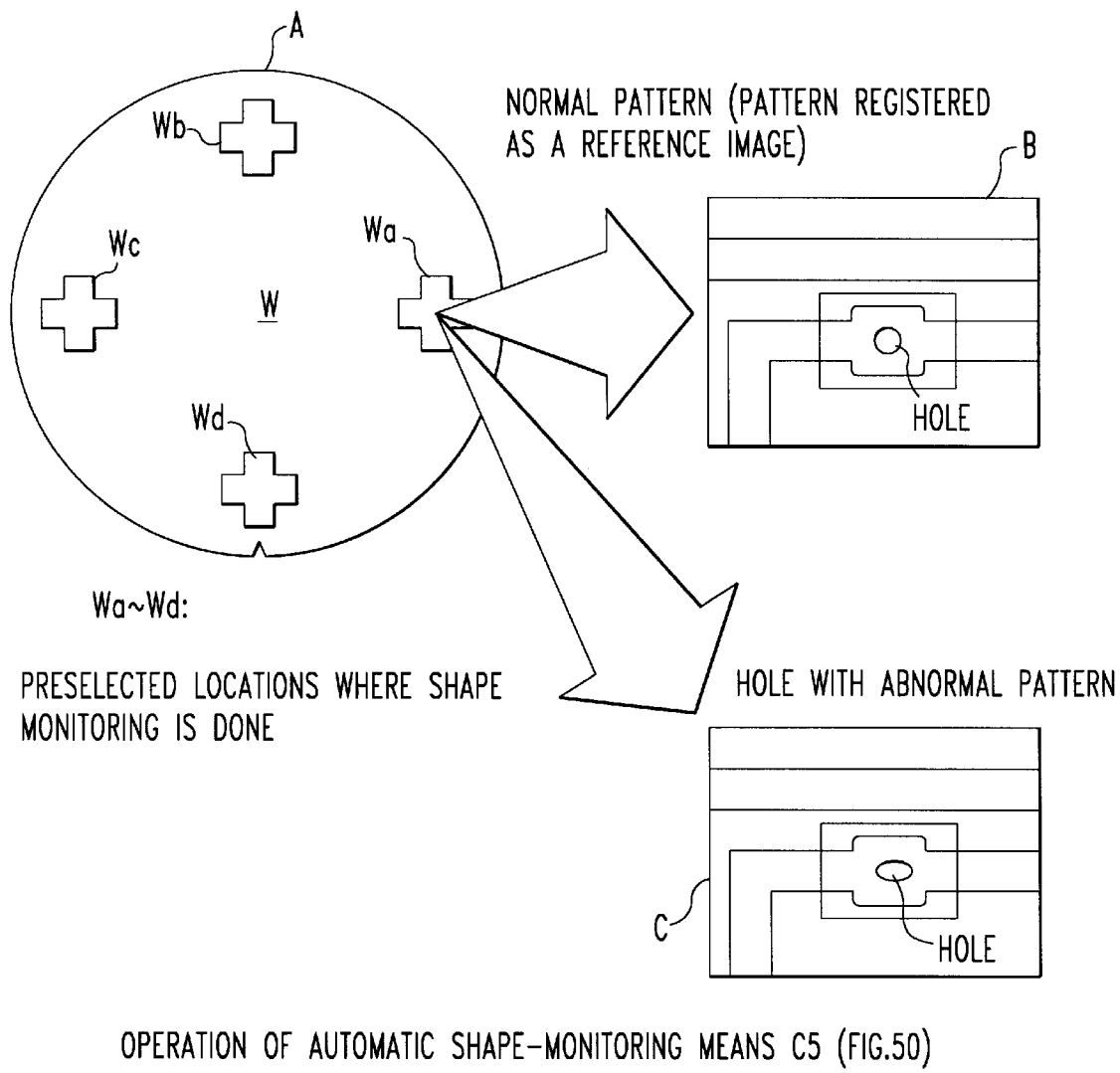
FIG. 23A is a diagram illustrating predetermined locations Wa-Wd of a wafer W at which shape-monitoring is done by the main function of an automatic shape-monitoring means C5.
FIG. 23B is a diagram showing a normal pattern image at the location Wa, the image being stored as a reference image.
FIG. 23C is a diagram similar to FIG. 23B, but in which a hole is patterned abnormally.
Figure 50:
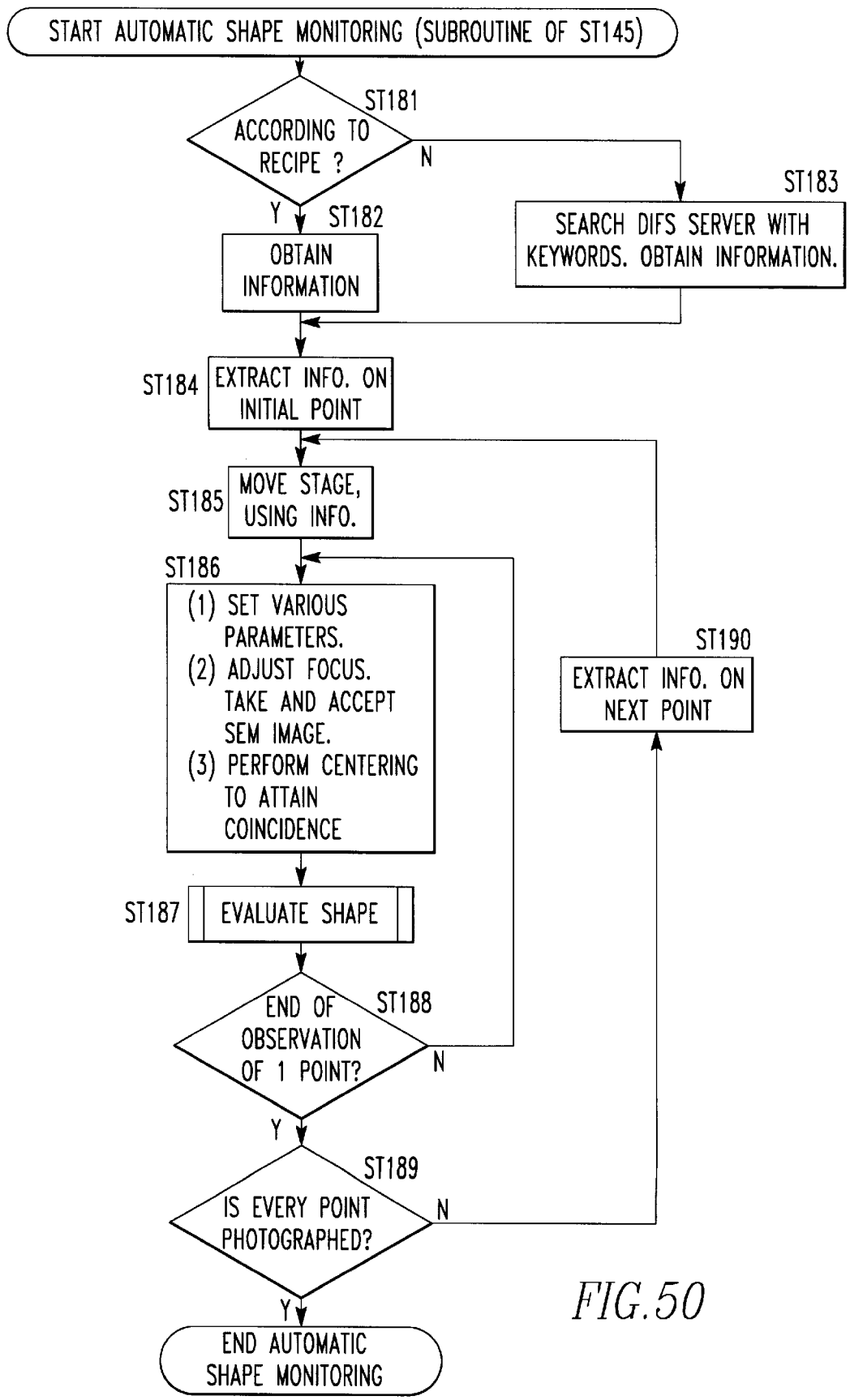
FIG. 50 is a flowchart illustrating a subroutine of step 145 to automatically monitor shapes.

(C5) Automatic Shape Monitoring Means C5 (FIGS. 23 and 50)

The essential function of the automatic shape monitoring means C5 is to monitor the shapes of patterned wafers. The monitoring means C5 is also capable of monitoring the shapes of unpatterned wafers.

FIGS. 23A–23C illustrate the main functions of the automatic shape monitoring means C5. FIG. 23A shows preselected portions Wa–Wd on the wafer W, the portions Wa–Wd being subjected to shape monitoring. FIG. 23B shows an example of an image of a normal pattern of Wa, the image being stored as a reference image. FIG. 23C shows an example of the image of the pattern of Wa having a defective hole.

The main function of the automatic shape monitoring means C5 consists of storing the image of the normal wafer W as the reference image, comparing the corresponding locations of wafers W in amount of features if the shape of a separate wafer W should be monitored, and judging the wafer to be defective if the difference in amount of features is in excess of a preset value, as shown in FIGS. 23A–23C.

The automatic shape monitoring means C5 has a function of judging whether a certain portion of a pattern formed on a wafer W is at fault, as illustrated in FIGS. 23A–23C. Besides, the monitoring means C5 has the following means C51–C54 to perform other functions described below.

Figure 56:
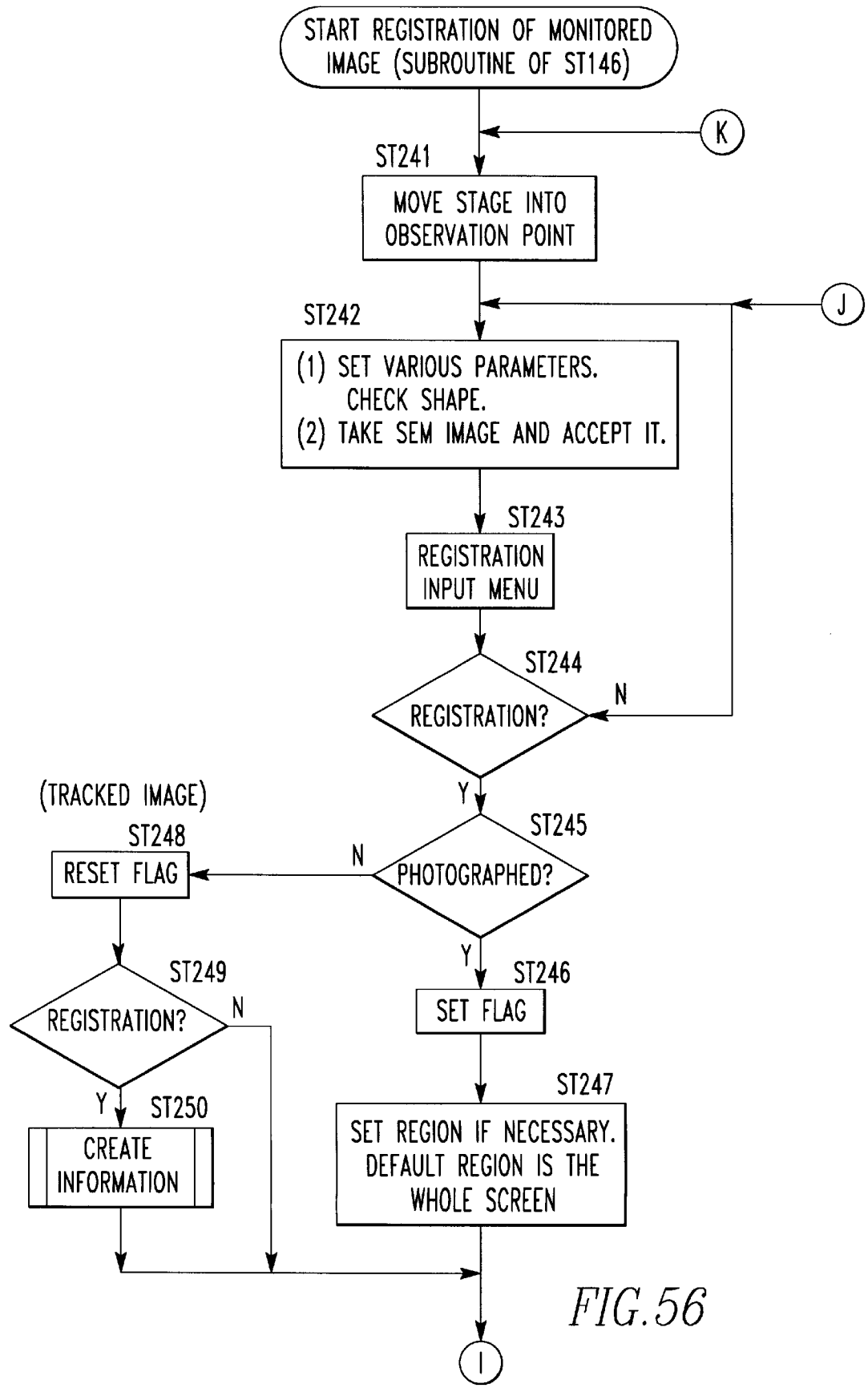
FIG. 56 is a flowchart illustrating the former half of the subroutine of FIG. 48 to register an image being monitored.
Figure 58:
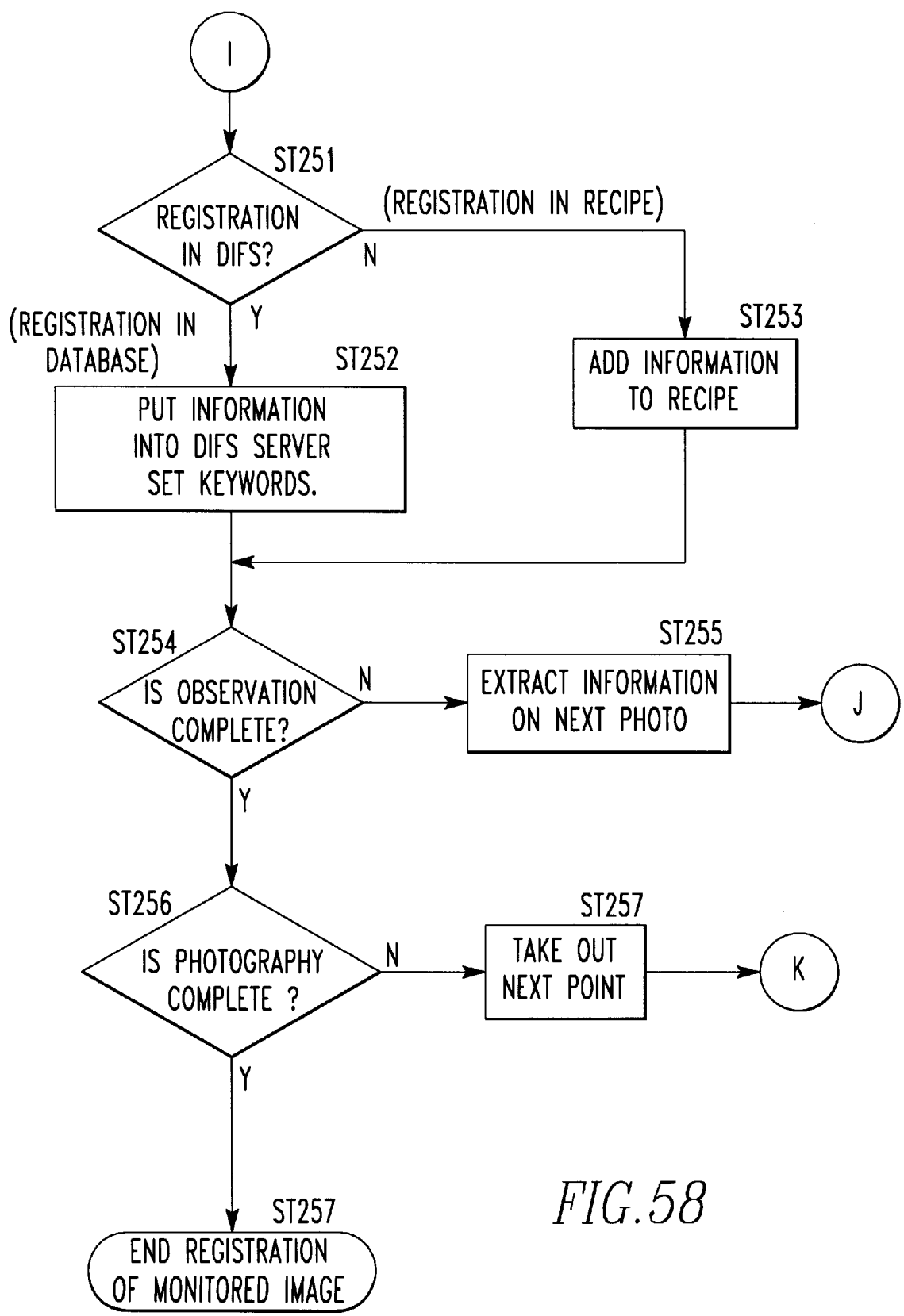
FIG. 58 is a flowchart illustrating processing performed subsequently to the processing of FIG. 56.
Figure 59:
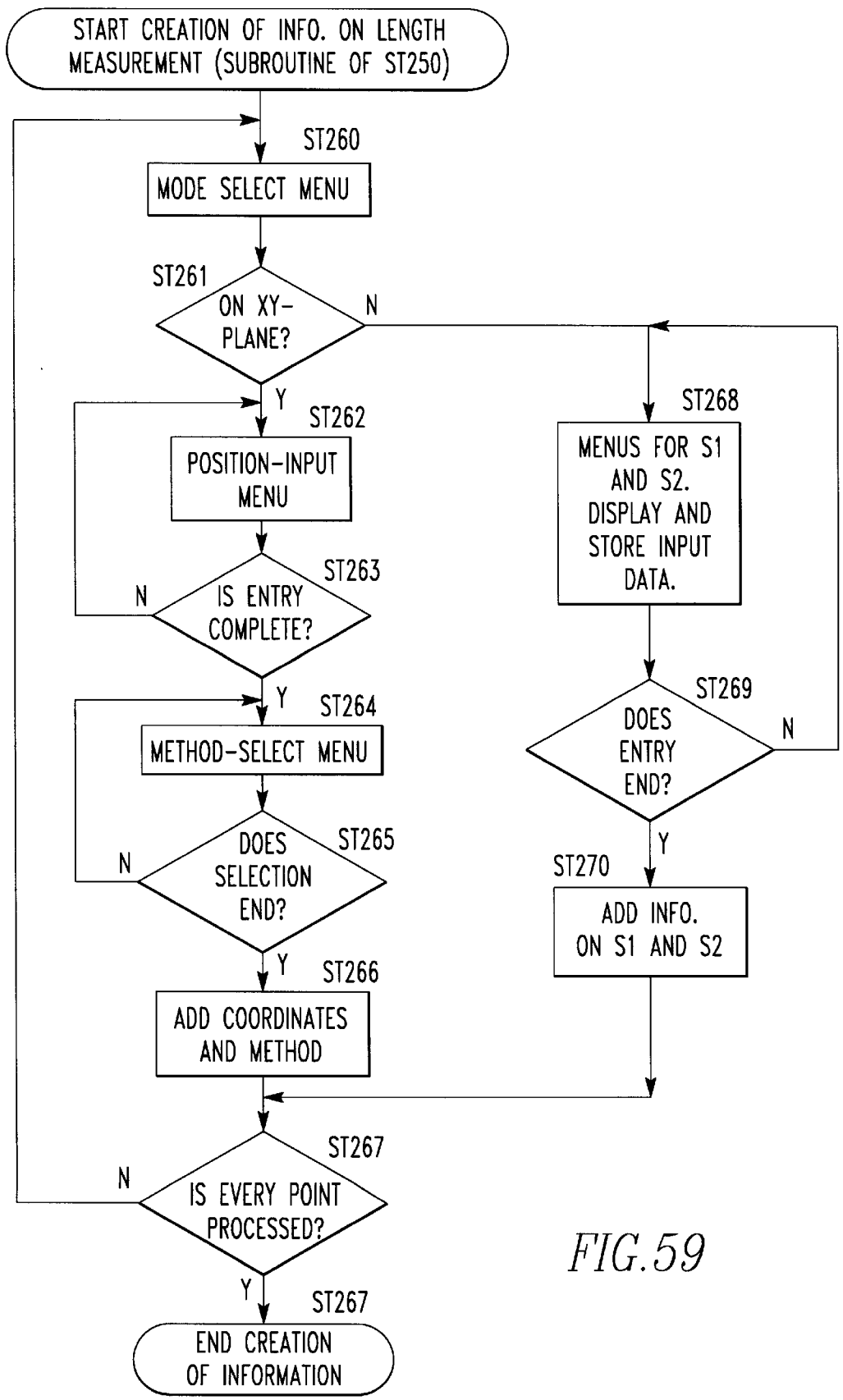
FIG. 59 is a flowchart illustrating a subroutine of step 250 to create information used to measure lengths.

(C51) Observed Point Information Registration-and-Managing Means C51 (FIGS. 24, 56, and 58)

The observed point information registration-and-managing means C51 searches for information about the positions of searched points, information about photographed images of the observed images (such as the accelerating voltage for the electron beam, magnification, tilt of the sample, rotation of the sample, brightness, contrast, etc.), and image information, and register them in the DIFS database (see steps 182, 183 of FIG. 50 and step 252 of FIG. 58). Information about the position of a portion that the operator want to observe is referred to as observed point positional information. Information about a photographed image of a point to be observed is referred to as photograph information. Information about images is referred to as observed point reference image information. These kinds of information are collectively referred to as observed point information.

Figure 24A:
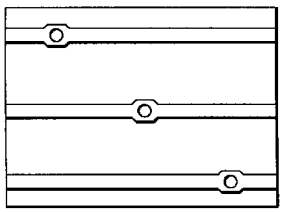
FIG. 24A is a diagram illustrating an image that is produced at a magnification of 3,000× and tracked by a function of an observational point information registration-and-management means C51.
Figure 24B:
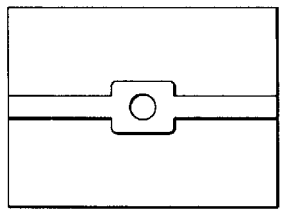
FIG. 24B is an image similar to FIG. 24A, but in which the magnification is 10,000×.
Figure 24C:
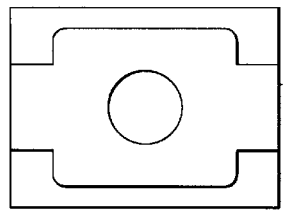
FIG. 24C is an image similar to FIG. 24A, but in which the magnification is 30,000×.
Figure 24D:
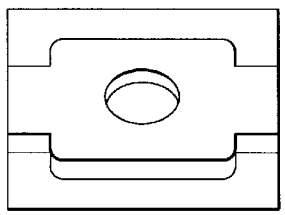
FIG. 24D is a diagram illustrating an image that has a tilted shape and is monitored by a function of the observational point information registration-and-management means C51.
Figure 24E:
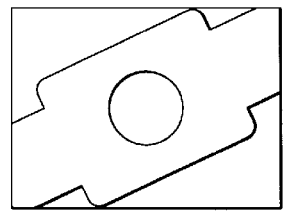
FIG. 24E is a diagram similar to FIG. 24D, but in which the monitored image has a rotated shape.
Figure 24F:
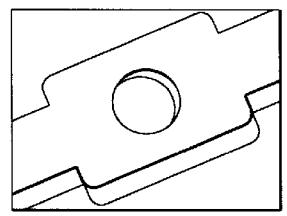
FIG. 24F is a diagram similar to FIG. 24D, but in which the monitored image has a rotated and tilted shape.

FIGS. 24A–24E illustrate the functions of the observed point information registration-and-managing means C51. FIG. 24A shows a tracked image at a magnification of 3,000×. FIG. 24B shows a tracked image at a magnification of 10,000×. FIG. 24C shows a tracked image at a magnification of 30,000×. FIG. 24D shows an image used to monitor the shape of a tilted sample. FIG. 24E shows an image used to monitor the shape of a rotated sample. FIG. 24F shows an image used to monitor the shape of a rotated and tilted sample.

In order to register the observed point information in the DIFS database, the review SEM reads an observed image registration image and takes a photograph (FIGS. 56 and 58). In the "observed image registration" menu, images which differ in magnification and tilt angle at each individual point can be registered. Therefore, for the same point, plural kinds of observed point information corresponding to different angles of view can be registered (FIGS. 24D, 24E, and 24F).

Instead of using the DIFS server 3, the shape maybe monitored, using observed point information (such as recipes) registered in a local database either of the host computer for computer-integrated manufacturing (CIM) or of a client, and the obtained, or observed, image can be registered in the DIFS server 3.

In registering the observed point information, information about observed points necessary for tracking can be registered, as well as locations at which shapes are monitored. For example, if the operator attempts to make an observation at a magnification of 30,000× at once, the desired observed point cannot be brought within the field of view due to the accuracy of the position of the stage, for example. For this reason, an image with a magnification of about 3,000× without tilt or rotation is first registered. Then, an image with a magnification of approximately 10,000× without tilt or rotation is registered. Thereafter, an image with a magnification of 30,000× without tilt or rotation is registered. If necessary, an observed image rotated or tilted is photographed. These kinds of information about the observed points are used as tracking information for finding out portions whose shapes should be monitored (FIGS. 24A, 24B, and 24C).

The observed point information can be searched for, using product numbers, lot numbers, wafer identification numbers, and observed point information names. The information is fetched from the database before the observed point is photographed automatically. Prior to execution of automatic shape monitoring, a recipe is created for the review SEM. At this time, information about observed points is established for each different wafer.

(C52) Automatic Observed Point Photographing Means C52 (FIG. 50)

The automatic observed point photographing means C52 has the following features:

(a) The observed point information established for each individual wafer is fetched from the database, and the wafer-supporting stage S is moved, using the information about the observed points.

(b) Conditions (such as accelerating voltage, magnification, tilt, rotation, brightness, and contrast) under which a tracked image is observed as shown in FIGS. 24A, 24B, and 24C are set into the SEM, the conditions being contained in the observed point information. The image is then accepted. Pattern comparison with the tracked image is done. Centering is performed until the tracked image is brought into the center. The tracking is performed in the order of FIGS. 24A, 24B and 24C, i.e., at a successively changed magnification, until an image close to the monitored image is obtained.

(c) Finally, the pattern is compared with the reference images at the observed points of FIGS. 24D, 24E, and 24F. Centering is done, and the image is photographed. Each time centering is done, automatic brightness adjustment and automatic focus adjustment are made. Data about the photographed image is automatically registered in the database. These operations are repeated for every observed point registered in the observed point information.

Figure 55:
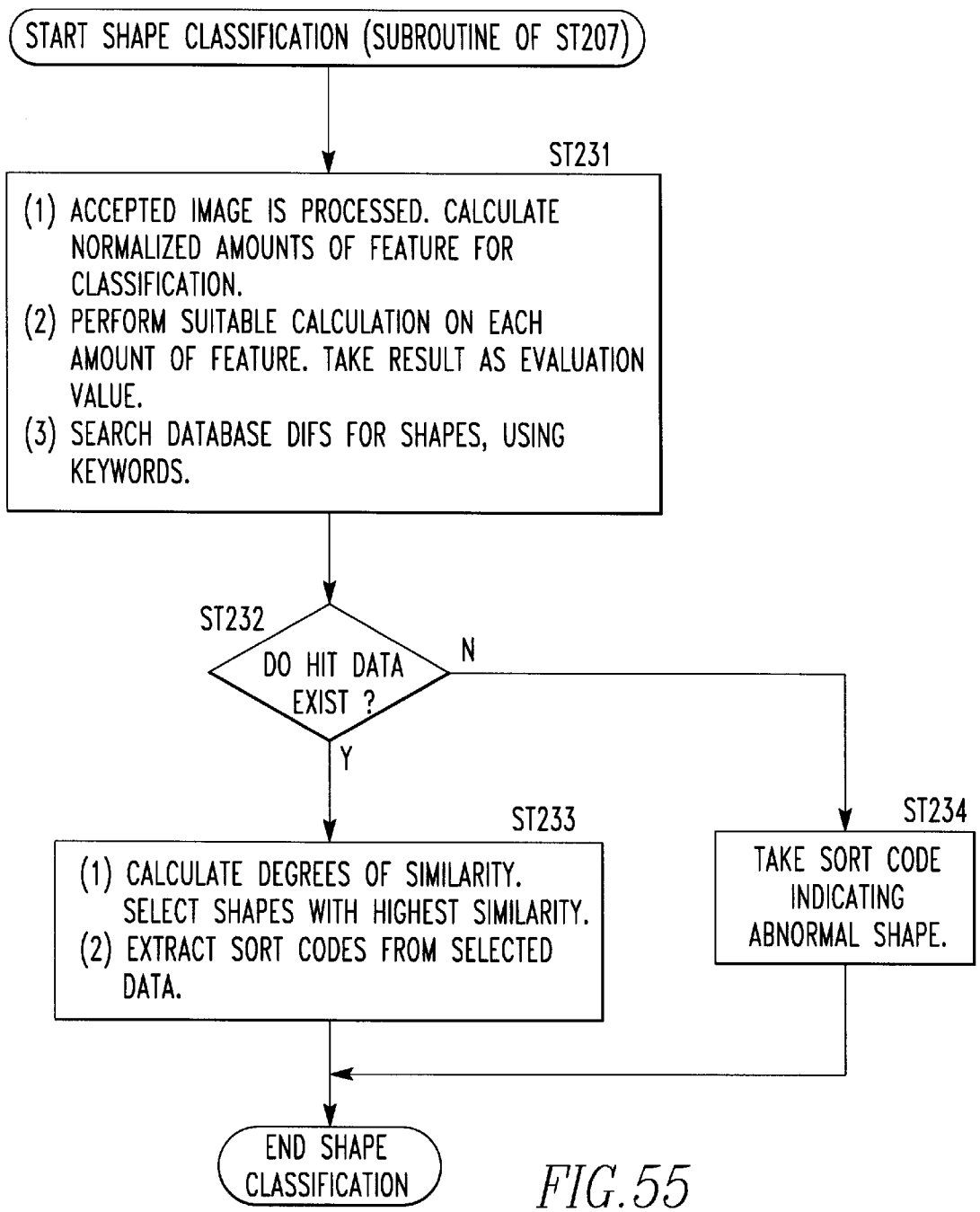
FIG. 55 is a flowchart illustrating a subroutine of step 207 of FIG. 51 to classify shapes.

(C53) Observed Image Comparing and Sorting Means C53 (FIG. 55)

When the observed point automatic photographing means C52 photographs an image, the observed image comparing and sorting means C53 orders a shape monitored image sorting means C82 to compare the photographed image with previously registered reference images and to give the same sort code to the monitored image as the reference image of the highest degree of similarity.

A rectangular region used for comparison can be established in each reference image. Both images are compared only within the established comparison region. Normal and abnormal shapes are registered as the reference images. Thus, it is possible to judge whether the photographed image has a normal shape or an abnormal shape. If the photographed image cannot be categorized, the image can be judged to be abnormal in shape. The results of the sorting and information necessary for the sorting are also registered in the database. The present function permits detection of the shapes of holes and the shapes of patterns including defective patterns.

This observed image comparing and sorting means C53 classifies observed images by the same method as used by a defect sorting means C8 (described later) and so the sorting method is not described here but will be described in detail in the column of the defect sorting means C8.

Figure 52:
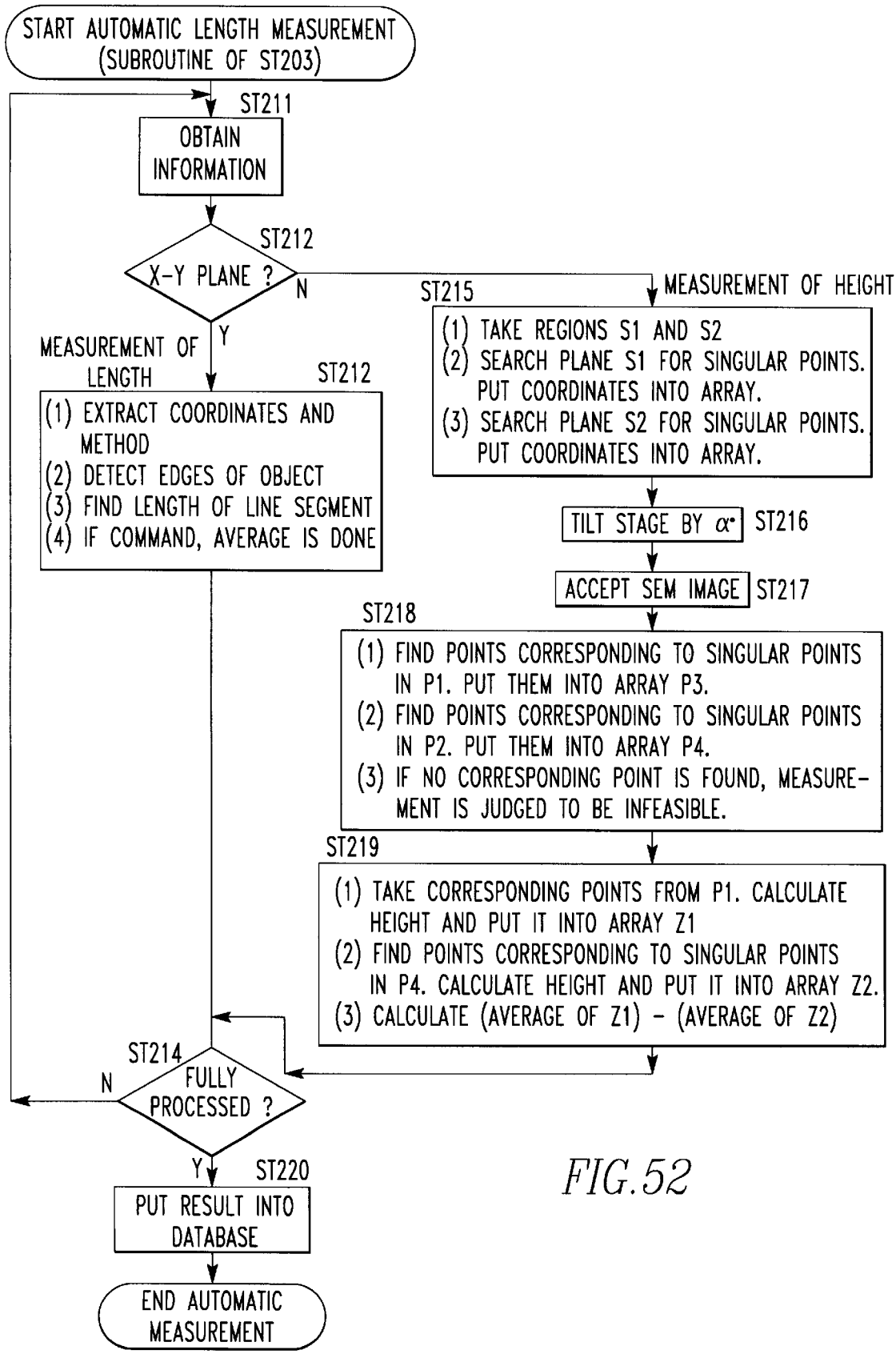
FIG. 52 is a flowchart illustrating a subroutine of step 203 to automatically measure lengths.

(C54) Automatic Observed Point Length Measuring Means C54 (FIGS. 25 and 52)

FIGS. 25A–25C illustrate the function of the automatic observed point length measuring means C54. FIG. 25A shows a measurement image used to make a measurement at a tilt angle of 0°. FIG. 25B shows a measurement image used to make a measurement at a tilt angle of α°. FIG. 25C illustrates a method of measuring film thicknesses and hole depths. The automatic observed point length measuring means C54 has the following functions.

(a) When an image is photographed by the observed point automatic photographing means C52, the distance is measured in the X-Y direction. For example, a linewidth or hole diameter as shown in FIG. 25A is measured. On the "observed image registration" menu of the observed point information registration-and-managing means C51, plural portions can be established as those subjected to length measurement.

(b) It has a function of measuring a distance in the Z-direction, e.g., a line thickness or hole depth as shown in FIG. 25B.

(c) It has a function of registering data obtained by the length measurement in the DIFS database. The registered data can be used to find the correlation with quality control or with inspection results.

In measuring a distance in the Z-direction, two rectangular planes (such as the top surface $Z_1$ or $Z_3$ of a pattern (e.g., a linear pattern) and a top surface $Z_2$ or $Z_4$ of the substrate) are specified as a height-measured region. The shape of the specified height-measured region can be circular or elliptical instead of rectangular. The film thickness and depth can be found by finding the average Z-coordinate of each specified plane ($z_1$, $Z_2$, $Z_3$, and $Z_4$) and performing subtractions. That is, the film thickness=$Z_1$–$Z_2$. The depth=$Z_3$–$Z_4$.

In finding the average Z-coordinate in a plane, feature points such as small processing nonuniformities, flaws, and dust within the Z-plane of the photographed image are emphasized by image processing. Then, the stage is tilted, and the image is photographed. This image is also processed by the same image processing technique. Thus, a plane Z' having the highest degree of correlation with the plane Z is detected. The average Z-coordinate $z_1$ is found from the amount of movement of the plane Z in the direction of tilt toward the plane Z'.

Figure 26:
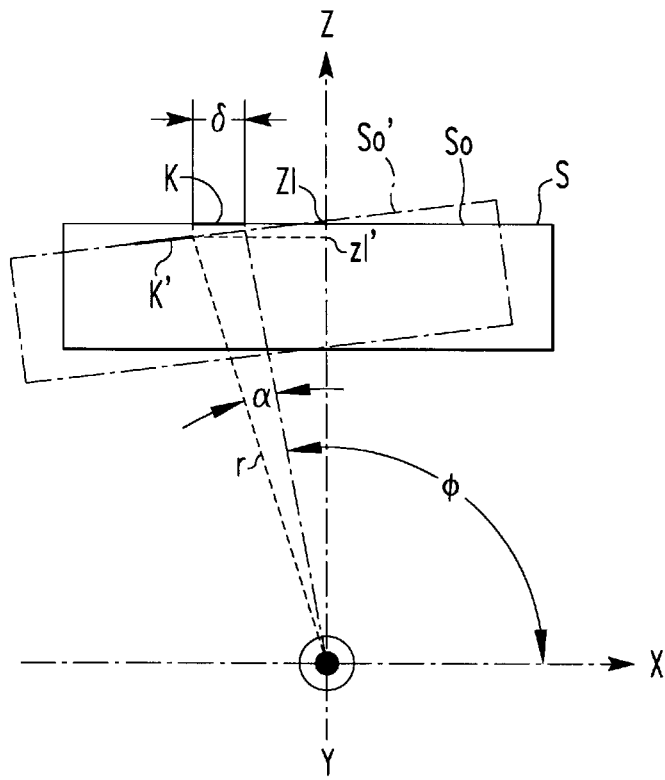
FIG. 26 is a diagram illustrating calculations of a film thickness and a hole depth performed by the observational point automatic length-measuring means C54.

FIG. 26 illustrates the function of the automatic observed point length measuring means C54. Examples of calculations performed to measure the film thickness and hole depth are given.

Assume that stage S is tilted at angle α and that plane $S_0$ has moved δ, as shown. Then, $$z1 = r\sin\phi$$

$$\delta = r\cos\phi - r\cos(\phi + \alpha)$$

$$= 2r\sin(\phi + \alpha/2)\sin(\alpha/2).$$

Therefore, z-coordinate of plane $S_0$ is given by $$z1 = r\sin\phi$$

$$= \delta\sin\phi / \{2\sin(\phi + \alpha/2)\sin(\alpha/2)\}$$

If $\phi = \pi/2$, $z_1$ is given by $z_1 = \delta/\sin\alpha$. Thus, $z_1$ can be found from both δ and α.

Parameters used in FIG. 26 are as follows:

$S_0$: a plane on the surface of the wafer W held on the wafer-supporting stage S tilted at an angle of 0° about the Y-axis.

K: specified height-measured region or defect on the plane $S_0$.

$z_1$: the Z-coordinate of the plane $S_0$.

$S_0'$: the position of the plane $S_0$ when the tilt angle about the Y-axis has varied from 0° to α°.

K': the position of the specified height-measured region or defect on the plane $S_0$ when the plane $S_0$ has tilted by α°.

r: the distance of the specified height-measured region or defect from the Y-axis.

φ: the angle made between a line segment YK shown in FIG. 26 and the X-axis.

α: the tilt angle of the wafer-supporting stage S about the Y-axis.

δ: the amount of movement of the specified height-measured region or defect K when the tilt angle of the stage S about the Y-axis has changed from 0° to α°.

In this case, the following relations hold:

$$z_1 = r\sin\phi$$

$$\delta = r\cos\phi - r\cos(\phi + \alpha)$$

$$= 2r(\phi + \alpha/2)\sin(\alpha/2)$$

Therefore, we have $$z_1 = r\sin\phi$$
$$= \delta\sin\phi / \{2\sin(\phi + \alpha/2)\sin(\alpha/2)\}$$

If $\phi$ is almost equal $\pi/2$, $z_1$ can be approximated by $$z_1 = \delta/\sin\alpha$$

Consequently, the $z_1$ that is the Z-coordinate of a plane to be measured (the surface of the specified height-measured region of defect K) can be found from the amount of movement $\delta$ of the specified height-measured region or defect K when the tilt angle is varied from 0° to $\alpha$°.

Figure 60:
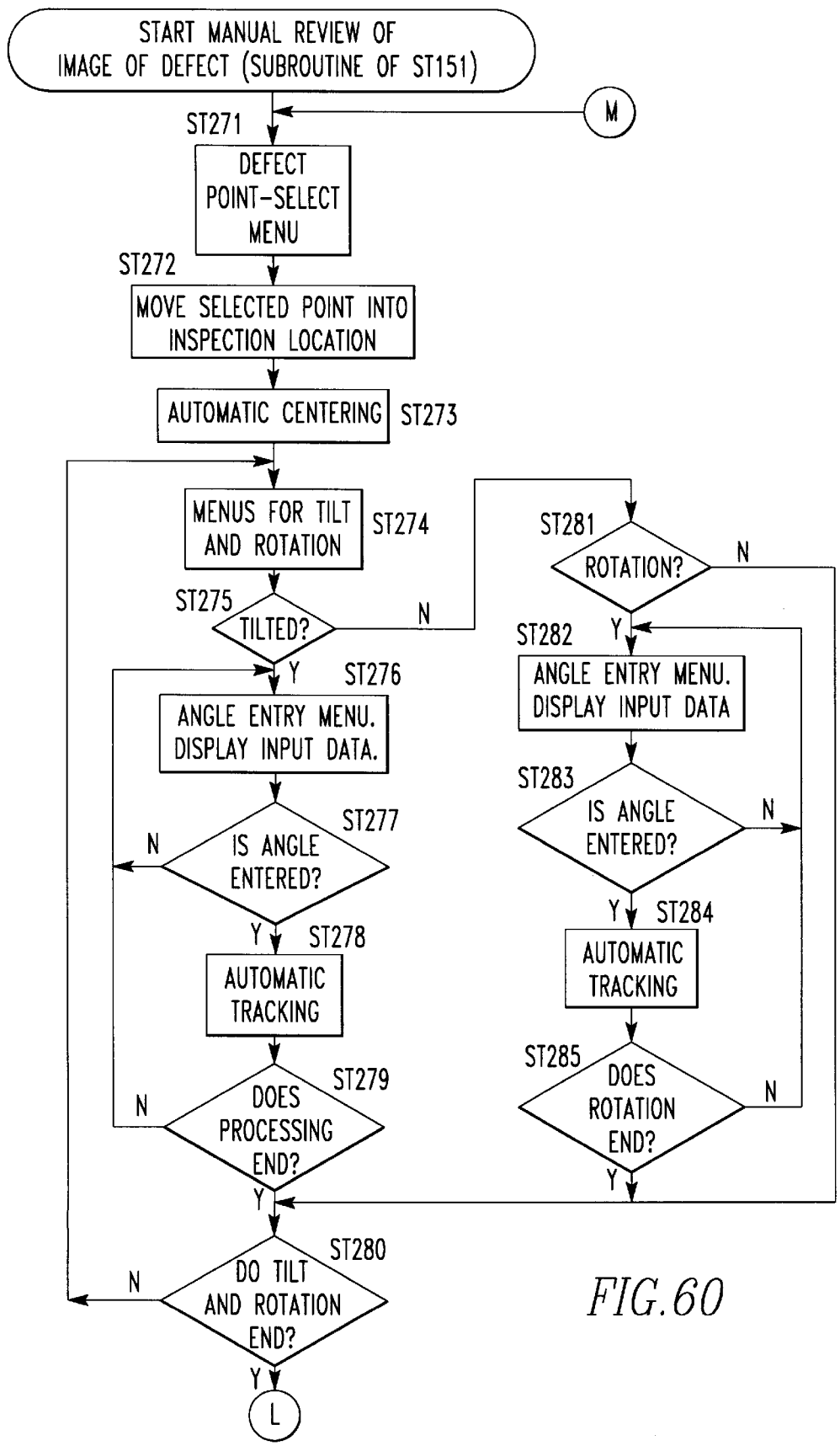
FIG. 60 is a flowchart illustrating a subroutine of step 151 to manually review defect images.

(C6) Manual Defect Image Review Executing Means C6 (FIG. 60)

This executing means C6 permits the user to manually select one of plural defects to be reviewed. This manual operation alone activates the function of the automatic centering means C11 (FIG. 16) of the commonly used function-realizing means C1. The defect image is brought into the screen center. Thus, an appropriate observed image is displayed. During the operation of this manual defect image review executing means C6, the user can manually review the selected defect image while selecting the functions of the means C11–C15 of the commonly used function-realizing means C1 described later.

Figure 62:
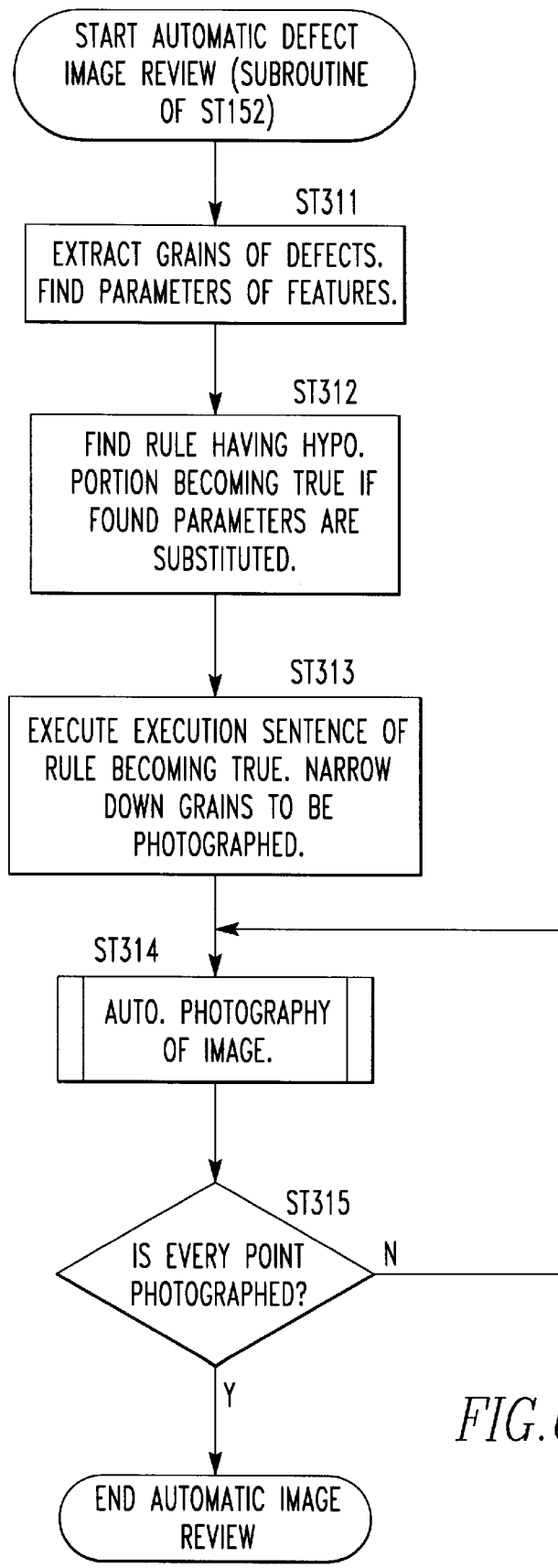
FIG. 62 is a flowchart illustrating a subroutine of step 152 of FIG. 48 to automatically review defect images.

(C7) Automatic Defect Image Review Executing Means C7 (FIG. 62)

The automatic defect image review executing means C7 has the following means C71–C76 to automatically load and unload wafers, make an automatic movement to an important defect, photograph the image under appropriate magnification, brightness, and focusing conditions (tilt/ rotation), and register the resulting information in the database.

Figure 27:
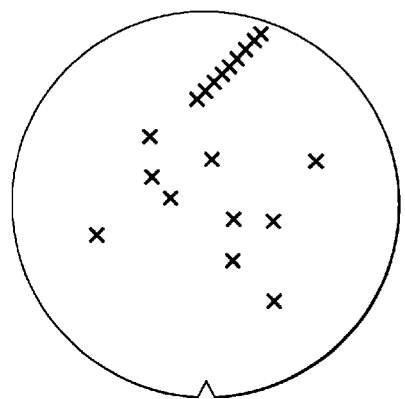
FIG. 27 is a diagram showing the distribution of foreign materials and defects.

(C71) Intelligent Defect Information Processing Means C71 (FIGS. 27 and 62)

This intelligent defect information processing means C71 has a function of recognizing the distribution of foreign materials or defects according to foreign material or defect information read from the DIFS server 3. The cause (scratches or falling of dust) can be estimated from the distribution of the foreign materials or defects (such as positions, shapes, or densities). According to the estimated cause, the priority can be given. Processing subsequent to (11) can be performed with respect to only important items.

FIG. 27 shows an example of the distribution of foreign materials or defects, and in which the defects are linearly distributed from the edges of a wafer. In this case, however, many scratches exist and so reviewing every defect belonging to this distribution will rarely produce useful information. Accordingly, it is common practice to review one point or so within this distribution. A decision is made as to whether it is a scratch. By making a judgment relying on the density or shape of the distribution, the number of points to be reviewed can be reduced greatly.

To perform such intelligent processing, rule-based deduction is performed. With rule-based deduction, appropriate processing is enabled if the conditions agree with contents described in the rules. For example, the following rules can be created.

Example 1 of Rule

Where something drags against the surface of the wafer W, a scratch may be formed. Often, the defect, or scratch, is distributed in an elongated region adjacent to the fringes of the wafer W. In this case, the review processing rule about defect points can be described as follows:

Rule (R1) "If defects having sizes greater than XX are distributed at an average density of YY, and if the ratio of the major diameter of the distribution profile to the minor diameter is in excess of 10 and the distribution is partly in contact with the circumference of the wafer, then defects inside this region having an average density of YY are sorted in increasing order."

(R2) With respect to the sorted top two, the following processing is performed.

(R21) Automatic photography is done at a tilt angle of 0°, with an angular position of 0°, and with a magnification of 5,000×.

(R22) Automatic photography is done at a tilt angle of 0°, with an angular position of 0°, and with a magnification of 20,000×.

(R23) Automatic photography is done at a tilt angle of 45°, with an angular position of 0°, and with a magnification of 20,000×."

Example 2 of Rule

During processing of the wafer W, dust attracted and collected falls from an air exhaust port and may adhere to a region of the wafer W that is located under the exhaust port, thus producing defects. In the case of such defects, even if every defect is obtained, useful information is rarely obtained. Therefore, it is considered that only one point in the distributed defects needs to be observed to make sure the sequence of observations. A rule governing this processing can be described as follows:

Pretreatment (i) A region of the wafer W having a density of more than $d_0$ is subjected to an observation. (ii) The coordinates ($X_0$, $Y_0$) of the center P of the observed region are found. (iii) The area S of the observed region is found. (iv) A defect point $P_d$ closest to the center P is found.

Rule

"If $S \geq S_0$, $X_1 < X_0 < X_2$, and $y_1 < y_0 < Y_2$ (R1), then the following steps are performed with respect to point $P_d$:

(R11) Automatic photography is done at a tilt angle of 0°, with an angular position of 0°, and with a magnification of 5,000×.

(R12) Automatic photography is done at a tilt angle of 0°, with an angular position of 0°, and with a magnification of 20,000×.

(R13) Automatic photography is done at a tilt angle of 30°, with an angular position of 0°, and with a magnification of 20,000×."

where a rectangular region given by $x_1 < x < x_2$ and $Y_1 < Y_0 < Y_2$ is close to the exhaust port, and $d_0$, $s_0$ are parameters set by the user empirically or experimentally.

Example 3 of Rule

For example, if dust adheres to the wafer W during pulling of the wafer in wet processing, repeating stripes of defects may be distributed on the wafer W at a constant density. In this case, if every defect is observed, useful information may rarely be obtained. Therefore, it is considered that only one point in the distributed defects needs to be observed to make sure the sequence of observations. A rule governing this processing can be described as follows:

Pretreatment (i) A region of the wafer W having a defect density of more than $d_1$ is treated as a region S of interest. (ii) The region S is subjected to two-dimensional Fourier transformation, thus obtaining data $S_f$. (iii) A point P having a maximum value $V_f$ on the $S_f$ is found, as well as the value $V_f$. (iv) A set Sfc of points lying on the $S_f$ and in a circle centered at the point P and having a radius of $r_1$ is found. (v) $S_{fc}$ is subjected to inverse two-dimensional Fourier transformation to find $S_m$. (vi) The region $S_m$ on the wafer W is searched for an arbitrary defect point $P_d$.

Rule (R1) "If $V_f > v_{f1}$, then the following steps are performed with respect to the point $P_d$:

(R11) Automatic photography is done at a tilt angle of 0°, with an angular position of 0°, and with a magnification of 5,000×.

(R12) Automatic photography is done at a tilt angle of 0°, with an angular position of 0°, and with a magnification of 25,000×.

(R13) Automatic photography is done at a tilt angle of 30°, with an angular position of 0°, and with a magnification of 250,000×.

(R14) Automatic photography is done at a tilt angle of 30°, with an angular position of 90°, and with a magnification of 250,000×."

where $d_1$, $r_1$, and $V_{f1}$ are parameters set by the user empirically or experimentally.

(C72) Automatic Defect Point Moving Means C72 (Steps 321 and 322 of FIG. 64)

The automatic defect point moving means C72 has a function of automatically moving any desired defect into the review position, or the inspection position illuminated with the electron beam, using information about the position of the defect to be reviewed. Automatic brightness/focusing adjustment may be made at a magnification of approximately 5,000×, depending on the accuracy of the position of the stage. The automatic centering function is used to automatically bring the defect point into the center of the viewing screen.

The automatic movement to the defect point is made, using the X-Y table. The automatic centering is done by adjusting the driving voltages applied to the deflection coils F6 and F7 for the electron beam.

Figure 70:
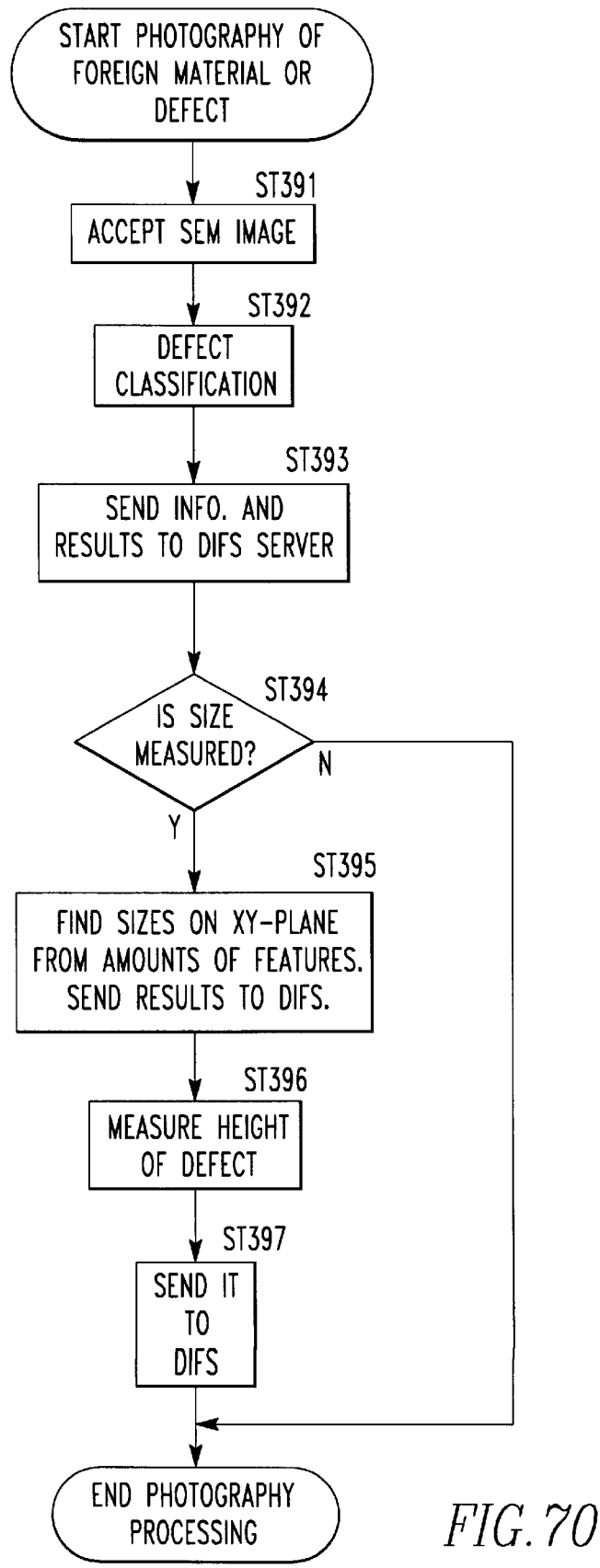
FIG. 70 is a flowchart illustrating subroutines of steps 296 and 329 of FIGS. 61 and 64, respectively, to photograph foreign materials and defect images.

(C73) Automatic Foreign Material/Defect Image Photographing Means C73 (FIG. 70)

An image has been moved into the review position by the automatic defect point moving means C72. The automatic foreign material/defect image photographing means C73 processes this image by image processing techniques to extract an image having a size adjusted to fitly enter the field of view by the field of view adjusting means, again performs automatic centering, and photographs the image. The photographed image is classified by a defect sorting means (described later), and is automatically sent to the DIFS server 3 together with the results of the sorting. The DIFS server 3 registers information about the transmitted, photographed image in the DIFS database. If the results of the sorting indicate that the image is not required to be photographed (e.g., the defect is a commonplace one and its kind is known), it is possible to avoid the registration in the database.

(C74) Automatic X-Ray Analysis Means C74 (Steps 330 and 331 of FIG. 64)

The automatic x-ray analysis means C74 makes an automatic x-ray analysis of the recognized defect portion and its surroundings by the use of the energy dispersive x-ray spectrometer (EDS) subsequently to the photographing of the defect image and sends the results of the analysis to the DIFS server 3.

(C75) Automatic Tilted Image Photographing Means C75 (FIG. 64)

The automatic tilted image photographing means C75 tilts the stage at an angle of 0°, detects the defect point, then tracks the defect image while gradually tilting the stage, and photographs the image when the tilt angle reaches a desired angle. The function of the "tilted image tracking means" is used for the tracking of the tilted image.

It seems that a bare wafer can be photographed by previously tilting the stage. It may not be easy to automatically detect defect points on a patterned wafer. In this case, the automatic tilted image photographing means C75 automatically photographs the tilted image.

(C76) Automatic Rotated Image Photographing Means C76 (FIG. 64)

When the operator wants to photograph the defect portion from various directions, the automatic rotated image photographing means C76 tilts and rotates the inspected part-holding member 65. For the rotation of the stage, the tilt angle is once returned to 0°, the defect point is recognized, and then the stage is rotated. The image is centered, and the stage is again tilted. Then, the tilted image is photographed. Where a danger exists of missing the defect as encountered when the tilt angle is small or no steps are present on the defect image, the image can be rotated while tilting it.

(C77) Automatic Defect Portion Measuring Portion C77 (FIG. 70)

The automatic defect portion measuring portion C77 automatically measures the size of a recognized defect portion (e.g., the lengths taken in the X- and Y-directions, respectively, the area of the defect portion, and the height of a stepped portion). To measure a height, the stage is slightly tilted, and a measurement is made by the same processing as done in the height measurement by the automatic observed point length measuring means C54. Before the measurement, the sizes and the positions of specified surfaces are set. The heights of the specified surfaces are also automatically found. The height of any defect portion above the substrate may be measured by calculating the difference between the height of the defeat portion and the height of the substrate.

(C8) Defect Sorting Means C8 (FIGS. 28, 29, 30, and 71)

The defect sorting means C8 classifies images photographed during the operation of a "manual defect review means" and the "automatic defect review means", classifies images photographed during the operation of the automatic shape monitoring means C5, and makes a decision as to whether each shape is normal or not. The defect sorting means C8 is composed of a defect image sorting means C81 and a shape monitoring image sorting means C82. Their functions are described below.

FIG. 28 illustrates processing for classifying defects. In FIG. 28, the amount of features (described later) and the evaluation value (described later) of round dust are found and previously stored in the image database of the DIFS server 3 for defect images and shape monitoring images. Also, the amount of features (described later) and the evaluation value (described later) of fibrous dust are found and previously stored in the image database of the DIFS server 3 for defect images and shape monitoring images. The amount of features and evaluation are stored in the DIFS server 3 by means (described later) for causing the server 3 to learn. The defect sorting means C8 has the following functions:

(a) It detects defect portions or shape-monitored portions of the image under inspection and finds the amount of various features of the portion of interest.

(b) Evaluation values indicating the degrees of similarity of this image to plural defect images or shape-monitored images are calculated from the amount of features of the image. The defect images or shaped-monitored images are given by means (described later) of the DISF server 3 for causing it to learn. These evaluation values are computed by appropriately processing the amounts of features (e.g., taking the sum of squares).

(c) The type of the defect image having an evaluation value closest to the defect image given to the controller is used as a candidate type in sorting various images.

Specifically, in classifying defect portions, the magnification and the evaluation value of each image are used as keywords or sortkeys. In classifying shapes, the coordinates of the center of each image are also used as keywords. The defect sorting database and the shape sorting database of the DIFS server 3 are searched for data about sorting of defect portions and shapes, respectively, using these two kinds of keywords, respectively. In performing a search, using the center coordinates, only a certain range is searched, because the stage involves errors.

Some data items are found, or hit, by the search. The degrees of similarity of these found items to the image found by (a) are calculated, using an appropriate evaluation function. For example, an evaluation function for finding the sum of squares of the differences between the amounts of features found in (a) and their corresponding amounts of features of the candidate types of sorting.

Then, the sort code attached to the candidate type that is judged to have the highest degree of similarity by the evaluation function is given to the inspected image of (a), for example, to minimize the sum of squares of the amounts of features.

(d) If the results of the sorting performed by the shape monitoring image sorting means indicate that the shape is abnormal, then the sorting issues a warning indicating abnormality. This sorting means can recognize abnormal shapes and classify them by causing the shape sorting and informing means (described later) to inform the shape monitoring image sorting means of abnormal shapes. Where defect images and shape monitoring images are registered in the DIFS server, the various amounts of features found as described above are registered at the same time. The server can search for similar images, using these amounts of features.

Method of Finding Amounts of Features and Evaluation Values for Defect Sorting

Figure 29:
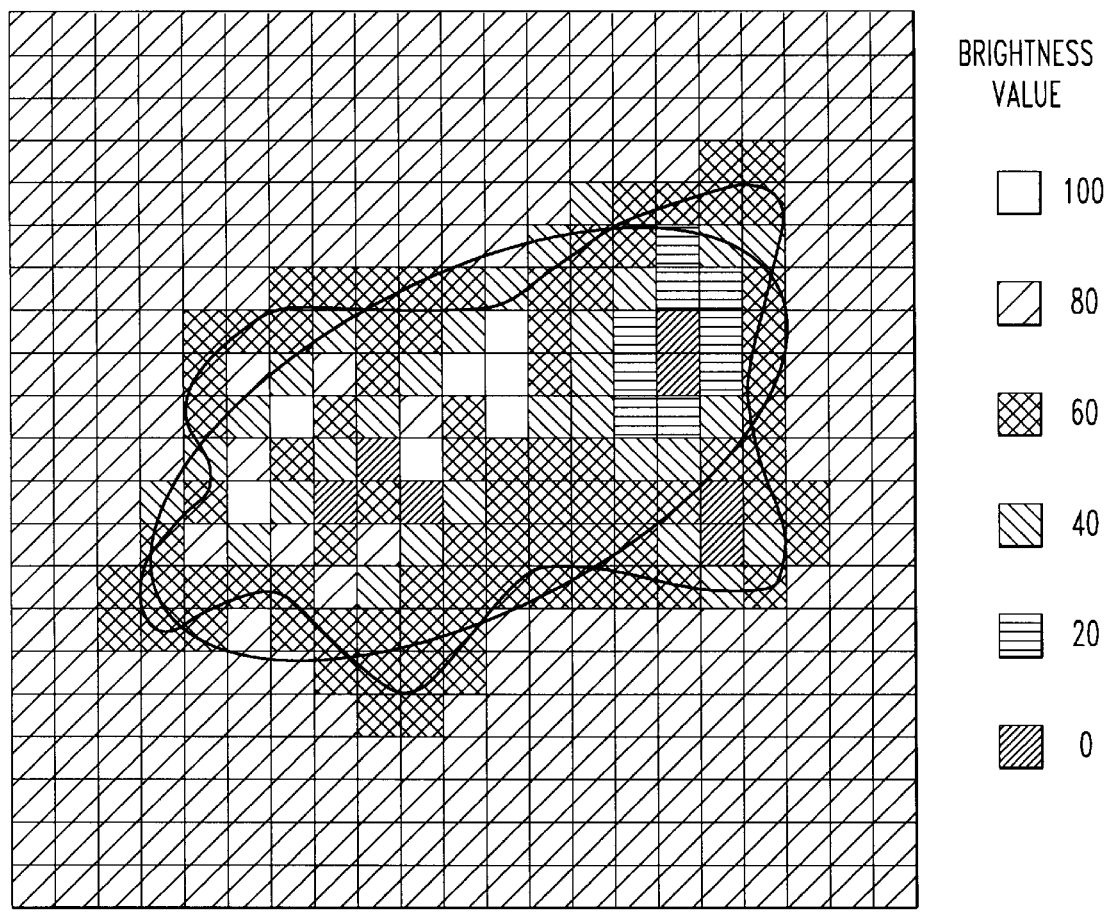
FIG. 29 is a diagram illustrating processing for classifying round defects.

FIG. 29 illustrates the amount of features and evaluation value of round dust or scratch, found in processing performed by the defect sorting means.

$x_1$=area of defect portion/area of rectangle circumscribing defect portion $x_2$=average brightness/(maximum brightness−minimum brightness)

$$x_3 = \sqrt{\{\sum (\text{brightness at point } Pn - \text{average brightness})^2\}} \Big/ (\text{average brightness} * \sqrt{N})$$

$$x_4 = \text{eccentricity}$$

$$= \sqrt{(1 - b^2/a^2)} \text{ when defect is approximated by ellipse}$$

$x_5$=length of circumference of ellipse/length of circumference of defect portion typical value=$X1^2+X2^2+X3^2+X4^2+X5^2$

X1=(13*17−(28+7+12+26))/(13*17)=(221−73)/221=0.670

X2=(100*7+80*8+60*81+40*31+20*9+0*7)/(7+8+81+31+9+7)/100=0.637

$$X3 = \sqrt{\begin{array}{l}\{(100-63.7)^2*7 + (80-63.7)^2*8 + \\ (60-63.7)^2*81 + (40-63.7)^2*31 + \\ (20-63.7)^2*9 + (0-63.7)^2*7\}\end{array}} \Big/ (63.7*\sqrt{143})$$

$$= \sqrt{75461.7}/761.7 = 274.7/761.7 = 0.360$$

$$X4 = \sqrt{(1-(20.0/41.25)^2)} = \sqrt{(1-0.235)} = 0.875$$

X5=45[pix]/58[pix]=0.672

Typical value=0.449+0.406+0.130+0.766+0.452=2.203.

Figure 30:
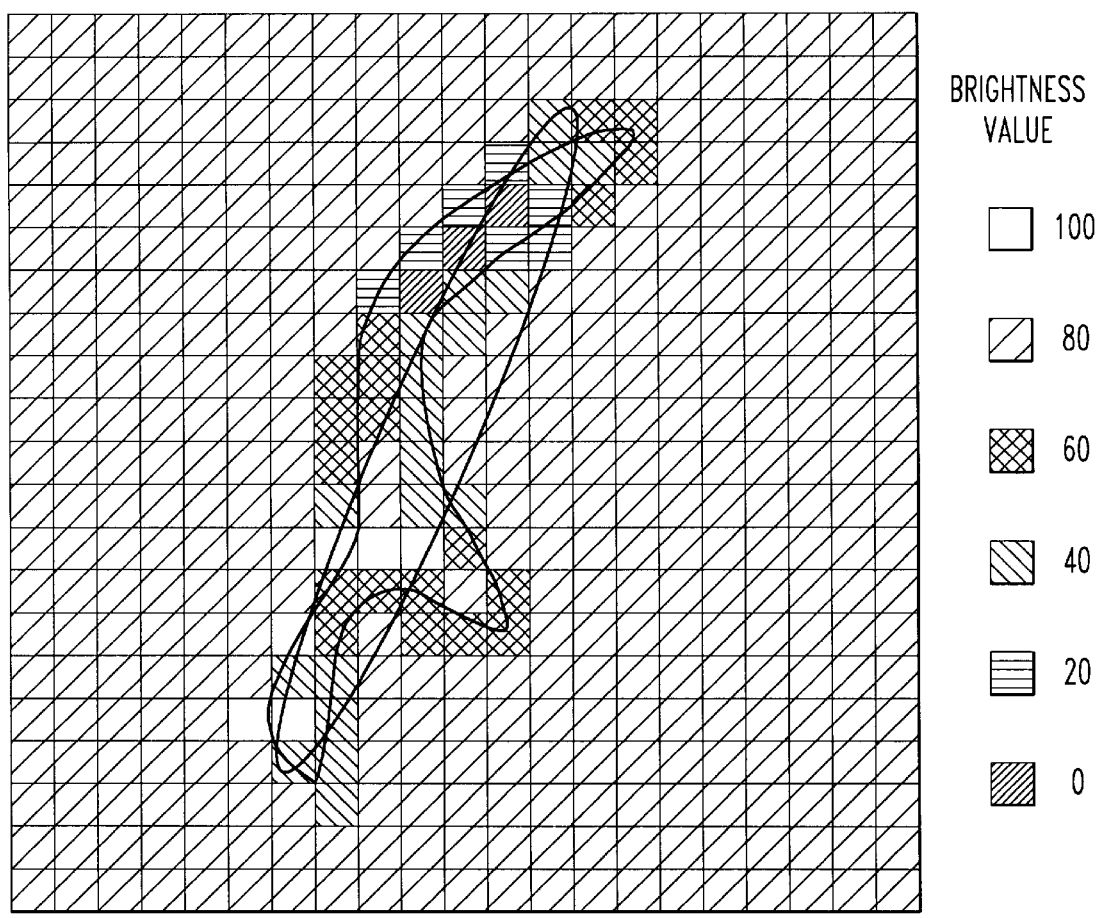
FIG. 30 is a diagram illustrating processing for classifying linear defects.

FIG. 30 illustrates the amount of features and evaluation value of fibrous dust or scratch.

$X_1$=area of defect portion/area of rectangle circumscribing defect portion $X_2$=average brightness/(maximum brightness−minimum brightness)

$$X_3 = \sqrt{\{\sum (\text{brightness at point } Pn - \text{average brightness})^2\}} \Big/ (\text{average brightness} * \sqrt{N})$$

$$X_4 = \text{eccentricity}$$

$$= \sqrt{(1-b^2/a^2)} \text{ when defect is approximated by ellipse}$$

$X_5$=length of circumference of ellipse/length of circumference of defect portion Typical value=$X_1^2+X_2^2+X_3^2+X_4^2+X_5^2$

X1=(10*17−57)/(10*17)=0.665

X2=(100*6+80*3+60*19+40*19+20*7+0*3)/(6+3+19+19+7+3)/100=0.505

$$X3 = \sqrt{\begin{array}{l}\{(100-50.5)^2*6 + (80-50.5)^2*3 + \\ (60-50.5)^2*19 + (40-50.5)^2*19 + \\ (20-50.5)^2*7 + (0-50.5)^2*3\}\end{array}} \Big/ (50.5*\sqrt{57})$$

$$= \sqrt{35284.3}/381.3 = 187.8/381.3 = 0.493$$

$$X4 = \sqrt{(1-(5.0/42.5)^2)} = \sqrt{(1-0.1384)} = 0.993$$

X5=43[pix]/50[pix]−0.86

Typical value=0.442+0.225+0.243+0.986+0.740=2.636.

In FIGS. 29 and 30, the amounts of features and evaluation values are found in the manner described below.

(1) A region (extracted region of a defect portion or evaluated region) in which the amount of features is to be found is established.

(2) Image processing of this region is performed to calculate normalized amounts of features $x_i$ (i=1, 2, 3, etc.). For example, in the case of sorting of defects, the following amounts of features are computed. What amounts of features $x_i$ should be adopted is determined, depending on experiment or experience.

(2-1) $x_1$=area of a defect portion/area of a rectangular portion circumscribing the defect portion (2-2) $x_2$=average brightness/(maximum brightness−minimum brightness)

$$(2\text{-}3)\quad x_3 = \frac{\sqrt{\sum(\text{brightness at point } Pn - \text{average brightness})^2}}{\text{average brightness} * \sqrt{N}}$$

where n is 1, 2, 3, ..., N (where N is the number of pixels in the defect portion).

$$(2\text{-}4)\quad x_4 = \text{eccentricity} = \sqrt{\frac{(1-b^2)}{a^2}}$$

where a is half of the length of the major axis and b is the half of the minor axis provided that the defect portion is approximated by an ellipse.

(2-5) $x_5$=circumference of the ellipse/circumference of defect portion (2-6) $x_6$= . . .

(3) evaluation value=$\Sigma x_i^2$ (where N is the number of features to be found)

(G) Functions of DIFS Server 3

The DIFS server 3 has a defect information managing means G1 (FIG. 11), a sorting informing means G2, a shape sorting informing means G22, a similar image seeking means G3, etc. These means G1–G3 are realized by a program loaded either in the ROM of the controller of the DIFS server 3 or in the memory Me connected with the controller.

Figure 37:
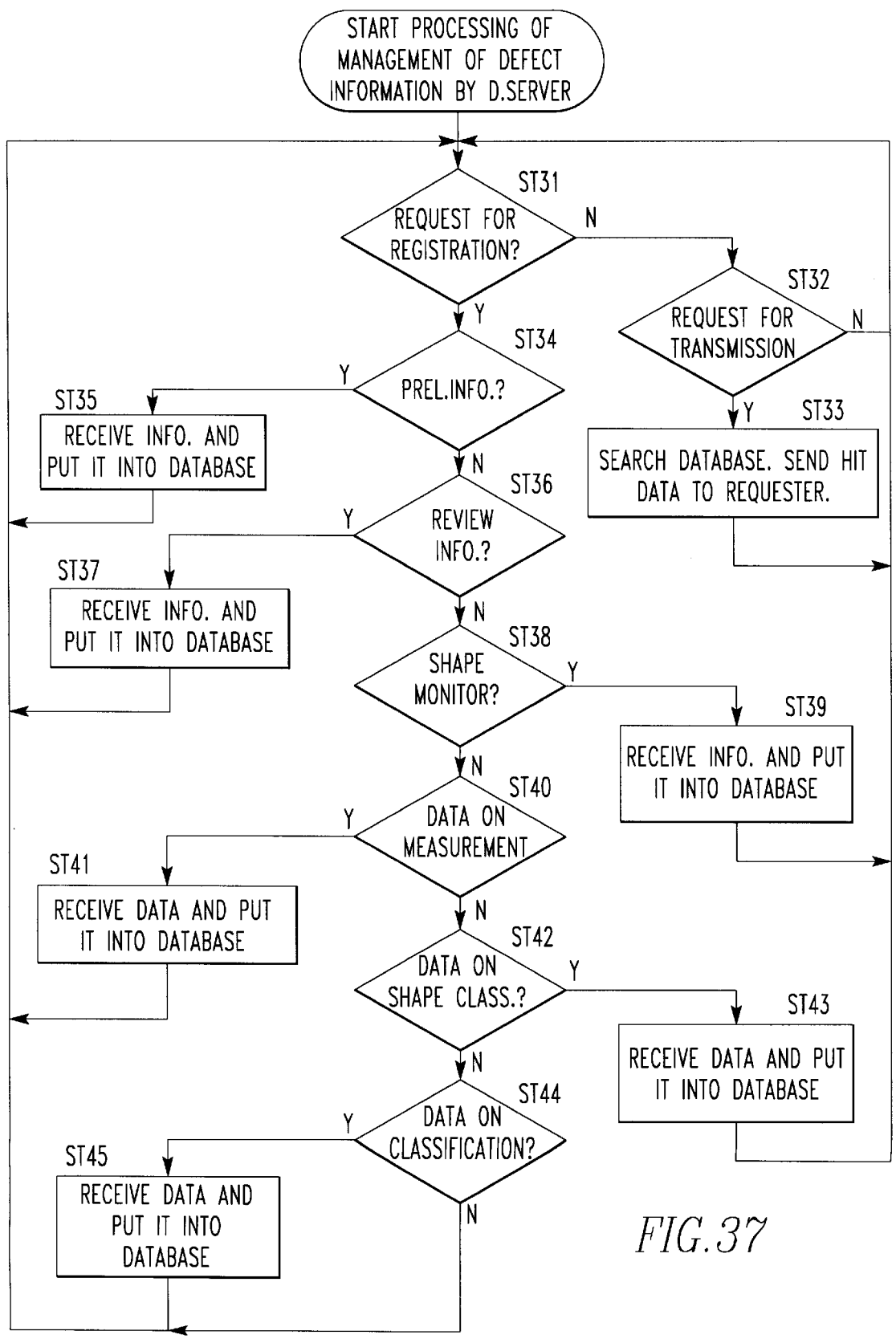
FIG. 37 is a flowchart illustrating information management of a defect information-managing means G1 of a DIFS server 3, the flowchart being executed by a program stored in a memory of the server 3.

(G1) Defect Information Managing Means G1 (FIG. 37)

The defect information managing means G1 saves preliminary inspection information obtained from the foreign material inspecting apparatus 1 or from the defect inspection apparatus 2 in the DIFS database, as well as the review information derived from the review SEM. The managing means G1 also functions to search the DIFS database for the preliminary inspection information by various attributes (e.g., product number, lot number, wafer identification number, defect class, size, data, and defect information name) at a request from a computer connected via the network N. The results of the search are sent back to the computer. Accordingly, the review SEM, for example, is capable of searching the DIFS server for the preliminary inspection information necessary for a review and of reading in the information.

Figure 38:
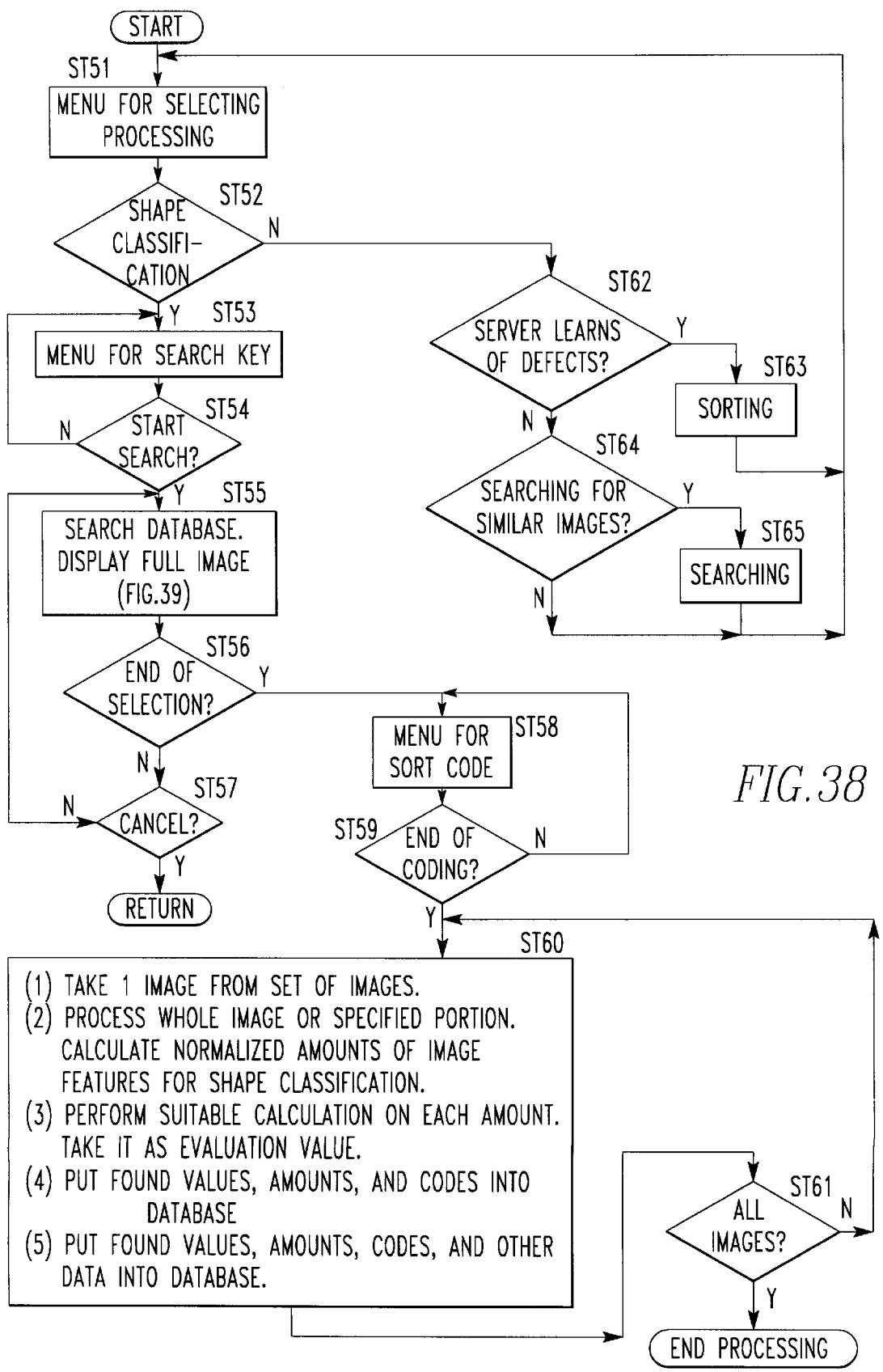
FIG. 38 is a flowchart illustrating processing of the DIFS server 3 to select procedures and to cause the apparatus to learn of sorting of shapes.
Figure 39:
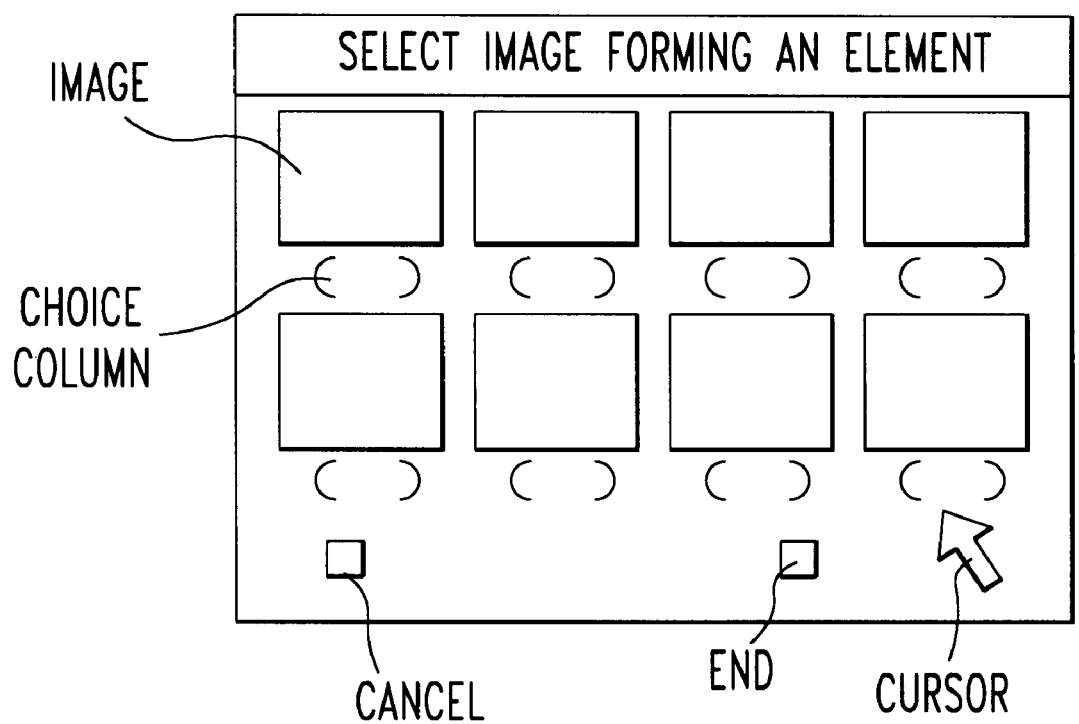
FIG. 39 is a diagram illustrating a menu displayed in step 55 of FIG. 38.
Figure 40:
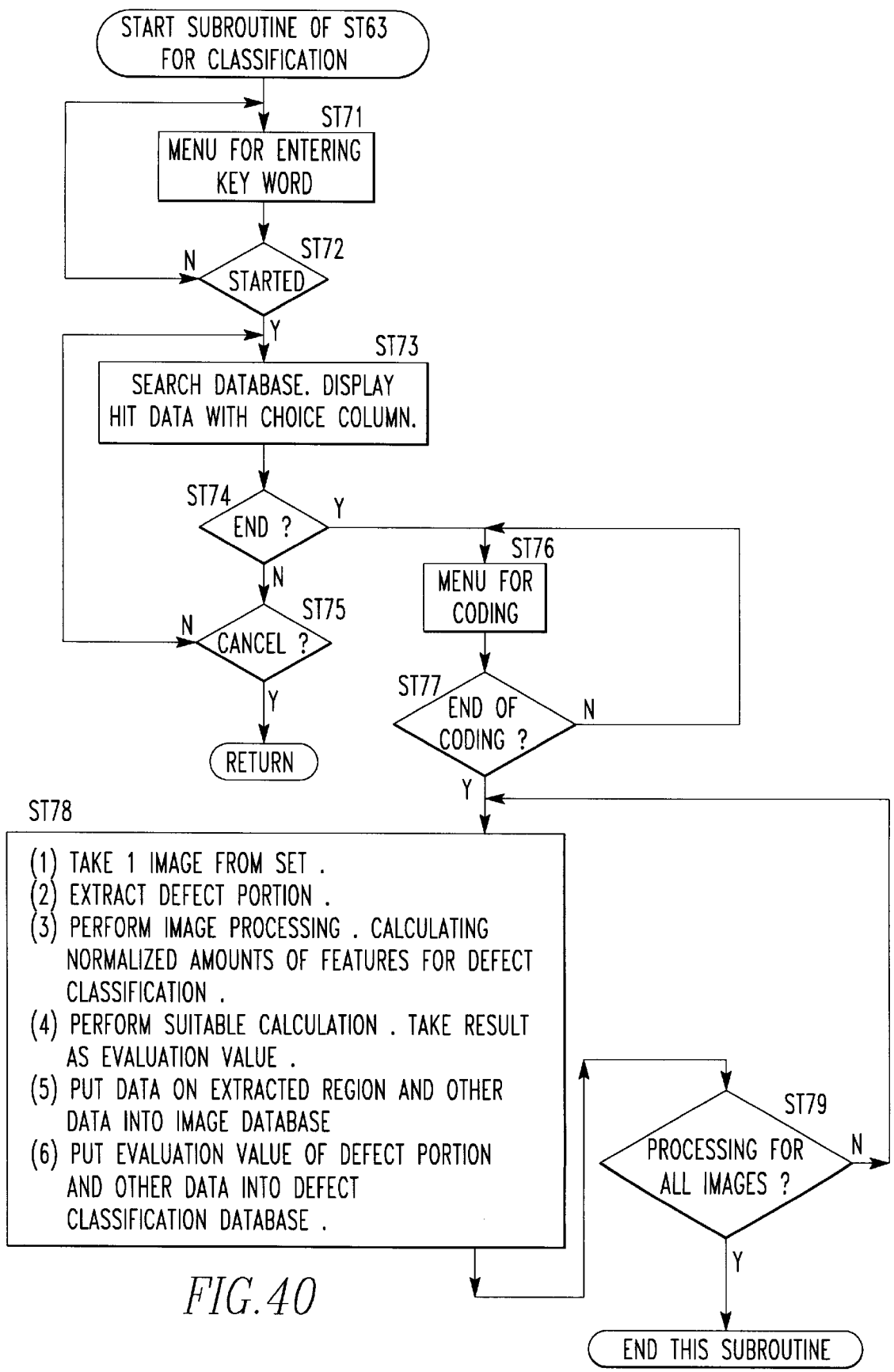
FIG. 40 is a flowchart illustrating processing for causing the server of learn of sorting of defects, the processing being performed subsequently to the processing of FIG. 38.

(G2) Sorting Informing Means G2 (FIGS. 38–40)

The sorting informing means G2 stores sorting information in the database of the DIFS server 3. This sorting information is necessary to classify images photographed during the operation of the manual defect review means or automatic defect review means or to classify images photographed during the operation of the automatic shape monitoring means C5 and to make a decision as to whether the shapes are normal or not (i.e., informing function and sorting function).

The sorting informing means G2 of the DIFS server 3 uses the images stored in the DIFS server 3 and fetches only images coincident with the contents of a desired sorting. One type is given to the set of images fetched to classify them. Also, the amounts of features of the images are calculated and stored. The obtained data is stored in the database of the DIFS server 3.

The amount of features of each defect image obtained by an inspection of the review SEM is calculated. Defect images can be easily classified by knowing to which class of the database does the defect image having the calculated amounts of features belong. The sorting informing means G2 comprises a shape sorting informing means G21 and a defect sorting and informing means G22, which are described in detail below.

(G21) Shape Sorting Informing Means G21 (FIGS. 38 and 39)

The shape sorting informing means G21 has a function of storing shape sorting information used by the automatic shape monitoring means C5 in memory (i.e., informing function and learning function). In a default condition, the whole image is treated in storing the information in the database, but only a rectangular region can be treated.

(G22) Defect Sorting Informing Means G22 (FIG. 40)

The sorting informing means G11 has a function of storing the amounts of features of images and sort codes, using images accepted in the DIFS server. In particular, only the images coincident with the contents of a desired type is fetched from the DIFS server, and a sort code given to the set of fetched images is stored. For example, only defect images that are certainly judged to be round defects are extracted, and the server is made to learn of this set. Similarly, the server can learn of various shapes. The functions of the shape sorting informing means G21 and of the defect sorting informing means G22 are described below.

(a) The image database of the DIFS server 3 is searched, by an arbitrary keyword, for images of defects produced by the same cause. Alternatively, the database is visually searched. In this way, the above-described defect images or images having the same shape are extracted, and a set is formed. A sort code is given to this set.

(b) The images are extracted one by one from the set. The following processing is performed for every component of the set.

(c) Where the server is made to learn of defects, defect portions are extracted from the extracted images. Where the server is caused to learn of shapes, a region in which shapes are evaluated is extracted.

(d) The extracted images undergo image processing operations to calculate normalized amounts of features of images. The amount of features of images may differ between where the server learns of defects and where the server learns of shapes.

(e) Appropriate calculations (e.g., taking the sum of squares) are performed on the amounts of features to produce evaluation values.

(f) To implement the function of searching for similar images by the use of the DIFS server 3, data indicating the extracted region, the evaluation value of each defect portion, the amounts of features of various images, and defect sort codes are stored in the image database of the DIFS server 3.

(g) To implement the defect-sorting function and the shape-sorting function, the found evaluation values, the amount of features of the images, sort codes, and the magnifications of the images are registered in the defect sorting database and in the image database of the DIFS server 3. The coordinates of the centers of the images are also registered in the shape sorting database.

Figure 41:
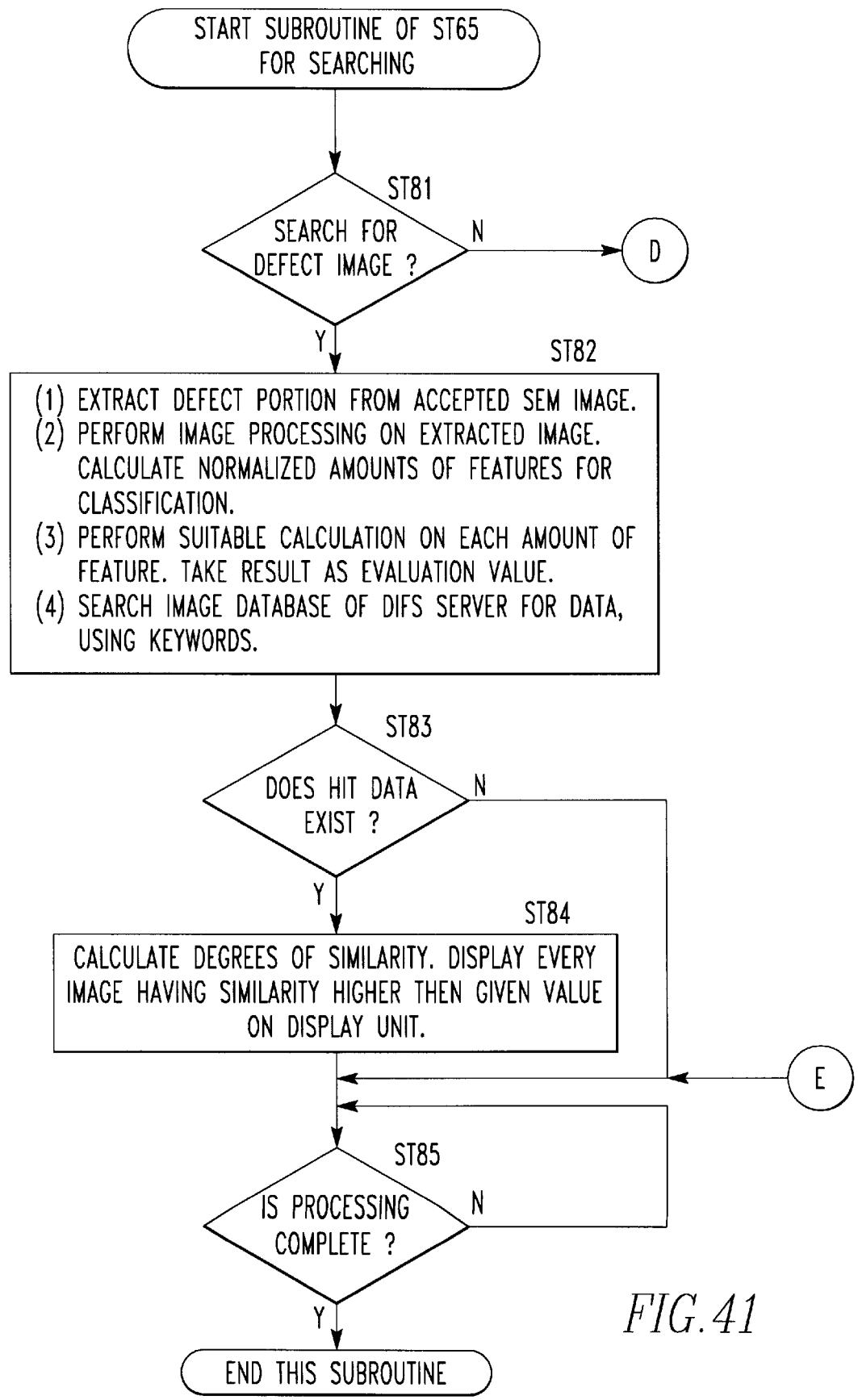
FIG. 41 is a flowchart illustrating processing for searching for similar images, the processing being performed subsequently to the processing of FIG. 38.
Figure 42:
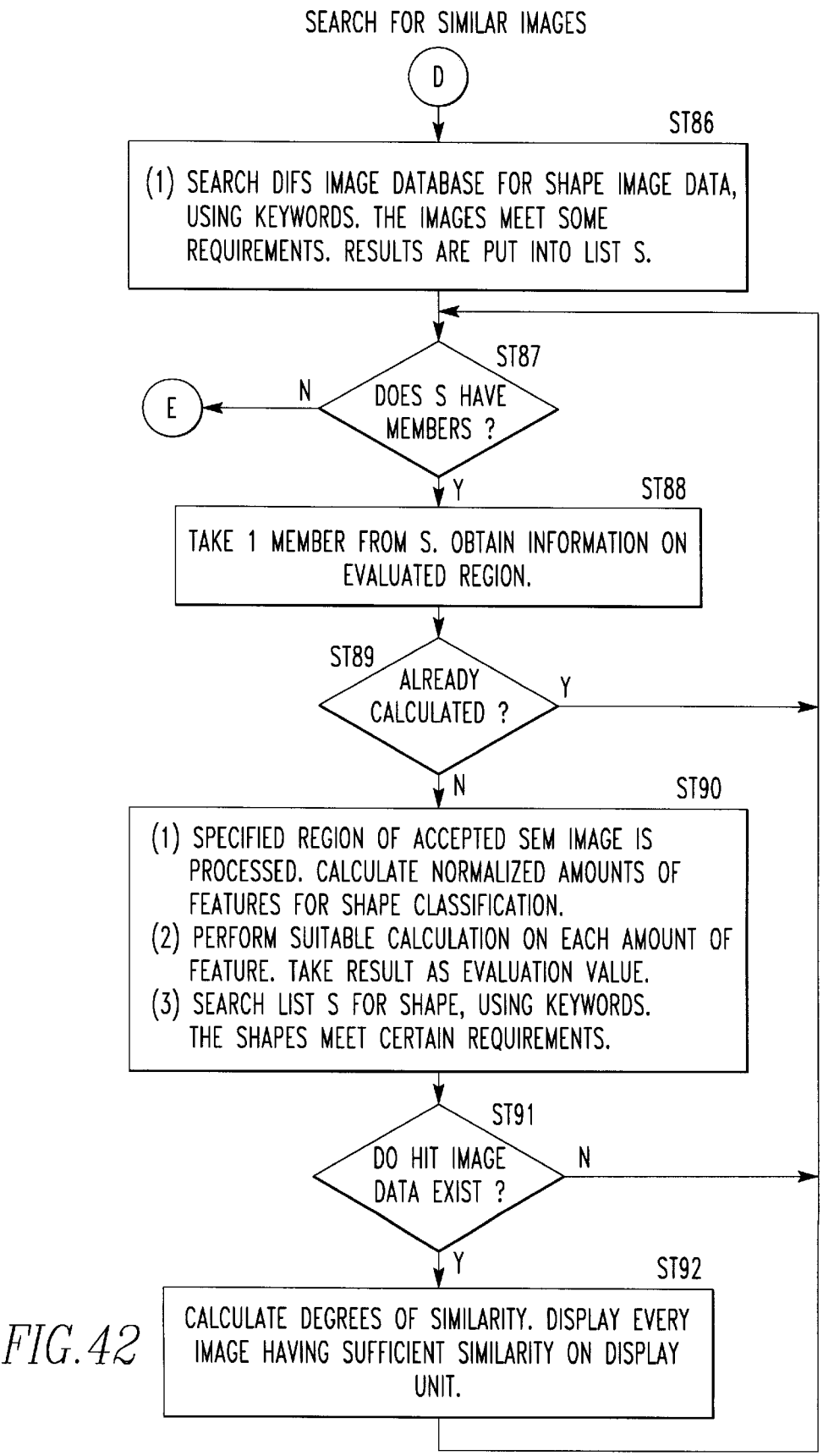
FIG. 42 is a flowchart illustrating processing for searching for similar images, the processing being performed subsequently to the processing of FIG. 41.

(G3) Similar Image Seeking Means G3 (FIGS. 41 and 42)

The similar image seeking means G3 comprises a similar image seeking means G31 for searching the database for defect images similar to the given defect image and displaying the discovered images and a shape monitoring image similar image seeking means G32 for searching the database for images similar to the given shape monitoring image and displaying the discovered images. These searches are performed in the manner described below.

(G31) Defect Image Similar Image Seeking means G31 (FIG. 41)

The defect image similar image seeking means G31 searches the database for images similar to the SEM image (or, defect image) of the accepted defect image and displays the discovered image. The details of this function are as follows.

(a) A defect portion is extracted from the accepted SEM (scanning electron microscope) image.

(b) The extracted image of the defect portion is processed by image processing techniques to calculate the normalized amounts of various features necessary for sorting of defects.

(c) Appropriate calculations (e.g., taking the sum of squares or performing the same calculations as the calculations used when the server was made to learn of shapes, for example) are performed to compute evaluation values.

(d) The image database of the DIFS server is searched for data about defect images having the same magnifications and having evaluation values lying in a tolerable range, using the magnification of the accepted SEM image and the found evaluation value as keywords.

(e) If hit data are discovered as a result of the search, the following operations are carried out. If no hit data are found, the search for images similar to the defect image is ended.

(f) The degrees of similarity of the amounts of features of various images obtained from the attributes of the hit image data to the amounts of the various images found in (b) are calculated. All image data having degrees of similarity higher than a given value are displayed on the display screen. In calculating the degrees of similarity, an appropriate evaluation function is used. For example, the evaluation function finds the sum of squares of the differences between the amounts of features of the various images found in (b) and the corresponding amounts of features of the hit image data.

(G32) Shape Monitoring Image Similar Image Seeking means G32 (FIG. 42)

The shape monitored image similar image seeking means G32 searches the database for images similar to the SEM image (shape-monitored image) of a shape-monitored portion and displays the discovered images. The details of the function are as follows.

(a) The image database of the DIFS server 3 is searched for shape image data having the same magnification and center coordinates lying in a tolerable range (generally, where the stage error is in a tolerable range), using the magnification of the image and the coordinates of the center of the image as keywords. The results of the search are entered in a list S that is an array of candidate data items.

(b) If the set S contains members or elements, the following operations are executed. If no members are present, nothing is searched for and thus the search for similar images is ended.

(c) One image forming a member of the set S is extracted. Information about an evaluated region established within the field of view of the review SEM during registration, i.e., the coordinates of diagonally opposite points of the image of the above-described member, is obtained (see FIG. 43).

(d) If calculations have been already performed for the evaluated region, it follows that the region has been already searched. Therefore, we go back to step (b). If no calculations have been performed about this region, the following operations are conducted.

(e) The accepted SEM image is processed by image processing techniques within the evaluated region obtained by (c) to calculate the normalized amounts of various features necessary for search for images similar to the shape-monitored image.

(f) Appropriate calculations (e.g., taking the sum of squares or performing the same calculations as the calculations used when the server was made to learn of shapes, for example) are performed to compute evaluation values.

(g) The set S is searched for shape sorting data which have the same magnification, have evaluation values lying within a tolerable range about the found evaluation value, and have center coordinates lying in a tolerable range, using the magnification of the image, the coordinates of the center of the image, and the evaluation value as keywords.

(h) If hit data are discovered as a result of the search, the following operations are carried out. If no hit data are found, the search for similar images is ended.

(i) The degrees of similarity of the amounts of features of various images obtained from the attributes of the hit image data to the amounts of the various images found in (e) are calculated. All image data having degrees of similarity higher than a given value are displayed on the display screen. In calculating the degrees of similarity, an appropriate evaluation function is used. For example, the evaluation function is used to find the sum of squares of the differences between the amounts of features of the various images found in (e) and the corresponding amounts of features of the hit image data.

Operation of the Embodiment

The operation of an embodiment of the present invention constructed as described thus far is described now.

(1) Before defects are reviewed, or a detailed inspection is performed, through the use of the review SEM, the following processing is carried out, using an optical defect inspection apparatus. In particular, the wafer cassette 13 is set on the defect inspection apparatus, and an inspection of defects is initiated. As soon as the defect inspection apparatus completes the wafer defect inspection, a file holding information about the defects is automatically registered in the DIFS server, along with product number, lot number, slot number, etc.

(2) Then, the wafer cassette 13 undergone the defect inspection by the defect inspection apparatus is placed in position within the review SEM. In FIG. 2, the cassette 13 holds plural stages of wafers and is placed on the recessed cassette placement portion 7a by the cassette-holding member 11 that moves along the transportation rails 10. This cassette 13 is pushed against the front end 7x and the left end 7y of the recessed portion 7a by the X-coordinate-positioning cylinder 14 and the Y-coordinate-positioning cylinder 15. In this way, the cassette is placed in position. The cassette sensor 8 supplies a cassette presence/absence signal to the SEM controller to permit the SEM controller to judge whether the cassette 13 is placed in position.

A bar code bearing a cassette identification number and printed on a bar code label stuck on a side surface of the cassette 13 is scanned by the cassette identification number reader 16 and supplied to the SEM controller. This SEM controller sends the applied cassette identification number to the host computer for computer-integrated manufacturing (CIM). The product number, lot number, etc. of each wafer are sent to the DIFS server 3 according to processing request slips obtained from the host computer for computer-integrated manufacturing (CIM). Preliminary inspection information about each wafer held at multiple stages within the cassette 13 is received from the DIFS server 3.

If the product numbers and lot numbers of the wafers (inspected parts) held in the cassette 13 are printed instead of printing only the cassette identification code or number on the bar code label stuck on a side surface of the cassette 13, the product numbers and lot numbers can be directly read.

(4) The review SEM searches the DIFS server by read product number and lot number and fetches registered files holding information about defects.

(5) Thereafter, wafers (or, inspected parts) are installed on the review SEM and move into the review position. The operation of the mechanism of the review SEM is next described.

In FIGS. 2–4, a wafer in a position W1 (FIG. 4) inside the cassette 13 is taken out by the externally moving arm 26 and moves into a position W2 inside the sample exchange chamber 7 through the external partitioning valve 18. The wafer is then once raised by the elevating rod 27 and lowered into a position W3 of FIG. 4 after the arm 26 has moved out. The wafer is placed on the internally moving arm 28, which in turn brings the wafer into the vacuum inspection chamber 6 and transfers the wafer to the inspected part-holding member 65 in a position indicated by the phantom line of FIG. 8.

After the inspected part-holding member 65 has been moved into the sample transfer position indicated by the phantom line of FIG. 8, the wafer W is placed on the inspected part-holding member 65 from the sample placement portions 28a of the internally moving arm 28 through the elevating table 66. Then, the wafer is placed in position by the positioning movable pins 68 etc., as already described in connection with FIG. 9.

Subsequently, the Y-motion table 56 and the X-motion table 63 are moved to bring the inspected part-holding member 65 into the working position (observational position) below the cooling plate 77. In this observational position, an electron beam is directed at the wafer W from the lower end of the microscope column 36 of the body 34 of the SEM.

At this time, the electron beam passes through the electron beam passage hole 79 in the cooling plate 77 and enters the wafer W. Heat from the cooling plate 77 is conducted to a thermally conductive mesh line 85, a thermally conductive rod 84, and an internal cylinder 83, and is absorbed by a refrigerant such as liquid nitrogen in a refrigerant container 81. Therefore, the cooling plate 77 is maintained at a low temperature. Thus, organic gases around the wafer are adsorbed on the cooling plate 77, preventing adhesion of contaminants to the wafer W. Secondary electrons emitted from the wafer W pass through the electron beam passage hole 79 and are detected by a secondary electron detector 87 received at the front end of the sensor-holding member 86. The output signal from the detector is sent to a measuring instrument (not shown) for an external secondary electron detector 88 via a transmission cable (not shown). An electron microscope image obtained in response to a scan made by the electron beam is displayed on the display device D.

The inspected portion of the wafer W is moved below the electron beam passage hole 79 by moving the Y-motion table 56 and the X-motion table 63. The inspected portion of the wafer W is scanned by the X-deflection coil F6 and the Y-deflection coil F7 shown in FIG. 10 to perform an inspection. During movement of the wafer W, the electron beam is directed at a given blank position by the action of a blanking coil F4 shown in FIG. 10 to prevent the wafer W from being illuminated. An image signal obtained by scanning the surface of the wafer W is supplied from the secondary electron detector 88 to the SEM controller and presented on the display device D. As a result, the human operator can observe and inspect the surface of the wafer W. Signals sent to and from the secondary electron detector 88 are stored in the SEM controller.

In FIG. 7, where the electron beam is directed at the wafer W while the tilt stage 37 is tilted, the electron beam hole 79 in the cooling plate slightly above the intersection of the tilting axis T (FIG. 8) of the wafer W and the electron beam rotates about the tilting axis T of the tilt stage 37 and tilts. As can be seen from FIG. 7, about half of the surface of the cooling plate 77 upwardly tilts or moves, and the remaining half downwardly tilts or moves. The half of the cooling plate tilting or moving upward moves toward the lower end portion of the SEM body located over the tilting axis T. The lower end portion of the microscope column 36 of the SEM body 34 tapers off downwardly. The distance between the sample surface and the top surface of the cooling plate is set to 2mm or less. Therefore, even if the SEM body 34 is close to the cooling plate 77, the upwardly tilting portion of the cooling plate 77 is placed along the tapering side surface of the lower end portion of the SEM body 34 without touching the lower end of the SEM body 34.

(6) The review SEM reviews (or, performs a detailed inspection of) each inspected part either in the manual mode or in the automatic mode and classifies the reviewed defects by making use of the operation of the above-described mechanism of the review SEM. The DIFS server 3 can make the server to learn of a method of sorting, search for similar images, and perform other operations.

Description, Using Flowcharts

Figure 31:
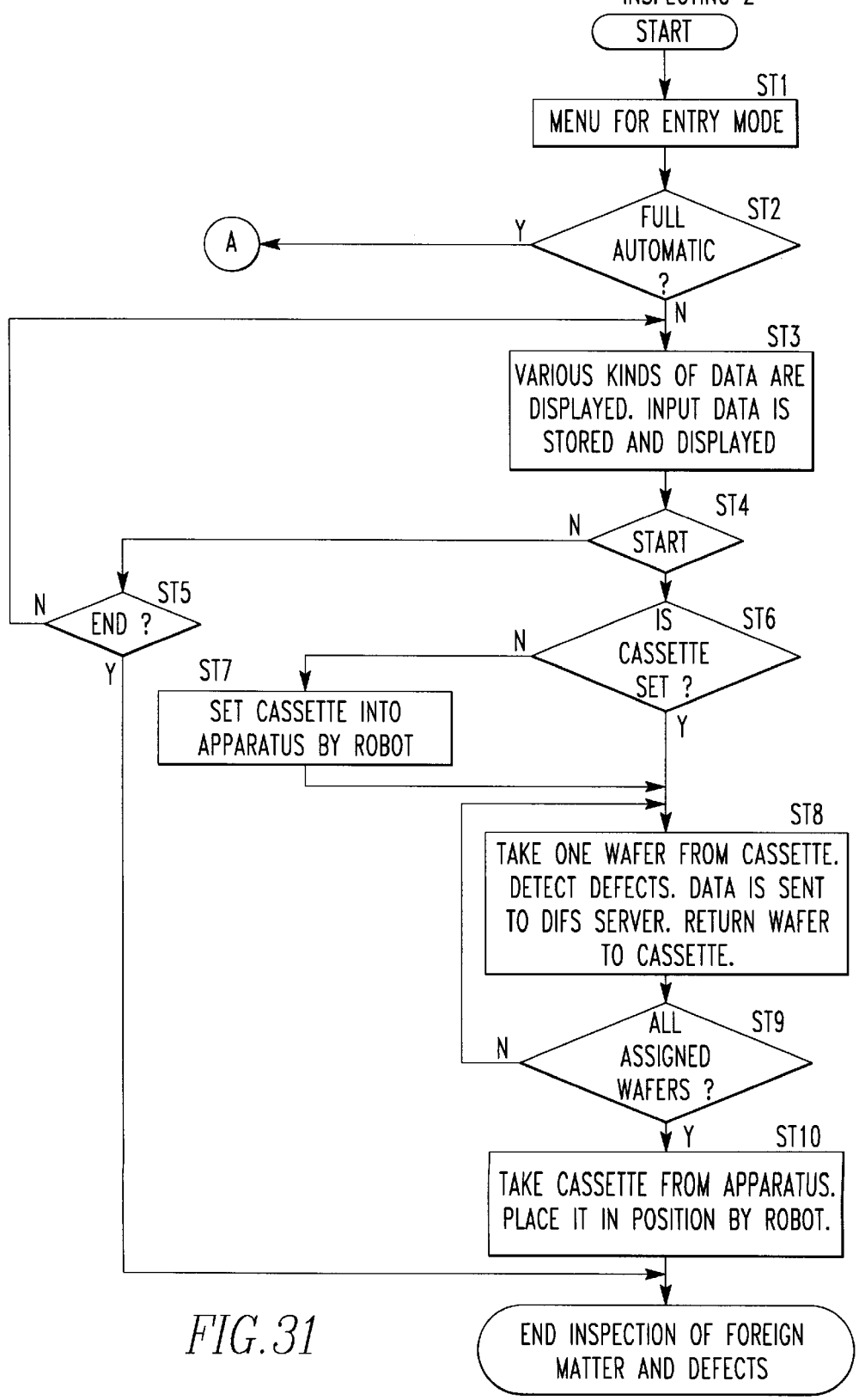
FIG. 31 is a flowchart illustrating processing performed by a foreign material-inspecting apparatus 1 and by a defect-inspecting apparatus 2.
Figure 33:
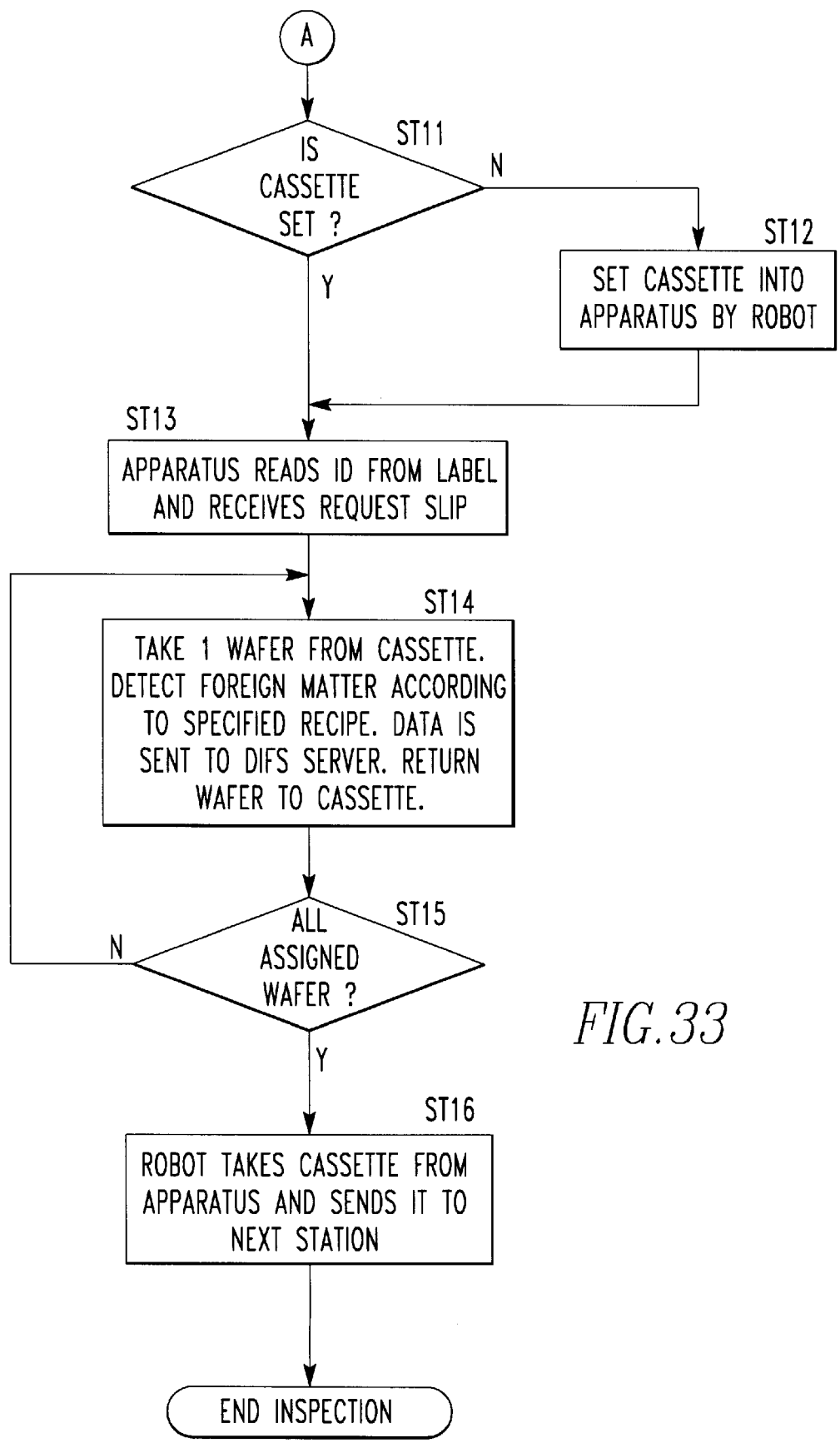
FIG. 33 is a flowchart illustrating processing performed subsequently to the processing of FIG. 31.

The operation of the part inspecting apparatus in accordance with the present invention is next described in detail, using flowcharts. FIG. 31 is a flowchart illustrating processing performed by the foreign material-inspecting apparatus 1 and the defect-inspecting apparatus 2. FIG. 32 illustrates a menu displayed in step 3 of FIG. 31. FIG. 33 is a flowchart illustrating processing performed subsequently to the processing illustrated in FIG. 31.

Since the foreign material-inspecting apparatus 1 and the defect-inspecting apparatus 2 perform inspection operations depicted by almost identical flowcharts, these inspection operations will be collectively referred to as the "foreign material/defect inspection flow". The inspecting apparatuses 1 and 2 will be collectively referred to as the "foreign material/defect-inspecting equipment."

In FIG. 31, when the power supply is turned on, the foreign material/defect-inspecting equipment starts the "foreign material/defect inspection flow". In step 1, a PROCESSING-SELECT menu is displayed to ask the user if there is any processing request slip in which information about the inspected part, or wafer, is registered.

In step 2, a decision is made as to whether the fully automated input mode has been selected. If the result is NO, control goes to step 3.

In step 3, the menu (FIG. 32) for entering wafer information about the foreign material/defect-inspecting equipment is displayed. If any input is present, input data is stored and displayed. Specifically, the product number, product lot number, wafer identification code or number (wafer-identifying number), processing steps for processing the wafer W, inspection recipe, etc. are assigned to slots. That is, information about the wafer W received in each individual slot of the cassette 13 is stored for each different slot. The inspection recipe describes parameters necessary for the foreign material/defect-inspecting equipment to execute the processing. For example, these parameters include the inspection mode of the detector, the inspection sensitivity, and inspected region.

In step 4, a decision is made as to whether an inspection is started according to the input data. This decision depends on whether the "start" is selected from the WAFER INFORMATION INPUT menu (FIG. 32) of step 3. If the result is NO, control proceeds to step 5. If the result is YES, control goes to step 6.

In step 5, a decision is made as to whether the processing is ended or not. This decision depends on whether the "end" is selected from the WAFER INFORMATION INPUT menu (FIG. 32) of step 3. If the result is NO, control goes back to step 3. If the result is YES, the inspection of foreign materials and defects is ended.

In step 6, a decision is made as to whether the cassette 13 is set. If the result is NO, control proceeds to step 7. If the result is YES, control goes to step 8.

In step 7, the inspected part-transporting device (19–28+ D3–D6+M3–M6) sets the cassette 13 holding the wafer W on the foreign material/defect-inspecting equipment. Control then goes to step 8.

In step 8, one wafer is taken from the cassette 13. Foreign materials and defects are detected. Data about the results of this detection is sent to the DIFS server 3. Then, the wafer W is returned to the cassette 13. The results Of the inspection of foreign materials contain the positions of foreign materials, the dimensions of the foreign materials taken in the X- and Y-directions, respectively, the areas of the foreign materials, and the features of the foreign materials.

In step 9, a decision is made as to whether all the assigned inspections of foreign materials and defects are finished. If the result is NO, control returns to step 8. If the result is YES, control goes back to step 10.

In step 10, the inspected part-transporting device takes the cassette 13 from the foreign material/defect-inspecting equipment and moves the cassette into a given position. Thus, the inspections of foreign materials and defects are ended.

In step 2, if the result is YES, control goes to step 11 of FIG. 33. In step 11, a decision is made as to whether the cassette 13 is in position. If the result is NO, control goes to step 12. If the result is YES, control proceeds to step 13.

In step 12, the inspected part-transporting device sets the cassette 13 holding th e wafer W in the foreign material/ defect-inspecting equipment. Control goes to step 13. In step 13, the foreign material/defect-inspecting equipment reads the identification number from the bar code on the label of the cassette 13. Then, the equipment receives an inquiry processing request slip from the host computer for computer-integrated manufacturing (CIM).

In step 14, one wafer W is taken from the cassette 13 according to the contents of the processing request slip. Foreign materials and defects are detected by a specified recipe. Data about the results of the inspection is sent to the DIFS server 3. The wafer W is returned to the cassette 13.

In step 15, a decision is made as to whether the assigned inspections of foreign materials and defects are all finished. If the result is NO, control goes back to step 14. If the result is YES, control proceeds to step 16.

In step 16, the inspected part-transporting device takes the cassette 13 from the foreign material/defect-inspecting equipment and moves into position. The inspections of foreign materials and defects are ended.

Figures 34, 35:
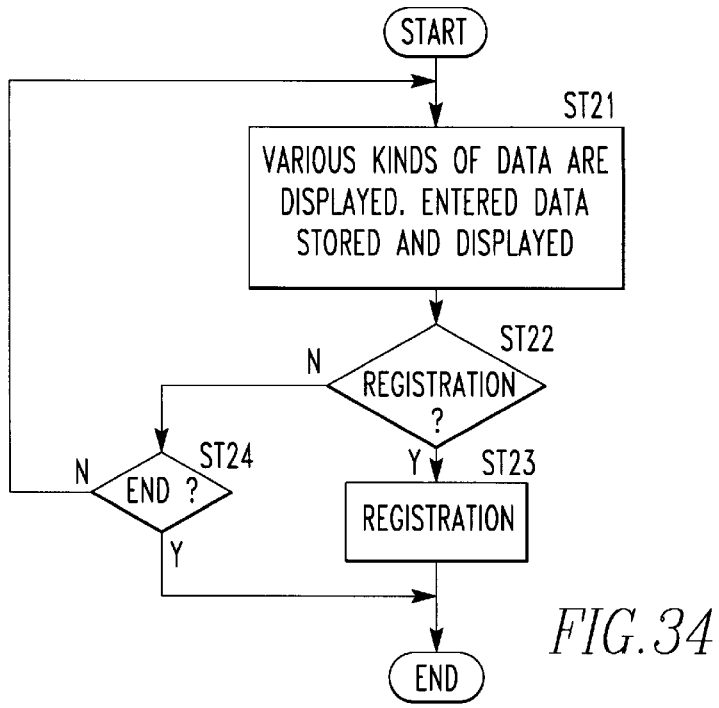
FIG. 34 is a flowchart illustrating processing for creating processing request slips, the processing being executed by a program stored in a memory of a host computer for CIM.
FIG. 35 is a diagram illustrating a menu for creating a processing request slip.
Figure 36:
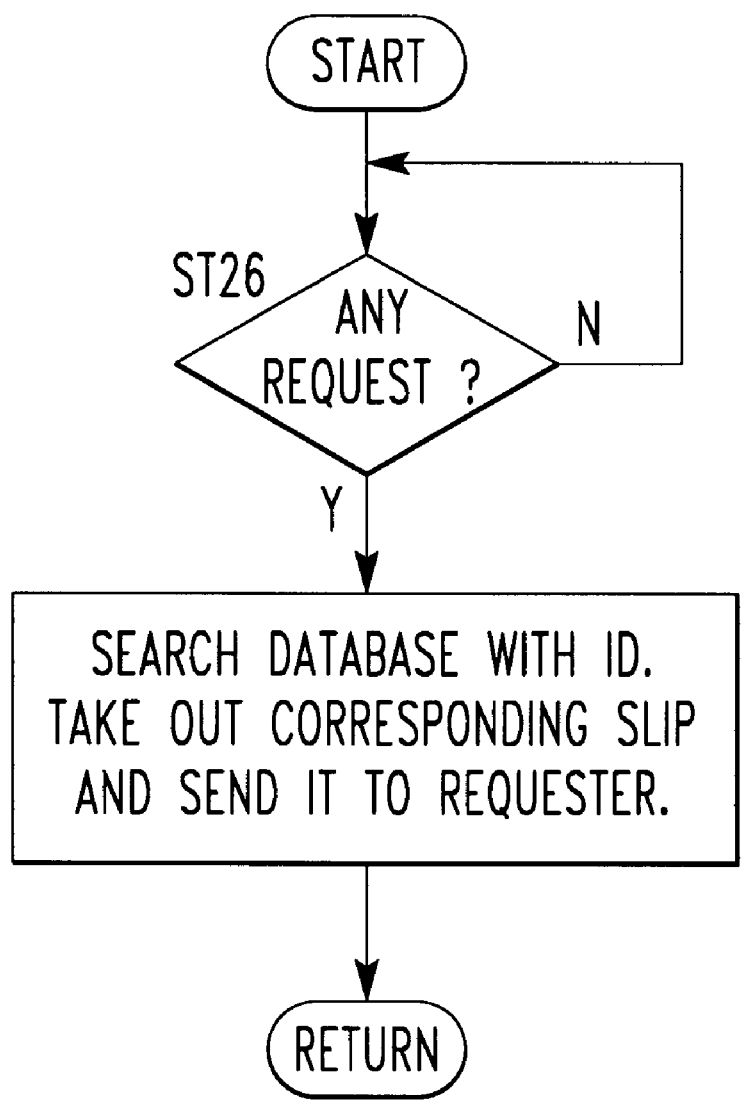
FIG. 36 is a flowchart illustrating processing for issuing processing request slips, the flowchart being stored in the memory of the host computer for CIM.

FIG. 34 is a flowchart illustrating the manner in which a processing request slip is created according to a program stored in the host computer for computer-integrated manufacturing (CIM). FIG. 35 illustrates a menu used in creating a processing request slip. FIG. 36 is a flowchart illustrating processing for issuing a processing request slip, the flowchart being stored in the memory of the host computer for computer-integrated manufacturing (CIM).

In FIG. 34, if the processing for creating a processing request slip starts, the WAFER INFORMATION INPUT menu for the host terminal (FIG. 32) is displayed (step 21). If any input is present, input data is stored and displayed. Specifically, the product number, product lot number, wafer identification code for number (wafer-identifying number), processing steps for processing the wafer W, inspection recipe, etc. are assigned to slots.

In step 22, a decision is made as to whether the input is registered. This decision depends on whether the "registration" is selected from the WAFER INFORMATION INPUT menu (FIG. 35) of step 21. If the result is YES, control proceeds to step 23. If the result is NO, control goes to step 24.

In step 23, the processing request slip is registered in the database or memory in the host computer for CIM, and then the processing for creating the processing request slip is ended.

In step 24, a decision is made as to whether the processing is ended or not. This decision depends on whether the "end" is selected from the WAFER INFORMATION INPUT menu (FIG. 35) of step 21. If the result is NO, control returns to step 21. If the result is YES, the processing for creating the processing request slip is ended.

In FIG. 36, if the processing for creating the processing request slip starts, a decision is made as to whether there is a request for a search (step 26). If the result is NO, step 26 is repeatedly executed. For example, the review SEM reads the cassette identification (ID) number. If the review SEM sends a request for transferring a processing request slip regarding the wafer W in the cassette whose identification number has been read, then the result of the decision made in step 26 is YES.

If the result of the decision made in step 26 is YES, the database of processing request slips is searched by cassette identification number. The corresponding processing request slip is taken and transmitted to the requester. If execution of step 27 ends, control goes back to step 26.

FIG. 37 illustrates a flowchart illustrating information management made by the defect information managing means G1 of the DIFS server in accordance with a program loaded in the memory of the DIFS server 3. The information management processing of the DIFS server 3 starts when the power supply is turned on.

In step 31, a decision is made as to whether there is any inspection result data registration request from the foreign material-detecting apparatus 1, the defect-inspection apparatus 2, the review SEM, or the like connected with the network N (FIGS. 1 and 13). If the result is NO, control returns to step 32.

In step 32, a decision is made as to whether there is any data transmission request. If the result is NO, control goes back to step 31. If the result is YES, the database corresponding to the request is searched by specified kind, lot number, wafer identification number, processing steps, date, etc. (step 33). The hit data is sent to the requester, such as the review SEM, client, or host computer, and then control goes back to step 31.

If the result of the decision made in step 31 is YES, control proceeds to step 34. In step 34, a decision is made as to whether the data urged to be registered is data about a preliminary inspection. If the result is YES, the data about a preliminary inspection is received (step 35) and registered in the preliminary inspection information database of the DIFS server 3. If the result of the decision made in step 34 is NO, control goes to step 36.

In step 36, a decision is made as to whether there exists any review information. If the result is YES, the review information is received in step 37 and registered in the review information database of the DIFS server 3.

If the result of the decision made in step 36 is NO, control proceeds to step 38. In step 38, a decision is made as to whether the information is information about shape monitoring. If the result is YES, data about monitoring of shape is received in step 39 and registered in the shape monitoring information database of the DIFS server 3, and control returns to step 31.

If the result of the decision made in step 38 is NO, control proceeds to step 40. In step 40, a decision is made as to whether the data is data about measurement of lengths (such as length, height, and area). If the result is YES, the data is received in step 41 and registered in the length-measuring database. Then, control goes back to step 31.

If the result of the decision made in step 4 0 is NO, control goes back to step 42. In step 42, a decision is made as to whether the data is about sorting of shapes. If the result is YES, the data is received (step 43) and registered in the shape sorting database. Then, control goes back to step 31. If the result is NO, control returns to step 44.

In step 44, a decision is made as to whether the data is defect sorting data. If the result is NO, control returns to step 31. If the result is YES, the data is received in step 45 and registered in the defect sorting database. Then, control goes to step 31.

Processing illustrated in FIGS. 38–42 is performed by the DIFS server 3 simultaneously with the processing of FIG. 37, i.e., by multitasking. FIG. 38 is a flowchart illustrating processing permitting the user to select desired processes from the processing of the DIFS server 3, as well as processing for causing the server to learn of shape sorting. FIG. 39 illustrates an image displayed in step 55 of FIG. 38. FIG. 40 is a flowchart illustrating processing for searching for similar images, subsequently to the processing of FIG. 38. FIG. 41 is a flowchart illustrating processing for searching for similar images, subsequently to the processing of FIG. 38. FIG. 42 is a flowchart illustrating processing for searching for similar images, subsequently to the processing of FIG. 41.

When the power supply of the DIFS server 3 is turned on, the processing of FIG. 33 starts. In the next steps 51–59, the following processing is executed.

(1) The image database or review information database of the DIFS server 3 is searched by arbitrary keyword. Alternatively, the search is made visually. A set of shape images belonging to the same type is created.

(2) A shape sort code is given to this set. The processing is as follows.

In step 51, a menu for selecting desired processing is displayed. This menu permits the user to select any one kind of processing from processing for causing the server to learn of shape sorting, processing for causing the server to learn of defect sorting, and processing for searching for similar images.

In step 52, a decision is made as to whether the processing for causing the server to learn of shape sorting is selected or not. If the result is YES, control proceeds to step 53.

In step 53, a menu for entering search keywords is displayed. The entered keyword or keywords are stored in memory.

In step 54, a decision is made as to whether the search is started or not. If the result is NO, control returns to step 53. If the result is YES, control goes back to step 55.

In step 55, the image database or review information database of the DIFS server 3 is searched. All hit images are displayed together with submenus. The display method is illustrated in FIG. 39, where a similar image is selected from every displayed image by clicking on an END icon with a mouse. The selection is canceled by clicking on a CANCEL icon with the mouse.

In step 56, a decision is made as to whether the selection ends. If the result is NO, a decision is made as to whether the selection is canceled or not in step 57.

In step 57, if the result is NO, control returns to step 55. If the result is YES, control goes to step 51.

In step 56, if the result is YES, control proceeds to step 58. In step 58, a menu for giving a shape sort code is displayed. The entered code is stored as a sort code for the image.

In step 59, a decision is made as to whether the processing for giving a code ends. If the result is NO, control goes back to step 58. If the result is YES, control proceeds to step 60, where the following processing is carried out.

(1) One image is extracted from a set of images.

(2) The whole surface of the extracted image or a specified evaluated region is processed by image processing techniques to calculate normalized amounts of image features for classifying shapes.

(3) Appropriate calculations (e.g., taking the sum of squares) are performed on the amounts of features to obtain an evaluation value.

(4) The found evaluation value, amounts of image features, and shape sort code are registered in the image database or in the review information database of the DIFS server 3.

(5) The found evaluation value, amounts of image features, the magnifications of images, and the coordinates of the centers of the images are registered in the shape sorting database of the DIFS server 3.

In step 61, a decision is made as to whether the processing has been performed for every image of the set. If the result is NO, control returns to step 60. If the result is YES, the processing for causing the server to learn of shape sorting is ended.

In step 52, if the result is NO, control proceeds to step 62, in which a decision is made as to whether it is the processing for causing the server to learn of defects. If the result is YES, the processing (FIG. 40) for causing the server to learn of defect sorting is executed in step 63, and control returns to step 51. If the result is NO, control proceeds to step 64.

In step 64, a decision is made as to whether it is the processing for searching for similar images. If the result is NO, control directly returns to step 51. If the result is YES, control goes back to step 51 after performing the processing for searching for similar images (illustrated in FIGS. 41 and 42).

FIG. 40 illustrates a subroutine of the processing for causing the server to learn of defect sorting of step 63 of FIG. 38.

Similarly to the processing of steps 53–59 of FIG. 38, steps 71–77 of FIG. 40 carry out the following processing.

(1) The image database of the DIFS server 3 is searched by arbitrary search keyword, or the database is visually searched. A set of images of defects induced by the same cause is created.

(2) A defect sort code is given to this set.

The following processing is performed in step 78.

(1) One image is extracted from a set of images.

(2) A defect portion is extracted from the extracted image.

(3) The extracted image is processed by image processing techniques to calculate normalized amounts of image features for sorting defects.

(4) Appropriate calculations (e.g., taking the sum of squares) are performed on the amounts of features to obtain an evaluation value.

(5) The found evaluation value, amounts of image features, and defect sort code are registered in the image database or review information database of the DIFS server 3.

(6) The evaluation value of the defect portion, amounts of image features, the defect sort code, and the magnification of the image are registered in the defect sorting database of the DIFS server 3.

In step 79, a decision is made as to whether every image of the set has been processed or not. If the result is NO, control returns to step 78. If the result is YES, the processing for causing the server to learn of defect sorting is ended.

Figure 43:
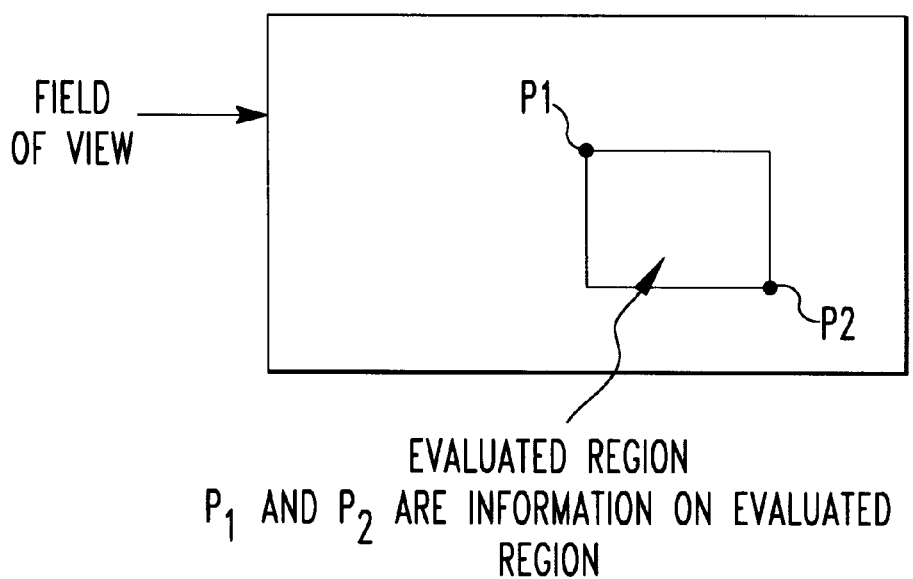
FIG. 43 is a diagram illustrating the field of view of an image produced by a review SEM, as well as an evaluated region.

FIG. 41 illustrates a subroutine for the processing for searching for similar images of step 65 of FIG. 38. FIG. 42 is a flowchart illustrating the processing for searching for similar images, subsequently to the processing of FIG. 41. FIG. 43 illustrates the field of view of the image on the review SEM and an evaluated region.

In step 81 of FIG. 41, a decision is made as to whether the processing is to search for defect images. If the result is YES, control proceeds to step 82, where the next processing is performed.

(1) A defect portion of the SEM image accepted by the review SEM is extracted.

(2) The extracted image of the defect portion is processed by image processing techniques to calculate normalized amounts of image features for classifying defects.

(3) Appropriate calculations (e.g., taking the sum of squares or performing the same calculations as used to cause the server to learn of something) are performed on the amounts of features to obtain an evaluation value.

(4) The image database of the DIFS server 3 is searched for data about defect images, using image magnification and evaluation as keywords, the defect images having the same image magnification and evaluation values that are in a tolerable range about the found evaluation value.

In step 83, a decision is made as to whether there exists any data hit by the search. If the result is NO, control goes to step 85. If the result is YES, control proceeds to step 84. In step 84, the following processing is carried out.

The degree of similarity of each image data item hit is calculated. Every image data item having a degree of similarity exceeding a given value is displayed on the display device. After finishing the processing of step 84, control goes to step 85. In step 85, a decision is made as to whether it is the processing for searching for similar images. If the result is NO, step 85 is repeatedly carried out. If the result is YES, the processing for searching for similar images is ended. In step 81, if the result is NO, control goes to step 86, where the following processing is executed.

(1) The image database of the DIFS server 3 is searched for data about the shapes of those images, using image magnification and image center coordinates as keywords which have the same image magnification and have center coordinates lying in a tolerable range.

(2) The results of the search are entered in a list or subset S. That is, the results are combined into a subset.

Instep 87, a decision is made as to whether the list S contains members. If the result is NO, control proceeds to step 85. If the result is YES, control goes to step 88.

In step 88, image data forming one member of the list S is extracted to obtain information about the evaluated region (FIG. 43).

In step 89, a decision is made as to whether the region is an evaluated region for which calculations have been already performed. If the result is YES, control goes back to step 87. If the result is NO, control proceeds to step 90, where the following processing is performed.

(1) A specified evaluated region of the accepted SEM image is processed by image processing techniques to calculate normalized amounts of image features for assorting shapes.

(2) Appropriate calculations (e.g., taking the sum of squares or performing the same calculations as used to cause the server to learn of something) on the amounts of features to obtain an evaluation value.

(3) The list S is searched for data about shape sorting, using image magnification, the image center coordinates, and evaluation as keywords. The data about shape sorting have the same image magnification and evaluation values that are in a tolerable range about the found evaluation value.

In step 91, a decision is made as to whether there exists any image data hit by the search. If the result is NO, control goes back to step 87. If the result is YES, control proceeds to step 92. In step 92, every image data item having a degree of similarity exceeding a given value is displayed on the display device. Control then goes back to step 87.

FIG. 44 is a flowchart illustrating the processing performed by the review SEM in accordance with a program stored either in the memory of the engineering workstation (EWS) or in the memory of the SEM controller. FIG. 45 is a flowchart illustrating the processing performed subsequently to the processing of FIG. 44. FIG. 46 illustrates the WAFER INFORMATION INPUT menu of step 103 of FIG. 44. FIG. 47 is a flowchart illustrating the processing performed subsequently to the processing of FIG. 44.

The processing of the review SEM of FIG. 44 is started when the power supply is turned on. In step 101, a MODE SELECT menu is displayed to prompt the user to choose between the automatic wafer information reacting mode and the manual input mode, to choose between the foreign material/defect observation mode and the shape monitoring mode, and to choose between the automatic review mode and the manual review mode. The meanings of these modes are as follows.

(1a) Automatic Wafer Information Reading Mode: The cassette identification number reader 16 reads the bar code BC (FIG. 2) from the label stuck on a side surface of the cassette 13 holding the inspected wafer. An inquiry into the host computer for CIM is made about the read cassette identification number. According to the obtained product number and lot number, information about the wafer held in the cassette 13 is read from the DIFS server 3.

(1b) Manual Wafer Information Input Mode: If no wafer information can be read from the cassette identification code, then information including product number and lot number necessary to read in the wafer information is entered through the WAFER INFORMATION INPUT menu (FIG. 46).

(2a) Foreign Material/Defect Observation Mode: A view, or detailed inspection, is made according to foreign material/defect information read from the DIFS server 3.

(2b) Shape Monitoring Mode: A specified observed point is automatically photographed or its dimensions are measured under specified conditions.

(2c) Shape Monitoring Image Registration Mode: An observed point image whose shape should be monitored an d conditions are manually registered.

(3a) Automatic Mode: The review is automatically made.

(3b) Manual Mode: The review is manually made.

In step 102, a decision is made as to whether the automatic reading mode is selected. If the result is NO, control goes to step 103. In step 103, the menu (FIG. 46) for entering wafer information into the review SEM is displayed. If any input exists, the input data is stored and displayed. That is, the product number of the wafer W, wafer identification number, processing steps used for the wafer, inspection recipe, etc. are allocated to the slots. The processing of this step 103 is similar to the processing of step 3. The menu for entering wafer information as shown in FIG. 46 is similar to the menu shown in FIG. 32.

In step 104, a decision is made according to input data as to whether an inspection should be started or not. This decision depends on whether the "start" is selected from the menu (FIG. 46) for entering wafer information in step 103. If the result is NO, control goes to step 105. If the result is YES, control proceeds to step 106.

In step 105, a decision is made as to whether the processing is ended. This decision depends on whether the "end" is selected from the menu (FIG. 46) for entering wafer information in step 103. If the result is NO, control returns to step 103. If the result is YES, the review is ended.

In step 106, a decision is made as to whether any cassette is set. If the result is NO, control goes to step 107. If the result is YES, control proceeds to step 111 of FIG. 45.

In step 107, the cassette-transporting device 9 (FIG. 2) places the cassette 13 holding the wafer W on the recessed cassette placement portion 7a of the review SEM. The X-positioning cylinder 14 and the Y-positioning cylinder 15 shown in FIG. 2B push the cassette 13 placed on the recessed placement portion 7a in the X- and Y-directions and place the cassette at the front end 7x and left end 7y of the recessed placement portion 7a.

In step 111 of FIG. 45, a decision is made as to whether the processing is an observation of foreign materials or defects. This decision depends on whether the foreign material/defect observation mode or the shape monitoring mode is selected from the menu for selecting a mode in step 101. If the result is YES, control goes to step 112. If the result is NO, control proceeds to step 114.

In step 112, an INSPECTION RESULT DATA request is sent to the DIFS server 3 for each individual slot. Data about hit inspection results is received and allocated to wafers. If two or more data items are hit, it means that same part is inspected twice or more, producing overlapping data items. Therefore, the operator makes a choice and assigns the data to wafers.

In step 113, a decision is made as to whether data about the inspection results have been allotted to every slot used. If the result is NO, control goes back to step 112. If the result is YES, control proceeds to step 114.

In step 114, one wafer is taken from a slot in the cassette 13 and set on the inspected part-holding member 65 (FIGS. 5, 7–9) of the review SEM.

In step 115, a review is made in a manner as described in connection with FIG. 48.

In step 116, a decision is made as to whether the review is finished for every assigned slot. If the result is NO, control goes back to step 114. If the result is YES, control returns to step 117.

In step 117, the cassette 13 is taken out of the recessed placement portion 7a and placed in position by the cassette-transporting device 9 etc. shown in FIG. 2.

The review processing is ended. In step 102, if the result is YES, control proceeds to step 121 of FIG. 47. In step 121, a decision is made as to whether any cassette is set. If the result is No, control goes to step 122. If the result is YES, control proceeds to step 123.

In step 122, the cassette-transporting device 9 (FIG. 2) places the cassette 13 holding the wafer W on the recessed cassette placement portion 7a of the review SEM and aligns the wafer to the front end 7x and left end 7y of the recessed placement portion 7a.

In step 123, the cassette identification number is read from the bar code (FIG. 2) on the cassette. In step 124, an inquiry into the host computer for CIM is made about the read cassette identification number. The product number of the wafer, lot number, wafer identification number, processing steps, recipe name, and other kinds of information about every slot are received and assigned to the slots.

In step 125, a decision is made as to whether the processing is an observation of foreign materials or defects. This decision depends on whether the foreign material/defect observation mode is selected from the MODE SELECTING menu of step 101 that permits a choice between the foreign material/defect observation mode and the shape monitoring mode. If the result is YES, control goes to step 126. If the result is NO, control proceeds to step 127.

In step 126, an INSPECTION RESULT DATA request is sent to the DIFS server 3 for each individual slot. The data includes data about the product number of the wafer W, lot number, wafer identification number, processing steps, etc. Data about hit inspection results is received and assigned to wafers. If two or more data items are hit, it means that same part is inspected twice or more, producing overlapping data items. Consequently, the finally obtained data item is adopted in the automatic mode.

Processing of steps 127–130 is similar to the processing of steps 114–117. FIG. 48 illustrates a subroutine for review processing of steps 115 and 128. When a review is started, the contents of a recipe assigned to the slot is read in step 141. Then, the SEM photography parameters such as accelerating voltage and probe current are tailored to the contents of the recipe.

In step 142, a decision is made as to whether monitoring of shapes is done. This decision depends on the choice between the foreign material/defect observation mode and the shape monitoring mode from the MODE SELECTING menu of step 101. If the result is YES, control goes to step 143.

In step 143, processing for aligning the wafer is performed. This processing is illustrated in the subroutine of the wafer alignment processing of FIG. 49.

In step 144, a decision is made as to whether the processing is registration of the image being monitored. This decision depends on whether the shape monitoring image registration mode is selected from the MODE SELECTING menu of step 101. If the result is NO, control proceeds to step 145. If the result is YES, control goes to step 146.

In step 145, automatic shape monitoring processing is performed according to the recipe. This processing is illustrated in the subroutine of tile automatic shape monitoring processing of FIG. 50.

In step 146, processing f or registering the image being monitored is performed. This processing is illustrated in the subroutine of the monitored image registration processing of FIG. 56.

In step 147, the wafer is taken from the review SEM and returned into the cassette 13.

In step 142, if the result is NO, control goes to step 148. In step 148, files containing the foreign material/defect inspection data assigned to the slots in step 112 or 126 is read into the foreign material/defect position information table.

In step 149, processing for aligning wafers is performed. This processing is similar to the processing of FIG. 143 and illustrated in the subroutine of the wafer alignment processing of FIG. 49.

In step 150, a decision is made as to whether it is a manual mode. This decision depends on the choice between the automatic mode and the manual mode from the MODE SELECTING menu of step 101. If the result is YES, control returns to step 151.

In step 151, processing for manually reviewing defect images is performed. This processing is illustrated in the subroutine of the manual defect image review processing illustrated in FIG. 60.

In step 150, if the result is NO, control proceeds to step 152. In step 152, processing for automatically reviewing defect images is performed. This processing is illustrated in the subroutine of the automatic defect image review processing of FIG. 62.

After the steps 151 and 152, processing of step 147 is performed and then the review is ended.

FIG. 49 illustrates a subroutine of step 143 for processing for aligning wafers.

In step 161, the wafer W is placed and held in position by the inspected part-holding member 65.

In step 162, a decision is made as to whether the wafer is a bare wafer. This decision is made according to the items described in the recipe or preliminary inspection information. If the result is YES, control goes back to step 163.

In step 163, edges of the outer periphery of the wafer are observed. The center of the wafer is found from the arcs of the edges. The deviation of the center is corrected. Then, an orientation flat state or notches formed in the wafer are detected, and the rotation of the wafer is corrected.

In step 164, a specified range is searched for foreign materials by foreign material data. The range is determined according to the recipe or system parameters.

In step 165, a decision is made as to whether two foreign materials spaced from each other by a distance more than a given value have been successfully searched for. If the result is NO, control goes to step 166, where the searched range is extended and then control returns to step 164.

In step 165, if the result is YES, control proceeds to step 167. In step 167, some foreign materials spaced from each other most remotely are selected. The field of view is moved into the point where the foreign material exists. The coordinates of the center of each foreign material are found. The misalignment is corrected to minimize the positional deviation. The processing for aligning wafers is ended.

In step 162, if the result is NO, control proceeds to step 168, where the following processing is carried out.

(1) The field of view being observed is moved into an alignment mark on the wafer W.

(2) Pattern matching with the alignment image is performed. The amount of deviation is stored in memory.

(3) Steps (1) and (2) above are carried out for plural alignment reference points. The deviation of the origin of the wafer and the angular position of the wafer are corrected to minimize the total amount of deviation.

In step 169, a decision is made as to whether a chip alignment is made. This decision depends on the items described in the recipe. If the result is NO, the processing for performing a wafer alignment is ended. If the result is YES, control goes to step 170, where the following processing is executed.

(1) Movement into the alignment mark position within the chip is made.

(2) Pattern matching with the alignment mark image is performed. The deviation is stored in memory.

(3) The steps (1) and (2) above are carried out for plural alignment marks (normally, two marks). The deviation of the origin of the wafer and the angular position of the wafer are corrected to minimize the total amount of deviation. Then, the alignment processing is ended.

FIG. 50 illustrates a subroutine for processing for automatically monitoring shapes of step 145. When this monitoring processing starts, a decision is made as to whether the shape monitoring is done according to the recipe (step 181). If the result is YES, control goes to step 183, where photography flag, observed point information, and length measurement information are obtained according to the recipe. If the result is NO, the DIFS server 3 is searched for photography flag, observed point information, and length measuring information by product number, lot number, wafer identification number, processing steps, observed point information name, etc.

In step 184, information about the initial observed point on the wafer is extracted. In step 185, the stage is moved according to the information about the observed point. In step 186, the following operations are successively executed.

(1) The accelerating voltage, magnification, tilt angle of the sample, angular position of the sample, brightness contrast, focusing, etc. are set according to the information about the photography.

(2) The focus is adjusted. An SEM image is photographed and accepted as an observed image.

(3) A centering operation is performed so that the observed image agrees with the observed point reference image.

In step 187, processing for evaluating the shape is performed. A subroutine of this step 187 is illustrated in FIG. 51.

In step 188, a decision is made as to whether the observation of one point is completed. If the result is NO, control goes back to step 186. If the result is YES, control proceeds to step 189.

In step 189, a decision is made as to whether the shapes of all observed points on the wafer have been photographed. If the result is NO, control goes to step 190.

In step 190, information about the next observed point is extracted. Control returns to step 185. Instep 189, if the result is YES, the processing for automatically monitoring shapes is ended.

FIG. 51 illustrates a subroutine for the processing for evaluating shapes in step 187 of FIG. 50. In step 201 of FIG. 51, an SEM image is accepted. In step 202, a decision is made as to whether there is any information about measurement of lengths. If the result is YES, the processing (step 203) for automatically measuring lengths is performed, and then control goes to step 204.

If the result is NO, control directly proceeds to step 204.

In step 204, a decision is made as to whether the photography flag is set (ON) or reset (OFF). If the flag is set, control goes to step 205, where a decision is made as to whether there exist any length measurement results. If the result is NO, the processing for evaluating shapes is ended. If the result is YES, the next processing is conducted in step 206.

(1) The results of the measurement of the lengths are registered in the DIFS server 3.

(2) At this time, product number, lot number, wafer identification number, processing steps, etc. are registered as keywords.

After completion of the processing of step 206, the processing for evaluating shapes is ended. In step 204, if the result is that the flag is set (ON), control goes to step 207.

In step 207, the processing for sorting shapes is performed. A subroutine of this step 207 is illustrated in FIG. 55. In step 208, the following processing is carried out.

(1) The results of the measurement of the lengths or the results of the sorting of shapes are registered in the DIFS server 3, together with the accepted SEM image.

(2) At this time, product number, lot number, wafer identification number, processing steps, etc. are registered as keywords.

After completion of the processing of step 208, the processing for evaluating shapes is ended.

Figure 53A:
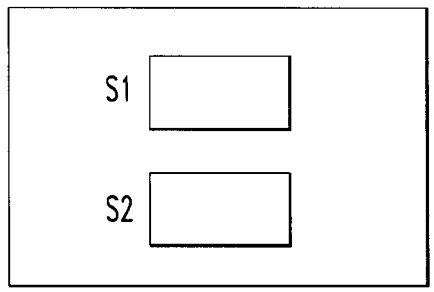
FIGS. 53A–53C are diagrams illustrating processing of the flowchart of FIG. 52.

FIG. 52 illustrates the subroutine of the processing (step 203) for automatically measuring lengths. FIGS. 53 and 54 illustrate the processing of the flowchart of FIG. 52.

In step 211 of FIG. 52, information about measurement of lengths is obtained. In step 212, a decision is made according to the recipe as to whether it is a measurement of a distance on the X-Y plane. If the result is YES, control goes to step 213, where the following processing is performed.

(1) Th e coordinates of the positions of two opposite ends of a line segment and a method of measurement are taken from the information about measurement of lengths.

(2) Edges of the object under inspection are detected by a method specified by the length measurement method by reference to the coordinates of the positions of the opposite ends of the line segment.

(3) The length of the line segment is found from the detected edges at the opposite ends of the line segment.

(4) Where the length measurement method commands averaging, the steps (2) and (3) above are repeated for the specified regions. Averaging processing is carried out to obtain results of the measurement of the line segment.

In step 214, a decision is made as to whether processing is done for all the information about the measurement of lengths. If the result is NO, control returns to step 211. In step 212, if the result is NO, control goes back to step 215, where the following processing is executed.

(1) Regions of height-measured planes S1 and S2 (FIG. 53A) are extracted from the information about the measurement of lengths.

Figure 53B:
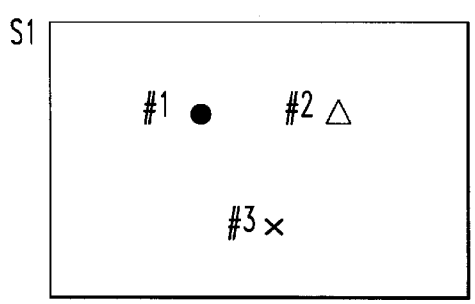

(2) The specified height-measured plane S1 is searched for minute singular points (such as scratches, dust, and nonuniformities) used for measurements of planes. The coordinates of the singular points are put in an array $P_1$ (FIG. 53B)

Figure 53C:
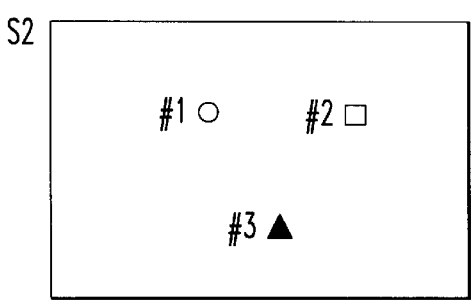

(3) Similarly, the specified height-measured plane S2 is searched for minute singular points used for measurements of planes. The coordinates of the singular points are put in an array $P_2$ (FIG. 53C).

Control then proceeds to step 216, where the stage is tilted at an angle of α°. In step 217, an SEM image is accepted. In step 218, the following processing is carried out.

Figure 54A:
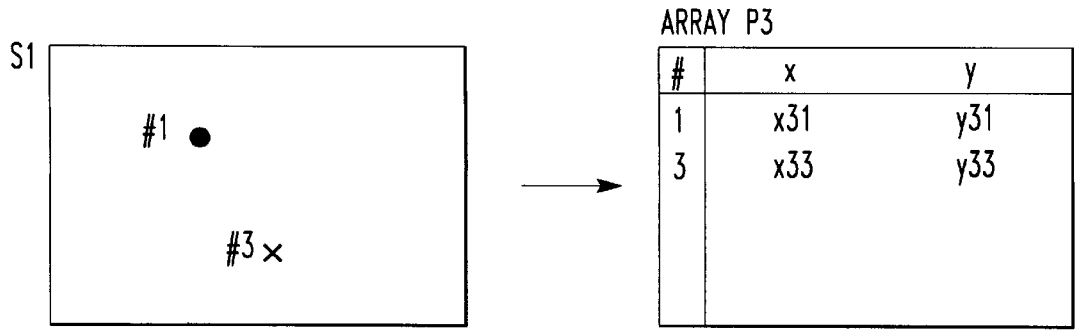
FIGS. 54A–54D are diagrams illustrating processing of the flowchart of FIG. 52.

(1) The specified height-measured plane S1 is searched for points corresponding to the singular points stored in the array $P_1$. The discovered singular points are put in an array $P_3$ (FIG. 54A).

Figure 54B:
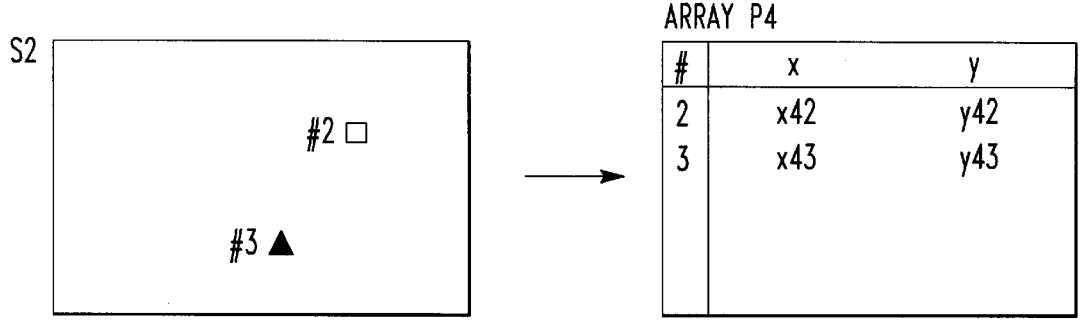

(2) Similarly, the specified height-measured plane S2 is searched for points corresponding to the singular points stored in the array $P_2$. The discovered singular points are put in an array $P_4$ (FIG. 54B).

(3) If any corresponding point is found neither in the array S1 nor S2, the measurement is judged to be impossible to perform.

Control then goes to step 219, where the following processing is performed.

Figure 54C:
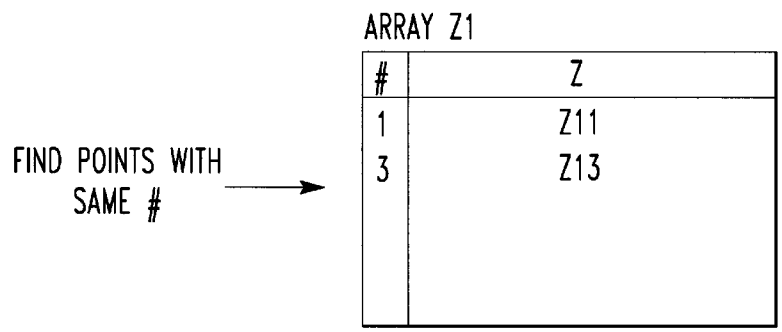

(1) Those points of the array $P_1$ which correspond to all points in the array $P_3$ are extracted. The height taken in the Z-direction is calculated from the information about these pairs of positions and put in an array $Z_1$ (FIG. 54C).

Figure 54D:
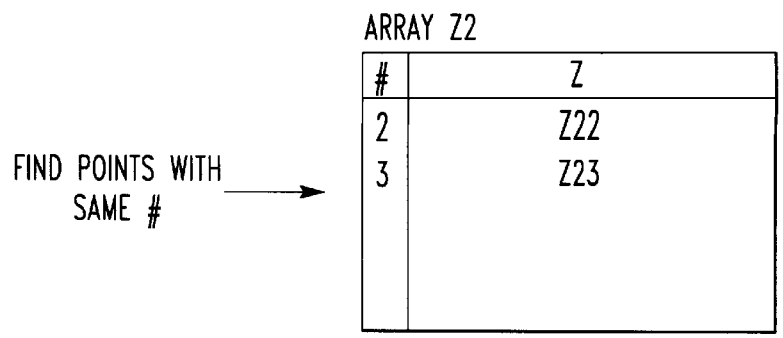

(2) Similarly, those points of the array $P_2$ which correspond to all points in the array $P_4$ are extracted. The height taken in the Z-direction is calculated from the information about these pairs of positions and put in an array $Z_2$ (FIG. 54D)

(3) (average of array $Z_1$)–(average of array $Z_2$) ={($Z_{11}$+$Z_{13}$)/2}–{($Z_{22}$+$Z_{23}$)/2} is calculated to obtain the final result of measurement of the height.

After completion of the processing of step 219, control goes to step 214. In step 214, if the result is YES, control proceeds to step 220, where the results of the measurement are sent to the DIFS server 3 and registered in the length measurement database of the server 3. Then, the processing for automatically measuring lengths is ended.

FIG. 55 illustrates a subroutine for processing for sorting shapes of step 207 of FIG. 51. In step 231 of FIG. 55, the following processing is performed.

(1) The whole surface of the SEM image accepted in step 201 or a specified evaluated region is processed by image processing techniques to calculate normalized amounts of image features for sorting shapes.

(2) Appropriate calculations (e.g., taking the sum of squares or performing the same calculations as used to cause the server to learn of something) are performed to obtain an evaluation value.

(3) The shape sorting database of the DIFS server 3 is searched for shape sorting data, using image magnification and image center coordinates, and the evaluation value as keywords. The shape sorting data have the same image magnification. The coordinates of the centers are in a tolerable range. The data have evaluation values lying in an allowable range about the found evaluation value.

On completion of the processing of step 231, control goes to step 232, where a decision is made as to whether there exist any data items hit by the search. If the result is YES, control goes to step 233, where the following processing is carried out.

(1) The degrees of similarity of the hit shape sorting data items are calculated. Those of the shape sorting data items which have the highest degree of similarity are selected.

(2) The sort codes of the selected shape sorting data items are extracted to obtain the result of the sorting.

In step 232, if the result is NO, control goes to step 234, where a sort code (e.g., ABNORMAL FORM) indicating an image having an abnormal form is taken as the result of the sorting. On completion of the step 233 or 234, the processing for sorting shapes is ended.

Figure 48:
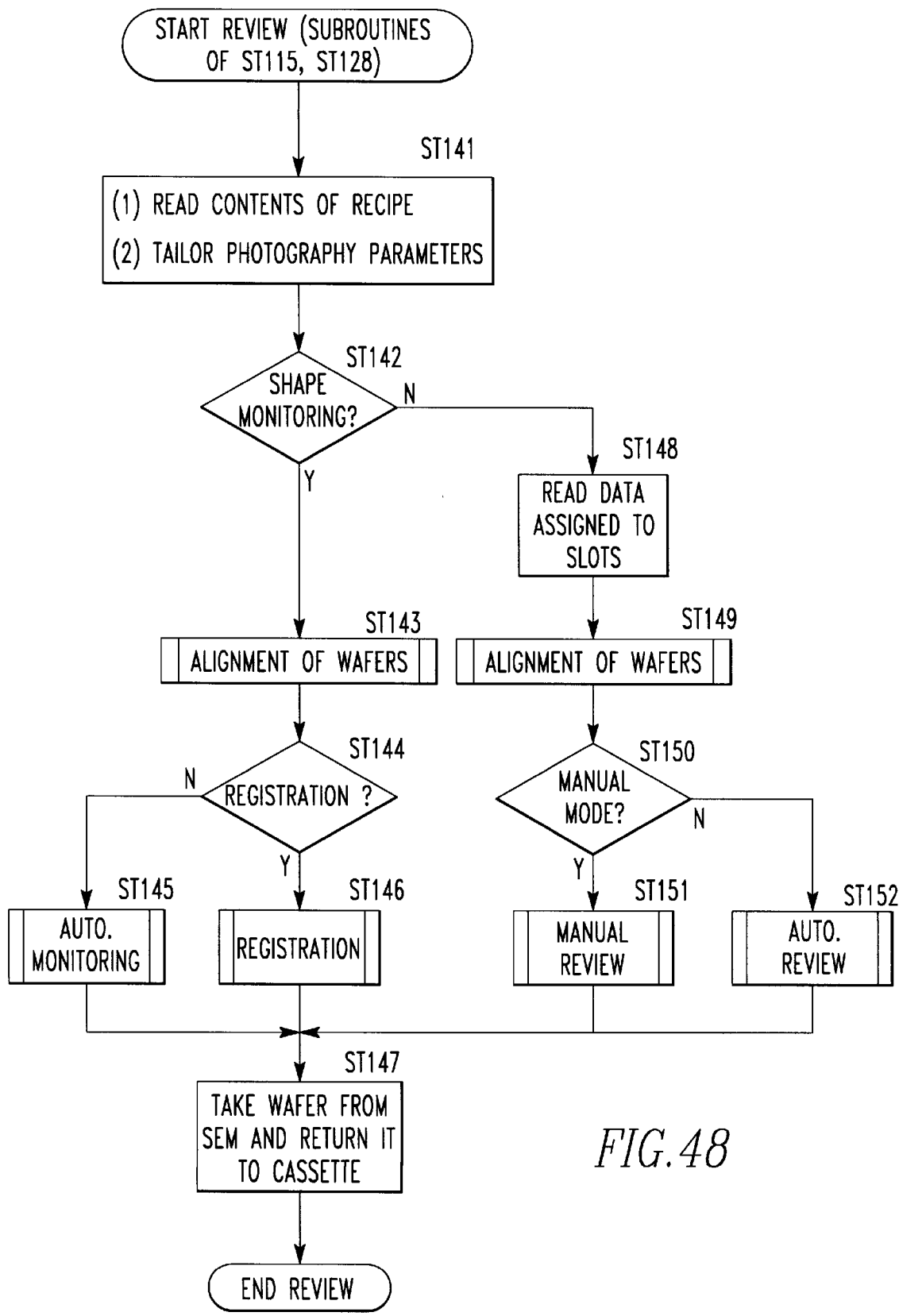
FIG. 48 is a flowchart illustrating a subroutine of steps 115 and 128 to make a review.
Figure 57:
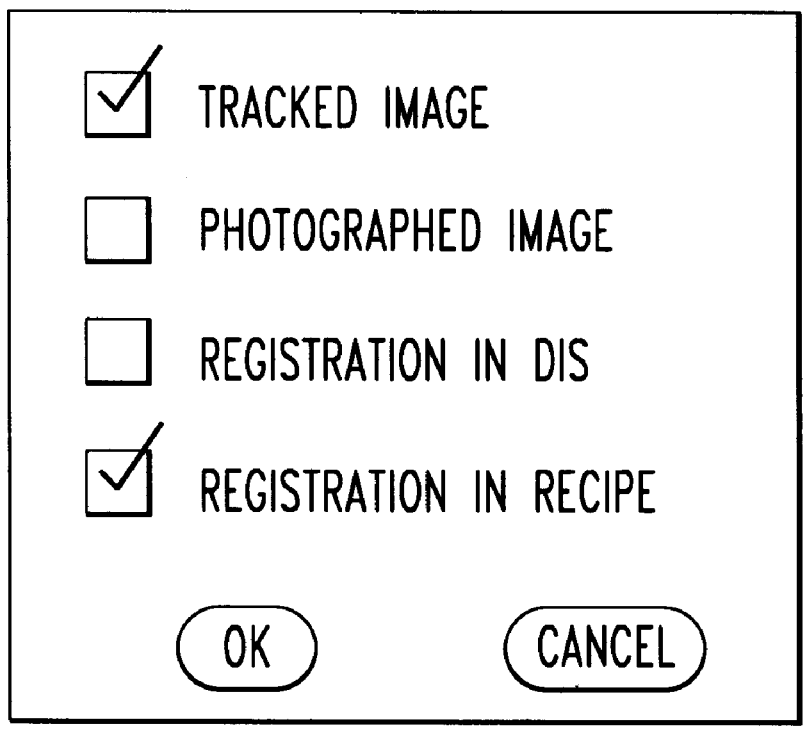
FIG. 57 is a diagram showing one example of a REGISTRATION INPUT menu displayed in step 244 of FIG. 56.

FIG. 56 illustrates the former half of the subroutine of the processing for registering monitored images of FIG. 48. FIG. 57 shows an example of a REGISTRATION INPUT menu displayed in step 244 of FIG. 56. FIG. 58 illustrates the processing performed subsequently to the processing of FIG. 56.

In step 241 of FIG. 56, the stage is moved into the observed point where shapes are monitored. In step 242, the following processing is executed.

(1) The field of view, focusing, accelerating voltage, magnification, tilt angle of the sample, angular position of the sample, brightness, contrast, etc. are set. The operator checks the shape on the CRT screen.

(2) An SEM image is photographed and accepted as an observed image.

In step 243, the REGISTRATION INPUT menu (FIG. 57) is displayed. In step 244, a decision is made as to whether the image being observed is registered. This decision depends on whether the operator has clicked on the "OK" icon of the REGISTRATION INPUT menu (FIG. 57). If the result is NO, control returns to step 242. If the result is YES, control proceeds to step 245.

In step 245, a decision is made as to whether the image is an image whose shape should be photographed. If the result is YES, control goes to step 246, where the photography flag is set (ON).

In step 247, a sorted and evaluated region is established, if necessary. The default sorted and evaluated region is the whole screen. Control then proceeds to step 251. In step 245, if the result is NO, control goes to step 248, where the photography flag is reset (OFF).

In step 249, a decision is made as to whether the processing is registration of information about measurement of lengths. This decision depends on whether the "length measurement information registration" is selected from the REGISTRATION INPUT menu (FIG. 57).

In step 249, if the result is YES, control goes to step 250, where information about length measurement is created. Then, control proceeds to step 251. If the result is NO, control directly goes to step 251.

In step 251 of FIG. 58, a decision is made as to whether registration into the DIFS server 3 is made. This decision depends on whether registration into the DIFS server is selected from the REGISTRATION INPUT menu (FIG. 57) or not. If the result is YES, control goes to step 252, where the following processing is performed.

(1) Photography flag, sorted and evaluated region, information about measurements of lengths, and information about an observed point are registered in the DIFS server 3.

(2) On registration, various items (such as product number, lot number, wafer identification number, processing steps, information about observed points, and name) are established as keywords.

In step 251, if the result is NO, control goes to step 253, where photography step, sorted and evaluated region, information about measurement of lengths, and information about observed points are added to the recipe, which in turn is stored in the memory of the engineering workstation (EWS) of FIG. 11 or in a disk.

On completion of the processing of step 252 or 253, control goes to step 254. In this step 254, a decision is made as to whether observation of one point is complete. If the result is NO, control goes to step 255, where information about the next photography is obtained. Then, control returns to step 242.

In step 254, if the result is YES, control proceeds to step 256, where a decision is made as to whether the shapes of all monitored points on the wafer have been photographed or registered. If the result is NO, control goes to step 257, in which information about the next observed point is read. Control then returns to step 241. In step 256, if the result is YES, the processing for registering a monitored image is ended.

FIG. 62 illustrates a subroutine illustrating processing (step 250 of FIG. 56) for creating information about measurement of lengths. In step 260 of FIG. 62, a menu is displayed to prompt the user to select a desired length measuring mode, i.e., a choice between measurement of a length on the X-Y plane and measurement of a height.

In step 261, a decision is made as to whether the processing is a measurement of a length on the X-Y plane. If the result is YES, control goes to step 262, where the menu for prompting the user to enter a measurement position is displayed. Then, control proceeds to step 263.

In step 263, a decision is made as to whether an input operation is complete. This decision depends on, for example, whether the positions of both ends of the measured point are specified with the mouse. If the result is NO, control goes back to step 262. If the result is YES, control proceeds to step 264, where a menu for prompting the user to select a desired method of measuring lengths is displayed. Then, control goes to step 265.

In step 265, a decision is made as to whether the selection is complete. If the result is NO, control returns to step 264. If the result is YES, control proceeds to step 266.

In step 266, the coordinates of both ends of the line segment and a method of measurement of lengths are added to the information about measurement of lengths.

In step 267, a decision is made as to whether every point to be measured has been processed or not. If the result is NO, control returns to step 260.

In step 261, if the result is NO, control proceeds to step 268, where menus for entering planes S1 and S2 for height measurement and input data are displayed and stored in memory. Rectangular, elliptical, or any other arbitrary form is specified as the planes S1 and S2.

In step 269, a decision is made as to whether the input operation is complete. This decision depends on the key operated on completion of the input operation for the planes S1 and S2 or whether any icon is selected. If the result is NO, control returns to step 268. If the result is YES, control proceeds to step 270.

In step 270, information about the planes S1 and S2 is added to the information about measurement of lengths. Then, control goes to step 267. In step 267, if the result of the decision is YES, the processing for creating information about measurement of lengths is ended.

Figure 61:
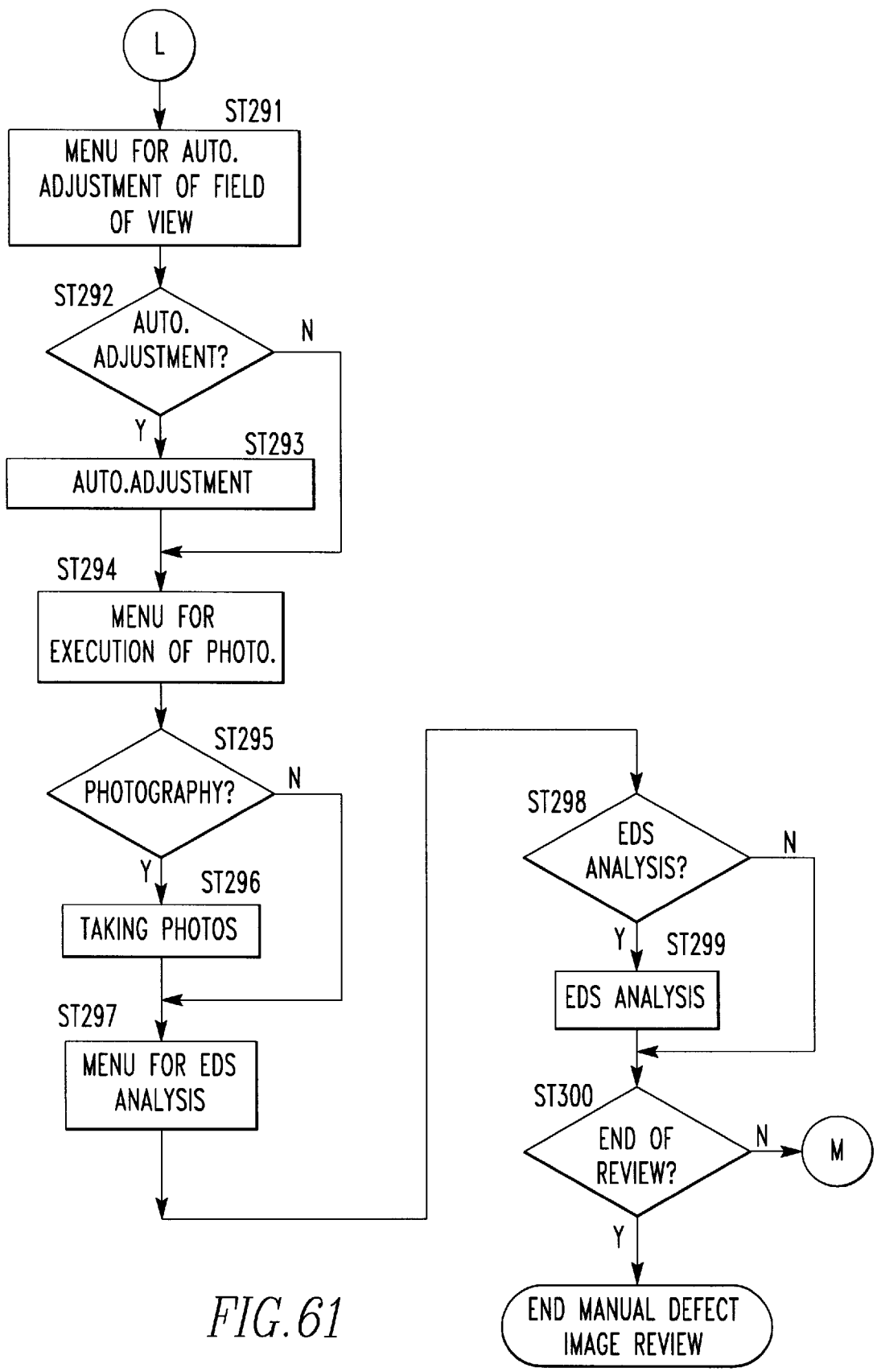
FIG. 61 is a flowchart illustrating processing performed subsequently to the processing of FIG. 60.

FIG. 60 is a subroutine for illustrating a manual review (step 151) of a defect image. FIG. 61 illustrates processing performed subsequently to the processing of FIG. 60.

In step 271, a menu is displayed to prompt the user to select a desired defect point to be inspected from the foreign material/defect inspection data read in step 148.

In step 272, the select ed defect point is moved into the inspection position. In step 273, the automatic centering is performed. This processing is illustrated in the subroutine of the automatic centering processing of FIG. 65.

In step 274, a menu for selecting tilt, rotation, and cancel is displayed. In step 275, a decision is made as to whether the tilt is selected. If the result is YES, control goes to step 276.

In step 276, a menu for prompting the user to enter a tilt angle is displayed. This menu contains an input submenu for entering the tilt angle of the tilt stage 37 (FIGS. 5 and 7) and an icon for selecting the end of an input operation. Also, data about the input (entered tilt angle) is displayed.

In step 277, a decision is made as to whether any tilt angle is entered. This decision depends on whether the icon for ending the input is selected or not. If the result of the decision is NO (i.e., "Input End" icon is not selected), control returns to step 276. If the result is YES, control proceeds to step 278.

In step 278, processing for automatically tracking a tilted image is performed. This processing is illustrated in the subroutine of the automatic tilted image tracking processing of FIG. 69.

In step 279, a decision is made as to whether the tilting processing is ended. This decision depends on a choice between an icon for selecting the end of the tilting processing and an icon for continuing the processing. If the result of the decision is NO, control goes back to step 276. If the result is YES, control proceeds to step 280.

In step 275, if the result is NO (i.e., tilting is not selected), control goes to step 281, where a decision is made as to whether rotation is selected or not. This decision depends on whether rotation is selected from a menu of step 274 for a choice among tilt, rotation, and cancel. If the "cancel" is selected from the menu of step 274, the result of the decision made in step 281 is NO. Control then goes to step 280. If the result of the decision made in step 281 is YES, control proceeds to step 282.

In step 282, a menu for prompting the user to enter an angle through which table is rotated is displayed. This menu contains an input submenu for entering an angle through which the rotating table 64 (FIGS. 5 and 7) is rotated and an icon for selecting the end of the input operation. Furthermore, data about the input (the angle through which the table is rotated) is displayed.

In step 283, a decision is made as to whether any angle is entered or not. This decision depends on whether the icon for ending the input is selected or not. If the result is NO (i.e., the end of the input is not selected), control goes back to step 282. If the result is YES, control proceeds to step 284.

In step 284, the processing for automatically tracking a rotated image is performed. This processing is illustrated in the subroutine of the automatic rotated image tracking processing of FIG. 68.

In step 285, a decision is made as to whether the rotating processing is ended. This decision depends on a choice between an icon for selecting the end of the rotating processing and an icon for selecting continuation of the processing. If the result of the decision is NO, control goes back to step 282. If the result is YES, control proceeds to step 280.

In step 280, a decision is made as to whether processing for tilting or rotation is ended. If the result is NO, control goes back to step 274. If the result is YES, control proceeds to step 291 of FIG. 61.

In step 291 of FIG. 61, a menu is displayed to permit the user to select execution of processing for automatically adjusting the field of view. In step 292, a decision is made as to whether the execution of the processing for automatic adjustment of the field of view is selected. If the result is YES, control goes to step 293. If the result is NO, control proceeds to step 294.

In step 293, the processing for automatically adjusting the field of view is carried out. This processing is illustrated in the subroutine of the processing (FIG. 67) for automatically adjusting the field of view. In step 294, a menu is displayed to permit the user to select execution of photography of a defect image. In step 295, a decision is made as to whether the execution of photography of a defect image is selected. If the result is NO, control goes to step 297. If the result is YES, control goes to step 296, where the processing for photographing a defect image is carried out. This processing is illustrated in the subroutine of the foreign material/defect image photographing processing of FIG. 70.

In step 297, a menu is displayed to permit the user to select execution of an EDS analysis. In step 298, a decision is made as to whether the execution of an EDS analysis is selected. If the result of the decision is NO, control goes to step 300. If the result is YES, control goes to step 299, where an EDS analysis is performed by the sequence described below.

(1) The composition of a central portion of a foreign material or defect and the composition of its outer portion are analyzed.

(2) If necessary, the spectrum of the outer portion is subtracted from the spectrum of the central portion to find a spectrum of only the foreign material or defect. The composition of only the foreign material or defect is analyzed.

In step 300, a decision is made as to whether the review is complete. This decision depends on whether the review of all slots to which data about the results of inspections are allotted in step 113 of FIG. 45 is complete. If the result of the decision is NO, control goes back to step 271. If the result is YES, the processing for manually reviewing a defect image is ended.

Figure 63:
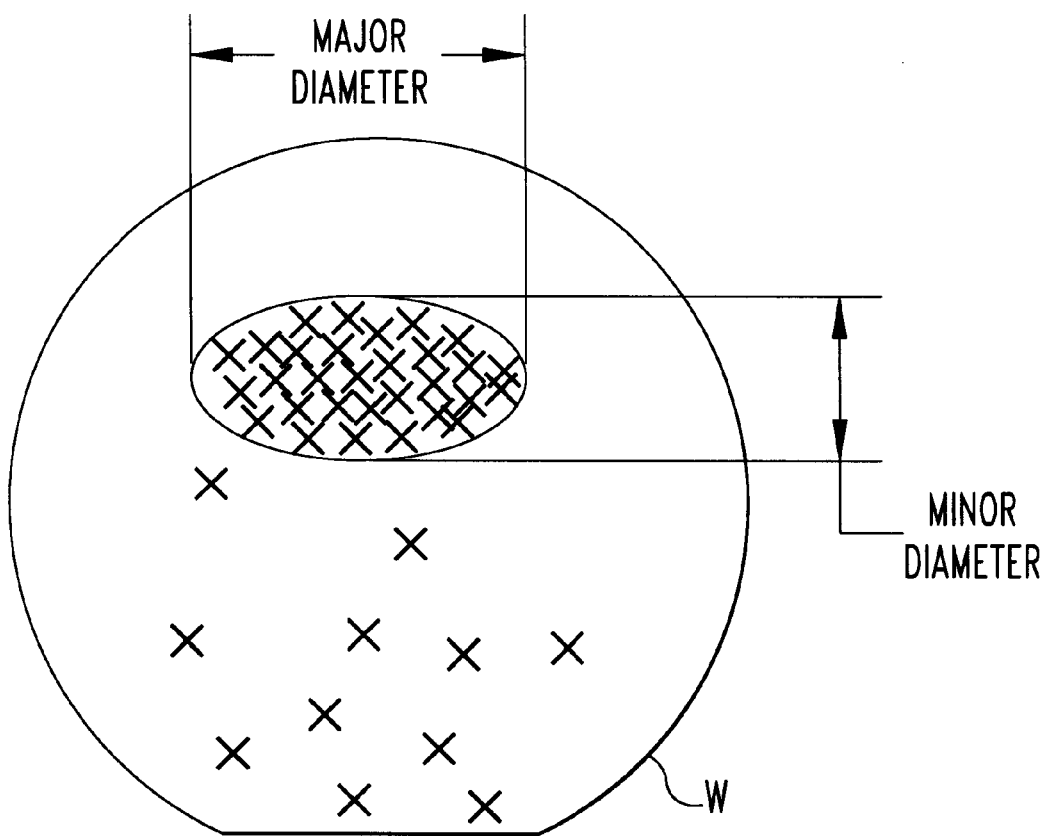
FIG. 63 is a diagram illustrating a distribution profile parameter of grains of defects.

FIG. 62 illustrates a subroutine of the automatic defect image review processing of step 152 illustrated in FIG. 48. FIG. 63 illustrates parameter of the profile of the distribution of grains of defect on the wafer W.

When the processing for automatically reviewing a defect image is started, control goes to step 311, where grains of foreign material or defect are extracted, and feature parameters of the grains are found. The feature parameters of the grains are as follows:

(1) average defect density=$N/\pi r^2 \cdot t$, where N is the number of defects within a radius of r and $\pi r^2 \cdot t$ is an area.

(2) distribution profile parameters (such as major diameter, minor diameter, area, and circumference)

For example, the major diameter of a distribution profile parameter is the major diameter (FIG. 63) of an ellipse approximating a region having an average defect density larger than the average value.

(3) a single isolated foreign material or defect within a radius of R (4) others In step 312, a defined rule base is searched for a rule having a hypothetical portion that becomes true if the found feature parameters are substituted. For the rule base, see "(C71) Intelligent Defect Information Processing Means C71 (FIG. 27)" described above.

In step 313, an execution sentence of the rule becoming true is executed, and grains are narrowed down to obtain those to be photographed. In step 314, the processing for automatically photographing foreign material or defect is processed. This processing is illustrated in a subroutine of the automatic foreign material/defect photographing processing of FIG. 64.

In step 315, a decision is made as to whether every point narrowed down has been photographed. If the result of the decision is NO, control goes back to step 314. If the result is YES, the processing for automatically reviewing a defect image is ended.

FIG. 64 illustrates a subroutine of the automatic foreign material/defect photographing processing of step 314 illustrated in FIG. 62. In FIG. t4, when the processing for automatically photographing foreign material or defect is started, control proceeds to step 321, an here a point of foreign material or defect is moved into the inspect ion position.

In step 322, the processing for automated centering is executed. This processing is illustrated in a subroutine of the automatic centering processing of FIG. 65. In step 323, the processing for automatically adjusting the field of view is carried out. This processing is illustrated in a subroutine of the automatic field of view adjusting processing of FIG. 67.

In step 324, the tilt angle of the tilt stage 37 and the angle through which the table 64 is rotated are read from photographic conditions (such as tilt angle, angle through which the table is rotated, and magnification) defined in the execution sentence of the rule base.

In step 325, a decision is made as to whether the defined angle through which the table is rotated is equal to 0° or not. If the result is YES, control proceeds to step 327. If the result is NO, control goes to step 326, where the processing for automatically tracking a rotated image is performed. This processing is illustrated in a subroutine of the automatic rotated image tracking processing of FIG. 68.

Control then goes to step 327, where a decision is made as to whether the tilt angle of the recipe is 0° or not. If the result of the decision is YES control goes to step 329. If the result is NO, control proceeds to step 328, where processing for automatically tracking a tilted image is performed. This processing is illustrated in a subroutine of the automatic tilted image tracking processing of FIG. 69. Control then goes to step 329, in which the processing for automatically photographing foreign material or defect is executed. This processing is illustrated in a subroutine of the foreign material/defect photographing processing of FIG. 70.

In step 330, a decision is made as to whether an EDS analysis is made. This decision depends on whether the execution sentence of the rule base specifies an EDS analysis. If the result is NO, the processing for automatically photographing foreign material or defect is ended. If the result is YES, control goes to step 331, where an automatic EDS analysis is made by the following sequence.

(1) A region of foreign material or defect is recognized by image processing techniques.

(2) The composition of the center of the foreign material or defect is analyzed. Also, the composition of an outer portion of the foreign material or defect is analyzed.

(3) If necessary, the spectrum of the outer portion is subtracted from the spectrum of the central portion to find a spectrum of only the foreign material or defect. The composition of only the foreign material or defect is analyzed.

(4) The results of the analysis are registered in the DIFS server.

On completion of the processing of step 331, control goes to step 332, where the results are registered in the DIFS server 3 and then the processing for automatically photographing foreign material or defect is ended.

FIG. 65 illustrates a subroutine for step 273 of FIG. 60 and for the automatic centering processing of step 322 of FIG. 64. This automatic centering processing is also executed in steps 363, 372, and 382 described later.

When the automatic centering processing of FIG. 65 is started, control goes to step 341, where processing for adjusting the image quality of an SEM image is carried out. This processing is illustrated in the subroutine for the SEM image quality adjusting processing of FIG. 66. In step 342, the following processing is carried out.

(1) An SEM image is accepted (i.e., digital image data is stored in memory).

(2) The coordinates of the center of foreign material or defect are found by image processing techniques.

(3) The electron beam or stage is moved to bring the center of the foreign material or defect into the screen center. This movement is made by moving the inspection location for the wafer W into the scanning center by the use of the X-deflection coil F6 and Y-deflection coil F7.

In step 343, the processing for adjusting the image quality of the SEM image is carried out. This processing is illustrated in a subroutine for the SEM image quality adjusting processing of FIG. 66. Thus, the processing for automatic centering ends.

Figure 66:
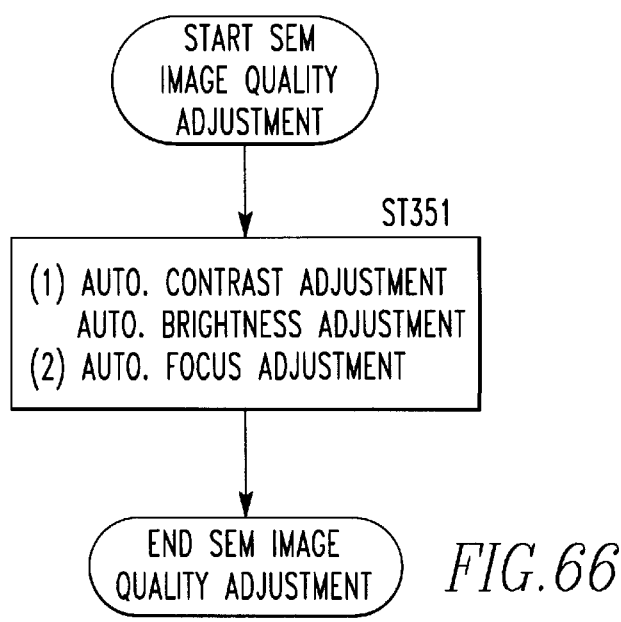
FIG. 66 is a flowchart illustrating subroutines of steps 341 and 343 of FIG. 65 to adjust SEM image quality, the subroutines being executed also in step 361.

FIG. 66 illustrates a subroutine for the SEM image quality adjusting processing of steps 341 and 343 of FIG. 65. This image quality adjusting processing is also executed in step 361 described later. When the SEM image quality adjusting processing of FIG. 66 begins, control goes to step 351, where the following steps are successively performed.

(1) Automatic contrast adjustment and automatic brightness adjustment are performed.

(2) Automatic focusing adjustment is made.

If the electron beam is not focused sufficiently, the steps (1) and (2) above can be repeatedly carried out. After completion of step 351, the processing for adjusting the image quality of an SEM image is ended.

FIG. 67 is a subroutine for the automatic field of view adjusting processing of step 293 of FIG. 61 and of step 323 of FIG. 64. When the automatic field of view adjusting processing starts, control goes to step 361, in which the SEM image quality adjusting processing is performed in the same way as the processing already described in connection with FIG. 66. In step 362, the following steps are successively executed.

(1) An SEM image is accepted.

(2) The size of a foreign material or defect portion is found by image processing techniques.

(3) The magnification is adjusted so that the foreign material or defect portion assumes an appropriate size on the display screen.

In step 363, the automatic centering processing is performed. This processing is illustrated in FIG. 65. After completion of this step 363, the automatic field of view adjusting processing is ended.

FIG. 68 is a subroutine for processing for automatically tracking a rotated image, the processing being illustrated in step 284 of FIG. 60 and in step 326 of FIG. 64. When the processing for automatically tracking a rotated image commences, control goes to step 371, where the rotating table 64 is rotated through a given angle stored in the recipe. For example, this angle is 5°. This angle can be determined by the following method from an amount of movement of an image when it is rotated through a minute angle (e.g., 0.1°).

In step 372, the processing for automatic centering is performed. This processing is illustrated in FIG. 65. In step 373, a decision is mace as to whether a desired angular position is reached. This angular position is specified in the recipe.

If the result of the decision made in step 373 is NO, control goes back to step 371. If the result is YES, the processing for automatically tracking a rotated image is ended.

FIG. 69 is a subroutine for the processing for automatically tracking a tilted image, the processing being illustrated in step 278 of FIG. 60 and in step 328 of FIG. 64. When the processing for automatically tracking a tilted image is started, control goes to step 381, where the tilt stage 37 is tilted at a given angle recorded in the recipes (say, 5°).

In step 382, the processing for automatic centering is carried out. This processing is illustrated in FIG. 65. In step 383, the thickness of a sample is corrected, using an amount of correction made for centering. In FIG. 26, the height, or a dimension taken in the direction of thickness, is given by $z=\delta/\sin \alpha$, where $\alpha$ is a distance traveled during the automatic centering processing of step 382 and $\alpha$ is a tilt angle made in step 381.

Then, a decision is made as to whether a desired tilt angle is reached (step 384). This tilt angle is specified in the recipe. If the result of the decision made in step 384 is NO, control goes back to step 381. If the result is YES, the processing for automatically tracking a tilted image is ended.

FIG. 70 is a subroutine for the processing for photographing foreign material or defect, the processing being illustrated in step 296 of FIG. 61 and in step 329 of FIG. 64. When this processing for automatically photographing foreign material or defect is started, control proceeds to step 391, where an SEM image is accepted. In step 392, the processing for sorting defects is performed. This processing is illustrated in the subroutine of FIG. 71 for automatically sorting foreign materials and defects.

In step 393, image information and the results of sorting are sent to the DIFS server to register them in this server. In step 394, a decision is made as to whether the size of a defect should be measured. If the result is NO, the processing for automatically photographing foreign material or defect is ended. If the result is YES, control proceeds to step 395.

In step 395, the size (length taken in the X-direction, length taken in the Y-direction, area, etc.) on the X-Y plane are found from the amount of features, which in turn is found in defect sorting of step 395. Data about the found size is sent to the DIFS server 3. In step 396, the height of the defect portion is measured. The results are transferred to the DIFS server 3. The processing for automatically photographing foreign material or defect is ended.

Figure 71:
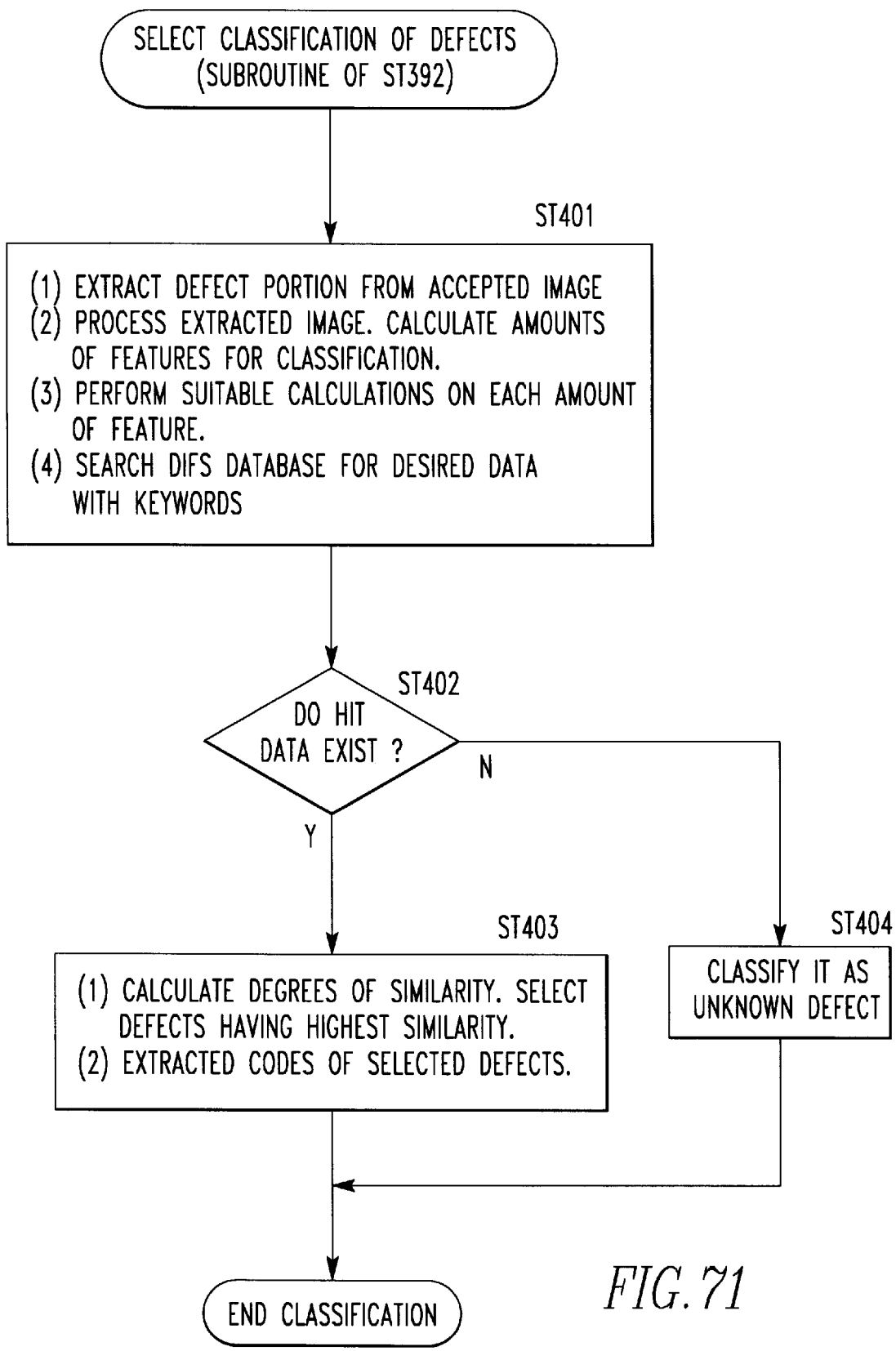
FIG. 71 is a flowchart illustrating a subroutine of step 392 of FIG. 70 to automatically classify foreign materials and defects.

FIG. 71 is a subroutine for processing of step 392 of FIG. 70 for sorting defects. In step 401 of FIG. 71, the following processing is carried out.

(1) A defect portion is extracted from an accepted SEM image.

(2) Normalized amounts of features used for defect sorting are calculated by image processing of the extracted image of the defect portion.

(3) Appropriate calculations (e.g., taking the sum of squares or performing the same calculations as used to cause the server to learn of something) are performed to obtain an evaluation value.

(4) The shape sorting database of the DIFS server 3 is searched for shape sorting data, using the image magnification and the evaluation value as keywords. The shape sorting data have the same image magnification. The coordinates of the centers are in a tolerable range. The data have evaluation values lying in an allowable range about the found evaluation value.

In step 402, a decision is made as to whether there exists any data hit by the search. If the result is NO, control goes to step 403. In step 403, the following processing is performed.

(1) The degrees of similarity of hit sorting data items about defects are calculated. Data items having the highest degree of similarity are selected. In computing the degrees of similarity, an appropriate evaluation function is used. For this purpose, the sum of squares of the differences between the amounts of features is calculated. The data item having the minimum value is taken as a data item having the highest degree of similarity. For calculation of degrees of similarity, refer to "(C8) Defect Sorting Means C8 (FIGS. 28, 29, and 30)" described above.

(2) The sort code of the selected defect sorting data item is extracted and used as the result of sorting.

In step 402, if the result of the decision is NO, control returns to step 404, where images incapable of being classified are given a sort code (e.g., UNKNOWN DEFECT) that is used as a sorting result. When the step 403 or 404 ends, the processing for sorting defects is ended.

Modified Embodiments

While the preferred embodiments of the part-inspecting system in accordance with the present invention have been described in detail, the invention is not limited to such embodiments but rather various changes and modifications are possible within the scope of the invention delineated by the appended claims. Modified embodiments of the invention are given below.

(H01) Device number, lot number, etc. can be printed on a label stuck on the cassette 13, as well as cassette number. In this case, the DIFS database can be searched for wafer information by device number or lot number read by the cassette identification reader 16, and the found wafer information can be read in.

(H02) The preliminary inspecting equipment (1, 2) of the part-inspecting system in accordance with the present invention can be dispensed with.

(H03) In the part-inspecting system in accordance with the present invention, defect information obtained by the review SEM can be stored in a database incorporated in the review SEM. In this case, the DIFS server can be omitted.

(H04) The cassette identification number reader for reading a bar code from a label on the cassette 13 can be omitted. In this case, requisite information needs to be entered manually.

(H05) Instead of the review SEM of the above embodiments, an optical review apparatus such as a confocal laser microscope can be used.

(H06) The part-inspecting system in accordance with the present invention can be composed of the preliminary inspecting equipment (1, 2), the optical review apparatus, and the review SEM.

The part-inspecting system in accordance with the present invention yields the following advantages.

(E01) It is possible to reduce the amount of operation that the operator must perform on the part-inspecting system.

(E02) Where the part search information input means is made of a means for reading a cassette identification number from a cassette holding a wafer, preliminary inspection information about the inspected part can be automatically read from the inspected part information database by the preliminary inspection information reading means.

(E03) A computer capable of accessing the inspected part information database can utilize the review information stored by the review information registration means in the inspected part information database.

(E04) Defects that need to be reviewed can be automatically selected from preliminary inspection information by the intelligent defect information processing means. This can reduce the amount of work that the operator must perform on the review SEM. Hence, the efficiency of the work can be enhanced.

(E05) The misalignment correcting means can bring the x- and y-coordinates of the part position reference position for an inspected part on the preliminary inspection apparatus into agreement with the X- and Y-coordinates of the part position reference point on the review SEM. Thus, the X- and Y-coordinates of a defect in the inspected part agree with the x- and y-coordinates. In this case, when the defect is moved into the review position on the XY-coordinate system on the review SEM, the x- and y-coordinates can be used intact.

Where the inspected part is a bare wafer having an arc, any deviation of the center can be corrected by detecting plural coordinates on the arc of the bare wafer by the misalignment correcting means for an unpatterned wafer and calculating the coordinates of the center of the wafer from the detected coordinates. Rotation of the wafer can be corrected by detecting an orientation flat state or notches.

(E06) A selected defect can be automatically moved into the review position by moving the XY-table (56+63) by means of the automatic defect point moving means according to positional information contained in the preliminary inspection information. In consequence, the amount of work that the operator must perform in operating the review SEM can be reduced.

(E07) The inspected part information database contains information about an observational position set for the inspected part, a reference image that is a normal scanning image in this observational position, and observational information including information about the magnification. The automatic profile monitoring means compares an image actually obtained from the observation position by scanning with the reference image. Consequently, it is easy to judge whether any defect is present on the scanning image Furthermore, defects can be categorized.

(E08) Since observational information contains information useful in identifying a portion whose lengths should be measured, the automatic length measuring means can automatically measure the lengths on the actually displayed image in the observational position identified by the information described above. An observational position is established on an inspected part. The thickness of the portion whose dimensions should be measured can be automatically found by finding two opposite end surfaces of the measured portion on the actually scanned image, taken in the direction of thickness, from a measured amount of movement of the scanned image when the tilt stage is tilted.

(E09) A defect can be automatically moved into the center of the scanned image by measuring the deviation of the center of the defect from the center of the scanned image after the defect has been moved into the review position by the automatic centering means.

(E010) Whenever the rotating table is tilted at an increment of angle by the rotated state centering operating means, the automatic centering means is operated to bring the defect into the center of the scanned image. The rotating table can be rotated through a specified angle without the defect moving off the scanned image.

(E011) Whenever the rotating table is tilted at an increment of angle by the tilted state centering operating means, the automatic centering means is operated to bring the defect into the center of the scanned image. The rotating table can be rotated through a specified angle without the defect moving off the scanned image.

(E012) Where automatic adjustment of the field of view as described above is commanded, the scanned image magnification determining means automatically adjusts the magnification of the scanned image according to the size of the defect on the scanned image. Therefore, the size of the defect displayed on the scanned image can be made appropriate.

(E013) The inspected part information database having a defect image sorting database stores scanned images of defects produced on the inspected part, the images being classified in terms of kind of defect. Therefore, the defect sorting means can compare an actual scanned image of an inspected part with scanned images of defects stored in the defect image sorting database and judge to what category of the database does the defect on the inspected part belong. Consequently) defects can be readily assorted.

The similar image search means can search the defect image sorting database for those images which are registered in this defect image sorting database and have evaluation values differing from uncoded electron microscope images of defects by values lying within a given range, and display the found images. Therefore, the microscope images of defects to which sort codes are not yet given can be easily classified by comparison with the images discovered by the search and displayed.

What is claimed is:

1. A part-inspecting system comprising:
   (1) do computer implemented defect image filing system having a memory storing an inspected part information database including:
      (a) a preliminary inspection information database for storing preliminary inspection information having part search information helpful in identifying defects on an already preliminarily inspected part, and positional information about positions of defects present on said inspected part determined on a preliminary inspection apparatus, and
      (b) a review information database for storing part search information useful in identifying said inspected part and review information obtained by a review inspection of said preliminarily inspected part;
   (2) a vacuum inspection chamber in which an inspected part-holding member may be disposed;
   (3) a review apparatus comprising:
      (a) a microscope and said vacuum inspection chamber,
      (b) an XY-table for moving said inspected part-holding member in X- and Y-directions perpendicular to each other to bring a desired portion of said inspected part into a review position,
      (c) a microscope image photographing means for creating a microscope image at a magnification set by a magnification setting means,
      (d) a part search information input means for entering information about a search for said inspected part set on said inspected part-holding member,
      (e) a part search information storage means for storing said information entered by said part search information input means, and
      (f) a preliminary information reading means for reading preliminary inspection information about a preliminary inspection of said inspected part from said inspected part database according to said information entered by said part search information input means;
   (4) a selecting means for selecting a defect to be reviewed from defects contained in said preliminary inspection information read in by said preliminary inspection reading means;
   (5) a review information registration means for storing review information obtained by reviewing said selected defect in said inspected part information database;
   (6) inspected part moving means for moving said XY-table to bring said inspected part held by said inspected part-holding member into target X- and Y-coordinates; and
   (7) a misalignment correcting means having:
      (a) set condition coordinate deviation amount detecting means for detecting amounts of deviations of x- and y-coordinates of a part position reference point on said preliminary inspection apparatus detected by said preliminary inspection apparatus from X- and Y-coordinates of said reference point on said review apparatus when said inspected part is set on said inspected part-holding member, and
      (b) reference point coinciding moving means for causing said inspected part to move distances equal to said detected amounts of deviations to bring said x- and y-coordinates of said reference point into agreement with said X- and Y-coordinates.

2. The part-inspecting system of claim 1, wherein said review apparatus consists of a scanning electron microscope used for reviews, and wherein said scanning electron microscope comprises an electron beam scanning device for scanning said inspected portion in a scanned range according to the magnification set by said magnification setting means with an electron beam, a particle detecting means for detecting particles emitted from a surface of said inspected part scanned by said electron beam scanning device, and a scanned image photographing means for creating a scanned image within a plane scanned by said electron beam from a scanning position of said electron beam and from an output signal from said particle detecting means.

3. The part-inspecting system of claim 1, wherein said review apparatus consists of an optical microscope used for reviews, and wherein said optical microscope photographs an optical image in said desired inspection position.

4. The part-inspecting system of any one of claims 1–3, wherein said misalignment correcting means has a reference point coordinate calculating means for calculating X- and Y-coordinates of said part position reference point from X- and Y-coordinates of plural part position detection positions on an arc on said inspected part provided that said inspected part is an unpatterned bare wafer having arc-shaped fringes, said arc having a center point at which said part position reference point is established.

5. The part-inspecting system of any one of claims 1–3, wherein said misalignment correcting means brings said x- and y-coordinates of said part position reference point of said inspected part into agreement with the X- and Y-coordinates provided that said inspected part is a patterned wafer and that said part position reference point is established on a certain pattern on said inspected part.

6. The part-inspecting system of claim 5, wherein said misalignment correcting means brings said x- and y-coordinates of said part position reference point of said inspected part into agreement with the X- and Y-coordinates provided that said inspected part is a wafer patterned into identical chips and that said part position reference point is established on a certain chip on said inspected part.

7. The part-inspecting system of claim 1, wherein said misalignment means is designed so that said part position reference point is established on a defect detected by said preliminary inspection apparatus for said inspected part.

8. A part-inspecting system comprising:
(1) a computer implemented defect image filing system having a memory storing an inspected part information database including:
    (a) a preliminary inspection information database for storing preliminary inspection information including part search information helpful in identifying defects on an already preliminarily inspected part, and positional information about positions of defects present on said inspected part, and information about sizes of said defects determined by a preliminary inspection apparatus, and
    (b) a review information database for storing part search information helpful in identifying said inspected part and review information obtained by a review inspection of said preliminarily inspected part;
(2) a vacuum inspection chamber in which an inspected part-holding member may be disposed;
(3) a review apparatus comprising:
    (a) a microscope and said vacuum inspection chamber,
    (b) an XY-table for moving said inspected part-holding member in X- and Y-directions perpendicular to each other to bring a desired portion of said inspected part into a review position,
    (c) a microscope image photographing means for creating a microscope image at a magnification set by a magnification setting means,
    (d) a part search information input means for entering information about a search for said inspected part set on said inspected part-holding member,
    (e) a part search information storage means for storing said information entered by said part search information input means, and
    (f) a preliminary information reading means for reading information about a preliminary inspection of said inspected part from said inspected part database according to said information entered by said part search information means;
(4) a selecting means for selecting a defect to be reviewed from defects contained in said preliminary inspection information read in by said preliminary inspection reading means;
(5) a review information registrations means for storing review information obtained by reviewing said selected defect in said inspected part information database;
(6) inspected part moving means for moving said XY-table to bring said inspected part held by said inspected part-holding member into target X- and Y-coordinates;
(7) set state coordinate deviation amount detecting means for detecting amounts of deviations of x- and y-coordinates of said part position reference point of said inspected part detected by said preliminary inspection apparatus from X- and Y-coordinates of said part position reference point on said review apparatus when said part is set on said inspected part-holding member; and
(8) target coordinate correcting means for correcting target coordinates of said part position reference point assumed after the movement of said inspected part according to said amounts of deviations of said inspected part.

9. The part-inspecting system of claim 8, further comprising a reference point coordinate calculating means for calculating X- and Y-coordinates of said part position reference point from X- and Y-coordinates of plural part position detection positions on an arc on said inspected part provided that said inspected part is an unpatterned bare wafer having arc-shaped fringes, said arc having a center point at which said part position reference point is established.

10. The part-inspecting system of claim 8, wherein said set state coordinate deviation amount detecting means are designed to detect amounts of deviations of said x- and y-coordinates of a pattern on said inspected part from X- and Y-coordinates of said pattern provided that said inspected part is a wafer patterned into fine lines and that said part position reference point is established on a given one of said fine lines.

11. The part-inspecting system of claim 10, wherein said set state coordinate deviation amount detecting means are designed to detect amounts of deviations of said x- and y-coordinates of a certain chip on said inspected part from X- and Y-coordinates of said pattern provided that said inspected part is a wafer patterned into identical chips and that part position reference points are established on certain chips of the inspected part.

12. The part-inspecting system of claim 8, wherein said part position reference point is established on a defect on said inspected part detected by said preliminary inspection apparatus, and wherein said set state coordinate deviation amount detecting means are designed to detect amounts of deviations of said x- and y-coordinates of said defect on said inspected part from X- and Y-coordinates of said defect on said review apparatus when said part is set in said inspected part-holding member.

13. A part-inspecting system comprising:
(1) a computer implemented defect image filing system having a memory storing an inspected part information database including:
    (a) a preliminary inspection information database for storing preliminary inspection information having part search information helpful in identifying defects on a preliminarily inspected part, and positional information about positions of defects present on said inspected part, and information about sizes of said defects determined on a preliminary inspection apparatus, and
    (b) a review information database for storing review information obtained by a review inspection of said preliminarily inspected part;
(2) a vacuum inspection chamber in which an inspected part-holding member may be disposed;

(3) a review apparatus comprising:
   (a) a microscope and said vacuum inspection chamber,
   (b) an XY-table for moving said inspected part-holding member in X- and Y-directions perpendicular to each other to bring a desired portion of said inspected part into a review position,
   (c) a microscope image photographing means for creating a microscope image at a magnification set by a magnification setting means,
   (d) a part search information input means for entering information about a search for said inspected part set on said inspected part-holding member,
   (e) a part search information storage means for storing said information entered by said part search information input means, and
   (f) a preliminary inspection information reading means for reading information about a preliminary inspection of said inspected part from said inspected part information database according to said information entered by said part search information input means;
(4) a review information registration means for storing review information obtained by reviewing a defect in said inspected part information database, said defect being selected from defects contained in said preliminary inspection information read by said preliminary inspection information reading means;
(5) a rotating table capable of adjusting the angular position of said inspected part-holding member about an axis of rotation perpendicular to said X- and Y-axes;
(6) an angular position specifying means for specifying the angular position of said rotating table;
(7) a rotation control means for rotating said rotating table so that said inspected part held by said inspected part-holding member moves into a target angular position specified by said angular position specifying means within an X-Y plane;
(8) a set state angular position detecting means for detecting the angular position of said inspected part within the X-Y plane when said inspected part is set on said inspected part-holding member;
(9) an angular position deviation detecting means for detecting amounts of deviations of x- and y-coordinates of the angular position of said inspected part on said preliminary inspection apparatus detected by said preliminary inspection apparatus from X- and Y-coordinates of the angular position of said part when said part is set; and
(10) a misalignment correcting means having an angular position coinciding rotating means for rotating said rotating table through an angle equal to said detected amount of deviation so that the x- and y-coordinates of said angular position of said inspected part agree with the X- and Y-coordinates of the angular position when the part is set.

14. The part-inspecting system of claim 13, wherein said set state angular position detecting means comprises:
   (a) a reference point coordinate calculating means for calculating X- and Y-coordinates of said part position reference point from X- and Y-coordinates of plural part position detection points on an arc on said inspected part provided that said inspected part is an unpatterned bare wafer having arc-shaped fringes, said arc having a center point at which said part position reference point is established, said arc having indicia indicating angular position detection points of said part;
   (b) angular position detection point coordinate detecting means for detecting X- and Y-coordinates of said part angular position detection points; and
   (c) means for detecting X- and Y-coordinates of the angular position of said inspected part from X- and Y-coordinates of said part position reference points and of said part angular position detection points when said inspected part is set on said inspected part-holding member.

15. The part-inspecting system of claim 13, wherein said set state angular position detecting means is designed to detect X- and Y-coordinates of part position detection points established on said inspected part where said inspected part is a patterned wafer and set on said inspected part-holding member and to determine the angular position of said wafer from the detected X- and Y-coordinates.

16. A part-inspecting system comprising:
(1) a computer implemented defect image filing system having a memory storing an inspected part information database including:
   (a) a preliminary inspection information database for storing preliminary inspection information having part search information helpful in identifying defects on a preliminarily inspected part, positional information about positions of defects present on said inspected part, and information about sizes of said defects determined on a preliminary inspection apparatus, and
   (b) a review information database for storing review information obtained by a review inspection of said preliminarily inspected part;
(2) a vacuum inspection chamber in which an inspected part-holding member is disposed;
(3) a review apparatus comprising:
   (a) a microscope and said vacuum inspection chamber,
   (b) an XY-table for moving said inspected part-holding member in X- and Y-directions perpendicular to each other to bring a desired portion of said inspected part held on said inspected part-holding member into a review position,
   (c) a microscope image photographing means for creating a microscope image at a magnification set by a magnification setting means,
   (d) a part search information input means for entering information about a search for said inspected part set on said inspected part-holding member,
   (e) a part search information storage means for storing said information entered by said part search information input means, and
   (f) a preliminary information reading means for reading information about a preliminary inspection of said inspected part from said inspected part database according to said information entered by said part search information input means;
(4) a review information registration means for storing review information obtained by reviewing a first defect in said inspected part information database, said first defect being selected from defects contained in said preliminary inspection information read by said preliminary information reading means;
(5) a rotating table capable of adjusting the angular position of said inspected part-holding member about an axis of rotation perpendicular to said X- and Y-axes;
(6) an angular position specifying means for specifying the angular position of said rotating table;
(7) a rotation control means for rotating said rotating table 0o that said inspected part held by said inspected part-holding member moves into X- and Y-coordinates of a target angular position corresponding to an angular position specified by said angular position specifying means;

(8) a set state angular position detecting means for detecting the X- and Y-coordinates of the angular position of said inspected part when said inspected part is set on said inspected part-holding member;

(9) an angular position deviation amount detecting means for detecting amounts of deviations of the x- and y-coordinates of the angular position of said inspected part on said preliminary inspection apparatus detected by said preliminary inspection apparatus from the X- and Y-coordinates of the angular position of said part when it is set; and

(10) target coordinate correcting means for correcting said target angular position of said inspected part during rotation of said inspected part according to the detected amounts of deviations.

17. A part-inspecting system comprising:

(1) a computer implemented defect image filing system having a memory storing an inspected part information database including:
  (a) a preliminary inspection information database for storing preliminary inspection information having part search information helpful in identifying defects on a preliminarily inspected part, positional information about positions of defects present on said inspected part, and information about sizes of said defects determined by a preliminary inspection apparatus, and
  (b) a review information database for storing review information obtained by a review inspection of said inspected part;

(2) a vacuum inspection chamber in which an inspected part-holding member may be disposed;

(3) a review apparatus comprising:
  (a) a microscope and said vacuum inspection chamber,
  (b) an XY-table for moving said inspected part-holding member in X- and Y-directions perpendicular to each other to bring a desired portion of said inspected part held on said inspected part-holding member into a review position,
  (c) a microscope image photographing means for creating a microscope image at a magnification set by a magnification setting means,
  (d) a part search information input means for entering information about a search for said inspected part set on said inspected part-holding member,
  (e) a part search information storage means for storing said information entered by said part search information input means, and
  (f) a preliminary information reading means for reading information about a preliminary inspection of said inspected part from said inspected part database according to said information entered by said part search information input means;

(4) a review information registration means for storing review information obtained by reviewing a first defect in said inspected part information database, said first defect being selected from defects contained in said preliminary inspection information;

said review information database holding information about an observational position set on said inspected part and observational information having amounts of features defined in terms of numerical values representing a reference image in said observational position, a magnification of said reference image, and features of images, said reference image being a normal microscope image in said observational position; and (5) an automatic shape monitoring means for comparing an evaluation value determined by an amount of features of an actual microscope image in the observational position set on said inspected part with a reference evaluation value determined according to the amount of features of said reference image and judging said image to be defective if the evaluation value of said image differs from said reference evaluation value by more than a given value.

18. The part-inspecting system of claim 17, wherein said automatic shape monitoring means has an automatic tracking means for displaying an actual microscope image at the same magnification as said reference image according to information about the magnification of said reference image.

19. The part-inspecting system of claim 17 or 18, wherein said inspected part information database has a defective shape monitoring database and a defective image sorting-and-registration means which, if the actual microscope image is judged to be defective, gives a sort code indicating a fault to said actual microscope image, and registers it in said defective image monitoring database.

20. A part-inspecting system (1) a computer implemented defect image filing system having a memory storing an inspected part information database including:
  (a) a preliminary inspection information database for storing preliminary inspection information having part search information helpful in identifying defects on a preliminarily inspected part, positional information about positions of defects present on said inspected part, and information about sizes of said defects determined on a preliminary inspection apparatus, and
  (b) a review information database for storing review information obtained by a review inspection of said preliminarily inspected part;

(2) a vacuum inspection chamber in which an inspected part-holding member may be disposed;

(3) a review apparatus comprising:
  (a) a scanning beam microscope having an optical axis and said vacuum inspection chamber,
  (b) an XY-table for moving said inspected part-holding member in X- and Y-directions perpendicular to each other to bring a desired portion of said inspected part held on said inspected part-holding member into a review position,
  (c) a microscope image photographing means for creating a microscope image at a magnification set by a magnification setting means,
  (d) a part search information input means for entering information about a search for said inspected part set on said inspected part-holding member,
  (e) a part search information storage means for storing said information entered by said part search information input means, and
  (f) a preliminary information reading means for reading information about a preliminary inspection of said inspected part from said inspected part database according to said information entered by said part search information input means;

(4) a review information registration means for storing review information obtained by reviewing a first defect in said inspected part information database, said first defect being selected from defects contained in said preliminary inspection information;

(5) observational information including identification information used to identify a portion whose dimensions should be measured; and (6) an automatic length measuring means for measuring dimensions of said portion identified by said identification information on an actual microscope image in an observational position set on said inspected part.

21. The part-inspecting system of claim 20, further comprising:
(7) a tilt stage capable of adjusting a tilt position of said inspected part-holding member about a tilting axis perpendicular to the optical axis of said microscope;
(8) a tilt angle specifying means for specifying a tilt angle of said tilt stage; and
(9) a tilt control means for tilting said tilt stage according to a tilt angle specified by said tilt angle specifying means;
said observational information including information used to identify a portion whose dimension taken in the direction of thickness perpendicular to a plane scanned by the electron beam is to be measured;
said automatic length measuring means being designed to calculate the dimension taken in the direction of thickness from measured amounts of movement of two opposite measurement points across an actual microscope image made when said tilt stage is tilted, said two opposite measurement points being established on their respective opposite end surfaces having two opposite ends, respectively, of said portion whose dimension is to be measured.

22. A part-inspecting system comprising:
(1) a computer implemented defect image filing system having a memory storing an inspected part information database including:
   (a) a preliminary inspection information database for storing preliminary inspection information having part search information helpful in identifying defects on a preliminarily inspected part, positional information about positions of defects present on said inspected part, and information about sizes of said defects determined on a preliminary inspection apparatus, and
   (b) a review information database for storing review information obtained by a review, or detailed inspection, of said inspected part;
(2) a vacuum inspection chamber in which an inspected part-holding member is disposed;
(3) a review apparatus comprising:
   (a) a microscope having an optical axis and said vacuum inspection chamber,
   (b) an XY-table for moving said inspected part-holding member in X- and Y-directions perpendicular to each other to bring a desired portion of said inspected part held on said inspected part-holding member into a review position,
   (c) a microscope image photographing means for creating a microscope image at a magnification set by a magnification setting means,
   (d) a part search information input means for entering information about a search for said inspected part set on said inspected part-holding member,
   (e) a part search information storage means for storing said information entered by said part search information input means, and
   (f) a preliminary information reading means for reading information about a preliminary inspection of said inspected part from said inspected part database according to said information entered by said part search information input means;
(4) a review information registration means for storing review information obtained by reviewing a first defect in said inspected part information database, said first defect being selected from defects contained in said preliminary inspection information; and
(5) an automatic defect moving means for moving said XY-table according to the positional information contained in said preliminary inspection information about said selected defect to bring the selected defect into said review position.

23. A part-inspecting system comprising:
(1) a computer implemented defect image filing system having a memory storing an inspected part information database including:
   (a) a preliminary inspection information database for storing preliminary inspection information having part search information helpful in identifying a preliminarily inspected part, positional information about positions of defects present on said inspected part, and information about sizes of said defects determined on a preliminary inspection apparatus, and
   (b) a review information database for storing review information obtained by a review inspection of said inspected part;
(2) a vacuum inspection chamber in which an inspected part-holding member may be disposed;
(3) a review apparatus comprising:
   (a) a microscope having an optical axis and said vacuum inspection chamber,
   (b) an XY-table for moving said inspected part-holding member in X- and Y-directions perpendicular to each other to bring a desired portion of said inspected part held on said inspected part-holding member into a review position,
   (c) a microscope image photographing means for creating a microscope image at a magnification set by a magnification setting means,
   (d) a part search information input means for entering information about a search for said inspected part set on said inspected part-holding member,
   (e) a part search information storage means for storing said information entered by said part search information input means, and
   (f) a preliminary information reading means for reading information about a preliminary inspection of said inspected part from said inspected part database according to said information entered by said part search information means;
(4) a review information registration means for storing review information obtained by reviewing a first defect in said inspected part information database, said first defect being selected from defects contained in said preliminary inspection information; and
(5) an automatic centering means having a defect center deviation amount measuring means for measuring an amount of deviation of a center of said defect from a center of the microscope image of the defect in said review position and a defect center moving means for causing said defect to move a distance equal to said measured amount of deviation, thus bringing the defect into the center of the microscope image.

24. The part-inspecting system of claim 23, further comprising:
(6) a rotating table capable of adjusting an angular position of said inspected part-holding member about an axis of rotation perpendicular to said X- and Y-axes;

(7) an angular position specifying means for specifying an angular position of said rotating table;

(8) a tilt control means for tilting said tilt stage according to a tilt angle specified by said tilt angle specifying means; and (9) a rotated image tracking means having a rotation control means for rotating said rotating table by tilting it by increments of angle until said table is rotated through an angle specified by said angular position specifying means, an incremental angle setting means for setting said increments of angle, and a rotated state centering operating means for operating said automatic centering means whenever said rotating table is rotated through said increment of angle.

25. The part-inspecting system of claim 23, further comprising:

(6) a tilt stage capable of adjusting a tilt position of said inspected part-holding member about a tilting axis perpendicular to the optical axis of said microscope;

(7) a tilt angle specifying means for specifying a tilt angle of said tilt stage; and (8) a rotated image tracking means having a tilt control means for tilting said rotating table by tilting it by increments of angle until said table is rotated through an angle specified by said tilt angle specifying means, an incremental angle setting means for setting said increments of angle, and a rotated state centering operating means for operating said automatic centering means whenever said rotating table is rotated through said increment of angle.

26. A part-inspecting system comprising:

(1) a computer implemented defect image filing system having a memory storing an inspected part information database including:

(a) a preliminary inspection information database for storing preliminary inspection information having part search information helpful in identifying defects on a preliminarily inspected part, positional information about positions of defects present on said inspected part, and information about sizes of said part determined on a preliminary inspection apparatus, and (b) a review information database for storing review information obtained by a review inspection of said inspected part;

(2) a vacuum inspection chamber in which an inspected part-holding member may be disposed;

(3) a review apparatus comprising:

(a) a microscope having an optical axis said vacuum inspection chamber, (b) an XY-table for moving said inspected part-holding member in X- and Y-directions perpendicular to each other to bring a desired portion of said inspected part held on said inspected part-holding member into a review position, (c) a microscope image photographing means for creating a microscope image at a magnification set by a magnification setting means, (d) a part search information input means for entering information about a search for said inspected part set on said inspected part-holding member, (e) a part search information storage means for storing said information entered by said part search information input means, and (f) a preliminary information reading means for reading information about a preliminary inspection of said inspected part from said inspected part database according to said information entered by said part search information input means;

(4) a review information registration means for storing review information obtained by reviewing a first defect in said inspected part information database, said first defect being selected from defects contained in said preliminary inspection information; and (5) an automatic field of view adjusting means comprising an automatic field of view adjustment commanding means for commanding automatic field of view adjustment so that a defect is displayed in appropriate size on said microscope image and said microscope magnification setting means for adjusting the magnification of the microscope image according to the size of the defect where the automatic field of view adjustment is commanded.

27. A part-inspecting system comprising:

(1) a computer implemented defect image filing system having a memory storing an inspected part information database including:

(a) a preliminary inspection information database for storing preliminary inspection information having part search information helpful in identifying defects on a preliminarily inspected part, positional information about positions of defects present on said inspected part, and information about sizes of said defects, and (b) a review information database for storing review information obtained by a review inspection of said inspected part;

(2) a vacuum inspection chamber in which an inspected part-holding member may be disposed;

(3) a review apparatus comprising:

(a) a microscope having an optical axis and said vacuum inspection chamber, (b) an XY-table for moving said inspected part-holding member in X- and Y-directions perpendicular to each other to bring a desired portion of said inspected part held on said inspected part-holding member into a review position, (c) a microscope image photographing means for creating a microscope image at a magnification set by a magnification setting means, (d) a part search information input means for entering information about a search for said inspected part set on said inspected part-holding member, (e) a part search information storage means for storing said information entered by said part search information input means, and (f) a preliminary information reading means for reading information about a preliminary inspection of said inspected part from said inspected part database according to said information entered by said part search information input means;

(4) a review information registration means for storing review information obtained by reviewing a first defect in said inspected part information database, said first defect being selected from defects contained in said preliminary inspection information;

said inspected part information database holding microscope images of defects produced on said inspected part together with sort codes representing kinds of the defects; and (5) a defect image sorting database holding amounts of features represented in terms of numerical values associated with sizes and shapes of said defects.

28. The part-inspecting system of claim 27, wherein said defect image sorting database holds numerical values associated with luminances of defects and representing amounts of features of the defects.

29. The part-inspecting system of claim 27 or 28, further comprising:
(6) an evaluation value calculating means for calculating an evaluation value from the amount of features of the microscope image of a defect on the inspected part before a sort code is given to the defect, said evaluation value being determined according to said amount of features; and
(7) a defect sorting means for giving the same sort code to the defect to which said sort code is not yet given as the code given to a defect that produces a small difference in evaluation value between the microscope image of a sort-coded defect stored in the defect image sorting database and the microscope image of the uncoded defect.

30. The part-inspecting system of claim 27 or 28, further comprising:
(6) an evaluation calculating means for calculating an evaluation value from the amount of features of the microscope image of an uncoded defect on the inspected part, said evaluation value being determined according to said amount of features; and
(7) similar image finding means for searching said defect image sorting database for images having evaluation values producing small differences with the evaluation value of the microscope image of the uncoded defect registered in the defect image sorting database and for displaying the found images, said small differences lying in a given range.

31. A part-inspecting system comprising:
(1) a computer implemented defect image filing system having a memory storing an inspected part information database including:
　(a) a preliminary inspection information database for storing preliminary inspection information having part search information helpful in identifying defects on a preliminarily inspected part, positional information about positions of defects present on said inspected part, and information about sizes of said defects determined on a preliminary inspection apparatus and
　(b) a review information database for storing review information obtained by a review inspection of said inspected part;
(2) a vacuum inspection chamber in which an inspected part-holding member may be disposed;
(3) a review apparatus comprising:
　(a) a microscope having an optical axis said vacuum inspection chamber,
　(b) an XY-table for moving said inspected part-holding member in X- and Y-directions perpendicular to each other to bring a desired portion of said inspected part held on said inspected part-holding member into a review position,
　(c) a microscope image photographing means for creating a microscope image at a magnification set by a magnification setting means,
　(d) a part search information input means for entering information about a search for said inspected part set on said inspected part-holding member,
　(e) a part search information storage means for storing said information entered by said part search information input means, and
　(f) a preliminary information reading means for reading information about a preliminary inspection of said inspected part from said inspected part database according to said information entered by said part search information input means;
(4) a review information registration means for storing review information obtained by reviewing a first defect in said inspected part information database, said first defect being selected from defects contained in said preliminary inspection information; and
(5) an intelligent defect information processing means for automatically selecting a defect to be reviewed from said preliminary inspection information.

32. The part-inspecting system of claim 31, wherein said intelligent defect information processing means has a condition validity judging means for judging whether a defect represented by said preliminary inspection information satisfies certain conditions and a review defect selecting means for selecting defects satisfying the certain conditions as defects to be reviewed.

33. The part-inspecting system of claim 31, wherein said intelligent defect information processing means is designed to select defects having sizes represented by said preliminary inspection information as defects required to be reviewed.

34. A part-inspecting system comprising:
(1) a computer implemented defect image filing system having a memory storing an inspected part information database including:
　(a) a preliminary inspection information database for storing preliminary inspection information having part search information helpful in identifying defects on a preliminarily inspected part, positional information about positions of defects present on said inspected part, and information about sizes of said defects determined on a preliminary inspection apparatus, and
　(b) a review information database for storing review information obtained by a review inspection of said inspected part;
(2) a vacuum inspection chamber in which an inspected part-holding member may be disposed;
(3) a review apparatus comprising:
　(a) a microscope having an optical axis and said vacuum inspection chamber,
　(b) an XY-table for moving said inspected part-holding member in X- and Y-directions perpendicular to each other to bring a desired portion of said inspected part held on said inspected part-holding member into a review position,
　(c) a microscope image photographing means for creating a microscope image at a magnification set by a magnification setting means,
　(d) a part search information input means for entering information about a search for said inspected part set on said inspected part-holding member,
　(e) a part search information storage means for storing said information entered by said part search information input means, and
　(f) a preliminary information reading means for reading information about a preliminary inspection of said inspected part from said inspected part database according to said information entered by said part search information input means;
(4) a review information registration means for storing review information obtained by reviewing a first defect in said inspected part information database, said first defect being selected from defects contained in said preliminary inspection information;
said review apparatus having a cassette placement portion mounted adjacent to said vacuum inspection chamber and an inspected part-transporting device for taking an inspected part from a cassette placed on said cassette placement portion, transporting the taken part to said inspected part-holding member, and transporting the part undergone an inspection from said inspected part-holding member to said cassette; and (5) a part search information input means having a search information detection device for detecting search information permitting a search for preliminary inspection information about the inspected part inside said cassette when the cassette having said search information in a detectable form is placed on said cassette placement portion.

35. The part-inspecting system of claim 34, wherein said search information detection device is made of a bar code reader for reading a bar code from a label stuck on an outer surface of said cassette, said bar code representing said search information.

36. A. part-inspecting system comprising:
(1) a computer implemented defect image filing system having a memory storing an inspected part information database including:
    (a) a preliminary inspection information database for storing preliminary inspection information having part search information helpful in identifying defects on a preliminarily inspected part, positional information about positions of defects present on said inspected part, and information about sizes of said defects determined on a preliminary inspection apparatus, and
    (b) a review information database for storing review information obtained by a review inspection of said inspected part;
(2) a vacuum inspection chamber in which an inspected part-holding member may be disposed;
(3) a review apparatus comprising:
    (a) a microscope and said vacuum inspection chamber,
    (b) an XY-table for moving said inspected part-holding member in X- and Y-directions perpendicular to each other to bring a desired portion of said inspected part held on said inspected part-holding member into a review position,
    (c) a microscope image photographing means for creating a microscope image at a magnification set by a magnification setting means,
    (d) a part search information input means for entering information about a search for said inspected part set on said inspected part-holding member,
    (e) a part search information storage means for storing said information entered by said part search information input means, and
    (f) a preliminary information reading means for reading information about a preliminary inspection of said inspected part from said inspected part database according to said information entered by said part search information input means;
(4) a review information registration means for storing review information obtained by reviewing a first defect in said inspected part information database, said first defect being selected from defects contained in said preliminary inspection information;
(5) an X-ray analyzer incorporated in said review apparatus and acting to make an X-ray analysis of an inspected part in said review position;
(6) an X-ray analysis execution judging means for judging whether execution of an X-ray analysis is specified; and (7) an automatic X-ray analysis execution means for automatically executing an X-ray analysis if execution of an X-ray analysis is specified.

37. An automated part-inspecting system comprising:
(1) a computer implemented defect image filing system having a memory storing an inspected part information database including:
    (a) a preliminary inspection information database for storing preliminary inspection information having part search information helpful in identifying defects on a preliminary inspected part, and positional information about positions of defects present on said inspected part determined on a preliminary inspection apparatus, and
    (b) a review information database for storing part search information useful in identifying said inspected part and review information obtained by a review inspection of said preliminary inspected part;
(2) a vacum inspection chamber in which an inspected part-holding member may be disposed;
(3) a computer directed review apparatus comprising:
    (a) a microscope and said vacum inspection chamber,
    (b) an XY-table for moving said inspected part-holding member in X- and Y-directions perpendiculr to each other to bring a desired portion of said inspected part into a review postion,
    (c) a microscope image photographing means for creating a microscope image at a magnification set by a magnification setting means,
    (d) a part search information input means for entering information about a search for said inspected part set on said inspected part-holding member,
    (e) a part search information storage means for storing said information entered by said part search information input means, and
    (f) a preliminary information reading means for automatically reading preliminary inspection information about a preliminary inspection of said inspected part from said inspected part database according to said information entered by said part search information input means;
(4) a selecting means for automatically selecting a defect to be reviewed from defects contained in said preliminary inspection information read in by said preliminary inspection reading means; and
(5) a review information registration means for storing review information obtained by reviewing said selected defect in said inspected part information database.

38. The part-inspected system of claim 37, wherein said review apparatus consists of a scanning electron microscope used for reviews, and wherein said scanning electron microscope comprises an electron beam scanning device for scanning said inspected portion in a scanned range according to the magnification set by said magnification setting means with an electron beam, a particle detecting means for detecting particles emitted from a surface of said inspected part scanned by said electron beam scanning device, and a scanned image photographing means for creating a scanned image within a plane scanned by said electron beam from a scanning position of said electron beam and from an output signal from said particle detecting means.

39. The part-inspecting system of of claim 37, wherein said review apparatus consists of an optical microscope used for reviews, and wherin said optical microscope photographs an optical image in said desired inspection position.

* * * * *

UNITED STATES PATENT AND TRADEMARK OFFICE
CERTIFICATE OF CORRECTION

PATENT NO. : 6,259,960 B1
DATED : July 10, 2001
INVENTOR(S) : Masayuki Inokuchi

It is certified that error appears in the above-identified patent and that said Letters Patent is hereby corrected as shown below:

Title Page,
Item [73] Assignee, "Joel Ltd." should read -- JEOL Ltd. --.
--[30] Foreign Application Priority Data
Nov. 1, 1996 (JP)................................8-307104--.
Item [57] ABSTRACT
Line 12, after "inspection reading" insert -- means --.
Line 14, after "discriminating" insert -- means --.

Column 3,
Line 27, "specific number." should read -- specified number. --.

Column 4,
Line 59, "100" should read -- 10° --.

Column 7,
Line 4,, "FIGS. 1-5, 9" should read -- FIGS. 1-5, a --.
Line 16, "(56+63on" should read -- (56+63 on --.

Column 9,
Line 26, "that the that the" should read -- that the --. (duplicate text)
Line 51, "part. (W)" should read -- part (W) -- (delete period).

Column 10,
Line 7, "where the reference" should read -- when the reference --.

Column 11,
Line 37, "means (C01)" should read -- means (C41) --.

Column 12,
Line 23, "microscope" should read -- microscope) --.

Column 15,
Line 43, "FIGS. 60 arid 64" should read -- FIGS. 60 and 64 --.

Column 16,
Lines 21-22, "$\theta = 3020$ ;" should read -- $\theta = 30°$; --.
Line 31, "electron bean" should read -- electron beam --.
Line 52, "display devie D1" should read -- display device D1 --.
Line 58, "refer to subheading" should read -- refer to subheadings --.

UNITED STATES PATENT AND TRADEMARK OFFICE
CERTIFICATE OF CORRECTION

PATENT NO. : 6,259,960 B1
DATED : July 10, 2001
INVENTOR(S) : Masayuki Inokuchi

It is certified that error appears in the above-identified patent and that said Letters Patent is hereby corrected as shown below:

Column 19,
Line 1, "find makes" should read -- and makes --.

Column 20,
Line 11, "across-sectional" should read -- a cross-sectional --.
Line 40, "there view SEM" should read -- the review SEM --.

Column 23,
Line 55, "Abase" should read -- A base --.

Column 24,
Line 15, "inposition" should read --in position--.

Column 25,
Line 3, "member E5" should read -- member 65 --.
Line 9, after "SEM controller" insert period (.).
Line 54, after "(FIG. 9B)" insert period (.).
Line 55, after "(FIG. 9C)" insert period (.).

Column 26,
Line 56, "if th e" should read -- if the --.

Column 27,
Line 36, at end of sentence, insert period (.)

Column 28,
Line 49, "inspectionposition" should read -- inspection position --.

Column 29,
Line 65, "coordinates were" should read -- coordinates where --.

Column 30,
Line 3, after "is" insert -- as follows: --.
Line 40, "$(X_{3, Y3})$" should read -- $(X_3, Y_3)$ --.

Column 36,
Line 55, "center ao" should read -- center $a_0$ --.
Line 59, "center position ao frcm" should read -- center position $a_0$ from --.

UNITED STATES PATENT AND TRADEMARK OFFICE
CERTIFICATE OF CORRECTION

PATENT NO. : 6,259,960 B1
DATED : July 10, 2001
INVENTOR(S) : Masayuki Inokuchi

It is certified that error appears in the above-identified patent and that said Letters Patent is hereby corrected as shown below:

<u>Column 44,</u>
Line 15, "of0°" should read -- of 0° --.
Line 39, "do" should read -- $d_0$ --.

<u>Column 45,</u>
Line 9, "A set Sfc" should read -- A set $S_{fc}$ --.
Line 20, "position of 0° ," should read -- position of 0°, -- (delete space).

<u>Column 46,</u>
Line 45, "height of the defeat" should read -- height of the defect --.

<u>Column 55,</u>
Line 11, "The results Of" should read -- The results of --.
Line 30, "th e wafer W" should read -- the wafer W --.

<u>Column 57,</u>
Line 7, "step 4 0" should read -- step 40 --.
Line 33, "FIG. 33" should read -- FIG 38 --.

<u>Column 59,</u>
Line 49, "Instep 87" should read -- In step 87 --.

<u>Column 60,</u>
Line 24, "reacting mode" should read -- reading mode --.
Lines 51-52, "an" and "d" should read -- and --.

<u>Column 61,</u>
Line 54, "is No," should read -- is NO, --.

<u>Column 62,</u>
Line 41, "tile automatic" should read -- the automatic --.
Line 43, "f or" should read -- for --.

<u>Column 63,</u>
Line 22, "In step 165 ," should read -- In step 165, -- (delete space).
Line 27, "In step 165 ," should read -- In step 165, -- (delete space).

UNITED STATES PATENT AND TRADEMARK OFFICE
CERTIFICATE OF CORRECTION

PATENT NO. : 6,259,960 B1
DATED : July 10, 2001
INVENTOR(S) : Masayuki Inokuchi

It is certified that error appears in the above-identified patent and that said Letters Patent is hereby corrected as shown below:

<u>Column 64,</u>
Line 29, "Instep 189," should read -- In step 189, --.

<u>Column 65,</u>
Line 6, "Th e" should read -- The --.
Line 31, after "53B)" insert period (.).
Line 60, after "54D)" insert period (.).

<u>Column 67,</u>
Line 59, "In step 265 ," should read -- In step 265, --.

<u>Column 68,</u>
Line 23, "select ed" should read -- selected --.

<u>Column 69,</u>
Line 61, "illustrates parameter" should read -- illustrates parameters --.

<u>Column 70,</u>
Line 31, "In FIG. t4" should read -- In FIG. 64 --.
Line 33, "an here" should read -- where --.

<u>Column 72,</u>
Line 19, "a decision is mace" should read -- a decision is made --.

<u>Column 74,</u>
Line 57, after "scanning image" insert period (.).

<u>Column 75,</u>
Line 35, "Consequently)" should read -- Consequently, --.
Line 47, "do computer" should read -- a computer --.

<u>Column 80,</u>
Line 63, paragraph (7), 0o" should read -- so -- .

UNITED STATES PATENT AND TRADEMARK OFFICE
CERTIFICATE OF CORRECTION

PATENT NO. : 6,259,960 B1
DATED : July 10, 2001
INVENTOR(S) : Masayuki Inokuchi

It is certified that error appears in the above-identified patent and that said Letters Patent is hereby corrected as shown below:

<u>Column 82,</u>
Line 21, after "system" insert -- comprising: --.

<u>Column 90,</u>
Line 61, "and wherin" should read -- and wherein --.

Signed and Sealed this

First Day of October, 2002

*Attest:*

*Attesting Officer*

JAMES E. ROGAN
*Director of the United States Patent and Trademark Office*